US012012457B1

(12) United States Patent
Kastelein et al.

(10) Patent No.: US 12,012,457 B1
(45) Date of Patent: Jun. 18, 2024

(54) IL23R BINDING MOLECULES AND METHODS OF USE

(71) Applicant: Synthekine, Inc., Menlo Park, CA (US)

(72) Inventors: Robert Kastelein, Menlo Park, CA (US); Patrick J. Lupardus, Menlo Park, CA (US); Deepti Rokkam, Menlo Park, CA (US)

(73) Assignee: Synthekine, Inc., Menlo Park, CA (US)

( * ) Notice: Subject to any disclaimer, the term of this patent is extended or adjusted under 35 U.S.C. 154(b) by 0 days.

(21) Appl. No.: 18/017,065

(22) PCT Filed: Aug. 5, 2021

(86) PCT No.: PCT/US2021/044835

§ 371 (c)(1),
(2) Date: Jan. 19, 2023

(87) PCT Pub. No.: WO2022/032023

PCT Pub. Date: Feb. 10, 2022

Related U.S. Application Data

(60) Provisional application No. 63/135,884, filed on Jan. 11, 2021, provisional application No. 63/078,745, filed on Sep. 15, 2020, provisional application No. 63/061,562, filed on Aug. 5, 2020.

(51) Int. Cl.
*C07K 16/28* (2006.01)

(52) U.S. Cl.
CPC .... *C07K 16/2866* (2013.01); *C07K 2317/569* (2013.01)

(58) Field of Classification Search
CPC ...................... C07K 16/2866; C07K 2317/569
See application file for complete search history.

(56) References Cited

U.S. PATENT DOCUMENTS

| | | | |
|---|---|---|---|
| 8,258,268 | B2 | 9/2012 | Wu et al. |
| 8,921,528 | B2 | 12/2014 | Holt et al. |
| 8,975,382 | B2 | 3/2015 | Revets et al. |
| 10,927,186 | B2 | 2/2021 | Roobrouck et al. |
| 2006/0024295 | A1 | 2/2006 | Brunetta |
| 2010/0297127 | A1 | 11/2010 | Ghilardi et al. |
| 2011/0028695 | A1 | 2/2011 | Revets et al. |
| 2011/0053865 | A1 | 3/2011 | Saunders et al. |
| 2011/0142831 | A1 | 6/2011 | Cua et al. |
| 2012/0082681 | A1 | 4/2012 | Carballido et al. |
| 2012/0201746 | A1 | 8/2012 | Liu et al. |
| 2012/0316324 | A1 | 12/2012 | Adams et al. |
| 2014/0065142 | A1 | 3/2014 | Roschke et al. |
| 2014/0099708 | A1 | 4/2014 | Carballido Herrera et al. |
| 2014/0170154 | A1 | 6/2014 | Presta |
| 2015/0079088 | A1 | 3/2015 | Lowman et al. |
| 2016/0046730 | A1 | 2/2016 | Ghayur et al. |
| 2016/0251440 | A1 | 9/2016 | Roobrouck et al. |
| 2017/0106051 | A1 | 4/2017 | Oh et al. |
| 2017/0298149 | A1 | 10/2017 | Baeuerle et al. |
| 2018/0362655 | A1 | 12/2018 | Wang et al. |
| 2019/0315864 | A1 | 10/2019 | Xu et al. |
| 2020/0157237 | A1 | 5/2020 | Regev et al. |
| 2023/0272093 | A1 | 8/2023 | Kastelein et al. |

FOREIGN PATENT DOCUMENTS

| | | | |
|---|---|---|---|
| CN | 103396482 | A | 11/2013 |
| CN | 111018985 | A | 4/2020 |
| WO | 2008011081 | A2 | 1/2008 |
| WO | 2009068631 | A1 | 6/2009 |
| WO | 2011/051327 | A2 | 5/2011 |
| WO | 2013006544 | A1 | 1/2013 |
| WO | 2013059299 | A1 | 4/2013 |
| WO | 2016097313 | A1 | 6/2016 |
| WO | 2017198212 | A1 | 11/2017 |
| WO | 2019129221 | A1 | 7/2019 |
| WO | 2020/052543 | A1 | 3/2020 |
| WO | 2020144164 | A1 | 7/2020 |
| WO | 2020187711 | A1 | 9/2020 |
| WO | 2022031929 | A1 | 2/2022 |
| WO | 2022031942 | A2 | 2/2022 |
| WO | 2022032042 | A1 | 2/2022 |
| WO | 2022055641 | A2 | 3/2022 |

OTHER PUBLICATIONS

UniProtKB A0A066RQT8, UniProtKB Accession No. A0A066RQT8, Sep. 3, 2014, retrieved from internet www.uniprot.org/uniprot/A0A066RQT8.

Biolegend, PE anti-mouse IL-23R Antibody, Catalog, Mar. 28, 2016, retrieved from the internet www.biolegend.com/en-us/global-elements/pdf-popup/pe-anti-mouse-il-23r-antibody-13084?filename=PE%20anti-mouse%20IL-23R%20Antibody.pdf&pdfgen=true.

Franke et al. Human and murine interleukin 23 receptors are novel substrates for a disintegrin and metalloproteases ADAM10 and ADAM17. Journal of Biological Chemistry. May 13, 2016;291(20):10551-61.

International Search Report in PCT/US2021/044835, dated Feb. 8, 2022, 17 pages.

UniProtKB A0A066RQT8, UniProtKB Accession Numner: A0A066RQT8, Sep. 3, 2014, retrieved from internet www.uniprot.org/uniprot/A0A066RQT8.

Wilton et al. sdAb-DB: the single domain antibody database. ACS Synthetic Biology. Nov. 16, 2018;7(11):2480-4.

U.S. Appl. No. 18/017,282 , Notice of Allowance, dated Aug. 24, 2023, 14 pages.

(Continued)

*Primary Examiner* — Ruixiang Li
(74) *Attorney, Agent, or Firm* — Kilpatrick Townsend & Stockton LLP

(57) ABSTRACT

The present disclosure relates to biologically active molecules comprising a single domain antibody (sdAb) that specifically binds to the extracellular domain of human IL23R, compositions comprising such antibodies, and methods of use thereof. Further disclosed are sequences of complementarity determining regions (CDR1, CDR2 and CDR3) and polypeptide sequences of human and mouse sdAbs.

42 Claims, No Drawings

Specification includes a Sequence Listing.

(56) References Cited

OTHER PUBLICATIONS

U.S. Appl. No. 18/018,448 , Non-Final Office Action, dated Sep. 25, 2023, 18 pages.
Application No. PCT/US2021/044674 , International Preliminary Report on Patentability, dated Feb. 16, 2023, 8 pages.
Application No. PCT/US2021/044674, International Search Report and Written Opinion, dated Jan. 19, 2022, 12 pages.
PCT/US2021/044674 , "Invitation To Pay Additional Fees And, Where Applicable, Protest Fee", Nov. 12, 2021, 2 pages.
Application No. PCT/US2021/044698 , International Preliminary Report on Patentability, dated Feb. 16, 2023, 9 pages.
Application No. PCT/US2021/044698 , International Search Report and Written Opinion, dated Feb. 1, 2022, 13 pages.
PCT/US2021/044698 , "Invitation to Pay Additional Fees And, Where Applicable Protest Fee", Nov. 9, 2021, 2 pages.
PCT/US2021/044835 , "Invitation to Pay Additional Fees and, Where Applicable, Protest Fee", Nov. 16, 2021, 3 pages.
Application No. PCT/US2021/044850 , International Preliminary Report on Patentability, dated Feb. 16, 2023, 6 pages.
Application No. PCT/US2021/044850 , International Search Report and Written Opinion, dated Jan. 6, 2022, 9 pages.
Application No. PCT/US2021/044855 , International Preliminary Report on Patentability, dated Feb. 16, 2023, 8 pages.
Application No. PCT/US2021/044855 , International Search Report and Written Opinion, dated Dec. 16, 2021, 11 pages.
Pingwara et al., "IFN-λ Modulates the Migratory Capacity of Canine Mammary Tumor Cells via Regulation of the Expression of Matrix Metalloproteinases and Their Inhibitors", Cells, vol. 10, No. 5, Apr. 23, 2021, pp. 1-15.

SEQUENCE LISTING

<160> NUMBER OF SEQ ID NOS: 335

<210> SEQ ID NO 1
<211> LENGTH: 629
<212> TYPE: PRT
<213> ORGANISM: Homo sapiens

<400> SEQUENCE: 1

Met Asn Gln Val Thr Ile Gln Trp Asp Ala Val Ile Ala Leu Tyr Ile
1 5 10 15

Leu Phe Ser Trp Cys His Gly Gly Ile Thr Asn Ile Asn Cys Ser Gly
20 25 30

His Ile Trp Val Glu Pro Ala Thr Ile Phe Lys Met Gly Met Asn Ile
35 40 45

Ser Ile Tyr Cys Gln Ala Ala Ile Lys Asn Cys Gln Pro Arg Lys Leu
50 55 60

His Phe Tyr Lys Asn Gly Ile Lys Glu Arg Phe Gln Ile Thr Arg Ile
65 70 75 80

Asn Lys Thr Thr Ala Arg Leu Trp Tyr Lys Asn Phe Leu Glu Pro His
85 90 95

Ala Ser Met Tyr Cys Thr Ala Glu Cys Pro Lys His Phe Gln Glu Thr
100 105 110

Leu Ile Cys Gly Lys Asp Ile Ser Ser Gly Tyr Pro Pro Asp Ile Pro
115 120 125

Asp Glu Val Thr Cys Val Ile Tyr Glu Tyr Ser Gly Asn Met Thr Cys
130 135 140

Thr Trp Asn Ala Gly Lys Leu Thr Tyr Ile Asp Thr Lys Tyr Val Val
145 150 155 160

His Val Lys Ser Leu Glu Thr Glu Glu Glu Gln Gln Tyr Leu Thr Ser
165 170 175

Ser Tyr Ile Asn Ile Ser Thr Asp Ser Leu Gln Gly Gly Lys Lys Tyr
180 185 190

Leu Val Trp Val Gln Ala Ala Asn Ala Leu Gly Met Glu Glu Ser Lys
195 200 205

Gln Leu Gln Ile His Leu Asp Asp Ile Val Ile Pro Ser Ala Ala Val
210 215 220

Ile Ser Arg Ala Glu Thr Ile Asn Ala Thr Val Pro Lys Thr Ile Ile
225 230 235 240

Tyr Trp Asp Ser Gln Thr Thr Ile Glu Lys Val Ser Cys Glu Met Arg
245 250 255

Tyr Lys Ala Thr Thr Asn Gln Thr Trp Asn Val Lys Glu Phe Asp Thr
260 265 270

Asn Phe Thr Tyr Val Gln Gln Ser Glu Phe Tyr Leu Glu Pro Asn Ile
275 280 285

Lys Tyr Val Phe Gln Val Arg Cys Gln Glu Thr Gly Lys Arg Tyr Trp
290 295 300

Gln Pro Trp Ser Ser Leu Phe Phe His Lys Thr Pro Glu Thr Val Pro
305 310 315 320

Gln Val Thr Ser Lys Ala Phe Gln His Asp Thr Trp Asn Ser Gly Leu
325 330 335

```
Thr Val Ala Ser Ile Ser Thr Gly His Leu Thr Ser Asp Asn Arg Gly
            340                 345                 350

Asp Ile Gly Leu Leu Leu Gly Met Ile Val Phe Ala Val Met Leu Ser
        355                 360                 365

Ile Leu Ser Leu Ile Gly Ile Phe Asn Arg Ser Phe Arg Thr Gly Ile
    370                 375                 380

Lys Arg Arg Ile Leu Leu Leu Ile Pro Lys Trp Leu Tyr Glu Asp Ile
385                 390                 395                 400

Pro Asn Met Lys Asn Ser Asn Val Val Lys Met Leu Gln Glu Asn Ser
                405                 410                 415

Glu Leu Met Asn Asn Asn Ser Ser Glu Gln Val Leu Tyr Val Asp Pro
            420                 425                 430

Met Ile Thr Glu Ile Lys Glu Ile Phe Ile Pro Glu His Lys Pro Thr
        435                 440                 445

Asp Tyr Lys Lys Glu Asn Thr Gly Pro Leu Glu Thr Arg Asp Tyr Pro
    450                 455                 460

Gln Asn Ser Leu Phe Asp Asn Thr Thr Val Val Tyr Ile Pro Asp Leu
465                 470                 475                 480

Asn Thr Gly Tyr Lys Pro Gln Ile Ser Asn Phe Leu Pro Glu Gly Ser
                485                 490                 495

His Leu Ser Asn Asn Asn Glu Ile Thr Ser Leu Thr Leu Lys Pro Pro
            500                 505                 510

Val Asp Ser Leu Asp Ser Gly Asn Asn Pro Arg Leu Gln Lys His Pro
        515                 520                 525

Asn Phe Ala Phe Ser Val Ser Ser Val Asn Ser Leu Ser Asn Thr Ile
    530                 535                 540

Phe Leu Gly Glu Leu Ser Leu Ile Leu Asn Gln Gly Glu Cys Ser Ser
545                 550                 555                 560

Pro Asp Ile Gln Asn Ser Val Glu Glu Glu Thr Thr Met Leu Leu Glu
                565                 570                 575

Asn Asp Ser Pro Ser Glu Thr Ile Pro Glu Gln Thr Leu Leu Pro Asp
            580                 585                 590

Glu Phe Val Ser Cys Leu Gly Ile Val Asn Glu Glu Leu Pro Ser Ile
        595                 600                 605

Asn Thr Tyr Phe Pro Gln Asn Ile Leu Glu Ser His Phe Asn Arg Ile
    610                 615                 620

Ser Leu Leu Glu Lys
625


<210> SEQ ID NO 2
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Gln Val Gln Leu Gln Glu Ser Gly Gly Gly Ser Val Gln Ala Gly Gly
1               5                   10                  15

Ser Leu Arg Leu Ser Cys Ala Ala Ser Gly Tyr Thr Tyr Cys Ser Tyr
            20                  25                  30

Asp Met Ser Trp Tyr Arg Gln Ala Pro Gly Lys Lys Arg Glu Phe Val
        35                  40                  45

Ser Ala Phe Asn Ser Asp Gly Thr Thr Ser Tyr Ala Asp Ser Val Lys
    50                  55                  60
```

```
Gly Arg Phe Thr Ile Ser Gln Asp Lys Ala Lys Asn Thr Val Tyr Leu
65                  70                  75                  80

Gln Met Asn Ser Leu Lys Pro Glu Asp Thr Ala Met Tyr Tyr Cys Lys
                85                  90                  95

Thr Asp Pro His Val Gln Ser Ser Gly Gly Tyr Cys Pro Pro Tyr Trp
            100                 105                 110

Gly Gln Gly Thr Gln Val Thr Val Ser Ser
        115                 120


<210> SEQ ID NO 3
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Gln Val Gln Leu Gln Glu Ser Gly Gly Gly Ser Val Gln Ala Gly Gly
1               5                   10                  15

Ser Leu Arg Leu Ser Cys Ala Ala Ser Gly Tyr Thr Tyr Cys Ser Tyr
            20                  25                  30

Asp Met Ser Trp Tyr Arg Gln Ala Pro Gly Lys Lys Arg Glu Phe Val
        35                  40                  45

Ser Ser Phe Asn Ser Asp Gly Ser Thr Ser Tyr Ala Asp Ser Val Lys
    50                  55                  60

Gly Arg Phe Thr Ile Ser Gln Asp Asn Ala Lys Asn Thr Val Tyr Leu
65                  70                  75                  80

Gln Met Asn Ser Leu Lys Pro Glu Asp Thr Ala Met Tyr Tyr Cys Lys
                85                  90                  95

Thr Asp Pro His Ala Asp Trp Gly Ala Pro Cys Gly Gly Asp Tyr Trp
            100                 105                 110

Gly Gln Gly Thr Gln Val Thr Val Ser Ser
        115                 120


<210> SEQ ID NO 4
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Gln Val Gln Leu Gln Glu Ser Gly Gly Gly Ser Val Gln Ala Gly Glu
1               5                   10                  15

Ser Leu Arg Leu Ser Cys Ala Ala Ser Gly Tyr Thr Tyr Cys Thr Tyr
            20                  25                  30

Asp Met Thr Trp Tyr Arg Gln Ala Pro Gly Lys Lys Arg Glu Phe Val
        35                  40                  45

Ser Gly Ile His Ser Asp Gly Thr Thr Ser Tyr Ala Asp Ser Val Lys
    50                  55                  60

Gly Arg Phe Thr Ile Ser Gln Asp Asn Ala Glu Asn Thr Val Tyr Leu
65                  70                  75                  80

Gln Met Asn Ser Leu Lys Pro Glu Asp Thr Ala Met Tyr Tyr Cys Lys
                85                  90                  95

Thr Asp Pro Ile Ala Thr Ile Thr Arg Arg Cys Asp Ser Tyr Trp Gly
            100                 105                 110
```

Gln Gly Thr Gln Val Thr Val Ser Ser
115 120

<210> SEQ ID NO 5
<211> LENGTH: 122
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 5

Gln Val Gln Leu Gln Glu Ser Gly Gly Gly Ser Val Gln Ala Gly Gly
1 5 10 15

Ser Leu Arg Leu Ser Cys Ala Ala Ser Gly Ser Thr Tyr Cys Thr Tyr
20 25 30

Asp Met Thr Trp Tyr Arg Gln Ala Pro Gly Lys Arg Arg Glu Phe Val
35 40 45

Ser Ala Ile Asn Ser Asp Gly Ser Thr Ser Tyr Ala Asp Ser Val Lys
50 55 60

Gly Arg Phe Thr Ile Ser Gln Asp Asn Ala Lys Asn Thr Val Tyr Leu
65 70 75 80

Gln Met Asn Ser Leu Lys Pro Glu Asp Thr Ala Met Tyr Tyr Cys Lys
85 90 95

Thr Asp Pro Asn Ser Gly Trp Gly Ala Pro Cys Gly Gly Asp Tyr Trp
100 105 110

Gly Gln Gly Thr Gln Val Thr Val Ser Ser
115 120

<210> SEQ ID NO 6
<211> LENGTH: 122
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 6

Gln Val Gln Leu Gln Glu Ser Gly Gly Gly Ser Val Gln Ala Gly Gly
1 5 10 15

Ser Leu Arg Leu Ser Cys Ala Ala Ser Gly Tyr Thr Tyr Cys Ser Tyr
20 25 30

Asp Met Ser Trp Tyr Arg Gln Ala Pro Gly Lys Lys Arg Glu Phe Val
35 40 45

Ser Ala Ile Ala Ser Asp Gly Ser Thr Ser Tyr Ala Asp Ser Leu Lys
50 55 60

Gly Arg Phe Thr Ile Ser Gln Asp Asn Ala Lys Asn Thr Val Tyr Leu
65 70 75 80

Gln Met Asn Ser Leu Lys Pro Glu Asp Thr Ala Met Tyr Tyr Cys Lys
85 90 95

Thr Asp Pro His Val Gln Ser Ser Gly Gly Tyr Cys Pro Pro Tyr Trp
100 105 110

Gly Gln Gly Thr Gln Val Thr Val Ser Ser
115 120

<210> SEQ ID NO 7
<211> LENGTH: 121
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 7

Gln Val Gln Leu Gln Glu Ser Gly Gly Gly Leu Val Gln Pro Gly Gly
1               5                   10                  15

Ser Leu Arg Leu Ser Cys Ala Ala Ser Gly Tyr Thr Tyr Cys Ser Tyr
            20                  25                  30

Asp Met Gly Trp Tyr Arg Gln Ala Pro Gly Lys Lys Arg Lys Phe Val
        35                  40                  45

Ser Ser Ile Asn Ser Asp Gly Thr Thr Ser Tyr Ala Asp Ser Val Lys
    50                  55                  60

Gly Arg Phe Thr Ile Ser Gln Asp Asn Ala Lys Asn Thr Val Tyr Leu
65                  70                  75                  80

Gln Met Asn Ser Leu Lys Pro Glu Asp Thr Ala Met Tyr Tyr Cys Lys
                85                  90                  95

Thr Asp Pro Gln Thr Arg Pro Gly Lys Pro Cys Ala Asp Tyr Trp Gly
            100                 105                 110

Gln Gly Thr Gln Val Thr Val Ser Ser
        115                 120


<210> SEQ ID NO 8
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Gln Val Gln Leu Gln Glu Ser Gly Gly Gly Ser Val Gln Ala Gly Gly
1               5                   10                  15

Ser Leu Arg Leu Ser Cys Ala Ala Ser Gly Tyr Thr Tyr Cys Asn Tyr
            20                  25                  30

Asp Ile Ala Trp Tyr Arg Gln Ala Pro Gly Lys Glu Arg Lys Phe Val
        35                  40                  45

Ser Ala Ile Ala Ser Asp Gly Ile Thr Ser Tyr Ala Asp Ser Val Lys
    50                  55                  60

Gly Arg Phe Thr Ile Ser Gln Asp Asn Ala Lys Asn Thr Val Tyr Leu
65                  70                  75                  80

Gln Met Asn Ser Leu Lys Pro Glu Asp Thr Ala Met Tyr Tyr Cys Lys
                85                  90                  95

Thr Asp Pro Ile Ser Thr Ile Thr Arg Ile Cys Asp Pro Tyr Trp Gly
            100                 105                 110

Gln Gly Thr Gln Val Thr Val Ser Ser
        115                 120


<210> SEQ ID NO 9
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Gln Val Gln Leu Gln Glu Ser Gly Gly Asp Ser Val Gln Ala Gly Gly
1               5                   10                  15
```

```
Ser Leu Arg Leu Ser Cys Ala Ala Ser Gly Tyr Thr Tyr Cys Ser Tyr
            20                  25                  30

Asp Met Lys Trp Tyr Arg Gln Ala Pro Gly Lys Glu Arg Glu Phe Val
        35                  40                  45

Ser Gly Ile Asp Ser Asp Gly Ser Ile Ser Tyr Ala Asp Ser Val Lys
    50                  55                  60

Gly Arg Phe Thr Ile Ser Gln Asp Asn Ala Lys Asn Thr Val Tyr Leu
65                  70                  75                  80

Gln Met Asn Ser Leu Lys Pro Glu Asp Thr Ala Met Tyr Tyr Cys Lys
                85                  90                  95

Thr Glu Gly Thr Ile Pro Val Gly Ala Cys Pro Asn Tyr Trp Gly Gln
            100                 105                 110

Gly Thr Gln Val Thr Val Ser Ser
        115                 120


<210> SEQ ID NO 10
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Gln Val Gln Leu Gln Glu Ser Gly Gly Gly Leu Val Gln Ala Gly Gly
1               5                   10                  15

Ser Leu Arg Leu Ser Cys Ala Ala Ser Gly Tyr Thr Tyr Cys Ser Tyr
            20                  25                  30

Asp Met Ser Trp Tyr Arg Gln Ala Pro Gly Lys Glu Arg Lys Phe Val
        35                  40                  45

Ser Ser Ile Asn Ser Asp Gly Thr Thr Ser Tyr Ala Asp Ser Val Lys
    50                  55                  60

Gly Arg Phe Thr Ile Ser Gln Asp Asn Ala Lys Asn Thr Val Tyr Leu
65                  70                  75                  80

Gln Met Asn Ser Leu Lys Pro Glu Asp Thr Ala Met Tyr Tyr Cys Lys
                85                  90                  95

Thr Asp Pro Gln Thr Arg Pro Gly Lys Pro Cys Ala Asp Tyr Trp Gly
            100                 105                 110

Gln Gly Thr Gln Val Thr Val Ser Ser
        115                 120


<210> SEQ ID NO 11
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Gln Val Gln Leu Gln Glu Ser Gly Gly Gly Ser Val Gln Ala Gly Gly
1               5                   10                  15

Ser Leu Lys Leu Ser Cys Ala Ala Ser Gly Tyr Thr Tyr Cys Asn Tyr
            20                  25                  30

Asp Ile Ala Trp Tyr Arg Gln Ala Pro Gly Lys Glu Arg Lys Phe Val
        35                  40                  45

Ser Ala Ile Ala Ser Asp Gly Ser Thr Ser Tyr Ala Asp Ser Val Lys
    50                  55                  60
```

```
Gly Arg Phe Thr Ile Ser Gln Asp Asn Ala Lys Asn Thr Val Tyr Leu
65                  70                  75                  80

Gln Met Asn Ser Leu Lys Pro Glu Asp Thr Ala Met Tyr Tyr Cys Lys
                85                  90                  95

Thr Asp Pro Ile Ala Thr Met Thr Arg Arg Cys Asp Pro Tyr Trp Gly
            100                 105                 110

Gln Gly Thr Gln Val Thr Val Ser Ser
        115                 120


<210> SEQ ID NO 12
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Gln Val Gln Leu Gln Glu Ser Gly Gly Gly Ser Val Gln Ala Gly Gly
1               5                   10                  15

Ser Leu Arg Leu Ser Cys Ala Ala Ser Gly Tyr Thr Tyr Cys Ser Tyr
            20                  25                  30

Asp Met Thr Trp Tyr Arg Gln Ala Pro Gly Lys Lys Arg Glu Phe Val
        35                  40                  45

Ser Ala Ile Asp Ser Asp Gly Ser Thr Ser Tyr Ala Asp Ser Val Lys
    50                  55                  60

Gly Arg Phe Thr Ile Ser Gln Asp Asn Ala Lys Asn Thr Val Tyr Leu
65                  70                  75                  80

Gln Met Asn Ser Leu Lys Pro Glu Asp Thr Ala Met Tyr Tyr Cys Lys
                85                  90                  95

Thr Asp Pro Ile Ala Thr Ile Ser Arg Arg Cys Asp Ser Tyr Trp Gly
            100                 105                 110

Gln Gly Thr Gln Val Thr Val Ser Ser
        115                 120


<210> SEQ ID NO 13
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Gln Val Gln Leu Gln Glu Ser Gly Gly Gly Ser Val Gln Ala Gly Gly
1               5                   10                  15

Ser Leu Arg Leu Ser Cys Ala Ala Ser Gly Tyr Thr Ser Ser Ser Arg
            20                  25                  30

Cys Met Gly Trp Phe Arg Gln Ala Pro Gly Lys Glu Arg Glu Gly Val
        35                  40                  45

Ala Arg Ile Tyr Thr Pro Thr Arg Thr Thr Trp Tyr Ala Asp Ser Val
    50                  55                  60

Lys Gly Arg Phe Thr Ile Ser Gln Asp Asn Ala Lys Asn Thr Val Tyr
65                  70                  75                  80

Leu Glu Met Ala Ser Leu Lys Pro Glu Asp Thr Ala Lys Tyr Phe Cys
                85                  90                  95

Ala Ala Gly Ala Ser Cys Ala Val Asp Leu Phe Ser Tyr Trp Gly Gln
            100                 105                 110
```

```
Gly Thr Gln Val Thr Val Ser Ser
        115                 120


<210> SEQ ID NO 14
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Gln Val Gln Leu Gln Glu Ser Gly Gly Gly Ser Val Gln Ala Gly Gly
1               5                   10                  15

Ser Leu Arg Leu Ser Cys Ala Ala Ser Gly Tyr Thr Tyr Cys Ser Tyr
            20                  25                  30

Asp Met Lys Trp Tyr Arg Gln Ala Pro Gly Lys Lys Arg Glu Phe Val
        35                  40                  45

Ser Ala Ile Asp Ser Asp Gly Ser Thr Ser Tyr Ala Asp Ser Val Lys
    50                  55                  60

Gly Arg Phe Thr Ile Ser Gln Asp Asn Ala Lys Asn Thr Val Tyr Leu
65                  70                  75                  80

Gln Met Asn Ser Leu Lys Pro Glu Asp Thr Ala Met Tyr Tyr Cys Lys
                85                  90                  95

Thr Glu Gly Thr Ile Pro Val Gly Val Cys Pro Asn Tyr Trp Gly Gln
            100                 105                 110

Gly Thr Gln Val Thr Val Ser Ser
        115                 120


<210> SEQ ID NO 15
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Gln Val Gln Leu Gln Glu Ser Gly Gly Gly Leu Val Gln Pro Gly Gly
1               5                   10                  15

Ser Leu Arg Leu Ser Cys Ala Ala Ser Gly Tyr Thr Tyr Cys Ser Tyr
            20                  25                  30

Asp Met Lys Trp Tyr Arg Gln Ala Pro Gly Lys Lys Arg Glu Phe Val
        35                  40                  45

Ser Ala Ile Asp Ser Asp Gly Ser Thr Ser Tyr Ala Asp Ser Val Lys
    50                  55                  60

Gly Arg Phe Thr Ile Ser Gln Asp Asn Ala Lys Asn Thr Val Tyr Leu
65                  70                  75                  80

Gln Met Asn Ser Leu Lys Pro Glu Asp Thr Ala Met Tyr Tyr Cys Lys
                85                  90                  95

Thr Glu Gly Thr Val Pro Val Gly Val Cys Pro Asn Tyr Trp Gly Gln
            100                 105                 110

Gly Thr Gln Val Thr Val Ser Ser
        115                 120


<210> SEQ ID NO 16
<211> LENGTH: 124
<212> TYPE: PRT
<213> ORGANISM: Artificial Sequence
<220> FEATURE:
```

<223> OTHER INFORMATION: Description of Artificial Sequence: Synthetic polypeptide

<400> SEQUENCE: 16

```
Gln Val Gln Leu Gln Glu Ser Gly Gly Gly Ser Val Gln Ala Gly Gly
1               5                   10                  15

Ser Leu Arg Leu Ser Cys Ala Ala Ser Pro Gly Thr Tyr Thr Ser Arg
            20                  25                  30

Tyr Met Gly Trp Phe Arg Gln Ala Pro Gly Lys Glu Arg Glu Gly Val
        35                  40                  45

Ala Thr Ile Trp Pro Ala Gly Gly Asn Thr Val Tyr Ala Asp Ser Val
    50                  55                  60

Lys Gly Arg Phe Thr Ile Ser Gln Asp Gly Ala Lys Lys Thr Val Tyr
65                  70                  75                  80

Leu Gln Met Asn Ser Leu Lys Pro Glu Asp Thr Ala Met Tyr Tyr Cys
                85                  90                  95

Ala Ala Ala Lys Tyr Gly Gly Thr Ser Leu Ala Pro Tyr Thr Tyr Asn
            100                 105                 110

Tyr Trp Gly Gln Gly Thr Gln Val Thr Val Ser Ser
        115                 120
```

<210> SEQ ID NO 17
<211> LENGTH: 121
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 17

```
Gln Val Gln Leu Gln Glu Ser Gly Gly Gly Ser Val Glu Ala Gly Gly
1               5                   10                  15

Ala Leu Thr Leu Ser Cys Val Ala Ser Gly Tyr Thr Tyr Cys Asn Tyr
            20                  25                  30

Asp Ile Ala Trp Tyr Arg Gln Ala Pro Gly Lys Glu Arg Lys Phe Val
        35                  40                  45

Ser Ala Ile Ala Ser Asp Gly Ser Thr Ser Tyr Ala Asp Ser Val Lys
    50                  55                  60

Gly Arg Phe Thr Ile Ser Gln Asp Asn Ala Lys Asn Thr Val Tyr Leu
65                  70                  75                  80

Gln Met Asn Ser Leu Lys Pro Glu Asp Thr Ala Met Tyr Tyr Cys Lys
                85                  90                  95

Thr Asp Pro Ile Ala Thr Met Thr Arg Arg Cys Asp Pro Tyr Trp Gly
            100                 105                 110

Gln Gly Thr Gln Val Thr Val Ser Ser
        115                 120
```

<210> SEQ ID NO 18
<211> LENGTH: 128
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 18

```
Gln Val Gln Leu Gln Glu Ser Gly Gly Gly Ser Val Gln Ala Gly Gly
1               5                   10                  15

Ser Leu Arg Leu Ser Cys Thr Ala Ser Gly Tyr Thr Phe Ser Thr Met
```

```
            20                  25                  30

Lys Tyr Met Gly Trp Phe Arg Gln Ala Pro Gly Lys Glu Arg Glu Gly
        35                  40                  45

Val Ala Ala Ile Trp Ile Ala Ala Gly Asn Thr Tyr Tyr Ala Asp Ser
    50                  55                  60

Val Lys Gly Arg Phe Thr Ile Ser Gln Asp Asn Thr Lys Asn Thr Val
65                  70                  75                  80

Tyr Leu Gln Met Asn Ser Leu Lys Pro Glu Asp Thr Ala Leu Tyr Tyr
                85                  90                  95

Cys Ala Ala Ala Arg Tyr Gly Phe Val Pro Ser Thr Trp Tyr Leu Pro
            100                 105                 110

Glu Arg Tyr Asn Tyr Trp Gly Gln Gly Thr Gln Val Thr Val Ser Ser
        115                 120                 125


<210> SEQ ID NO 19
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Gln Val Gln Leu Gln Glu Ser Gly Gly Gly Ser Val Gln Ala Gly Gly
1               5                   10                  15

Ser Leu Arg Leu Ala Cys Ala Ala Ser Gly Tyr Thr Tyr Cys Asn Tyr
            20                  25                  30

Asp Ile Ala Trp Tyr Arg Gln Ala Pro Gly Lys Glu Arg Lys Phe Val
        35                  40                  45

Ser Ala Ile Ala Ser Asp Gly Ser Thr Ser Tyr Ala Asp Ser Val Lys
    50                  55                  60

Gly Arg Phe Thr Ile Ser Gln Asp Asn Ala Lys Asn Thr Val Tyr Leu
65                  70                  75                  80

Gln Met Asn Ser Leu Lys Pro Glu Asp Thr Ala Met Tyr Tyr Cys Lys
                85                  90                  95

Thr Asp Pro Ile Ala Thr Met Thr Arg Arg Cys Asp Pro Tyr Trp Gly
            100                 105                 110

Gln Gly Thr Gln Val Thr Val Ser Ser
        115                 120


<210> SEQ ID NO 20
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Gln Val Gln Leu Gln Glu Ser Gly Gly Gly Ser Val Gln Ala Gly Gly
1               5                   10                  15

Ser Leu Arg Leu Ser Cys Ala Ala Ser Gly Tyr Thr Ser Cys Ser Tyr
            20                  25                  30

Asp Met Ser Trp Tyr Arg Gln Ala Pro Gly Lys Lys Arg Glu Phe Val
        35                  40                  45

Ser Ala Ile His Ser Asp Gly Thr Thr Ser Tyr Ala Asp Ser Met Lys
    50                  55                  60

Gly Arg Phe Thr Ile Ser Gln Asp Asn Ala Lys Asn Thr Val Tyr Leu
```

```
65                  70                  75                  80

Gln Met Asn Ser Leu Lys Pro Glu Asp Thr Ala Met Tyr Tyr Cys Lys
                85                  90                  95

Thr Asp Pro Asn Tyr Ser Asp His Val Cys Pro Pro Tyr Trp Gly Arg
            100                 105                 110

Gly Thr Gln Val Thr Val Ser Ser
        115                 120
```

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 21

```
Tyr Thr Tyr Cys Ser Tyr Asp Met Ser
1               5
```

<210> SEQ ID NO 22
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 22

```
Ala Phe Asn Ser Asp Gly Thr Thr Ser Tyr Ala Asp Ser Val Lys Gly
1               5                   10                  15
```

<210> SEQ ID NO 23
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 23

```
Asp Pro His Val Gln Ser Ser Gly Gly Tyr Cys Pro Pro Tyr
1               5                   10
```

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 24

```
Tyr Thr Tyr Cys Ser Tyr Asp Met Ser
1               5
```

<210> SEQ ID NO 25
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 25

```
Ser Phe Asn Ser Asp Gly Ser Thr Ser Tyr Ala Asp Ser Val Lys Gly
```

1 5 10 15

<210> SEQ ID NO 26
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 26

Asp Pro His Ala Asp Trp Gly Ala Pro Cys Gly Gly Asp Tyr
1 5 10

<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 27

Tyr Thr Tyr Cys Thr Tyr Asp Met Thr
1 5

<210> SEQ ID NO 28
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 28

Gly Ile His Ser Asp Gly Thr Thr Ser Tyr Ala Asp Ser Val Lys Gly
1 5 10 15

<210> SEQ ID NO 29
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 29

Asp Pro Ile Ala Thr Ile Thr Arg Arg Cys Asp Ser Tyr
1 5 10

<210> SEQ ID NO 30
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 30

Ser Thr Tyr Cys Thr Tyr Asp Met Thr
1 5

<210> SEQ ID NO 31
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 31

Ala Ile Asn Ser Asp Gly Ser Thr Ser Tyr Ala Asp Ser Val Lys Gly
1 5 10 15

<210> SEQ ID NO 32
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 32

Asp Pro Asn Ser Gly Trp Gly Ala Pro Cys Gly Gly Asp Tyr
1 5 10

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 33

Tyr Thr Tyr Cys Ser Tyr Asp Met Ser
1 5

<210> SEQ ID NO 34
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 34

Ala Ile Ala Ser Asp Gly Ser Thr Ser Tyr Ala Asp Ser Leu Lys Gly
1 5 10 15

<210> SEQ ID NO 35
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 35

Asp Pro His Val Gln Ser Ser Gly Gly Tyr Cys Pro Pro Tyr
1 5 10

<210> SEQ ID NO 36
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 36

Tyr Thr Tyr Cys Ser Tyr Asp Met Gly
1 5

<210> SEQ ID NO 37

```
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Ser Ile Asn Ser Asp Gly Thr Thr Ser Tyr Ala Asp Ser Val Lys Gly
1               5                   10                  15


<210> SEQ ID NO 38
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Asp Pro Gln Thr Arg Pro Gly Lys Pro Cys Ala Asp Tyr
1               5                   10


<210> SEQ ID NO 39
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Tyr Thr Tyr Cys Asn Tyr Asp Ile Ala
1               5


<210> SEQ ID NO 40
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Ala Ile Ala Ser Asp Gly Ile Thr Ser Tyr Ala Asp Ser Val Lys Gly
1               5                   10                  15


<210> SEQ ID NO 41
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Asp Pro Ile Ser Thr Ile Thr Arg Ile Cys Asp Pro Tyr
1               5                   10


<210> SEQ ID NO 42
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42
```

Tyr Thr Tyr Cys Ser Tyr Asp Met Lys
1 5

<210> SEQ ID NO 43
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 43

Gly Ile Asp Ser Asp Gly Ser Ile Ser Tyr Ala Asp Ser Val Lys Gly
1 5 10 15

<210> SEQ ID NO 44
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 44

Glu Gly Thr Ile Pro Val Gly Ala Cys Pro Asn Tyr
1 5 10

<210> SEQ ID NO 45
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 45

Tyr Thr Tyr Cys Ser Tyr Asp Met Ser
1 5

<210> SEQ ID NO 46
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 46

Ser Ile Asn Ser Asp Gly Thr Thr Ser Tyr Ala Asp Ser Val Lys Gly
1 5 10 15

<210> SEQ ID NO 47
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 47

Asp Pro Gln Thr Arg Pro Gly Lys Pro Cys Ala Asp Tyr
1 5 10

<210> SEQ ID NO 48
<211> LENGTH: 9
<212> TYPE: PRT
<213> ORGANISM: Artificial Sequence
<220> FEATURE:

<223> OTHER INFORMATION: Description of Artificial Sequence: Synthetic peptide

<400> SEQUENCE: 48

Tyr Thr Tyr Cys Asn Tyr Asp Ile Ala
1 5

<210> SEQ ID NO 49
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 49

Ala Ile Ala Ser Asp Gly Ser Thr Ser Tyr Ala Asp Ser Val Lys Gly
1 5 10 15

<210> SEQ ID NO 50
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 50

Asp Pro Ile Ala Thr Met Thr Arg Arg Cys Asp Pro Tyr
1 5 10

<210> SEQ ID NO 51
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 51

Tyr Thr Tyr Cys Ser Tyr Asp Met Thr
1 5

<210> SEQ ID NO 52
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 52

Ala Ile Asp Ser Asp Gly Ser Thr Ser Tyr Ala Asp Ser Val Lys Gly
1 5 10 15

<210> SEQ ID NO 53
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 53

Asp Pro Ile Ala Thr Ile Ser Arg Arg Cys Asp Ser Tyr
1 5 10

<210> SEQ ID NO 54
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 54

Tyr Thr Ser Ser Ser Arg Cys Met Gly
1 5

<210> SEQ ID NO 55
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 55

Arg Ile Tyr Thr Pro Thr Arg Thr Thr Trp Tyr Ala Asp Ser Val Lys
1 5 10 15

Gly

<210> SEQ ID NO 56
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 56

Gly Ala Ser Cys Ala Val Asp Leu Phe Ser Tyr
1 5 10

<210> SEQ ID NO 57
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 57

Tyr Thr Tyr Cys Ser Tyr Asp Met Lys
1 5

<210> SEQ ID NO 58
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 58

Ala Ile Asp Ser Asp Gly Ser Thr Ser Tyr Ala Asp Ser Val Lys Gly
1 5 10 15

<210> SEQ ID NO 59
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 59

Glu Gly Thr Ile Pro Val Gly Val Cys Pro Asn Tyr
1 5 10

<210> SEQ ID NO 60
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 60

Tyr Thr Tyr Cys Ser Tyr Asp Met Lys
1 5

<210> SEQ ID NO 61
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 61

Ala Ile Asp Ser Asp Gly Ser Thr Ser Tyr Ala Asp Ser Val Lys Gly
1 5 10 15

<210> SEQ ID NO 62
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 62

Glu Gly Thr Val Pro Val Gly Val Cys Pro Asn Tyr
1 5 10

<210> SEQ ID NO 63
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 63

Gly Thr Tyr Thr Ser Arg Tyr Met Gly
1 5

<210> SEQ ID NO 64
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 64

Thr Ile Trp Pro Ala Gly Gly Asn Thr Val Tyr Ala Asp Ser Val Lys
1 5 10 15

Gly

<210> SEQ ID NO 65
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 65

Ala Lys Tyr Gly Gly Thr Ser Leu Ala Pro Tyr Thr Tyr Asn Tyr
1 5 10 15

<210> SEQ ID NO 66
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 66

Tyr Thr Tyr Cys Asn Tyr Asp Ile Ala
1 5

<210> SEQ ID NO 67
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 67

Ala Ile Ala Ser Asp Gly Ser Thr Ser Tyr Ala Asp Ser Val Lys Gly
1 5 10 15

<210> SEQ ID NO 68
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 68

Asp Pro Ile Ala Thr Met Thr Arg Arg Cys Asp Pro Tyr
1 5 10

<210> SEQ ID NO 69
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 69

Tyr Thr Phe Ser Thr Met Lys Tyr Met Gly
1 5 10

<210> SEQ ID NO 70
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 70

Ala Ile Trp Ile Ala Ala Gly Asn Thr Tyr Tyr Ala Asp Ser Val Lys
1 5 10 15

Gly

<210> SEQ ID NO 71
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 71

Ala Arg Tyr Gly Phe Val Pro Ser Thr Trp Tyr Leu Pro Glu Arg Tyr
1 5 10 15

Asn Tyr

<210> SEQ ID NO 72
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 72

Tyr Thr Tyr Cys Asn Tyr Asp Ile Ala
1 5

<210> SEQ ID NO 73
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 73

Ala Ile Ala Ser Asp Gly Ser Thr Ser Tyr Ala Asp Ser Val Lys Gly
1 5 10 15

<210> SEQ ID NO 74
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 74

Asp Pro Ile Ala Thr Met Thr Arg Arg Cys Asp Pro Tyr
1 5 10

<210> SEQ ID NO 75
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 75

Tyr Thr Ser Cys Ser Tyr Asp Met Ser
1 5

<210> SEQ ID NO 76
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 76

Ala Ile His Ser Asp Gly Thr Thr Ser Tyr Ala Asp Ser Met Lys Gly
1 5 10 15

<210> SEQ ID NO 77
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 77

Asp Pro Asn Tyr Ser Asp His Val Cys Pro Pro Tyr
1 5 10

<210> SEQ ID NO 78
<211> LENGTH: 366
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 78
caggttcagc tgcaagagag cgggggtggg tctgtgcagg ctggtggcag cttgcgcctt 60
agttgcgcgg cttctggtta tacttattgt tcctacgata tgtcatggta tcgtcaggct 120
cctggcaaga aacgggagtt cgtctctgcc ttcaactccg atggcaccac tagctatgca 180
gattctgtga aaggcagatt caccatctct caggacaagg ccaagaatac cgtgtacctc 240
cagatgaaca gcctgaagcc agaggatacc gctatgtact attgcaagac agatcctcac 300
gtgcaatcct ctggtggcta ctgtccgccc tactggggcc agggcacaca ggtaacggtt 360
agttcc 366

<210> SEQ ID NO 79
<211> LENGTH: 366
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 79
caggtgcagc tccaggaatc tggcggaggt tccgtgcagg ccggtggcag cctgaggctc 60
agctgcgccg cgtccgggta tacctactgt tcctacgata tgtcctggta tcggcaggct 120
ccgggtaaaa agagagagtt tgtgtccagc tttaacagcg acggcagtac atcttacgct 180
gactccgtga agggtcgctt caccattagc caggataacg caaaaaacac agtgtacctt 240
cagatgaaca gtctgaagcc agaggacacc gccatgtatt actgcaagac ggacccgcac 300
gctgattggg gtgccccttg cgggggcgat tattggggcc aaggcaccca ggtgactgtt 360
tcttcc 366

<210> SEQ ID NO 80

<211> LENGTH: 363
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 80

```
caggtgcagc tccaggaatc tgggggcggt tctgtgcaag cgggcgagag cctgagactg      60

agctgcgccg cgagcggcta cacctactgt acctatgaca tgacttggta cagacaggcc     120

cccggaaaaa agcgcgagtt cgtcagcggt atccatagcg acggtactac ctcttacgca     180

gattccgtga aaggccgctt cacaatttct caggacaatg ccgaaaacac cgtgtacctc     240

cagatgaact ccctgaagcc agaggatacc gcgatgtatt actgcaagac agaccccatc     300

gccaccatca cccgccggtg cgactcatac tgggggcagg gcactcaggt cacagtctca     360

tct                                                                   363
```

<210> SEQ ID NO 81
<211> LENGTH: 366
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 81

```
caggtgcaac ttcaggaatc aggaggcggt agtgtgcaag cgggcggaag tctgcgcctg      60

agctgcgctg cctccgggag cacgtattgt acgtatgata tgacgtggta caggcaggcc     120

cctggcaagc gcagggagtt cgtgagtgca atcaactcag atggcagcac ctcttatgct     180

gacagcgtga aagggagatt cactatctcc caggacaacg caaaaaacac cgtctatctc     240

cagatgaact ctctgaagcc cgaagacacc gcgatgtatt actgtaagac tgatcctaac     300

agcggatggg gcgctccttg cggtggcgat tattggggac agggcaccca agtgacagtt     360

agcagc                                                                366
```

<210> SEQ ID NO 82
<211> LENGTH: 366
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 82

```
caggtgcagc ttcaggaaag cggtgggggc tccgtccagg caggcggttc ccttcgcctt      60

tcttgtgccg cttctggtta tacttactgt tcatacgata tgtcttggta tcgccaggct     120

cccggcaaaa agcgtgagtt cgtctctgcc atcgcctccg atggctcaac gtcctacgcg     180

gacagtctca agggtcgctt caccatttcc caggataatg caaagaacac cgtgtatctc     240

cagatgaact cactgaagcc cgaagacaca gccatgtact attgcaagac tgacccacac     300

gtacagtctt ccggcggata ctgcccacct tactggggac agggaaccca ggtgacagtg     360

agttct                                                                366
```

<210> SEQ ID NO 83
<211> LENGTH: 363
<212> TYPE: DNA
<213> ORGANISM: Artificial Sequence
<220> FEATURE:

<223> OTHER INFORMATION: Description of Artificial Sequence: Synthetic
      polynucleotide

<400> SEQUENCE: 83
caggtgcagc ttcaggaaag tggcgggggt ctggtgcagc cgggcgggtc cctccggctg 60
tcctgtgctg ccagcggcta cacctattgc agctatgata tgggctggta tcgccaggcc 120
cctggaaaaa agagaaagtt tgtgtccagc attaacagcg atgggaccac ttcttacgct 180
gacagtgtta aagggcgttt cacgatctcc caggacaacg ctaaaaacac cgtgtatctc 240
cagatgaata gcctgaagcc cgaggacacc gcaatgtatt actgtaaaac tgacccccag 300
acacgtcccg gtaagccatg tgctgattat tggggccagg ggacccaggt gaccgtcagc 360
tcc 363

<210> SEQ ID NO 84
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 84
caggtgcagc tccaggagtc cggtggcggg tctgtccaag ctggcggttc ccttcgcctg 60
tcctgtgcag ccagtggata tacgtattgc aactacgaca tcgcctggta tagacaggcc 120
cctggcaaag agcgcaagtt cgtatccgca atcgccagtg acggtatcac ctcttatgct 180
gactctgtga agggtcggtt cactatctcc caggataacg ctaagaacac agtctacctc 240
cagatgaaca gcttgaagcc ggaggacact gcgatgtact attgcaagac tgatccgatt 300
tccaccatca caaggatctg cgacccgtac tggggccagg gcacccaagt gactgtgtca 360
tca 363

<210> SEQ ID NO 85
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 85
caagtgcagt tgcaggagag cggtggcgat tctgtgcagg ccggaggctc cctccgcctg 60
tcctgtgccg cttcaggcta cacgtattgt tcttatgata tgaagtggta tcgccaggcc 120
ccaggtaagg aacgcgagtt cgtcagcggt attgattccg acggcagtat tagctacgcc 180
gactccgtga aaggccgctt cacaattagc caggacaacg cgaaaaacac cgtgtacctc 240
cagatgaact ctctgaagcc agaggatacc gccatgtact attgcaagac tgagggcact 300
atccccgtag gtgcatgtcc taactactgg ggccagggca ctcaggtaac cgtcagtagc 360

<210> SEQ ID NO 86
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 86
caagtccagc tccaggagag cggcggtggc ttggtgcagg ccggtggctc cctgagactg 60
agctgtgcag cctccgggta tacatattgc agctacgaca tgagttggta tcgccaggca 120
ccgggcaagg agagaaagtt tgtgtcctct atcaattcag atggcacaac ctcctacgcc 180
gactcagtca agggtcgttt cactatttct caggacaacg ctaagaacac cgtgtacctc 240
cagatgaaca gcctgaagcc tgaggatacg gccatgtact attgcaaaac tgacccccag 300
actagacctg gcaagccgtg cgcggactat tggggtcagg gcacgcaagt caccgtgtcc 360
tca 363

<210> SEQ ID NO 87
<211> LENGTH: 363
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 87
caggtgcagt tgcaggagag cggcggaggg tctgtgcagg ctggaggtag cctgaagctg 60
tcctgtgctg ccagcggcta cacctactgt aactacgata tcgcgtggta tcggcaagcg 120
cccggcaaag agcgtaagtt cgtgtccgct atcgcctccg atggctctac ttcctatgcc 180
gacagcgtta aaggtcgctt caccatctcc caagacaacg ccaaaaatac agtgtatctt 240
cagatgaact ctctgaaacc cgaggatact gcgatgtatt actgcaagac tgatccaatc 300
gctaccatga ccaggcgctg cgacccttac tggggccagg gcacccaggt gacggtatcc 360
tca 363

<210> SEQ ID NO 88
<211> LENGTH: 363
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 88
caagtccagc ttcaggagtc tggtgggggc tctgtccagg ccgggggctc tctgagactg 60
tcttgtgcag cctccgggta cacctactgt tcctatgaca tgacttggta tcgtcaagca 120
cctggcaaaa agcgtgagtt cgtgtctgcc atcgactccg acggctctac ctcctacgcc 180
gactctgtga aaggtaggtt cacaatctcc caggataacg caaagaatac tgtgtacttg 240
cagatgaact ccttgaagcc cgaggatact gccatgtact attgcaagac agaccctatt 300
gctactatct ctcgtaggtg tgatagttac tggggacaag gcacccaggt taccgtatcc 360
agt 363

<210> SEQ ID NO 89
<211> LENGTH: 360
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 89
caggtgcagc tccaagaatc tggtggaggg tcagtgcagg ccggaggcag cctgcgcctg 60
tcttgcgctg caagcggtta caccagctcc tctcgctgta tgggatggtt ccggcaagct 120
ccgggcaagg aaagggaagg agtcgctcgt atctacaccc caaccagaac tacgtggtac 180
gccgatagcg tcaaggggcg cttcaccatc agccaggata acgccaagaa taccgtgtac 240
ctggagatgg ccagcctcaa gccagaggac acggcgaagt atttttgcgc tgccggggcg 300
tcctgcgccg tggatttgtt ctcttactgg ggtcagggca ctcaggtcac cgtgtcaagc 360

<210> SEQ ID NO 90
<211> LENGTH: 360
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 90
caggttcagc tccaggagtc cggcggtggc tctgtgcagg ccggtggctc cctgagactg 60
tcctgcgcgg cttcaggata cacgtactgc tcctatgata tgaagtggta tcgtcaggct 120
ccaggcaaaa agagggagtt cgtgagcgcg attgattccg atgggagtac ctcctacgcg 180
gactctgtga agggacgctt tactatttcc caggacaacg cgaagaatac ggtctacctg 240
caaatgaact ccctcaagcc ggaggatacc gctatgtatt actgtaaaac cgagggaaca 300
attcctgtcg gcgtctgccc taattattgg gggcagggca cacaagtgac tgtctcctcc 360

<210> SEQ ID NO 91
<211> LENGTH: 360
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 91
caagtccagc tgcaagagtc tggtgggggc ctggtgcaac caggggggcag cttgagactc 60 tcctgcgctg ccagcgggta tacatactgt agctatgata tgaagtggta caggcaagcc 120
cctggcaaaa agcgcgagtt cgtgtccgcc atcgactccg acggttccac tagctacgcg 180
gattccgtga agggaaggtt cactatttct caggataacg ccaagaacac cgtctacctc 240
cagatgaact ccctgaagcc agaggacacc gccatgtact attgtaagac cgagggcaca 300
gtgcctgtgg gcgtctgtcc aaattattgg ggtcaaggca cccaggtcac agtatcctct 360

<210> SEQ ID NO 92
<211> LENGTH: 372
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 92
caagtgcagc tgcaagagag cggtggcggg tccgtgcaag caggtggctc cttgcgcctg 60
tcctgcgctg ccagccccgg cacctacaca tcccgttata tgggatggtt tcgccaggca 120
cctggaaagg aacgcgaggg ggttgcgact atctggcccg ctggcggtaa caccgtttac 180
gccgatagcg tgaaagggcg cttcaccatt agtcaagacg gggccaaaaa gaccgtgtac 240
ctccagatga actccctgaa acctgaagac actgctatgt actattgtgc cgcagctaag 300
tacggcggga ctagcctggc tccttacaca tataactact ggggccaagg cacccaggtg 360
acagtctctt ct 372

<210> SEQ ID NO 93
<211> LENGTH: 363
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 93
caggtccaac tccaggaatc cggtgggggc agcgtcgagg ccgggggcgc actcaccctc 60
tcctgcgtcg caagcggcta tacgtactgt aactacgaca ttgcttggta tcgccaggcc 120
ccaggcaagg agcgcaagtt cgtttccgcc atcgcctctg atggaagcac aagttacgca 180
gattccgtga aaggccggtt cacaatctca caggacaacg ctaagaacac cgtctacttg 240
cagatgaaca gtctgaagcc cgaagacacc gccatgtatt actgcaagac cgatcccatc 300
gccactatga cacgtcgctg tgacccctac tggggccaag gcactcaggt gaccgtgagt 360
tcc 363

<210> SEQ ID NO 94
<211> LENGTH: 384
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 94
caggtacagc tccaagaatc tggcggtggc tccgtgcagg ccggtggctc cttgcgtctg 60
tcctgcaccg ccagtggata tactttctcc accatgaagt acatgggatg gttccgccag 120
gctccgggaa aggagaggga gggcgttgcg gccatttgga tcgccgctgg caacacttat 180
tacgccgatt ccgtgaaagg ccgctttacc atttcccagg acaacacaaa gaacaccgtt 240
tacctccaga tgaatagcct gaagccagag gataccgccc tctactattg cgcggcagcc 300
aggtacggct ttgtccccag cacttggtat ctccccgagc gttacaacta ttggggccag 360
ggaactcagg tgactgtcag ttcc 384

<210> SEQ ID NO 95
<211> LENGTH: 363
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 95
caggtgcagt tgcaggagtc cggcggtggg tctgtgcagg cgggcgggag cctgcgcttg 60
gcctgcgccg caagcggtta tacctactgc aattacgaca tcgcgtggta tcggcaggcc 120
cccggtaagg agcgtaagtt cgtgtccgcc atcgcgtctg acggaagcac ctcttatgcc 180
gatagcgtga aaggaagatt tacaatctcc caggataacg ccaaaaacac cgtctatttg 240
cagatgaata gtctgaagcc agaggacacg gctatgtatt actgcaagac cgatccaatc 300
gctaccatga ccaggcgctg cgacccatat tggggccagg gcacgcaggt caccgtatcc 360
tcc 363

<210> SEQ ID NO 96
<211> LENGTH: 360
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 96

```
caggtccagt tgcaggaaag cggcggtgga tcagtccagg ctggtgggag tctgcgtctg     60

agctgtgctg ccagcggtta tacatcctgc tcttacgata tgtcttggta cagacaggcc    120

cctggcaaga aaagagagtt cgtttccgcc attcatagtg atggcacaac ctcctacgcc    180

gacagcatga aggggaggtt cactatctcc caggataatg ctaagaatac cgtttatctc    240

cagatgaact cactgaaacc ggaggacacc gcaatgtact attgcaagac ggaccctaac    300

tactcagacc acgtgtgccc gccttactgg ggacgcggta ctcaagtgac tgtgtcaagc    360
```

<210> SEQ ID NO 97
<211> LENGTH: 116
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 97

```
Gln Val Gln Leu Gln Glu Ser Gly Gly Gly Ser Val Gln Ala Gly Gly
1               5                   10                  15

Ser Leu Arg Leu Ser Cys Ala Ala Ser Gly Tyr Thr Tyr Ser Ser Cys
            20                  25                  30

Thr Met Gly Trp Tyr Arg Gln Ala Pro Gly Lys Glu Arg Glu Leu Val
        35                  40                  45

Ser Met Leu Ile Ser Asp Gly Ser Thr Phe Tyr Ala Asp Ser Val Lys
    50                  55                  60

Gly Arg Phe Thr Phe Ser Gln Glu Tyr Ala Lys Asn Thr Val Tyr Leu
65                  70                  75                  80

Gln Met Asn Ser Leu Lys Pro Glu Asp Thr Ala Met Tyr Tyr Cys Gly
                85                  90                  95

Cys Ala Thr Leu Gly Ser Arg Thr Val Trp Gly Gln Gly Thr Gln Val
            100                 105                 110

Thr Val Ser Ser
        115
```

<210> SEQ ID NO 98
<211> LENGTH: 116
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 98

```
Gln Val Gln Leu Gln Glu Ser Gly Gly Gly Ser Val Gln Ala Gly Gly
1               5                   10                  15

Ser Leu Thr Leu Ser Cys Thr Ala Pro Gly Phe Thr Phe Arg Leu Ala
            20                  25                  30

Ala Met Arg Trp Val Arg Gln Ala Pro Gly Lys Gly Leu Glu Trp Val
        35                  40                  45

Ser Gly Ile Asp Ser Arg Gly Ser Thr Ile Tyr Ala Asp Ser Val Lys
    50                  55                  60

Gly Arg Phe Thr Ile Ser Lys Asp Asn Ala Lys Asn Thr Leu Tyr Leu
65                  70                  75                  80
```

```
Gln Leu Asn Ser Leu Lys Thr Glu Asp Thr Ala Met Tyr Tyr Cys Ala
                85                  90                  95

Gln Gly Val Tyr Gly Asp Thr Tyr Ser Gly Ser Gln Gly Thr Gln Val
            100                 105                 110

Thr Val Ser Ser
        115


<210> SEQ ID NO 99
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Gln Val Gln Leu Gln Glu Ser Gly Gly Gly Ser Val Gln Ala Gly Gly
1               5                   10                  15

Ser Leu Arg Leu Ser Cys Thr Ala Ser Val Asn Thr Tyr Cys Glu Tyr
            20                  25                  30

Asn Met Ser Trp Tyr Arg Gln Ala Pro Gly Lys Glu Arg Glu Phe Val
        35                  40                  45

Ser Gly Val Asp Ser Asp Gly Ser Thr Arg Tyr Ser Glu Ser Val Lys
    50                  55                  60

Gly Arg Phe Thr Ile Ser Gln Asp Asn Ala Lys Asn Thr Met Tyr Leu
65                  70                  75                  80

Gln Met Asn Gly Leu Lys Pro Glu Asp Thr Ala Met Tyr Tyr Cys Lys
                85                  90                  95

Thr Tyr Val Cys Thr Phe Cys Ser Gly Asn Ser Cys Tyr Tyr Glu Tyr
            100                 105                 110

Lys Tyr Tyr Tyr Glu Gly Gln Gly Thr Gln Val Thr Val Ser Ser
        115                 120                 125


<210> SEQ ID NO 100
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Gln Val Gln Leu Gln Glu Ser Gly Gly Gly Ser Val Gln Ala Gly Gly
1               5                   10                  15

Ser Leu Arg Leu Ser Cys Ala Ala Ser Gly Tyr Thr Tyr Ser Asn Asn
            20                  25                  30

Cys Met Gly Trp Phe Arg Gln Ala Pro Gly Lys Asp Arg Glu Arg Ile
        35                  40                  45

Ala Asn Ile Tyr Thr Gly Gly Gly Arg Thr Thr Tyr Ala Asp Ser Val
    50                  55                  60

Lys Gly Arg Phe Thr Ile Ser Gln Asp Ser Ala Lys Ser Thr Val Tyr
65                  70                  75                  80

Leu Gln Met Asn Ser Leu Lys Pro Glu Asp Thr Ala Met Tyr Tyr Cys
                85                  90                  95

Ala Ala Gly Ser Cys Gly Ser Ala Arg Ser Glu Tyr Ser Tyr Trp Gly
            100                 105                 110

Gln Gly Thr Gln Val Thr Val Ser Ser
        115                 120
```

<210> SEQ ID NO 101
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 101

```
Gln Val Gln Leu Gln Glu Ser Gly Gly Gly Ser Val Gln Ala Gly Gly
1               5                   10                  15

Ser Leu Arg Leu Ser Cys Ala Ala Ser Gly Tyr Thr Phe Cys Met Ala
            20                  25                  30

Trp Phe Arg Gln Ala Pro Gly Lys Glu Arg Glu Gly Val Ala Arg Phe
        35                  40                  45

Tyr Thr Arg Asp Gly Tyr Thr Tyr Tyr Ser Asp Ser Val Lys Gly Arg
    50                  55                  60

Phe Thr Ile Ser Gln Asn Asn Ala Lys Asn Thr Leu Tyr Leu Gln Met
65                  70                  75                  80

Asn Ser Leu Lys Ser Glu Asp Thr Ala Met Tyr Tyr Cys Ala Ala Asp
                85                  90                  95

Leu Ala Arg Cys Ser Ser Asn Lys Asn Asp Phe Arg Tyr Trp Gly Gln
            100                 105                 110

Gly Thr Gln Val Thr Val Ser Ser
        115                 120
```

<210> SEQ ID NO 102
<211> LENGTH: 127
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 102

```
Gln Val Gln Leu Gln Glu Ser Gly Gly Gly Ser Val Gln Ala Gly Gly
1               5                   10                  15

Ser Leu Arg Leu Ser Cys Ala Ala Ser Gly Tyr Thr Ser Gly Asn Tyr
            20                  25                  30

Trp Met Gly Trp Phe Arg Gln Ala Pro Gly Lys Glu Arg Glu Gly Val
        35                  40                  45

Ala Thr Leu Trp Thr Gly Gly Ala Ser Thr Phe Tyr Gly Asp Ser Val
    50                  55                  60

Lys Gly Arg Phe Thr Ile Ser Arg Asp Asn Phe Lys Asn Thr Leu Tyr
65                  70                  75                  80

Leu Gln Met Asn Ser Leu Lys Val Glu Asp Thr Ala Met Tyr Tyr Cys
                85                  90                  95

Ala Ala Asp Pro Ala Leu Arg Leu Gly Ala Asn Ile Leu Arg Pro Ala
            100                 105                 110

Glu Tyr Lys Tyr Trp Gly Gln Gly Thr Gln Val Thr Val Ser Ser
        115                 120                 125
```

<210> SEQ ID NO 103
<211> LENGTH: 118
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 103

```
Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Arg Ser
            20                  25                  30

Ala Met Thr Trp Val Arg Gln Ala Pro Gly Lys Gly Leu Asp Trp Val
        35                  40                  45

Ser Gly Ile Asp Ser Gly Gly Thr Thr Val Tyr Ala Asp Ser Val Lys
    50                  55                  60

Gly Arg Phe Thr Ile Ser Arg Asp Ser Ala Lys Asn Thr Leu Tyr Leu
65                  70                  75                  80

Gln Met Asn Ser Leu Lys Thr Glu Asp Thr Ala Val Tyr Tyr Cys Ala
                85                  90                  95

Ile Gly Leu Pro Trp Gly Asn Thr Trp Arg Thr Arg Gly Gln Gly Thr
            100                 105                 110

Gln Val Thr Val Ser Ser
        115
```

<210> SEQ ID NO 104
<211> LENGTH: 116
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 104

```
Gln Val Gln Leu Gln Glu Ser Gly Gly Gly Ser Val Gln Ala Gly Gly
1               5                   10                  15

Ser Leu Arg Leu Ser Cys Thr Ala Ser Arg Tyr Thr Tyr Ser Ser Cys
            20                  25                  30

Thr Met Gly Trp Tyr Arg Gln Ala Pro Gly Lys Glu Arg Glu Leu Val
        35                  40                  45

Ser Met Val Phe Ser Asp Gly Ser Thr Phe Tyr Ala Asp Ser Val Lys
    50                  55                  60

Gly Arg Phe Thr Phe Ser Gln Glu Asn Ala Lys Asn Thr Val Tyr Leu
65                  70                  75                  80

Gln Met Asn Ser Leu Lys Pro Glu Asp Thr Ala Met Tyr Tyr Cys Gly
                85                  90                  95

Cys Ala Thr Leu Gly Ser Arg Thr Ile Trp Gly Gln Gly Thr Gln Val
            100                 105                 110

Thr Val Ser Ser
        115
```

<210> SEQ ID NO 105
<211> LENGTH: 116
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 105

```
Gln Val Gln Leu Gln Glu Ser Gly Gly Gly Leu Val Gln Pro Gly Gly
1               5                   10                  15

Ser Leu Arg Leu Ser Cys Ala Thr Ser Gly Phe Thr Phe Arg Leu Thr
            20                  25                  30

Ala Met Arg Trp Val Arg Gln Ala Pro Gly Lys Gly Val Glu Trp Val
```

```
        35                  40                  45

Ser Gly Ile Asp Ser Ala Gly Ser Thr Ile Tyr Ala Asp Ser Val Lys
    50                  55                  60

Gly Arg Phe Thr Ile Ser Lys Asp Asn Ala Lys Asn Thr Leu Tyr Leu
65                  70                  75                  80

Gln Met Asn Ser Leu Lys Thr Glu Asp Thr Ala Met Tyr Tyr Cys Ala
                85                  90                  95

Gln Gly Val Tyr Gly Asp Thr Tyr Ser Gly Ser Gln Gly Thr Gln Val
            100                 105                 110

Thr Val Ser Ser
        115


<210> SEQ ID NO 106
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Gln Val Gln Leu Gln Glu Ser Gly Gly Gly Ser Val Gln Ala Gly Gly
1               5                   10                  15

Ser Leu Arg Leu Ser Cys Ala Ala Ser Gly Asp Thr Tyr Ser Ser Cys
            20                  25                  30

Thr Met Gly Trp Tyr Arg Gln Ala Pro Gly Lys Glu Arg Asp Leu Val
        35                  40                  45

Ser Met Leu Met Gly Asp Gly Ser Thr Phe Tyr Ala Asp Ser Val Lys
    50                  55                  60

Gly Arg Phe Thr Phe Ser Gln Glu Asn Ala Lys Asn Thr Val Tyr Leu
65                  70                  75                  80

Gln Met Asn Ser Leu Lys Pro Glu Asp Thr Ala Met Tyr Tyr Cys Gly
                85                  90                  95

Cys Ala Thr Leu Gly Ser Arg Thr Ile Trp Gly Gln Gly Thr Gln Val
            100                 105                 110

Thr Val Ser Ser
        115


<210> SEQ ID NO 107
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Gln Val Gln Leu Gln Glu Ser Gly Gly Gly Ser Val Gln Ala Gly Gly
1               5                   10                  15

Ser Leu Arg Leu Ser Cys Ala Ala Ser Gly Tyr Thr Tyr Ser Ser Cys
            20                  25                  30

Thr Met Gly Trp Tyr Arg Gln Ala Pro Gly Lys Glu Arg Glu Leu Val
        35                  40                  45

Ser Met Leu Ile Ser Asp Gly Ser Thr Phe Tyr Ala Asp Ser Val Lys
    50                  55                  60

Gly Arg Phe Thr Phe Ser Gln Glu Asn Ala Lys Ser Thr Val Tyr Leu
65                  70                  75                  80

Gln Met Asn Ser Leu Lys Pro Glu Asp Thr Ala Met Tyr Tyr Cys Gly
```

```
                85                  90                  95

Cys Ala Thr Leu Gly Ser Arg Thr Val Trp Gly Gln Gly Thr Gln Val
            100                 105                 110

Thr Val Ser Ser
        115


<210> SEQ ID NO 108
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

Gln Val Gln Leu Gln Glu Ser Gly Gly Gly Ser Val Gln Ala Gly Gly
1               5                   10                  15

Ser Leu Arg Leu Ser Cys Ala Ala Ser Gly Tyr Thr Tyr Ser Ser Cys
            20                  25                  30

Thr Met Gly Trp Tyr Arg Gln Ala Pro Gly Lys Glu Arg Glu Leu Val
        35                  40                  45

Ser Met Leu Ile Ser Asp Gly Ser Thr Phe Tyr Ala Asp Ser Val Lys
    50                  55                  60

Gly Arg Phe Thr Phe Ser Gln Glu Asn Ala Lys Asn Thr Val Tyr Leu
65                  70                  75                  80

Gln Met Asn Ser Leu Lys Pro Glu Asp Thr Ala Met Tyr Tyr Cys Gly
                85                  90                  95

Cys Ala Thr Leu Gly Ser Arg Thr Val Trp Gly Gln Gly Thr Gln Val
            100                 105                 110

Thr Val Ser Ser
        115


<210> SEQ ID NO 109
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Gln Val Gln Leu Gln Glu Ser Gly Gly Gly Leu Val Gln Pro Gly Gly
1               5                   10                  15

Ser Leu Arg Leu Ser Cys Ala Thr Ser Gly Phe Thr Phe Arg Leu Ala
            20                  25                  30

Ala Met Arg Trp Val Arg Gln Ala Pro Gly Lys Gly Leu Glu Trp Val
        35                  40                  45

Ser Gly Ile Asp Ser Arg Gly Ser Thr Ile Tyr Ala Asp Ser Val Lys
    50                  55                  60

Gly Arg Phe Thr Ile Ser Lys Asp Asn Ala Lys Asn Thr Leu Tyr Leu
65                  70                  75                  80

Gln Leu Asn Ser Leu Lys Thr Glu Asp Thr Ala Met Tyr Tyr Cys Ala
                85                  90                  95

Gln Gly Val Tyr Gly Asp Thr Tyr Ser Gly Ser Gln Gly Thr Gln Val
            100                 105                 110

Thr Val Ser Ser
        115
```

<210> SEQ ID NO 110
<211> LENGTH: 118
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 110

```
Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Arg Thr Ser
            20                  25                  30

Ala Met Thr Trp Val Arg Gln Ala Pro Gly Lys Gly Leu Asp Trp Val
        35                  40                  45

Ser Gly Ile Asp Ser Gly Gly Thr Thr Val Tyr Ala Asp Ser Val Lys
    50                  55                  60

Gly Arg Phe Thr Ile Ser Arg Asp Ser Ala Lys Asn Thr Leu Tyr Leu
65                  70                  75                  80

Gln Met Asn Ser Leu Lys Thr Glu Asp Thr Ala Val Tyr Tyr Cys Ala
                85                  90                  95

Met Gly Leu Pro Trp Gly Asn Thr Trp Arg Thr Arg Gly Gln Gly Thr
            100                 105                 110

Gln Val Thr Val Ser Ser
        115
```

<210> SEQ ID NO 111
<211> LENGTH: 116
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 111

```
Gln Val Gln Leu Gln Glu Ser Gly Gly Gly Ser Val Gln Ala Gly Gly
1               5                   10                  15

Ser Leu Arg Leu Ser Cys Ala Ala Ser Gly Tyr Thr Tyr Ser Ser Cys
            20                  25                  30

Thr Met Gly Trp Tyr Arg Gln Ala Pro Gly Lys Glu Arg Glu Leu Val
        35                  40                  45

Ser Met Val Phe Ser Asp Gly Ser Thr Phe Tyr Ala Asp Ser Val Lys
    50                  55                  60

Gly Arg Phe Thr Phe Ser Gln Glu Asn Ala Lys Asn Thr Val Tyr Leu
65                  70                  75                  80

Gln Met Asn Ser Leu Lys Pro Glu Asp Thr Ala Met Tyr Tyr Cys Gly
                85                  90                  95

Cys Ala Thr Leu Gly Ser Arg Thr Ile Trp Gly Gln Gly Thr Gln Val
            100                 105                 110

Thr Val Ser Ser
        115
```

<210> SEQ ID NO 112
<211> LENGTH: 116
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 112

```
Gln Val Gln Leu Gln Glu Ser Gly Gly Gly Ser Val Gln Ala Gly Gly
1               5                   10                  15

Ser Leu Arg Leu Ser Cys Ala Ala Ser Gly Asp Thr Tyr Ser Ser Cys
            20                  25                  30

Thr Met Gly Trp Tyr Arg Gln Ala Pro Gly Lys Glu Arg Asp Leu Val
        35                  40                  45

Ser Met Leu Met Gly Asp Gly Ser Thr Phe Tyr Ala Asp Ser Val Lys
    50                  55                  60

Gly Arg Phe Thr Phe Ser Gln Glu Asn Ala Lys Asn Thr Val Tyr Leu
65                  70                  75                  80

Gln Met Asn Asn Leu Lys Pro Glu Asp Thr Ala Met Tyr Tyr Cys Gly
                85                  90                  95

Cys Ala Thr Leu Gly Ser Arg Thr Ile Trp Gly Gln Gly Thr Gln Val
            100                 105                 110

Thr Val Ser Ser
        115


<210> SEQ ID NO 113
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Gln Val Gln Leu Gln Glu Ser Gly Gly Gly Ser Val Gln Ala Gly Gly
1               5                   10                  15

Ser Leu Arg Leu Ser Cys Ala Ala Ser Gly Phe Thr Phe Arg Leu Thr
            20                  25                  30

Ala Met Arg Trp Val Arg Gln Ala Pro Gly Lys Gly Leu Glu Trp Val
        35                  40                  45

Ser Gly Ile Asp Ser Arg Gly Ser Thr Ile Tyr Ala Asp Ser Val Lys
    50                  55                  60

Gly Arg Phe Thr Ile Ser Lys Asp Asn Ala Lys Asn Thr Leu Tyr Leu
65                  70                  75                  80

Gln Leu Asn Ser Leu Lys Thr Glu Asp Thr Ala Met Tyr Tyr Cys Ala
                85                  90                  95

Gln Gly Val Tyr Gly Asp Thr Tyr Ser Gly Ser Gln Gly Thr Gln Val
            100                 105                 110

Thr Val Ser Ser
        115


<210> SEQ ID NO 114
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Arg Leu Thr
            20                  25                  30

Ala Met Arg Trp Val Arg Gln Ala Pro Gly Lys Gly Leu Glu Trp Val
        35                  40                  45
```

```
Ser Gly Ile Asp Ser Arg Gly Ser Thr Ile Tyr Ala Asp Ser Val Lys
    50                  55                  60

Gly Arg Phe Thr Ile Ser Lys Asp Asn Ala Lys Asn Thr Leu Tyr Leu
65                  70                  75                  80

Gln Leu Asn Ser Leu Lys Thr Glu Asp Thr Ala Met Tyr Tyr Cys Ala
                85                  90                  95

Gln Gly Val Tyr Gly Asp Thr Tyr Ser Gly Ser Gln Gly Thr Gln Val
            100                 105                 110

Thr Val Ser Ser
        115


<210> SEQ ID NO 115
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Arg Leu Ser
            20                  25                  30

Ala Met Arg Trp Val Arg Gln Ala Pro Gly Lys Gly Leu Glu Trp Val
        35                  40                  45

Ser Gly Ile Asp Ser Arg Gly Ser Thr Ile Tyr Ala Asp Ser Val Lys
    50                  55                  60

Gly Arg Phe Thr Ile Ser Lys Asp Asn Ala Lys Asn Thr Leu Tyr Leu
65                  70                  75                  80

Gln Leu Asn Ser Leu Lys Thr Glu Asp Thr Ala Met Tyr Tyr Cys Ala
                85                  90                  95

Gln Gly Val Tyr Gly Asp Thr Tyr Ser Gly Ser Gln Gly Thr Gln Val
            100                 105                 110

Thr Val Ser Ser
        115


<210> SEQ ID NO 116
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ser
            20                  25                  30

Ala Met Thr Trp Val Arg Gln Ala Pro Gly Lys Gly Leu Asp Trp Val
        35                  40                  45

Ser Gly Ile Asp Ser Gly Gly Thr Thr Val Tyr Ala Asp Ser Val Lys
    50                  55                  60

Gly Arg Ala Thr Ile Leu Lys Asp Asn Ala Lys Asn Thr Leu Tyr Leu
65                  70                  75                  80

Gln Met Asn Ser Leu Lys Thr Glu Asp Thr Ala Val Tyr Tyr Cys Ala
                85                  90                  95
```

```
Thr Gly Leu Pro Trp Gly Asn Thr Trp Arg Thr Arg Gly Gln Gly Thr
            100                 105                 110

Gln Val Thr Val Ser Ser
        115


<210> SEQ ID NO 117
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

Gln Val Gln Leu Gln Glu Ser Gly Gly Gly Leu Val Gln Pro Gly Gly
1               5                   10                  15

Ser Leu Arg Leu Ser Cys Ala Thr Ser Gly Phe Thr Phe Ser Ser Ser
            20                  25                  30

Ala Met Thr Trp Val Arg Gln Ala Pro Gly Lys Gly Leu Asp Trp Val
        35                  40                  45

Ser Gly Ile Asp Ser Gly Gly Thr Thr Val Tyr Ala Asp Ser Val Lys
    50                  55                  60

Gly Arg Phe Thr Ile Ser Lys Asp Asn Ala Lys Asn Thr Leu Tyr Leu
65                  70                  75                  80

Gln Met Asn Ser Leu Lys Thr Glu Asp Thr Ala Val Tyr Tyr Cys Ala
                85                  90                  95

Thr Gly Leu Pro Trp Gly Asn Thr Trp Arg Thr Thr Gly Gln Gly Thr
            100                 105                 110

Gln Val Thr Val Ser Ser
        115


<210> SEQ ID NO 118
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Gln Val Gln Leu Gln Glu Ser Gly Gly Gly Ser Val Gln Ala Gly Gly
1               5                   10                  15

Ser Leu Arg Leu Ser Cys Ala Ala Ser Gly Tyr Thr Phe Cys Met Ala
            20                  25                  30

Trp Phe Arg Gln Ala Pro Gly Lys Glu Arg Glu Gly Val Ala Arg Phe
        35                  40                  45

Tyr Thr Arg Asp Ser Tyr Thr Tyr Tyr Ser Asp Ser Val Lys Gly Arg
    50                  55                  60

Phe Thr Ile Ser Gln Asn Asn Ala Lys Asn Thr Leu Tyr Leu Gln Met
65                  70                  75                  80

Asn Ser Leu Lys Ser Glu Asp Thr Ala Met Tyr Tyr Cys Ala Ala Asp
                85                  90                  95

Leu Thr Arg Cys Ser Ser Asn Lys Asn Asp Phe Arg Tyr Trp Gly Gln
            100                 105                 110

Gly Thr Gln Val Thr Val Ser Ser
        115                 120


<210> SEQ ID NO 119
```

```
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Asn Phe Arg Leu Tyr
            20                  25                  30

Ala Met Arg Trp Val Arg Gln Ala Pro Gly Lys Gly Val Glu Trp Val
        35                  40                  45

Ser Gly Ile Asp Ser Gly Gly Ser Thr Ile Tyr Ala Asp Ser Val Lys
    50                  55                  60

Gly Arg Phe Thr Ile Ser Lys Asp Asn Ala Lys Asn Thr Leu Tyr Leu
65                  70                  75                  80

Gln Leu Asn Ser Leu Lys Thr Glu Asp Thr Ala Met Tyr Tyr Cys Ala
                85                  90                  95

Gln Gly Val Tyr Gly Asp Thr Tyr Ser Gly Ser Gln Gly Thr Gln Val
            100                 105                 110

Thr Val Ser Ser
        115


<210> SEQ ID NO 120
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

Gln Val Gln Leu Gln Glu Ser Gly Gly Gly Ser Val Gln Ala Gly Gly
1               5                   10                  15

Ser Leu Arg Leu Ser Cys Ala Val Ser Gly Tyr Thr Phe Cys Met Ala
            20                  25                  30

Trp Phe Arg Gln Ala Pro Gly Lys Glu Arg Glu Gly Val Ala Arg Phe
        35                  40                  45

Tyr Thr Arg Asp Gly Tyr Thr Tyr Tyr Ser Gly Ser Val Lys Gly Arg
    50                  55                  60

Phe Thr Ile Ser Gln Asn Asn Ala Lys Asn Thr Leu Tyr Leu Gln Met
65                  70                  75                  80

Asn Ser Leu Lys Ser Glu Asp Thr Ala Met Tyr Tyr Cys Ala Ala Asp
                85                  90                  95

Leu Thr Arg Cys Ser Ser Asn Lys Asn Asp Phe Arg Tyr Trp Gly Gln
            100                 105                 110

Gly Thr Gln Val Thr Val Ser Ser
        115                 120


<210> SEQ ID NO 121
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121
```

```
Gln Val Gln Leu Gln Glu Ser Gly Gly Gly Ser Val Gln Ala Gly Gly
1               5                   10                  15

Ser Leu Arg Leu Ser Cys Ala Ala Ser Gly Tyr Thr Tyr Ser Ser Cys
            20                  25                  30

Thr Met Gly Trp Tyr Arg Gln Ala Pro Gly Lys Glu Arg Glu Leu Val
        35                  40                  45

Ser Met Leu Ile Ser Asp Gly Ser Thr Phe Tyr Ala Asp Ser Val Lys
    50                  55                  60

Gly Arg Phe Thr Phe Ser Gln Glu Asn Ala Lys Asn Thr Val Tyr Leu
65                  70                  75                  80

Gln Met Asn Ser Leu Lys Pro Glu Asp Thr Ala Met Tyr Phe Cys Gly
                85                  90                  95

Cys Ala Thr Leu Gly Ser Arg Thr Val Trp Gly Gln Gly Thr Gln Val
            100                 105                 110

Thr Val Ser Ser
        115


<210> SEQ ID NO 122
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Gln Val Gln Leu Gln Glu Ser Gly Gly Gly Ser Val Gln Ala Gly Gly
1               5                   10                  15

Ser Leu Arg Leu Ser Cys Ala Ala Ser Gly Tyr Thr Phe Cys Met Ala
            20                  25                  30

Trp Phe Arg Gln Ala Pro Gly Lys Glu Arg Glu Gly Val Ala Arg Phe
        35                  40                  45

Tyr Thr Arg Asp Gly Tyr Thr Tyr Tyr Ser Asp Ser Val Lys Gly Arg
    50                  55                  60

Phe Thr Ile Ser Gln Asn Asn Ala Lys Asn Thr Leu Tyr Leu Gln Met
65                  70                  75                  80

Asn Ser Leu Lys Ser Glu Asp Thr Ala Met Tyr Tyr Cys Ala Ala Asp
                85                  90                  95

Leu Thr Arg Cys Ser Ser Asn Lys Asn Asp Phe Arg Tyr Trp Gly Gln
            100                 105                 110

Gly Thr Gln Val Thr Val Ser Ser
        115                 120


<210> SEQ ID NO 123
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

Gln Val Gln Leu Gln Glu Ser Gly Gly Gly Ser Val Gln Ala Gly Gly
1               5                   10                  15

Ser Leu Arg Leu Ser Cys Ala Ala Ser Gly Tyr Thr Tyr Ser Ser Cys
            20                  25                  30

Thr Met Gly Trp Tyr Arg Gln Ala Pro Gly Lys Glu Arg Glu Leu Val
        35                  40                  45
```

```
Ser Met Leu Ile Ser Asp Gly Ser Thr Phe Tyr Ala Asp Ser Val Lys
    50                  55                  60

Gly Arg Phe Thr Ser Ser Gln Glu Asn Ala Lys Asn Thr Val Tyr Leu
65                  70                  75                  80

Gln Met Asn Ser Leu Lys Pro Glu Asp Thr Ala Met Tyr Tyr Cys Gly
                85                  90                  95

Cys Ala Thr Leu Gly Ser Arg Thr Val Trp Gly Gln Gly Thr Gln Val
            100                 105                 110

Thr Val Ser Ser
        115


<210> SEQ ID NO 124
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Arg Leu Thr
            20                  25                  30

Ala Met Arg Trp Val Arg Gln Ala Pro Gly Lys Gly Leu Glu Trp Val
        35                  40                  45

Ser Gly Ile Asp Ser Arg Gly Ser Thr Ile Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Leu Asn Ser Leu Lys Thr Glu Asp Ala Ala Met Tyr Tyr Cys Ala
                85                  90                  95

Gln Gly Val Tyr Gly Asp Thr Tyr Ser Gly Ser Gln Gly Thr Gln Val
            100                 105                 110

Thr Val Ser Ser
        115


<210> SEQ ID NO 125
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Thr Ser
            20                  25                  30

Ala Met Thr Trp Val Arg Gln Ala Pro Gly Lys Gly Leu Asp Trp Val
        35                  40                  45

Ser Gly Ile Asp Ser Gly Gly Thr Thr Val Tyr Ala Asp Ser Val Lys
    50                  55                  60

Gly Arg Phe Thr Ile Ser Lys Asp Asn Ala Lys Asn Thr Leu Tyr Leu
65                  70                  75                  80

Gln Met Asn Ser Leu Lys Thr Glu Asp Thr Ala Val Tyr Tyr Cys Ala
                85                  90                  95
```

```
Thr Gly Leu Pro Trp Gly Asn Thr Trp Arg Thr Arg Gly Gln Gly Thr
            100                 105                 110

Gln Val Thr Val Ser Ser
        115


<210> SEQ ID NO 126
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Arg Leu Thr
            20                  25                  30

Ala Met Arg Trp Val Arg Gln Ala Pro Gly Lys Gly Leu Glu Trp Val
        35                  40                  45

Ser Gly Ile Asp Ser Arg Gly Ser Thr Ile Tyr Ala Asp Ser Val Lys
    50                  55                  60

Gly Arg Phe Thr Ile Ser Lys Asp Asn Ala Lys Asn Thr Leu Tyr Leu
65                  70                  75                  80

Gln Leu Asn Ser Leu Lys Thr Glu Asp Thr Ala Met Tyr Tyr Cys Ala
                85                  90                  95

Gln Gly Val Tyr Gly Asp Thr Tyr Ser Gly Ser Leu Gly Thr Gln Val
            100                 105                 110

Thr Val Ser Ser
        115


<210> SEQ ID NO 127
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Arg Leu Thr
            20                  25                  30

Ala Met Arg Trp Val Arg Gln Ala Pro Gly Lys Gly Leu Glu Trp Val
        35                  40                  45

Ser Gly Ile Asp Ser Arg Gly Ser Thr Ile Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Leu Asn Ser Leu Lys Thr Glu Asp Thr Ala Met Tyr Tyr Cys Ala
                85                  90                  95

Gln Gly Val Tyr Gly Asp Thr Tyr Ser Gly Ser Gln Gly Thr Gln Val
            100                 105                 110

Thr Val Ser Ser
        115


<210> SEQ ID NO 128
<211> LENGTH: 118
```

<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 128

```
Gln Val Gln Leu Gln Glu Ser Gly Gly Gly Leu Val Arg Pro Gly Gly
1               5                   10                  15

Ser Leu Arg Leu Ser Cys Ala Ala Ser Gly Phe Thr Phe Ser Arg Ser
            20                  25                  30

Ala Met Thr Trp Val Arg Gln Ala Pro Gly Lys Gly Leu Asp Trp Val
        35                  40                  45

Ser Gly Ile Asp Ser Gly Gly Thr Thr Val Tyr Ala Asp Ser Val Lys
    50                  55                  60

Gly Arg Phe Thr Ile Ser Arg Asp Ser Ala Lys Asn Thr Leu Tyr Leu
65                  70                  75                  80

Gln Met Asn Ser Leu Lys Thr Glu Asp Thr Ala Val Tyr Tyr Cys Ala
                85                  90                  95

Ile Gly Leu Pro Trp Gly Asn Thr Trp Arg Thr Arg Gly Gln Gly Thr
            100                 105                 110

Gln Val Thr Val Ser Ser
        115
```

<210> SEQ ID NO 129
<211> LENGTH: 118
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 129

```
Gln Val Gln Leu Gln Glu Ser Gly Gly Gly Leu Val Gln Pro Gly Gly
1               5                   10                  15

Ser Leu Arg Leu Ser Cys Thr Thr Ser Gly Phe Thr Phe Ser Ser Ser
            20                  25                  30

Ala Met Thr Trp Val Arg Gln Ala Pro Gly Lys Gly Leu Asp Trp Val
        35                  40                  45

Ser Gly Ile Asp Ser Gly Gly Thr Thr Val Tyr Ala Asp Ser Val Lys
    50                  55                  60

Gly Arg Phe Thr Ile Ser Lys Asp Asn Ala Lys Asn Thr Leu Tyr Leu
65                  70                  75                  80

Gln Met Asn Ser Leu Lys Thr Glu Asp Thr Ala Val Tyr Tyr Cys Ala
                85                  90                  95

Thr Gly Leu Pro Trp Gly Asn Thr Trp Arg Thr Thr Gly Gln Gly Thr
            100                 105                 110

Gln Val Thr Val Ser Ser
        115
```

<210> SEQ ID NO 130
<211> LENGTH: 116
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 130

```
Gln Val Gln Leu Gln Glu Ser Gly Gly Gly Leu Val Gln Pro Gly Gly
```

```
1               5                   10                  15

Ser Leu Arg Leu Ser Cys Ala Ala Ser Gly Phe Thr Phe Arg Leu Thr
            20                  25                  30

Ala Met Arg Trp Val Arg Gln Ala Pro Gly Lys Gly Leu Glu Trp Val
        35                  40                  45

Ser Gly Ile Asp Ser Arg Gly Ser Thr Ile Tyr Ala Asp Ser Val Lys
    50                  55                  60

Gly Arg Phe Thr Ile Ser Lys Asp Asn Ala Lys Asn Thr Leu Tyr Leu
65                  70                  75                  80

Gln Leu Asn Ser Leu Lys Thr Glu Asp Thr Ala Met Tyr Tyr Cys Ala
                85                  90                  95

Gln Gly Val Tyr Gly Asp Thr His Ser Gly Ser Gln Gly Thr Gln Val
            100                 105                 110

Thr Val Ser Ser
        115


<210> SEQ ID NO 131
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

Gln Val Gln Leu Gln Glu Ser Gly Gly Gly Leu Val Gln Pro Gly Gly
1               5                   10                  15

Ser Leu Arg Leu Ala Cys Ser Ala Ser Gly Phe Thr Phe Ser Ser Ser
            20                  25                  30

Ala Met Thr Trp Val Arg Gln Ala Pro Gly Lys Gly Leu Asp Trp Val
        35                  40                  45

Ser Gly Ile Asp Ser Gly Gly Thr Thr Val Tyr Ala Asp Ser Val Lys
    50                  55                  60

Gly Arg Ala Thr Ile Leu Lys Asp Asn Ala Lys Asn Thr Leu Tyr Leu
65                  70                  75                  80

Gln Met Asn Ser Leu Lys Thr Glu Asp Thr Ala Val Tyr Tyr Cys Ala
                85                  90                  95

Thr Gly Leu Pro Trp Gly Asn Thr Trp Arg Thr Arg Gly Gln Gly Thr
            100                 105                 110

Gln Val Thr Val Ser Ser
        115


<210> SEQ ID NO 132
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

Gln Val Gln Leu Gln Glu Ser Gly Gly Gly Ser Val Gln Ala Gly Gly
1               5                   10                  15

Ser Leu Arg Leu Ser Cys Ala Ala Ser Gly Asp Thr Tyr Ser Ser Cys
            20                  25                  30

Thr Met Gly Trp Tyr Arg Gln Ala Pro Gly Lys Glu Arg Asp Leu Val
        35                  40                  45

Ser Met Val Phe Ser Asp Gly Ser Thr Phe Tyr Ala Asp Ser Val Lys
```

```
    50                  55                  60

Gly Arg Phe Thr Phe Ser Gln Glu Asn Ala Lys Asn Thr Val Tyr Leu
65                  70                  75                  80

Gln Met Asn Ser Leu Lys Pro Glu Asp Thr Ala Met Tyr Tyr Cys Gly
                85                  90                  95

Cys Ala Thr Leu Gly Ser Arg Thr Ile Trp Gly Gln Gly Thr Gln Val
            100                 105                 110

Thr Val Ser Ser
        115


<210> SEQ ID NO 133
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

Gln Val Gln Leu Gln Glu Ser Gly Gly Gly Leu Val Gln Pro Gly Gly
1               5                   10                  15

Ser Leu Arg Leu Ser Cys Ala Thr Ser Gly Phe Thr Phe Ser Ser Gly
            20                  25                  30

Ala Met Thr Trp Val Arg Gln Ala Pro Gly Lys Gly Leu Asp Trp Val
        35                  40                  45

Ser Gly Ile Asp Ser Gly Gly Thr Thr Val Tyr Ala Asp Ser Val Lys
    50                  55                  60

Gly Arg Phe Thr Ile Ser Lys Asp Asn Ala Lys Asn Thr Leu Tyr Leu
65                  70                  75                  80

Gln Met Asn Ser Leu Lys Thr Glu Asp Thr Ala Val Tyr Tyr Cys Ala
                85                  90                  95

Thr Gly Leu Pro Trp Gly Asn Thr Trp Arg Thr Thr Gly Gln Gly Thr
            100                 105                 110

Gln Val Thr Val Ser Ser
        115


<210> SEQ ID NO 134
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Thr Ser
            20                  25                  30

Ala Met Thr Trp Val Arg Gln Ala Pro Gly Lys Gly Leu Asp Trp Val
        35                  40                  45

Ser Gly Ile Asp Ser Gly Gly Thr Thr Val Tyr Ala Asp Ser Val Lys
    50                  55                  60

Gly Arg Phe Thr Ile Ser Lys Asp Asn Ala Lys Asn Thr Leu Tyr Leu
65                  70                  75                  80

Gln Met Asn Ser Leu Lys Thr Glu Asp Thr Ala Val Tyr Tyr Cys Ala
                85                  90                  95

Thr Gly Leu Pro Trp Gly Asn Ile Trp Arg Thr Arg Gly Gln Gly Thr
```

```
            100                 105                 110

Gln Val Thr Val Ser Ser
        115


<210> SEQ ID NO 135
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Arg Ser
            20                  25                  30

Ala Met Thr Trp Val Arg Gln Ala Pro Gly Lys Gly Leu Asp Trp Val
        35                  40                  45

Ser Gly Ile Asp Ser Gly Gly Thr Thr Val Tyr Ala Asp Ser Val Lys
    50                  55                  60

Gly Arg Phe Thr Ile Ser Arg Asp Ser Ala Lys Asn Thr Leu Tyr Leu
65                  70                  75                  80

Gln Met Asn Gly Leu Lys Thr Glu Asp Thr Ala Val Tyr Tyr Cys Ala
                85                  90                  95

Ile Gly Leu Pro Trp Gly Asn Thr Trp Arg Thr Arg Gly Gln Gly Thr
            100                 105                 110

Gln Val Thr Val Ser Ser
        115


<210> SEQ ID NO 136
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Arg Leu Thr
            20                  25                  30

Ala Met Arg Trp Val Arg Gln Ala Pro Gly Lys Gly Leu Glu Trp Val
        35                  40                  45

Ser Gly Ile Asp Ser Arg Gly Ser Thr Ile Tyr Ala Asp Ser Val Lys
    50                  55                  60

Gly Arg Phe Thr Ile Ser Lys Asp Asn Ala Lys Asn Thr Leu Tyr Leu
65                  70                  75                  80

Gln Leu Asn Ser Leu Lys Ser Glu Asp Thr Ala Met Tyr Tyr Cys Ala
                85                  90                  95

Gln Gly Val Tyr Gly Asp Thr Tyr Ser Gly Ser Gln Gly Thr Gln Val
            100                 105                 110

Thr Val Ser Ser
        115


<210> SEQ ID NO 137
<211> LENGTH: 118
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 137

```
Gln Val Gln Leu Gln Glu Ser Gly Gly Gly Leu Val Gln Pro Gly Gly
1               5                   10                  15

Ser Leu Arg Leu Thr Cys Ala Ala Ser Gly Phe Thr Phe Ser Thr Ser
            20                  25                  30

Ala Met Thr Trp Val Arg Gln Ala Pro Gly Lys Gly Leu Asp Trp Val
        35                  40                  45

Ser Gly Ile Asp Ser Gly Gly Thr Thr Val Tyr Ala Asp Ser Val Lys
    50                  55                  60

Gly Arg Phe Thr Ile Ser Lys Asp Asn Ala Lys Asn Thr Leu Tyr Leu
65                  70                  75                  80

Gln Met Asn Ser Leu Lys Thr Glu Asp Thr Ala Val Tyr Tyr Cys Ala
                85                  90                  95

Thr Gly Leu Pro Trp Gly Asn Thr Trp Arg Thr Arg Gly Gln Gly Thr
            100                 105                 110

Gln Val Thr Val Ser Ser
        115
```

<210> SEQ ID NO 138
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

```
Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Arg Trp Val Arg Gln Ala Pro Gly Lys Gly Leu Glu Trp Val
        35                  40                  45

Ser Gly Ile Asp Ser Arg Gly Ser Thr Ile Tyr Ala Asp Ser Val Lys
    50                  55                  60

Gly Arg Phe Thr Ile Ser Lys Asp Asn Ala Lys Asn Thr Leu Tyr Leu
65                  70                  75                  80

Gln Leu Asn Ser Leu Lys Thr Glu Asp Thr Ala Met Tyr Tyr Cys Ala
                85                  90                  95

Gln Gly Val Tyr Gly Asp Thr Tyr Ser Gly Ser Gln Gly Thr Gln Val
            100                 105                 110

Thr Val Ser Ser
        115
```

<210> SEQ ID NO 139
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

```
Gln Val Gln Leu Gln Glu Ser Gly Gly Gly Ser Val Gln Ala Gly Gly
1               5                   10                  15
```

```
Ser Leu Arg Leu Ser Cys Ala Ala Ser Gly Tyr Thr Phe Cys Met Ala
            20                  25                  30

Trp Phe Arg Gln Ala Pro Gly Lys Glu Arg Glu Gly Val Ala Arg Phe
        35                  40                  45

Tyr Thr Arg Asp Gly Tyr Thr Tyr Tyr Ser Asp Ser Val Lys Gly Arg
    50                  55                  60

Phe Thr Ile Ser Gln Asp Asn Ala Lys Asn Thr Leu Tyr Leu Gln Met
65                  70                  75                  80

Asn Ser Leu Lys Ser Glu Asp Thr Ala Met Tyr Tyr Cys Ala Ala Asp
                85                  90                  95

Leu Thr Arg Cys Ser Ser Asn Lys Asn Asp Phe Arg Tyr Trp Gly Gln
            100                 105                 110

Gly Thr Gln Val Thr Val Ser Ser
        115                 120


<210> SEQ ID NO 140
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Arg Leu Ser
            20                  25                  30

Ala Met Arg Trp Val Arg Gln Ala Pro Gly Lys Gly Phe Glu Trp Val
        35                  40                  45

Ser Gly Ile Asp Ser Arg Gly Ser Thr Ile Tyr Ala Asp Ser Val Lys
    50                  55                  60

Gly Arg Phe Thr Ile Ser Lys Asp Asn Ala Lys Asn Thr Leu Tyr Leu
65                  70                  75                  80

Gln Leu Asn Ser Leu Lys Thr Glu Asp Thr Ala Met Tyr Tyr Cys Ala
                85                  90                  95

Gln Gly Val Tyr Gly Asp Thr Tyr Ser Gly Ser Gln Gly Thr Gln Val
            100                 105                 110

Thr Val Ser Ser
        115


<210> SEQ ID NO 141
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Arg Leu Ser
            20                  25                  30

Ala Met Arg Trp Val Arg Gln Ala Pro Gly Lys Gly Leu Glu Trp Val
        35                  40                  45

Ser Gly Ile Asp Ser Arg Gly Ser Thr Ile Tyr Ala Asp Ser Val Glu
    50                  55                  60
```

```
Gly Arg Phe Thr Ile Ser Lys Asp Asn Ala Lys Asn Thr Leu Tyr Leu
65                  70                  75                  80

Gln Leu Asn Ser Leu Lys Thr Glu Asp Thr Ala Met Tyr Tyr Cys Ala
                85                  90                  95

Gln Gly Val Tyr Gly Asp Thr Tyr Ser Gly Ser Gln Gly Thr Gln Val
            100                 105                 110

Thr Val Ser Ser
        115


<210> SEQ ID NO 142
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Arg Leu Ser
            20                  25                  30

Ala Met Arg Trp Val Arg Gln Ala Pro Gly Lys Gly Leu Glu Trp Val
        35                  40                  45

Ser Gly Ile Asp Ser Arg Gly Ser Thr Ile Tyr Ala Asp Ser Val Lys
    50                  55                  60

Gly Arg Phe Thr Ile Ser Lys Asp Asp Ala Lys Asn Thr Leu Tyr Leu
65                  70                  75                  80

Gln Leu Asn Ser Leu Lys Thr Glu Asp Thr Ala Met Tyr Tyr Cys Ala
                85                  90                  95

Gln Gly Val Tyr Gly Asp Thr Tyr Ser Gly Ser Gln Gly Thr Gln Val
            100                 105                 110

Thr Val Ser Ser
        115


<210> SEQ ID NO 143
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Tyr Thr Tyr Ser Ser Cys Thr Met Gly
1               5


<210> SEQ ID NO 144
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Met Leu Ile Ser Asp Gly Ser Thr Phe Tyr Ala Asp Ser Val Lys Gly
1               5                   10                  15


<210> SEQ ID NO 145
<211> LENGTH: 8
```

<212> TYPE: PRT
<213> ORGANISM: Artificial Sequence
<220> FEATURE:
<223> OTHER INFORMATION: Description of Artificial Sequence: Synthetic peptide

<400> SEQUENCE: 145

Ala Thr Leu Gly Ser Arg Thr Val
1 5

<210> SEQ ID NO 146
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 146

Phe Thr Phe Arg Leu Ala Ala Met Arg
1 5

<210> SEQ ID NO 147
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 147

Gly Ile Asp Ser Arg Gly Ser Thr Ile Tyr Ala Asp Ser Val Lys Gly
1 5 10 15

<210> SEQ ID NO 148
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 148

Gly Val Tyr Gly Asp Thr Tyr Ser
1 5

<210> SEQ ID NO 149
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 149

Asn Thr Tyr Cys Glu Tyr Asn Met Ser
1 5

<210> SEQ ID NO 150
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 150

Gly Val Asp Ser Asp Gly Ser Thr Arg Tyr Ser Glu Ser Val Lys Gly 1 5 10 15

<210> SEQ ID NO 151
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 151

Tyr Val Cys Thr Phe Cys Ser Gly Asn Ser Cys Tyr Tyr Glu Tyr Lys
1 5 10 15

Tyr Tyr Tyr

<210> SEQ ID NO 152
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 152

Tyr Thr Tyr Ser Asn Asn Cys Met Gly
1 5

<210> SEQ ID NO 153
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 153

Asn Ile Tyr Thr Gly Gly Gly Arg Thr Thr Tyr Ala Asp Ser Val Lys
1 5 10 15

Gly

<210> SEQ ID NO 154
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 154

Gly Ser Cys Gly Ser Ala Arg Ser Glu Tyr Ser Tyr
1 5 10

<210> SEQ ID NO 155
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 155

Tyr Thr Phe Cys Met Ala
1 5

<210> SEQ ID NO 156
<211> LENGTH: 17

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 156

Arg Phe Tyr Thr Arg Asp Gly Tyr Thr Tyr Tyr Ser Asp Ser Val Lys
1 5 10 15

Gly

<210> SEQ ID NO 157
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 157

Asp Leu Ala Arg Cys Ser Ser Asn Lys Asn Asp Phe Arg Tyr
1 5 10

<210> SEQ ID NO 158
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 158

Tyr Thr Ser Gly Asn Tyr Trp Met Gly
1 5

<210> SEQ ID NO 159
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 159

Thr Leu Trp Thr Gly Gly Ala Ser Thr Phe Tyr Gly Asp Ser Val Lys
1 5 10 15

Gly

<210> SEQ ID NO 160
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 160

Asp Pro Ala Leu Arg Leu Gly Ala Asn Ile Leu Arg Pro Ala Glu Tyr
1 5 10 15

Lys Tyr

<210> SEQ ID NO 161
<211> LENGTH: 9
<212> TYPE: PRT
<213> ORGANISM: Artificial Sequence
<220> FEATURE:

<223> OTHER INFORMATION: Description of Artificial Sequence: Synthetic peptide

<400> SEQUENCE: 161

Phe Thr Phe Ser Arg Ser Ala Met Thr
1 5

<210> SEQ ID NO 162
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 162

Gly Ile Asp Ser Gly Gly Thr Thr Val Tyr Ala Asp Ser Val Lys Gly
1 5 10 15

<210> SEQ ID NO 163
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 163

Gly Leu Pro Trp Gly Asn Thr Trp Arg Thr
1 5 10

<210> SEQ ID NO 164
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 164

Tyr Thr Tyr Ser Ser Cys Thr Met Gly
1 5

<210> SEQ ID NO 165
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 165

Met Val Phe Ser Asp Gly Ser Thr Phe Tyr Ala Asp Ser Val Lys Gly
1 5 10 15

<210> SEQ ID NO 166
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 166

Ala Thr Leu Gly Ser Arg Thr Ile
1 5

<210> SEQ ID NO 167
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 167

Phe Thr Phe Arg Leu Thr Ala Met Arg
1               5

<210> SEQ ID NO 168
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 168

Gly Ile Asp Ser Ala Gly Ser Thr Ile Tyr Ala Asp Ser Val Lys Gly
1               5                   10                  15

<210> SEQ ID NO 169
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 169

Gly Val Tyr Gly Asp Thr Tyr Ser
1               5

<210> SEQ ID NO 170
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 170

Asp Thr Tyr Ser Ser Cys Thr Met Gly
1               5

<210> SEQ ID NO 171
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 171

Met Leu Met Gly Asp Gly Ser Thr Phe Tyr Ala Asp Ser Val Lys Gly
1               5                   10                  15

<210> SEQ ID NO 172
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 172

Ala Thr Leu Gly Ser Arg Thr Ile
1 5

<210> SEQ ID NO 173
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 173

Tyr Thr Tyr Ser Ser Cys Thr Met Gly
1 5

<210> SEQ ID NO 174
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 174

Met Leu Ile Ser Asp Gly Ser Thr Phe Tyr Ala Asp Ser Val Lys Gly
1 5 10 15

<210> SEQ ID NO 175
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 175

Ala Thr Leu Gly Ser Arg Thr Val
1 5

<210> SEQ ID NO 176
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 176

Tyr Thr Tyr Ser Ser Cys Thr Met Gly
1 5

<210> SEQ ID NO 177
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 177

Met Leu Ile Ser Asp Gly Ser Thr Phe Tyr Ala Asp Ser Val Lys Gly
1 5 10 15

<210> SEQ ID NO 178
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 178

Ala Thr Leu Gly Ser Arg Thr Val
1 5

<210> SEQ ID NO 179
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 179

Phe Thr Phe Arg Leu Ala Ala Met Arg
1 5

<210> SEQ ID NO 180
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 180

Gly Ile Asp Ser Arg Gly Ser Thr Ile Tyr Ala Asp Ser Val Lys Gly
1 5 10 15

<210> SEQ ID NO 181
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 181

Gly Val Tyr Gly Asp Thr Tyr Ser
1 5

<210> SEQ ID NO 182
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 182

Phe Thr Phe Arg Thr Ser Ala Met Thr
1 5

<210> SEQ ID NO 183
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 183

Gly Ile Asp Ser Gly Gly Thr Thr Val Tyr Ala Asp Ser Val Lys Gly
1 5 10 15

<210> SEQ ID NO 184
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 184

Gly Leu Pro Trp Gly Asn Thr Trp Arg Thr
1 5 10

<210> SEQ ID NO 185
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 185

Tyr Thr Tyr Ser Ser Cys Thr Met Gly
1 5

<210> SEQ ID NO 186
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 186

Met Val Phe Ser Asp Gly Ser Thr Phe Tyr Ala Asp Ser Val Lys Gly
1 5 10 15

<210> SEQ ID NO 187
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 187

Ala Thr Leu Gly Ser Arg Thr Ile
1 5

<210> SEQ ID NO 188
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 188

Asp Thr Tyr Ser Ser Cys Thr Met Gly
1 5

<210> SEQ ID NO 189
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 189

Met Leu Met Gly Asp Gly Ser Thr Phe Tyr Ala Asp Ser Val Lys Gly
1 5 10 15

<210> SEQ ID NO 190
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 190

Ala Thr Leu Gly Ser Arg Thr Ile
1 5

<210> SEQ ID NO 191
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 191

Phe Thr Phe Arg Leu Thr Ala Met Arg
1 5

<210> SEQ ID NO 192
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 192

Gly Ile Asp Ser Arg Gly Ser Thr Ile Tyr Ala Asp Ser Val Lys Gly
1 5 10 15

<210> SEQ ID NO 193
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 193

Gly Val Tyr Gly Asp Thr Tyr Ser
1 5

<210> SEQ ID NO 194
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 194

Phe Thr Phe Arg Leu Thr Ala Met Arg
1 5

<210> SEQ ID NO 195
<211> LENGTH: 16
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 195

Gly Ile Asp Ser Arg Gly Ser Thr Ile Tyr Ala Asp Ser Val Lys Gly
1               5                   10                  15


<210> SEQ ID NO 196
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Gly Val Tyr Gly Asp Thr Tyr Ser
1               5


<210> SEQ ID NO 197
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Phe Thr Phe Arg Leu Ser Ala Met Arg
1               5


<210> SEQ ID NO 198
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Gly Ile Asp Ser Arg Gly Ser Thr Ile Tyr Ala Asp Ser Val Lys Gly
1               5                   10                  15


<210> SEQ ID NO 199
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Gly Val Tyr Gly Asp Thr Tyr Ser
1               5


<210> SEQ ID NO 200
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Phe Thr Phe Ser Ser Ser Ala Met Thr
1               5
```

<210> SEQ ID NO 201
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 201

Gly Ile Asp Ser Gly Gly Thr Thr Val Tyr Ala Asp Ser Val Lys Gly
1 5 10 15

<210> SEQ ID NO 202
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 202

Gly Leu Pro Trp Gly Asn Thr Trp Arg Thr
1 5 10

<210> SEQ ID NO 203
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 203

Phe Thr Phe Ser Ser Ser Ala Met Thr
1 5

<210> SEQ ID NO 204
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 204

Gly Ile Asp Ser Gly Gly Thr Thr Val Tyr Ala Asp Ser Val Lys Gly
1 5 10 15

<210> SEQ ID NO 205
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 205

Gly Leu Pro Trp Gly Asn Thr Trp Arg Thr
1 5 10

<210> SEQ ID NO 206
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 206

Tyr Thr Phe Cys Met Ala
1 5

<210> SEQ ID NO 207
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 207

Arg Phe Tyr Thr Arg Asp Ser Tyr Thr Tyr Tyr Ser Asp Ser Val Lys
1 5 10 15

Gly

<210> SEQ ID NO 208
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 208

Asp Leu Thr Arg Cys Ser Ser Asn Lys Asn Asp Phe Arg Tyr
1 5 10

<210> SEQ ID NO 209
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 209

Phe Asn Phe Arg Leu Tyr Ala Met Arg
1 5

<210> SEQ ID NO 210
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 210

Gly Ile Asp Ser Gly Gly Ser Thr Ile Tyr Ala Asp Ser Val Lys Gly
1 5 10 15

<210> SEQ ID NO 211
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 211

Gly Val Tyr Gly Asp Thr Tyr Ser
1 5

<210> SEQ ID NO 212
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 212

Tyr Thr Phe Cys Met Ala
1 5

<210> SEQ ID NO 213
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 213

Arg Phe Tyr Thr Arg Asp Gly Tyr Thr Tyr Tyr Ser Gly Ser Val Lys
1 5 10 15

Gly

<210> SEQ ID NO 214
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 214

Asp Leu Thr Arg Cys Ser Ser Asn Lys Asn Asp Phe Arg Tyr
1 5 10

<210> SEQ ID NO 215
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 215

Tyr Thr Tyr Ser Ser Cys Thr Met Gly
1 5

<210> SEQ ID NO 216
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 216

Met Leu Ile Ser Asp Gly Ser Thr Phe Tyr Ala Asp Ser Val Lys Gly
1 5 10 15

<210> SEQ ID NO 217
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 217

Ala Thr Leu Gly Ser Arg Thr Val
1 5

<210> SEQ ID NO 218
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 218

Tyr Thr Phe Cys Met Ala
1 5

<210> SEQ ID NO 219
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 219

Arg Phe Tyr Thr Arg Asp Gly Tyr Thr Tyr Tyr Ser Asp Ser Val Lys
1 5 10 15

Gly

<210> SEQ ID NO 220
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 220

Asp Leu Thr Arg Cys Ser Ser Asn Lys Asn Asp Phe Arg Tyr
1 5 10

<210> SEQ ID NO 221
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 221

Tyr Thr Tyr Ser Ser Cys Thr Met Gly
1 5

<210> SEQ ID NO 222
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 222

Met Leu Ile Ser Asp Gly Ser Thr Phe Tyr Ala Asp Ser Val Lys Gly
1 5 10 15

<210> SEQ ID NO 223
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 223

Ala Thr Leu Gly Ser Arg Thr Val
1               5

<210> SEQ ID NO 224
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 224

Phe Thr Phe Arg Leu Thr Ala Met Arg
1               5

<210> SEQ ID NO 225
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 225

Gly Ile Asp Ser Arg Gly Ser Thr Ile Tyr Ala Asp Ser Val Lys Gly
1               5                   10                  15

<210> SEQ ID NO 226
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 226

Gly Val Tyr Gly Asp Thr Tyr Ser
1               5

<210> SEQ ID NO 227
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 227

Phe Thr Phe Ser Thr Ser Ala Met Thr
1               5

<210> SEQ ID NO 228
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 228

Gly Ile Asp Ser Gly Gly Thr Thr Val Tyr Ala Asp Ser Val Lys Gly
1 5 10 15

<210> SEQ ID NO 229
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 229

Gly Leu Pro Trp Gly Asn Thr Trp Arg Thr
1 5 10

<210> SEQ ID NO 230
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 230

Phe Thr Phe Arg Leu Thr Ala Met Arg
1 5

<210> SEQ ID NO 231
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 231

Gly Ile Asp Ser Arg Gly Ser Thr Ile Tyr Ala Asp Ser Val Lys Gly
1 5 10 15

<210> SEQ ID NO 232
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 232

Gly Val Tyr Gly Asp Thr Tyr Ser
1 5

<210> SEQ ID NO 233
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 233

Phe Thr Phe Arg Leu Thr Ala Met Arg
1 5

<210> SEQ ID NO 234
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 234

Gly Ile Asp Ser Arg Gly Ser Thr Ile Tyr Ala Asp Ser Val Lys Gly
1 5 10 15

<210> SEQ ID NO 235
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 235

Gly Val Tyr Gly Asp Thr Tyr Ser
1 5

<210> SEQ ID NO 236
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 236

Phe Thr Phe Ser Arg Ser Ala Met Thr
1 5

<210> SEQ ID NO 237
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 237

Gly Ile Asp Ser Gly Gly Thr Thr Val Tyr Ala Asp Ser Val Lys Gly
1 5 10 15

<210> SEQ ID NO 238
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 238

Gly Leu Pro Trp Gly Asn Thr Trp Arg Thr
1 5 10

<210> SEQ ID NO 239
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 239

Phe Thr Phe Ser Ser Ser Ala Met Thr
1 5

<210> SEQ ID NO 240
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 240

Gly Ile Asp Ser Gly Gly Thr Thr Val Tyr Ala Asp Ser Val Lys Gly
1 5 10 15

<210> SEQ ID NO 241
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 241

Gly Leu Pro Trp Gly Asn Thr Trp Arg Thr
1 5 10

<210> SEQ ID NO 242
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 242

Phe Thr Phe Arg Leu Thr Ala Met Arg
1 5

<210> SEQ ID NO 243
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 243

Gly Ile Asp Ser Arg Gly Ser Thr Ile Tyr Ala Asp Ser Val Lys Gly
1 5 10 15

<210> SEQ ID NO 244
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 244

Gly Val Tyr Gly Asp Thr His Ser
1 5

<210> SEQ ID NO 245
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 245

Phe Thr Phe Ser Ser Ser Ala Met Thr
1 5

<210> SEQ ID NO 246
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 246

Gly Ile Asp Ser Gly Gly Thr Thr Val Tyr Ala Asp Ser Val Lys Gly
1 5 10 15

<210> SEQ ID NO 247
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 247

Gly Leu Pro Trp Gly Asn Thr Trp Arg Thr
1 5 10

<210> SEQ ID NO 248
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 248

Asp Thr Tyr Ser Ser Cys Thr Met Gly
1 5

<210> SEQ ID NO 249
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 249

Met Val Phe Ser Asp Gly Ser Thr Phe Tyr Ala Asp Ser Val Lys Gly
1 5 10 15

<210> SEQ ID NO 250
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 250

Ala Thr Leu Gly Ser Arg Thr Ile
1 5

<210> SEQ ID NO 251
<211> LENGTH: 9
<212> TYPE: PRT

<213> ORGANISM: Artificial Sequence
<220> FEATURE:
<223> OTHER INFORMATION: Description of Artificial Sequence: Synthetic
peptide

<400> SEQUENCE: 251

Phe Thr Phe Ser Ser Gly Ala Met Thr
1 5

<210> SEQ ID NO 252
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 252

Gly Ile Asp Ser Gly Gly Thr Thr Val Tyr Ala Asp Ser Val Lys Gly
1 5 10 15

<210> SEQ ID NO 253
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 253

Gly Leu Pro Trp Gly Asn Thr Trp Arg Thr
1 5 10

<210> SEQ ID NO 254
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 254

Phe Thr Phe Ser Thr Ser Ala Met Thr
1 5

<210> SEQ ID NO 255
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 255

Gly Ile Asp Ser Gly Gly Thr Thr Val Tyr Ala Asp Ser Val Lys Gly
1 5 10 15

<210> SEQ ID NO 256
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 256

Gly Leu Pro Trp Gly Asn Ile Trp Arg Thr
1 5 10

<210> SEQ ID NO 257
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 257

Phe Thr Phe Ser Arg Ser Ala Met Thr
1               5

<210> SEQ ID NO 258
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 258

Gly Ile Asp Ser Gly Gly Thr Thr Val Tyr Ala Asp Ser Val Lys Gly
1               5                   10                  15

<210> SEQ ID NO 259
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 259

Gly Leu Pro Trp Gly Asn Thr Trp Arg Thr
1               5                   10

<210> SEQ ID NO 260
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 260

Phe Thr Phe Arg Leu Thr Ala Met Arg
1               5

<210> SEQ ID NO 261
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 261

Gly Ile Asp Ser Arg Gly Ser Thr Ile Tyr Ala Asp Ser Val Lys Gly
1               5                   10                  15

<210> SEQ ID NO 262
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 262

Gly Val Tyr Gly Asp Thr Tyr Ser
1 5

<210> SEQ ID NO 263
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 263

Phe Thr Phe Ser Thr Ser Ala Met Thr
1 5

<210> SEQ ID NO 264
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 264

Gly Ile Asp Ser Gly Gly Thr Thr Val Tyr Ala Asp Ser Val Lys Gly
1 5 10 15

<210> SEQ ID NO 265
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 265

Gly Leu Pro Trp Gly Asn Thr Trp Arg Thr
1 5 10

<210> SEQ ID NO 266
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 266

Phe Thr Phe Ser Asn Tyr Ala Met Arg
1 5

<210> SEQ ID NO 267
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 267

Gly Ile Asp Ser Arg Gly Ser Thr Ile Tyr Ala Asp Ser Val Lys Gly
1 5 10 15

<210> SEQ ID NO 268
<211> LENGTH: 8

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 268

Gly Val Tyr Gly Asp Thr Tyr Ser
1 5

<210> SEQ ID NO 269
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 269

Tyr Thr Phe Cys Met Ala
1 5

<210> SEQ ID NO 270
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 270

Arg Phe Tyr Thr Arg Asp Gly Tyr Thr Tyr Tyr Ser Asp Ser Val Lys
1 5 10 15

Gly

<210> SEQ ID NO 271
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 271

Asp Leu Thr Arg Cys Ser Ser Asn Lys Asn Asp Phe Arg Tyr
1 5 10

<210> SEQ ID NO 272
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 272

Phe Thr Phe Arg Leu Ser Ala Met Arg
1 5

<210> SEQ ID NO 273
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 273

```
Gly Ile Asp Ser Arg Gly Ser Thr Ile Tyr Ala Asp Ser Val Lys Gly
1               5                   10                  15


<210> SEQ ID NO 274
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 274

Gly Val Tyr Gly Asp Thr Tyr Ser
1               5


<210> SEQ ID NO 275
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 275

Phe Thr Phe Arg Leu Ser Ala Met Arg
1               5


<210> SEQ ID NO 276
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 276

Gly Ile Asp Ser Arg Gly Ser Thr Ile Tyr Ala Asp Ser Val Glu Gly
1               5                   10                  15


<210> SEQ ID NO 277
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 277

Gly Val Tyr Gly Asp Thr Tyr Ser
1               5


<210> SEQ ID NO 278
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 278

Phe Thr Phe Arg Leu Ser Ala Met Arg
1               5


<210> SEQ ID NO 279
<211> LENGTH: 16
<212> TYPE: PRT
<213> ORGANISM: Artificial Sequence
```

<220> FEATURE:
<223> OTHER INFORMATION: Description of Artificial Sequence: Synthetic peptide

<400> SEQUENCE: 279

Gly Ile Asp Ser Arg Gly Ser Thr Ile Tyr Ala Asp Ser Val Lys Gly
1 5 10 15

<210> SEQ ID NO 280
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 280

Gly Val Tyr Gly Asp Thr Tyr Ser
1 5

<210> SEQ ID NO 281
<211> LENGTH: 347
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 281
caagtgcagc tgcaagaatc tggcggaggc ttgtgcaagc tggcggttcc ttgcgtctga 60
gctgcgccgc atctgggtat acctacagta gctgcacaat gggttggtat agacaagcgc 120
ccggtaagga gcgggaactg gtgtccatgc tgatctctga cggcagtact ttttacgccg 180
actccgtgaa gggcagattc acattctccc aggagtacgc caagaacacc gtctaccttc 240
agatgaacag tctgaagcct gaggacaccg ctatgtacta ttgcggctgc gcaacgctcg 300
gctcccgcac ggtctggggt cagggcaccc aggtcaccgt gtcctct 347

<210> SEQ ID NO 282
<211> LENGTH: 348
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 282
caggttcagc ttcaggagtc tggtggcggt tccgtacagg ccgggggctc ccttactctc 60
agctgtaccg cgccgggttt tactttccgg ttggcggcca tgcgctgggt tcgccaggct 120
ccgggaaaag gactggagtg ggttagcggc attgattcca ggggctccac catctatgcc 180
gactctgtga aggggaggtt cacaattagc aaagataatg ccaaaaacac tctttacctt 240
cagctcaatt ctttgaaaac tgaggatact gcaatgtatt actgcgccca gggcgtatac 300
ggcgacactt actccgggag ccaaggaaca caggtgactg tatcttct 348

<210> SEQ ID NO 283
<211> LENGTH: 381
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 283
caggtccagt tgcaagagtc agggggtggg tccgtacagg caggaggttc cctccgcctc 60
agctgcactg cctctgtcaa cacatactgc gaatacaata tgtcctggta tcggcaggcc 120
cctggcaagg agagagagtt cgtgtccggc gttgactctg atggttccac ccgctacagc 180
gagagcgtta aggggcgctt caccatctcc caggacaacg ccaagaacac tatgtacctc 240
cagatgaatg gtctgaagcc cgaggacacc gctatgtact attgtaagac atacgtttgt 300
accttctgtt caggcaacag ctgctactat gaatataagt actattacga gggccaggga 360
acgcaggtta ccgtatcctc t 381

<210> SEQ ID NO 284
<211> LENGTH: 363
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 284
caggtgcaac tccaggagtc cggcgggggt agcgtccagg ctgggggctc cctccgcctg 60
agttgtgctg ccagcggtta tacttactct aataattgca tgggctggtt taggcaagct 120
ccgggcaagg accgcgagag aattgccaat atctacacag gaggtggcag aactacctac 180
gcagatagtg tgaagggccg gttcaccatt tctcaggaca gtgcgaagtc cactgtgtac 240
ctccagatga actcactgaa gccggaggac accgcgatgt attactgcgc cgctggctcc 300
tgtgggagcg ctcgttccga atactcatac tggggccagg gcacccaggt gaccgtgtcc 360
tcc 363

<210> SEQ ID NO 285
<211> LENGTH: 360
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 285
caagtgcagc tccaggaatc tgggggcggg tctgtccaag ctggcgggag cctccgcctg 60
agttgtgctg cctctgggta caccttttgt atggcttggt tccgccaagc gcctgggaag 120
gaacgcgagg gtgtcgcacg cttctataca cgtgatggat acacatatta ctctgacagc 180
gttaagggca gattcactat ctctcagaat aacgctaaga ataccctcta cttgcagatg 240
aactctctga aagcgagga caccgctatg tactattgcg cagcggattt ggcccgctgt 300
tccagcaaca agaatgactt tcgttactgg ggtcagggga cacaggtgac agttagtagc 360

<210> SEQ ID NO 286
<211> LENGTH: 381
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 286
caggtccagc tccaggagtc aggaggtggc tccgttcagg ctggtggctc cctccggctg 60
tcctgtgccg caagcggata cacgtctgga aactactgga tgggatggtt ccgtcaagcc 120
cccggcaaag aacgcgaggg cgtggctact ctgtggactg gtggagcctc aaccttctac 180
ggcgactctg ttaagggccg tttcaccatt agtcgcgata acttcaaaaa cacactctac 240
cttcagatga actccctgaa ggtcgaggat acagccatgt attactgcgc cgctgaccct 300
gccctgcgtc tgggagctaa catcctgcgc cctgctgaat acaaatattg gggtcaaggg 360
acacaggtga ctgtcagctc a 381

<210> SEQ ID NO 287
<211> LENGTH: 354
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 287
caggtgcagc tccaggagtc cggcggtggc ctggtacagc ccggtggcag cttgcgcctg 60
agctgcgccg cttctggatt tacattctcc cgcagcgcca tgacatgggt tcgccaggct 120
ccaggcaagg gcctcgactg ggtgtccggc attgacagtg gcggaactac cgtgtacgca 180
gattctgtta agggaagatt caccatctcc cgcgactccg ccaagaacac cctgtacttg 240
caaatgaaca gcctcaagac agaagacaca gccgtgtatt actgtgccat cggactgccg 300
tggggcaaca catggcgtac caggggacag ggcacacagg tgacagtctc ctca 354

<210> SEQ ID NO 288
<211> LENGTH: 348
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 288
caggtgcagt tgcaggagtc cggcggaggc agcgtgcaag ccggaggtag cctccgcctg 60
agctgcacag cgagccgcta cacctatagc agttgcacta tgggttggta tcgtcaggcc 120
cccggcaagg agagggaact cgtgtcaatg gtgttttctg acggttccac cttctacgcc 180
gactccgtta aaggtcggtt caccttctct caggaaaacg ccaaaaacac cgtgtacctc 240
cagatgaact ccctgaaacc cgaggatacc gctatgtact attgcggatg cgctacactc 300
ggctcaagaa ctatctgggg ccaaggcact caggtgactg tctcctcc 348

<210> SEQ ID NO 289
<211> LENGTH: 348
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 289
caggtgcagc tccaggaaag cggaggtggc ctcgtgcagc ctggtggctc cctgagactg 60
tcttgcgcaa catctggatt caccttcagg ctcactgcta tgcgttgggt gagacaagcc 120
ccagggaagg gcgtcgaatg ggtgtctgga atcgactccg ctggctctac gatctacgcc 180
gacagcgtga agggccgctt cactatctcc aaagataatg ctaagaacac tctgtatctg 240
caaatgaaca gcctcaaaac cgaagacaca gctatgtact attgtgcgca gggtgtctac 300
ggtgatacct acagcggttc tcagggcact caggtgacgg tgtccagc 348

<210> SEQ ID NO 290
<211> LENGTH: 348
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 290
caggtccagc tccaggagag cggcgggggc agcgtgcagg ctgggggttc cctgagactg 60
tcctgtgctg cctccggcga tacctacagt tcatgtacta tgggctggta tcgccaggct 120
ccgggcaagg agcgcgacct cgtgagcatg ttgatgggcg atggtagcac cttttacgcc 180
gatagtgtga agggccgttt cacctttagc caggagaacg ctaaaaacac tgtgtacttg 240
cagatgaaca gcttgaagcc cgaggacact gcaatgtatt actgtggctg cgccacgctg 300
ggctcccgca caatttgggg ccagggcacc caggtgaccg tttctagc 348

<210> SEQ ID NO 291
<211> LENGTH: 348
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 291
caggtccagc tccaggaaag cggcggtgga agcgtgcagg ccggtggcag tcttcgcctg 60
tcttgcgctg cgtctggtta cacctactcc tcatgcacta tgggttggta caggcaggcc 120
ccagggaagg agcgcgagct ggtatccatg ctcatttctg acgggtccac cttctacgcc 180
gattctgtca agggcaggtt taccttttcc caggaaaacg ccaagtccac tgtctatctg 240
caaatgaact ccttgaagcc cgaagacact gccatgtatt actgtggctg tgcgacgctt 300
ggctcaagga cggtgtgggg ccagggcacg caggtaaccg tttccagc 348

<210> SEQ ID NO 292
<211> LENGTH: 348
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 292
caggtgcagc tccaagagtc tggcggaggc tccgtgcagg ctggcgggag cctgcgcttg 60
tcctgcgcag ccagcggcta tacctactcc tcttgtacta tgggctggta taggcaagcg 120
cctggcaagg agcgcgaact cgtcagcatg ttgatctctg acggaagcac cttctacgct 180
gattctgtga aggggcgttt taccttcagc caggagaacg ctaagaacac cgtgtacctc 240
cagatgaact ctctgaaacc tgaagatacc gctatgtact attgcggatg cgctaccctg 300
ggttctagga ccgtttgggg tcagggaaca caggtgacag tatcttcc 348

<210> SEQ ID NO 293
<211> LENGTH: 348
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 293

```
caggtccagc tccaggaatc tggcgggggc ctcgtgcaac caggggggttc cctgagattg     60

tcttgcgcaa ccagtggttt taccttccgc ctcgctgcca tgcgttgggt gcggcaagcg    120

cccggcaagg gcctggagtg ggtgtctggg attgattctc ggggctccac aatctacgcg    180

gacagcgtca agggtcgctt cactatctct aaggacaatg ctaagaacac tctgtacctt    240

cagttgaact ctctgaaaac cgaggatacc gctatgtatt actgtgctca gggagtgtat    300

ggcgatacat actccggctc ccaggggacg caagtgactg tgagttct                 348
```

<210> SEQ ID NO 294
<211> LENGTH: 354
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 294

```
caggtgcagc ttcaggagtc cggcgggggc ctggttcagc ccggtgggtc cctgcgcctg     60

tcatgcgcag cttccggctt cacctttagg acatctgcca tgacttgggt gcgtcaggct    120

cctggcaagg gcctcgactg ggtgagcggc atcgacagcg gggaaccac agtgtatgcc    180

gactccgtca agggacgctt caccattagc cgcgactccg ccaagaacac cctctacctt    240

cagatgaaca gcctgaagac ggaagacacc gccgtttatt actgcgcaat ggggctgcct    300

tggggcaaca cctggaggac tcggggccag ggaactcagg tgaccgtgtc ttcc          354
```

<210> SEQ ID NO 295
<211> LENGTH: 348
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 295

```
caggtgcagc ttcaggagtc aggcgggggc agcgtgcagg ccggaggctc cttgaggctg     60

agttgcgcgg ccagcggcta cacatattct agctgcacaa tggggtggta tcgccaggca    120

cccggaaagg agagggaact cgtgtctatg gtgttctctg acggctccac attctacgcc    180

gattctgtga agggccggtt taccttctca caggagaatg ccaaaaacac cgtgtatctc    240

cagatgaact ctttgaagcc agaggacaca gccatgtatt actgtggatg cgctaccctg    300

ggctcccgta ccatctgggg tcagggcacc caggtgactg tcagctct                 348
```

<210> SEQ ID NO 296
<211> LENGTH: 348
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 296

```
caagtccagc tccaggagag cgggggcggt tccgtccagg cgggcggaag cctccgcctt     60

tcatgtgcag ctagtggcga cacgtacagc tcctgtacta tgggctggta caggcaggcc    120

ccaggtaagg agcgcgatct ggtgtctatg ctgatgggcg acggcagtac cttttacgct    180

gatagcgtca agggccgttt caccttttct caggagaacg ccaagaatac cgtctatctt    240

caaatgaata acctcaagcc agaagatact gctatgtact attgtggttg tgccaccctg    300
```

gggtccagaa caatctgggg acagggcacc caggtcactg tgtcctct 348

<210> SEQ ID NO 297
<211> LENGTH: 348
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 297
caagtccagc ttcaggagtc tggcgggggc tcagtgcaag caggaggtag cctgaggctg 60
agctgcgctg ccagtggttt tactttccgc ctcaccgcca tgcgctgggt gcgccaggcc 120
cccggcaagg gcctggagtg ggtgagcgga atcgactcca ggggcagcac tatttatgcc 180
gactcagtga aggggagatt tactatctcc aaggacaatg caaaaaacac cctttacctt 240
caactgaact ctttgaagac cgaggacacg gccatgtatt actgcgcaca gggagtctac 300
ggggacacct actctggctc tcagggcacc caggtcactg tgtctagc 348

<210> SEQ ID NO 298
<211> LENGTH: 348
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 298
caagtccagc tccaggagag cggcgggggc ctggtgcagc ccggtggctc tttgaggctc 60
agctgtgctg cctccggctt cacattccgc ctgactgcaa tgcgttgggt gaggcaggct 120
cctggcaagg gtctggagtg ggtctctggt atcgacagta gaggctccac catctacgca 180
gatagcgtaa agggacgctt caccatctcc aaagataacg ctaagaacac cctctacctc 240
cagcttaaca gcctgaagac cgaggacaca gctatgtact attgtgcaca aggcgtctac 300
ggcgatacct attccggttc ccagggcact caggtgaccg tctcctcc 348

<210> SEQ ID NO 299
<211> LENGTH: 348
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 299
caggttcagc ttcaggagag cggcggtggc ctggtccaac ctgggggaag cctccgtctg 60
agctgcgccg catctggatt cacctttagg ctgtcagcta tgcgctgggt ccgtcaggcc 120
ccagggaagg gcctggaatg ggttagcggg atcgactctc gcgggtctac gatttatgcc 180
gactcagtca aggggcgctt cacgatctct aaggacaacg ctaagaacac cctgtacttg 240
cagctgaaca gcctgaagac cgaggatacg gctatgtatt actgtgcgca gggggtctac 300
ggggacacct actcaggatc acagggcacc caagtgaccg tgagttcc 348

<210> SEQ ID NO 300
<211> LENGTH: 354
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 300
caggtacagc tccaggagtc cggcggaggc cttgtgcagc ctggtggctc cttgagactg 60
agctgtgccg cttccggttt tacattctcc agctcagcca tgacatgggt gagacaggcc 120
cctggaaagg gactggactg ggtttctggc attgactcag gggcacgac cgtgtatgct 180 gactctgtta agggccgcgc caccatcctc aaggacaacg ctaagaacac actctacctc 240
cagatgaact ccctgaagac tgaggacaca gctgtctact attgtgctac tggtctgcct 300
tggggtaaca cctggcggac caggggccag ggcactcagg tgactgtctc ctca 354

<210> SEQ ID NO 301
<211> LENGTH: 354
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 301
caggtgcagc tccaggagtc aggcggtgga ctcgttcagc cgggtggctc cctgcgcctc 60
agttgtgcga cctctggctt taccttctcc agctccgcta tgacctgggt gaggcaagca 120
cctgggaagg gcctcgattg ggtctccggc attgattctg gaggcaccac tgtctacgcc 180
gacagcgtga agggcagatt cacaatcagt aaggacaacg ctaagaacac tctgtacctg 240
caaatgaaca gcctgaagac cgaggacacc gctgtttatt actgcgcaac gggactgcct 300
tggggtaata cttggaggac taccggccag ggaactcagg tgactgtgag ttcc 354

<210> SEQ ID NO 302
<211> LENGTH: 360
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 302
caggtgcagc tccaggaatc cggtggaggc tccgtgcaag cgggcgggtc cctgcgcctc 60
agctgtgcag cttctggcta taccttctgc atggcctggt ttcgccaggc ccctgggaag 120
gagagggagg gggtggcccg cttttacact agagacagct atacttacta tagcgactcc 180
gtgaaggggc gctttacgat tagccagaat aacgccaaga ataccttgta cctccagatg 240
aatagtctga agtccgagga caccgccatg tattactgtg ctgccgacct tacgaggtgc 300
agctccaata agaacgactt ccgctactgg ggccagggta ctcaggtcac tgtgtccagc 360

<210> SEQ ID NO 303
<211> LENGTH: 348
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 303
caagtgcagc tccaggaaag cggaggcggt ctggtccaac caggagggtc cctgcgtctg 60
tcctgcgcgg cctccggctt taatttcaga ctgtatgcga tgcgttgggt tcgtcaagcg 120
cccggtaagg gcgtggagtg ggtgtccggt atcgactcag gaggctctac catctatgct 180
gactctgtga agggccgctt taccatcagc aaggacaacg ctaaaaatac cctgtacttg 240

```
cagctgaact ctctgaaaac cgaggacact gccatgtatt actgcgccca gggtgtgtac    300

ggcgacacct actctggttc ccaaggcacc caggtgacgg tctcctcc                 348


<210> SEQ ID NO 304
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 304

caagtgcagc tccaggagag cggtggcggt tctgtgcaag cgggtgggtc cctgcggctg     60

agctgcgctg tgtctggtta taccttctgt atggcctggt tccgccaggc tccgggaaag    120

gagcgcgaag gcgtggctcg gttctacacc agagacggtt acacatacta ttccggcagc    180

gtgaagggca ggttcacgat cagccagaat aacgctaaaa acaccctgta cctgcaaatg    240

aacagcctga agagcgagga taccgcgatg tattactgcg cagccgactt gaccagatgc    300

tcttccaaca aaaacgactt ccgctactgg ggtcagggca cccaagtcac tgtgtcctcc    360


<210> SEQ ID NO 305
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 305

caagtccagc tccaggagag tggaggcgga agcgtgcagg ccggtggctc cctgagactt     60

tcatgcgcag cgtccggcta tacatattct tcctgcacta tgggctggta cagacaagcg    120

ccgggcaagg agcgtgagtt ggtgagtatg ctcatcagcg atggcagtac cttttatgcg    180

gactctgtca agggccgctt caccttctct caagagaacg ctaaaaacac agtttacctc    240

cagatgaact ccctgaagcc cgaagacact gccatgtatt tttgtgggtg tgccactctt    300

ggctccagga cggtgtgggg ccagggcacc caggttaccg tgagcagt                 348


<210> SEQ ID NO 306
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 306

caggtccagc tgcaagagtc tggagggggc agcgtgcagg ctggcggttc tctgcgcctg     60

agctgcgctg cgagtgggta cactttctgt atggcatggt ttcgccaagc tcccggtaag    120

gagcgcgaag gtgtggcccg cttttatact agggacggtt acacatatta ctcagactct    180

gtgaagggcc gttttaccat ttcccaaaac aatgcaaaaa acaccctgta ccttcagatg    240

aactctctca aaagcgagga tactgctatg tattactgcg ccgcagacct gaccagatgt    300

tcatccaata agaatgactt ccgctactgg ggccaaggga cccaggtgac cgtgagcagt    360


<210> SEQ ID NO 307
<211> LENGTH: 348
<212> TYPE: DNA
<213> ORGANISM: Artificial Sequence
```

<220> FEATURE:
<223> OTHER INFORMATION: Description of Artificial Sequence: Synthetic
polynucleotide

<400> SEQUENCE: 307
caggtccagc tgcaagaatc tggtgggggt tccgtgcaag ccggaggcag cctgaggctc 60
agctgcgccg caagcggata cacatattcc tcttgcacta tgggttggta tcgccaggcc 120
ccaggcaagg aacgtgagct ggtctctatg ctcatcagtg atggcagcac cttttacgct 180
gattctgtga agggcagatt tacctcttcc caggagaacg ctaaaaacac tgtgtacctt 240
cagatgaaca gcctgaagcc agaggacacc gcgatgtact attgcggctg cgcaaccctg 300
gggagcagga cagtgtgggg gcagggcaca caggtgaccg tctcctca 348

<210> SEQ ID NO 308
<211> LENGTH: 348
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 308
caggtccagc tgcaagagag cggaggcggg ctcgtgcagc cgggtggcag cctgcgcctt 60
tcctgcgctg cgtctggctt caccttcagg ctcaccgcta tgagatgggt tagacaagct 120
cccggcaagg gtctggaatg ggtgagcggc atcgacagca gaggtagcac gatctacgct 180
gattccgtca agggacggtt cacaatttcc agagacaacg ccaagaacac actgtacctt 240
cagttgaact ccctgaagac cgaagacgcc gctatgtact attgtgcgca gggcgtgtac 300
ggcgatacct actcaggctc ccagggcacc caggtaacgg tgagttcc 348

<210> SEQ ID NO 309
<211> LENGTH: 354
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 309
caggtacagc tgcaagagag tggcggaggc ctcgttcaac ccggagggag tctgcgcctg 60
tcttgtgctg cctccggctt cacctttttcc acttccgcta tgacctgggt caggcaggcc 120
cccggcaagg gactggactg ggtaagtggc atcgactccg gtggcactac cgtgtacgcg 180
gactccgtga aaggccgctt cactattagc aaggacaacg ctaaaaacac actctacctc 240
cagatgaaca gcctcaagac agaggacact gccgtgtact attgcgcgac cggcctgcct 300
tggggcaaca cctggcgcac aagaggtcaa gggacacagg tcactgtgag cagc 354

<210> SEQ ID NO 310
<211> LENGTH: 348
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 310
caggtgcagc tgcaagaaag cggaggcgga cttgttcagc ctgggggctc cttgcggctg 60
tcctgtgctg cctcaggctt tacttttcgt ctgacagcca tgcggtgggt gcggcaggcc 120
cctggcaagg gtctcgaatg ggtttccggt attgactctc gcggctctac tatctacgcc 180
gactctgtga agggccgttt caccatctcc aaggataatg ccaaaaacac gctgtacttg 240
cagcttaata gcttgaagac cgaggatacg gccatgtact attgtgctca gggcgtttac 300
ggcgacactt attctggctc ccttggcacg caggtcacgg tttctagc 348

<210> SEQ ID NO 311
<211> LENGTH: 348
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 311
caggtgcagc tccaggagag cggaggcgga ctggtgcagc caggtggcag cctgaggctc 60
tcctgtgcgg cctcaggttt tacctttcgc ctgacagcca tgcggtgggt cagacaagcg 120
cctgggaaag gtctggagtg ggtgtctggt atcgactctc gcggttccac catctacgcc 180
gattctgtga aggggcgctt tacaattagc cgcgacaacg ccaagaacac cctgtacctc 240
cagctcaatt ccctgaagac cgaggacacc gcgatgtact attgtgcgca aggcgtctat 300
ggggatacct atagcggttc tcagggaacc caggtgactg tttccagc 348

<210> SEQ ID NO 312
<211> LENGTH: 354
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 312
caggtgcagc tccaggaatc tgggggaggc ctggttcgcc ctgggggtag cctgagactg 60
agctgtgcag cctctggatt cactttctcc cgttccgcaa tgacctgggt ccgccaggcc 120
ccaggcaagg ggttggattg ggtgtctggc attgattccg gggcaccac tgtgtacgcg 180 gactccgtga agggccgctt caccatcagc cgcgatagcg ccaaaaacac gctgtatctc 240
cagatgaaca gcctgaagac cgaggacact gccgtctact attgtgctat cggcctgccc 300
tggggcaaca catggcgtac acgcggtcag ggcacgcagg tgaccgtgtc ttct 354

<210> SEQ ID NO 313
<211> LENGTH: 354
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 313
caggtccagc ttcaggaaag cggaggcgga ctggtgcagc ccggaggcag tctgcgtctc 60
agctgtacga ccagcgggtt tactttctct agtagcgcaa tgacttgggt gaggcaggct 120
ccgggcaagg gtctggactg ggtcagcggt atcgacagcg gcgggacgac tgtgtatgcc 180
gattcagtga aaggacggtt cactatctca aaggacaacg ccaaaaacac actgtacctt 240
cagatgaact ccctgaagac cgaagacaca gcggtgtatt actgcgccac agggttgcct 300
tggggcaaca cttggcgcac cactggacaa gggacgcagg tgaccgtttc ctct 354

<210> SEQ ID NO 314

<211> LENGTH: 348
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 314

```
caggtgcagc tccaagagag tggcggaggc ctggtgcagc ccggtggctc tctgaggttg     60

tcttgtgctg cctctggctt taccttcaga ctgacagcca tgcgctgggt ccgccaggct    120

cctggtaagg gactggagtg ggtaagcggt atcgactcca gagggagcac catctatgct    180

gattccgtta agggacggtt caccatctct aaggataatg ccaagaacac cctgtatctc    240

cagttgaact ccctgaaaac cgaggacacc gcgatgtact attgcgcaca gggcgtgtat    300

ggcgacactc acagcggctc tcaaggcacc caggtgaccg tgtcttcc                 348
```

<210> SEQ ID NO 315
<211> LENGTH: 354
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 315

```
caggtccagc tccaagaatc cggcggaggg ctggtacagc caggaggcag tcttaggctg     60

gcttgctctg cgtccggctt cacattttcc agctctgcca tgacctgggt gcgccaggca    120

cccggaaagg gcctggactg ggtgagcggg attgatagcg gaggcaccac ggtgtatgct    180

gacagtgtaa aaggacgcgc cactatcctg aaggacaatg ccaagaacac cctctatttg    240

cagatgaaca gcctgaagac tgaagatact gctgtgtatt actgtgcaac gggcctgcct    300

tggggaaaca cttggcggac gcggggccag ggcacgcagg tgaccgtgtc ttcc          354
```

<210> SEQ ID NO 316
<211> LENGTH: 348
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 316

```
caggttcagc tgcaagaatc tggtggcgga agcgtgcaag cgggtggctc tcttcgtctc     60

tcttgtgctg catccggcga cacctacagc tcctgcacaa tggggtggta tcgtcaggcc    120

cctggcaagg agcgggatct ggtcagcatg gtcttctctg acggcagcac attctacgct    180

gactccgtca agggacgttt caccttctct caggagaacg cgaagaatac tgtgtatctt    240

cagatgaaca gcctgaagcc ggaggataca gcaatgtatt actgcggttg cgcgaccctg    300

ggtagcagga ccatctgggg tcaaggcacc caggtgacag tgtcctcc                 348
```

<210> SEQ ID NO 317
<211> LENGTH: 354
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 317

```
caggtccagc ttcaggaatc aggaggcggg cttgtgcagc cgggaggcag cctgcgcctg     60
```

tcctgcgcaa cctccggctt taccttctcc agcggagcca tgacctgggt gcggcaggcc 120
cccggtaagg gcctggattg ggtgtctggc atcgactccg gcggaaccac tgtgtacgct 180
gattctgtga agggtcgctt cacaattagt aaggacaacg ctaagaacac cctgtacctc 240
cagatgaact cattgaagac agaggatacc gccgtgtact attgtgcaac cggcctcccc 300
tgggggaaca cctggcgcac cactggtcag ggaacacaag taaccgtgag cagc 354

<210> SEQ ID NO 318
<211> LENGTH: 354
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 318
caggtccagc tccaggagag tggcgggga ctcgtgcagc ctggtggctc tttgcgcctg 60
agctgcgcgg caagcggatt tacattttcc accagtgcta tgacctgggt gcgccaggct 120
cccggcaagg gactggactg ggtaagcggt attgattccg gcggaacgac tgtgtacgct 180
gatagcgtaa agggccgctt taccatcagc aaagacaacg ccaaaaatac cctttacctg 240
caaatgaact ctttgaagac ggaggacacc gctgtgtatt actgcgccac tggcctccct 300
tggggcaaca tctggagaac ccgtggtcag ggcacccagg ttaccgtgtc ctcc 354

<210> SEQ ID NO 319
<211> LENGTH: 354
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 319
caggtccaac tccaggagtc cggcggaggc ttggtgcagc ctggaggctc tctgcggctg 60
tcctgcgccg catcaggttt tacgttttct cggtctgcca tgacctgggt cagacaggca 120
ccaggcaagg gcctggattg ggtgtccggt attgactctg gtggcactac cgtgtatgcc 180
gactccgtta agggccgttt caccatctcc agggactctg ccaagaacac attgtatttg 240
caaatgaacg gcctcaaaac tgaggacacc gcagtctact attgtgcaat cgggcttccg 300
tggggcaaca cgtggagaac caggggccag gggactcagg tcaccgtgtc atcc 354

<210> SEQ ID NO 320
<211> LENGTH: 348
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 320
caggtccagc tccaggagtc aggtggaggc ctggtgcaac ccggaggctc cctccgcctg 60
tcctgtgcag cctccggctt tacctttcgc ctgaccgcga tgaggtgggt tcggcaggcc 120
cctggcaaag ggctggagtg ggttagcggc atcgactcca ggggctccac catttacgcc 180
gactctgtca aggggcgttt caccatttct aaggacaacg ctaagaatac cctctacctc 240
cagctcaact ccctgaagag tgaagacacc gccatgtatt actgtgccca gggcgtctac 300
ggagacactt acagcgggtc ccagggtact caggtgaccg tgtcttcc 348

<210> SEQ ID NO 321
<211> LENGTH: 354
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 321
caagtccagt tgcaggagtc aggaggtggc ctggtgcaac ccggtggctc cctccgtctg 60
acctgcgctg cgtctggttt cactttctca acttcagcta tgacatgggt ccgccaggca 120
ccggggaagg gcctcgactg ggtatctggg atcgacagcg gaggcaccac tgtctatgcc 180
gattccgtga aaggacgctt cactattagc aaggacaacg ctaaaaacac cctgtatttg 240
cagatgaata gcctcaaaac tgaagatact gccgtttact attgcgccac tggcctcccc 300
tggggcaaca cctggcgcac aaggggtcag ggtactcagg taaccgtgtc ctct 354

<210> SEQ ID NO 322
<211> LENGTH: 348
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 322
caggtgcagc tgcaagagtc cggtggcggt ctggtgcagc ccggaggcag tctgaggctc 60
tcctgcgctg cctctggatt caccttcagc aactacgcta tgcgctgggt gcggcaggcc 120
cccggcaagg gcctggagtg ggtcagtggc atcgacagtc gcggaagtac tatttatgcc 180
gactccgtga agggaaggtt cactatttcc aaggacaacg ccaaaaacac tctgtacttg 240
cagctgaact ccttgaagac tgaggacact gccatgtact attgcgccca gggagtctat 300
ggggacacct attccgggag ccagggcact caggtgaccg tgtcaagt 348

<210> SEQ ID NO 323
<211> LENGTH: 360
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 323
caggttcagc tccaggaatc cggtggaggg tccgtgcagg ccgggggcag cctgagactg 60
tcctgtgctg cctctggtta tacgttttgc atggcgtggt tccggcaggc tcctggaaaa 120
gagcgcgagg gcgtggcaag attctacact agagatggtt acacctatta ctccgactct 180
gtcaagggga ggtttaccat ctctcaggac aacgccaaga acactttgta cctccagatg 240
aactccctga agtctgagga caccgccatg tattactgtg cagccgatct gacccggtgc 300
agttccaaca agaacgattt ccgctattgg ggccagggca cacaggtcac agtctcctcc 360

<210> SEQ ID NO 324
<211> LENGTH: 348
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 324

```
caagtacagc tccaagagtc tgggggaggt cttgtgcagc ccggaggctc tttgcgtctg     60
tcatgtgcgg ccagcggatt cacattcagg ctgtctgcaa tgcgttgggt gcgccaagcg    120
cctggcaagg ggtttgaatg ggtgtctgga attgattccc gtggctctac catctatgcc    180
gattctgtta aaggccgctt taccatctcc aaggataacg caaaaaacac actgtacttg    240
cagctgaata gcctgaaaac tgaggacacc gctatgtatt actgcgctca gggagtgtat    300
ggcgacactt attccggcag ccagggcact caggtgacag ttagctcc                 348
```

<210> SEQ ID NO 325
<211> LENGTH: 348
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 325

```
caggtgcagc tccaggagtc cggcggtgga ctcgtgcaac ccggcggttc ccttagattg     60
tcttgcgccg cttcaggttt tacctttcgc ttgtccgcta tgcggtgggt tcgccaagcg    120
ccaggaaaag gcctggagtg ggtctccggt attgattcca gaggctccac catctacgcc    180
gactctgtcg agggcaggtt caccatcagc aaggacaacg caaagaacac cctgtatctt    240
cagcttaata gtctgaagac cgaggacact gcgatgtatt actgcgctca gggagtgtac    300
ggtgatacct actccggctc ccagggaact caggtgaccg tctccagc                 348
```

<210> SEQ ID NO 326
<211> LENGTH: 348
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 326

```
caagttcagt tgcaggagag cggagggggc ctggttcagc cgggaggctc cctgaggctg     60
tcctgcgctg cgagtggctt cacttttagg ttgtccgcta tgcgctgggt gcgccaggct    120
cctgggaagg gtctggagtg ggtgtctggg attgactcca gaggtagtac catttacgcc    180
gactccgtca agggacgctt caccatctcc aaggacgatg ccaagaacac cctgtatctc    240
cagctgaact cactcaagac cgaagacacg gcaatgtatt actgtgccca gggtgtgtat    300
ggtgacactt actctggctc tcagggcact caagtgaccg tttcttcc                 348
```

<210> SEQ ID NO 327
<211> LENGTH: 332
<212> TYPE: PRT
<213> ORGANISM: Homo sapiens

<400> SEQUENCE: 327

```
Gly Ile Thr Asn Ile Asn Cys Ser Gly His Ile Trp Val Glu Pro Ala
1               5                   10                  15

Thr Ile Phe Lys Met Gly Met Asn Ile Ser Ile Tyr Cys Gln Ala Ala
            20                  25                  30

Ile Lys Asn Cys Gln Pro Arg Lys Leu His Phe Tyr Lys Asn Gly Ile
        35                  40                  45

Lys Glu Arg Phe Gln Ile Thr Arg Ile Asn Lys Thr Thr Ala Arg Leu
    50                  55                  60
```

```
Trp Tyr Lys Asn Phe Leu Glu Pro His Ala Ser Met Tyr Cys Thr Ala
65                  70                  75                  80

Glu Cys Pro Lys His Phe Gln Glu Thr Leu Ile Cys Gly Lys Asp Ile
                85                  90                  95

Ser Ser Gly Tyr Pro Pro Asp Ile Pro Asp Glu Val Thr Cys Val Ile
            100                 105                 110

Tyr Glu Tyr Ser Gly Asn Met Thr Cys Thr Trp Asn Ala Gly Lys Leu
        115                 120                 125

Thr Tyr Ile Asp Thr Lys Tyr Val Val His Val Lys Ser Leu Glu Thr
    130                 135                 140

Glu Glu Glu Gln Gln Tyr Leu Thr Ser Ser Tyr Ile Asn Ile Ser Thr
145                 150                 155                 160

Asp Ser Leu Gln Gly Gly Lys Lys Tyr Leu Val Trp Val Gln Ala Ala
                165                 170                 175

Asn Ala Leu Gly Met Glu Glu Ser Lys Gln Leu Gln Ile His Leu Asp
            180                 185                 190

Asp Ile Val Ile Pro Ser Ala Ala Val Ile Ser Arg Ala Glu Thr Ile
        195                 200                 205

Asn Ala Thr Val Pro Lys Thr Ile Ile Tyr Trp Asp Ser Gln Thr Thr
    210                 215                 220

Ile Glu Lys Val Ser Cys Glu Met Arg Tyr Lys Ala Thr Thr Asn Gln
225                 230                 235                 240

Thr Trp Asn Val Lys Glu Phe Asp Thr Asn Phe Thr Tyr Val Gln Gln
                245                 250                 255

Ser Glu Phe Tyr Leu Glu Pro Asn Ile Lys Tyr Val Phe Gln Val Arg
            260                 265                 270

Cys Gln Glu Thr Gly Lys Arg Tyr Trp Gln Pro Trp Ser Ser Leu Phe
        275                 280                 285

Phe His Lys Thr Pro Glu Thr Val Pro Gln Val Thr Ser Lys Ala Phe
    290                 295                 300

Gln His Asp Thr Trp Asn Ser Gly Leu Thr Val Ala Ser Ile Ser Thr
305                 310                 315                 320

Gly His Leu Thr Ser Asp Asn Arg Gly Asp Ile Gly
                325                 330


<210> SEQ ID NO 328
<211> LENGTH: 644
<212> TYPE: PRT
<213> ORGANISM: Mus musculus

<400> SEQUENCE: 328

Met Ser His Leu Thr Leu Gln Leu His Val Val Ile Ala Leu Tyr Val
1               5                   10                  15

Leu Phe Arg Trp Cys His Gly Gly Ile Thr Ser Ile Asn Cys Ser Gly
            20                  25                  30

Asp Met Trp Val Glu Pro Gly Glu Ile Phe Gln Met Gly Met Asn Val
        35                  40                  45

Ser Ile Tyr Cys Gln Glu Ala Leu Lys His Cys Arg Pro Arg Asn Leu
    50                  55                  60

Tyr Phe Tyr Lys Asn Gly Phe Lys Glu Glu Phe Asp Ile Thr Arg Ile
65                  70                  75                  80

Asn Arg Thr Thr Ala Arg Ile Trp Tyr Lys Gly Phe Ser Glu Pro His
                85                  90                  95

Ala Tyr Met His Cys Thr Ala Glu Cys Pro Gly His Phe Gln Glu Thr
```

```
            100                 105                 110

Leu Ile Cys Gly Lys Asp Ile Ser Ser Gly His Pro Pro Asp Ala Pro
        115                 120                 125

Ser Asn Leu Thr Cys Val Ile Tyr Glu Tyr Ser Gly Asn Met Thr Cys
    130                 135                 140

Thr Trp Asn Thr Gly Lys Pro Thr Tyr Ile Asp Thr Lys Tyr Ile Val
145                 150                 155                 160

His Val Lys Ser Leu Glu Thr Glu Glu Glu Gln Gln Tyr Leu Ala Ser
                165                 170                 175

Ser Tyr Val Lys Ile Ser Thr Asp Ser Leu Gln Gly Ser Arg Lys Tyr
            180                 185                 190

Leu Val Trp Val Gln Ala Val Asn Ser Leu Gly Met Glu Asn Ser Gln
        195                 200                 205

Gln Leu His Val His Leu Asp Asp Ile Val Ile Pro Ser Ala Ser Ile
    210                 215                 220

Ile Ser Arg Ala Glu Thr Thr Asn Asp Thr Val Pro Lys Thr Ile Val
225                 230                 235                 240

Tyr Trp Lys Ser Lys Thr Met Ile Glu Lys Val Phe Cys Glu Met Arg
                245                 250                 255

Tyr Lys Thr Thr Thr Asn Gln Thr Trp Ser Val Lys Glu Phe Asp Ala
            260                 265                 270

Asn Phe Thr Tyr Val Gln Gln Ser Glu Phe Tyr Leu Glu Pro Asp Ser
        275                 280                 285

Lys Tyr Val Phe Gln Val Arg Cys Gln Glu Thr Gly Lys Arg Asn Trp
    290                 295                 300

Gln Pro Trp Ser Ser Pro Phe Val His Gln Thr Ser Gln Glu Thr Gly
305                 310                 315                 320

Lys Arg Asn Trp Gln Pro Trp Ser Ser Pro Phe Val His Gln Thr Ser
                325                 330                 335

Gln Thr Val Ser Gln Val Thr Ala Lys Ser Ser His Glu Pro Gln Lys
            340                 345                 350

Met Glu Met Leu Ser Ala Thr Ile Phe Arg Gly His Pro Ala Ser Gly
        355                 360                 365

Asn His Gln Asp Ile Gly Leu Leu Ser Gly Met Val Phe Leu Ala Ile
    370                 375                 380

Met Leu Pro Ile Phe Ser Leu Ile Gly Ile Phe Asn Arg Ser Leu Arg
385                 390                 395                 400

Ile Gly Ile Lys Arg Lys Val Leu Leu Met Ile Pro Lys Trp Leu Tyr
                405                 410                 415

Glu Asp Ile Pro Asn Met Glu Asn Ser Asn Val Ala Lys Leu Leu Gln
            420                 425                 430

Glu Lys Ser Val Phe Glu Asn Asp Asn Ala Ser Glu Gln Ala Leu Tyr
        435                 440                 445

Val Asp Pro Val Leu Thr Glu Ile Ser Glu Ile Ser Pro Leu Glu His
    450                 455                 460

Lys Pro Thr Asp Tyr Lys Glu Glu Arg Leu Thr Gly Leu Leu Glu Thr
465                 470                 475                 480

Arg Asp Cys Pro Leu Gly Met Leu Ser Thr Ser Ser Ser Val Val Tyr
                485                 490                 495

Ile Pro Asp Leu Asn Thr Gly Tyr Lys Pro Gln Val Ser Asn Val Pro
            500                 505                 510

Pro Gly Gly Asn Leu Phe Ile Asn Arg Asp Glu Arg Asp Pro Thr Ser
        515                 520                 525
```

```
Leu Glu Thr Thr Asp Asp His Phe Ala Arg Leu Lys Thr Tyr Pro Asn
    530                 535                 540

Phe Gln Phe Ser Ala Ser Ser Met Ala Leu Leu Asn Lys Thr Leu Ile
545                 550                 555                 560

Leu Asp Glu Leu Cys Leu Val Leu Asn Gln Gly Glu Phe Asn Ser Leu
                565                 570                 575

Asp Ile Lys Asn Ser Arg Gln Glu Glu Thr Ser Ile Val Leu Gln Ser
            580                 585                 590

Asp Ser Pro Ser Glu Thr Ile Pro Ala Gln Thr Leu Leu Ser Asp Glu
        595                 600                 605

Phe Val Ser Cys Leu Ala Ile Gly Asn Glu Asp Leu Pro Ser Ile Asn
    610                 615                 620

Ser Tyr Phe Pro Gln Asn Val Leu Glu Ser His Phe Ser Arg Ile Ser
625                 630                 635                 640

Leu Phe Gln Lys


<210> SEQ ID NO 329
<211> LENGTH: 351
<212> TYPE: PRT
<213> ORGANISM: Mus musculus

<400> SEQUENCE: 329

Gly Ile Thr Ser Ile Asn Cys Ser Gly Asp Met Trp Val Glu Pro Gly
1               5                   10                  15

Glu Ile Phe Gln Met Gly Met Asn Val Ser Ile Tyr Cys Gln Glu Ala
            20                  25                  30

Leu Lys His Cys Arg Pro Arg Asn Leu Tyr Phe Tyr Lys Asn Gly Phe
        35                  40                  45

Lys Glu Glu Phe Asp Ile Thr Arg Ile Asn Arg Thr Thr Ala Arg Ile
    50                  55                  60

Trp Tyr Lys Gly Phe Ser Glu Pro His Ala Tyr Met His Cys Thr Ala
65                  70                  75                  80

Glu Cys Pro Gly His Phe Gln Glu Thr Leu Ile Cys Gly Lys Asp Ile
                85                  90                  95

Ser Ser Gly His Pro Pro Asp Ala Pro Ser Asn Leu Thr Cys Val Ile
            100                 105                 110

Tyr Glu Tyr Ser Gly Asn Met Thr Cys Thr Trp Asn Thr Gly Lys Pro
        115                 120                 125

Thr Tyr Ile Asp Thr Lys Tyr Ile Val His Val Lys Ser Leu Glu Thr
    130                 135                 140

Glu Glu Glu Gln Gln Tyr Leu Ala Ser Ser Tyr Val Lys Ile Ser Thr
145                 150                 155                 160

Asp Ser Leu Gln Gly Ser Arg Lys Tyr Leu Val Trp Val Gln Ala Val
                165                 170                 175

Asn Ser Leu Gly Met Glu Asn Ser Gln Gln Leu His Val His Leu Asp
            180                 185                 190

Asp Ile Val Ile Pro Ser Ala Ser Ile Ile Ser Arg Ala Glu Thr Thr
        195                 200                 205

Asn Asp Thr Val Pro Lys Thr Ile Val Tyr Trp Lys Ser Lys Thr Met
    210                 215                 220

Ile Glu Lys Val Phe Cys Glu Met Arg Tyr Lys Thr Thr Thr Asn Gln
225                 230                 235                 240

Thr Trp Ser Val Lys Glu Phe Asp Ala Asn Phe Thr Tyr Val Gln Gln
                245                 250                 255
```

```
Ser Glu Phe Tyr Leu Glu Pro Asp Ser Lys Tyr Val Phe Gln Val Arg
            260                 265                 270

Cys Gln Glu Thr Gly Lys Arg Asn Trp Gln Pro Trp Ser Ser Pro Phe
        275                 280                 285

Val His Gln Thr Ser Gln Glu Thr Gly Lys Arg Asn Trp Gln Pro Trp
    290                 295                 300

Ser Ser Pro Phe Val His Gln Thr Ser Gln Thr Val Ser Gln Val Thr
305                 310                 315                 320

Ala Lys Ser Ser His Glu Pro Gln Lys Met Glu Met Leu Ser Ala Thr
                325                 330                 335

Ile Phe Arg Gly His Pro Ala Ser Gly Asn His Gln Asp Ile Gly
            340                 345                 350


<210> SEQ ID NO 330
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 330

His His His His His His
1               5


<210> SEQ ID NO 331
<211> LENGTH: 8
<212> TYPE: PRT
<213> ORGANISM: Artificial Sequence
<220> FEATURE:
<223> OTHER INFORMATION: Description of Artificial Sequence: Synthetic
      8xHis tag

<400> SEQUENCE: 331

His His His His His His His His
1               5


<210> SEQ ID NO 332
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (1)..(40)
<223> OTHER INFORMATION: This sequence may encompass 1-10
      "Gly Gly Gly Ser" repeating units

<400> SEQUENCE: 332

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly Gly Ser
            20                  25                  30

Gly Gly Gly Ser Gly Gly Gly Ser
        35                  40


<210> SEQ ID NO 333
<211> LENGTH: 50
<212> TYPE: PRT
<213> ORGANISM: Artificial Sequence
<220> FEATURE:
<223> OTHER INFORMATION: Description of Artificial Sequence: Synthetic
```

polypeptide
<220> FEATURE:
<221> NAME/KEY: SITE
<222> LOCATION: (1)..(50)
<223> OTHER INFORMATION: This sequence may encompass 1-10
"Gly Gly Gly Ser Gly" repeating units

<400> SEQUENCE: 333

Gly Gly Gly Ser Gly Gly Gly Gly Ser Gly Gly Gly Gly Ser Gly Gly
1 5 10 15

Gly Gly Ser Gly Gly Gly Gly Ser Gly Gly Gly Gly Ser Gly Gly Gly
20 25 30

Gly Ser Gly Gly Gly Gly Ser Gly Gly Gly Gly Ser Gly Gly Gly Gly
35 40 45

Ser Gly
50

<210> SEQ ID NO 334
<211> LENGTH: 40
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<221> NAME/KEY: SITE
<222> LOCATION: (1)..(40)
<223> OTHER INFORMATION: This sequence may encompass 1-10
"Gly Gly Ser Gly" repeating units

<400> SEQUENCE: 334

Gly Gly Ser Gly Gly Gly Ser Gly Gly Gly Ser Gly Gly Gly Ser Gly
1 5 10 15

Gly Gly Ser Gly Gly Gly Ser Gly Gly Gly Ser Gly Gly Gly Ser Gly
20 25 30

Gly Gly Ser Gly Gly Gly Ser Gly
35 40

<210> SEQ ID NO 335
<211> LENGTH: 6
<212> TYPE: PRT
<213> ORGANISM: Artificial Sequence
<220> FEATURE:
<223> OTHER INFORMATION: Description of Artificial Sequence: Synthetic
His tag
<220> FEATURE:
<221> NAME/KEY: SITE
<222> LOCATION: (1)..(6)
<223> OTHER INFORMATION: This sequence may encompass 3-6 residues

<400> SEQUENCE: 335

His His His His His His
1 5

IL23R BINDING MOLECULES AND METHODS OF USE

CROSS-REFERENCES TO RELATED APPLICATIONS

This application is a national stage application under 35 U.S.C. 371 of PCT/US2021/044835, filed Aug. 5, 2021, which claims priority to U.S. Provisional Application No. 63/061,562, filed Aug. 5, 2020, U.S. Provisional Application No. 63/078,745, filed Sep. 15, 2020, and U.S. Provisional Application No. 63/135,884, filed Jan. 11, 2021, the disclosures of which are hereby incorporated by reference in their entirety for all purposes.

SEQUENCE LISTING

The instant application contains a Sequence Listing which has been submitted electronically in ASCII format and is hereby incorporated by reference in its entirety. Said ASCII copy, created on Jan. 18, 2023, is named 1361752-SL.txt and is 186,876 bytes in size.

FIELD OF THE INVENTION

The present disclosure relates to biologically active molecules comprising a single domain antibody that specifically binds to the extracellular domain of the IL23R, compositions comprising such single domain antibodies, and methods of use thereof.

BACKGROUND

IL23 is a heterodimeric cytokine comprise of the p19 and p40 subunits produced by dendritic cells, macrophages and neutrophils. IL23 binds to the IL23 receptor, a heterodimeric complex of IL12 receptor subunit beta-1 (IL12Rβ1 or IL12RB1) and IL23R receptor subunit. IL23 binds IL23R with an affinity of 44 nM but binds to IL12Rβ1 with a significantly lower affinity of 2 μM. There is no apparent direct binding of IL23R to IL12Rβ1, the completion of the IL23:IL23R:IL12Rβ1 complex mediated by the initial formation of the IL23:IL23R complex which in turn binds to IL12Rβ1. The IL23R binds primarily to the p19 subunit of the IL23 cytokine while the p40 subunit binds primarily to IL12Rβ1.

In addition to forming one of the components of the IL12 receptor, IL12Rβ1 is also a component of the IL23 receptor. IL12Rβ1 (also known as CD212) is a constitutively expressed type I transmembrane protein that belongs to the hemopoietin receptor superfamily. IL12Rβ1 binds with low affinity to IL23. IL12Rβ1 is required for high-affinity binding to the IL12p40 subunit and it is associated with the Janus kinase (Jak) family member Tyk-2. The binding IL12p40 and IL12p35 to IL12Rβ1 and IL12Rβ2, respectively results in the activation of the Tyk-2 and Jak-2 Janus kinases, induces STAT4 phosphorylation which in turn regulates IFNgmama gene transcription. The p40 subunit of the IL23 and IL12 cytokines provides the majority of binding sites for IL12Rβ1.

An antibody against p40, which blocks both IL23 and IL12 demonstrated activity in clinical trials of Crohn's disease. Selective blockade of the IL23R receptor activity by molecules that selectively bind to IL23R inhibit the by IL23p19/IL23R may provide more limited organ specific targeting o inflammatory disease without more widespread effects associate with inhibition of the p40/IL12 pathway. Additionally it has been shown that anti-IL23R, but not anti-IL23p19, partially suppressed lung metastases in tumor-bearing mice neutralized for IL12p40. Additionally it has been shown that IL23R has tumor-promoting effects that are partially independent of IL23p19. Consequently, the blockade of IL23R activity by molecules that selectively bind to IL23R is potentially effective in the suppression of tumor metastases. Yan, et al (2018) *Cancer Immunol Res* 6(8); 978-87.

Although monoclonal antibodies are the most widely used reagents for the detection and quantification of proteins, monoclonal antibodies are large molecules of about 150 kDa and it sometimes limits their use in assays with several reagents competing for close epitopes recognition. A unique class of immunoglobulin containing a heavy chain domain and lacking a light chain domain (commonly referred to as heavy chain" antibodies (HCAbs) is present in camelids, including dromedary camels, Bactrian camels, wild Bactrian camels, llamas, alpacas, vicuñas, and guanacos as well as cartilaginous fishes such as sharks. The isolated variable domain region of HCAbs is known as a VHH (an abbreviation for "variable-heavy-heavy" reflecting their architecture) or Nanobody® (Ablynx). Single domain VHH antibodies possesses the advantage of small size (~12-14 kD), approximately one-tenth the molecular weight a conventional mammalian IgG class antibody) which facilitates the binding of these VHH molecules to antigenic determinants of the target which may be inaccessible to a conventional monoclonal IgG format (Ingram et al., 2018). Furthermore, VHH single domain antibodies are frequently characterized by high thermal stability facilitating pharmaceutical distribution to geographic areas where maintenance of the cold chain is difficult or impossible. These properties, particularly in combination with simple phage display discovery methods that do not require heavy/light chain pairing (as is the case with IgG antibodies) and simple manufacture (e.g., in bacterial expression systems) make VHH single domain antibodies useful in a variety of applications including the development of imaging and therapeutic agents.

SUMMARY OF THE INVENTION

The present disclosure provides polypeptides that specifically bind to the extracellular domain of IL23R.

The present disclosure provides a IL23R binding molecule that specifically bind to the extracellular domain of IL23R (e.g., human IL23R).

In some embodiments, the IL23R binding molecule comprises a single domain antibody (sdAb) that specifically binds to the extracellular domain of the human IL23R.

In some embodiments, the IL23R binding molecule is a sdAb, the sdAb comprising a set of CDRs corresponding to CDR1, CDR2, and CDR3 as shown in a row of Table 1 below.

In some embodiments, the IL23R binding molecule comprises a CDR1, a CDR2, and a CDR3 as described in a row of Table 1A below, in which the CDR1, CDR2, and CDR3 can each, independently, comprise at least 90% (e.g., 91%, 92%, 93%, 94%, 95%, 96%, 97%, 98%, 99%, or 100%) sequence identity, or have 0, 1, 2, or 3 amino acid changes, optionally conservative amino acid changes, relative to the sequence described in a row of Table 1 below.

In some embodiments, the IL23R binding molecule consists of, optionally consists essentially of, or optionally comprises a single domain antibody (sdAb) having at least 80%, alternatively at least 85%, alternatively at least 90%, alternatively at least 95%, alternatively at least 98%, alternatively at least 99% identity (or being identical except for 1, 2, 3, or 4 amino acids that optionally are conserved substitutions) or 100% identity to a polypeptide sequence of any one of SEQ ID NOS:2-20, as shown in Table 1 below.

TABLE 1 hIL23R ECD Generated VHHs and CDRs

| Name | VHH Amino Acid Sequence (CDRs underlined | CDR1 | CDR2 | CDR3 |
|---|---|---|---|---|
| hIL23R VHH1 | QVQLQESGGGSVQAGGSLRLSCAASGYTYCSYDMSWYRQAPGKKREFVSAFNSDGTTSYADSVKGRFTISQDKAKNTVYLQMNSLKPEDTAMYYCKTDPHVQSSGGYCPPYWGQGTQVTVSS (SEQ ID NO: 2) | YTYCSYDMS (SEQ ID NO: 21) | AFNSDGTTSYADSVKG (SEQ ID NO: 22) | DPHVQSSGGYCPPY (SEQ ID NO: 23) |
| hIL23R VHH2 | QVQLQESGGGSVQAGGSLRLSCAASGYTYCSYDMSWYRQAPGKKREFVSSFNSDGSTSYADSVKGRFTISQDNAKNTVYLQMNSLKPEDTAMYYCKTDPHADWGAPCGGDYWGQGTQVTVSS (SEQ ID NO: 3) | YTYCSYDMS (SEQ ID NO: 24) | SFNSDGSTSYADSVKG (SEQ ID NO: 25) | DPHADWGAPCGGDY (SEQ ID NO: 26) |
| hIL23R VHH3 | QVQLQESGGGSVQAGESLRLSCAASGYTYCTYDMTWYRQAPGKKREFVSGIHSDGTTSYADSVKGRFTISQDNAENTVYLQMNSLKPEDTAMYYCKTDPIATITRRCDSYWGQGTQVTVSS (SEQ ID NO: 4) | YTYCTYDMT (SEQ ID NO: 27) | GIHSDGTTSYADSVKG (SEQ ID NO: 28) | DPIATITRRCDSY (SEQ ID NO: 29) |
| hIL23R VHH4 | QVQLQESGGGSVQAGGSLRLSCAASGSTYCTYDMTWYRQAPGKRREFVSAINSDGSTSYADSVKGRFTISQDNAKNTVYLQMNSLKPEDTAMYYCKTDPNSGWGAPCGGDYWGQGTQVTVSS (SEQ ID NO: 5) | STYCTYDMT (SEQ ID NO: 30) | AINSDGSTSYADSVKG (SEQ ID NO: 31) | DPNSGWGAPCGGDY (SEQ ID NO: 32) |
| hIL23R VHH5 | QVQLQESGGGSVQAGGSLRLSCAASGYTYCSYDMSWYRQAPGKKREFVSAIASDGSTSYADSLKGRFTISQDNAKNTVYLQMNSLKPEDTAMYYCKTDPHVQSSGGYCPPYWGQGTQVTVSS (SEQ ID NO: 6) | YTYCSYDMS (SEQ ID NO: 33) | AIASDGSTSYADSLKG (SEQ ID NO: 34) | DPHVQSSGGYCPPY (SEQ ID NO: 35) |
| hIL23R VHH6 | QVQLQESGGGLVQPGGSLRLSCAASGYTYCSYDMGWYRQAPGKKRKFVSSINSDGTTSYADSVKGRFTISQDNAKNTVYLQMNSLKPEDTAMYYCKTDPQTRPGKPCADYWGQGTQVTVSS (SEQ ID NO: 7) | YTYCSYDMG (SEQ ID NO: 36) | SINSDGTTSYADSVKG (SEQ ID NO: 37) | DPQTRPGKPCADY (SEQ ID NO: 38) |
| hIL23R VHH7 | QVQLQESGGGSVQAGGSLRLSCAASGYTYCNYDIAWYRQAPGKERKFVSAIASDGITSYADSVKGRFTISQDNAKNTVYLQMNSLKPEDTAMYYCKTDPISTITRICDPYWGQGTQVTVSS (SEQ ID NO: 8) | YTYCNYDIA (SEQ ID NO: 39) | AIASDGITSYADSVKG (SEQ ID NO: 40) | DPISTITRICDPY (SEQ ID NO: 41) |
| hIL23R VHH8 | QVQLQESGGDSVQAGGSLRLSCAASGYTYCSYDMKWYRQAPGKEREFVSGIDSDGSISYADSVKGRFTISQDNAKNTVYLQMNSLKPEDTAMYYCKTEGTIPVGACPNYWGQGTQVTVSS (SEQ ID NO: 9) | YTYCSYDMK (SEQ ID NO: 42) | GIDSDGSISYADSVKG (SEQ ID NO: 43) | EGTIPVGACPNY (SEQ ID NO: 44) |
| hIL23R VHH9 | QVQLQESGGGLVQAGGSLRLSCAASGYTYCSYDMSWYRQAPGKERKFVSSINSDGTTSYADSVKGRFTISQDNAKNTVYLQMNSLKPEDTAMYYCKTDPQTRPGKPCADYWGQGTQVTVSS (SEQ ID NO: 10) | YTYCSYDMS (SEQ ID NO: 45) | SINSDGTTSYADSVKG (SEQ ID NO: 46) | DPQTRPGKPCADY (SEQ ID NO: 47) |

TABLE 1-continued

| hIL23R ECD Generated VHHs and CDRs | | | | |
|---|---|---|---|---|
| Name | VHH Amino Acid Sequence (CDRs underlined | CDR1 | CDR2 | CDR3 |
| hIL23R VHH10 | QVQLQESGGGSVQAGGSLKLSCAASGYTYCNYDIAWYRQAPGKERKFVSAIASDGSTSYADSVKGRFTISQDNAKNTVYLQMNSLKPEDTAMYYCKTDPIATMTRRCDPYWGQGTQVTVSS (SEQ ID NO: 11) | YTYCNYDIA (SEQ ID NO: 48) | AIASDGSTSYADSVKG (SEQ ID NO: 49) | DPIATMTRRCDPY (SEQ ID NO: 50) |
| hIL23R VHH11 | QVQLQESGGGSVQAGGSLRLSCAASGYTYCSYDMTWYRQAPGKKREFVSAIDSDGSTSYADSVKGRFTISQDNAKNTVYLQMNSLKPEDTAMYYCKTDPIATISRRCDSYWGQGTQVTVSS (SEQ ID NO: 12) | YTYCSYDMT (SEQ ID NO: 51) | AIDSDGSTSYADSVKG (SEQ ID NO: 52) | DPIATISRRCDSY (SEQ ID NO: 53) |
| hIL23R VHH12 | QVQLQESGGGSVQAGGSLRLSCAASGYTSSSRCMGWFRQAPGKEREGVARIYTPTRTTWYADSVKGRFTISQDNAKNTVYLEMASLKPEDTAKYFCAAGASCAVDLFSYWGQGTQVTVSS (SEQ ID NO: 13) | YTSSSRCMG (SEQ ID NO: 54) | RIYTPTRTTWYADSVKG (SEQ ID NO: 55) | GASCAVDLFSY (SEQ ID NO: 56) |
| hIL23R VHH13 | QVQLQESGGGSVQAGGSLRLSCAASGYTYCSYDMKWYRQAPGKKREFVSAIDSDGSTSYADSVKGRFTISQDNAKNTVYLQMNSLKPEDTAMYYCKTEGTIPVGVCPNYWGQGTQVTVSS (SEQ ID NO: 14) | YTYCSYDMK (SEQ ID NO: 57) | AIDSDGSTSYADSVKG (SEQ ID NO: 58) | EGTIPVGVCPNY (SEQ ID NO: 59) |
| hIL23R VHH14 | QVQLQESGGGLVQPGGSLRLSCAASGYTYCSYDMKWYRQAPGKKREFVSAIDSDGSTSYADSVKGRFTISQDNAKNTVYLQMNSLKPEDTAMYYCKTEGTVPVGVCPNYWGQGTQVTVSS (SEQ ID NO: 15) | YTYCSYDMK (SEQ ID NO: 60) | AIDSDGSTSYADSVKG (SEQ ID NO: 61) | EGTVPVGVCPNY (SEQ ID NO: 62) |
| hIL23R VHH15 | QVQLQESGGGSVQAGGSLRLSCAASPGTYTSRYMGWFRQAPGKEREGVATIWPAGGNTVYADSVKGRFTISQDGAKKTVYLQMNSLKPEDTAMYYCAAAKYGGTSLAPYTYNYWGQGTQVTVSS (SEQ ID NO: 16) | GTYTSRYMG (SEQ ID NO: 63) | TIWPAGGNTVYADSVKG (SEQ ID NO: 64) | AKYGGTSLAPYTYNY (SEQ ID NO: 65) |
| hIL23R VHH16 | QVQLQESGGGSVEAGGALTLSCVASGYTYCNYDIAWYRQAPGKERKFVSAIASDGSTSYADSVKGRFTISQDNAKNTVYLQMNSLKPEDTAMYYCKTDPIATMTRRCDPYWGQGTQVTVSS (SEQ ID NO: 17) | YTYCNYDIA (SEQ ID NO: 66) | AIASDGSTSYADSVKG (SEQ ID NO: 67) | DPIATMTRRCDPY (SEQ ID NO: 68) |
| hIL23R VHH17 | QVQLQESGGGSVQAGGSLRLSCTASGYTFSTMKYMGWFRQAPGKEREGVAAIWIAAGNTYYADSVKGRFTISQDNTKNTVYLQMNSLKPEDTALYYCAAARYGFVPSTWYLPERYNYWGQGTQVTVSS (SEQ ID NO: 18) | YTFSTMKYMG (SEQ ID NO: 69) | AIWIAAGNTYYADSVKG (SEQ ID NO: 70) | ARYGFVPSTWYLPERYNY (SEQ ID NO: 71) |
| hIL23R VHH18 | QVQLQESGGGSVQAGGSLRLACAASGYTYCNYDIAWYRQAPGKERKFVSAIASDGSTSYADSVKGRFTISQDNAKNTVYLQMNSLKPEDTAMYYCKTDPIATMTRRCDPYWGQGTQVTVSS (SEQ ID NO: 19) | YTYCNYDIA (SEQ ID NO: 72) | AIASDGSTSYADSVKG (SEQ ID NO: 73) | DPIATMTRRCDPY (SEQ ID NO: 74) |

TABLE 1-continued

| hIL23R ECD Generated VHHs and CDRs | | | | |
|---|---|---|---|---|
| Name | VHH Amino Acid Sequence (CDRs underlined | CDR1 | CDR2 | CDR3 |
| hIL23R VHH19 | QVQLQESGGGSVQAGGSLRLS CAASGYTSCSYDMSWYRQAP GKKREFVSAIHSDGTTSYADS MKGRFTISQDNAKNTVYLQMN SLKPEDTAMYYCKTDPNYSDH VCPPYWGRGTQVTVSS (SEQ ID NO: 20) | YTSCSYDMS (SEQ ID NO: 75) | AIHSDGTTSYA DSMKG (SEQ ID NO: 76) | DPNYSDHVCP PY (SEQ ID NO: 77) |

In some embodiments, the foregoing sets of CDRs are incorporated in a humanized VHH framework to provide "humanized" sdAb IL23R binding molecules.

The disclosure further provides methods of chemical or recombinant processes for the preparation of the IL23R binding molecules of the present disclosure.

The disclosure further provides nucleic acids encoding the IL23R binding molecules. Table 2 below provides examples of DNA sequences encoding IL23R binding molecules as described herein.

TABLE 2

| DNA Sequences Encoding VHHs of Table 1 | |
|---|---|
| Name | DNA Sequence |
| hIL23R VHH1 | CAGGTTCAGCTGCAAGAGAGCGGGGGTGGGTCTGTGCAGGCTGGTGGCAGC TTGCGCCTTAGTTGCGCGGCTTCTGGTTATACTTATTGTTCCTACGATATGTC ATGGTATCGTCAGGCTCCTGGCAAGAAACGGGAGTTCGTCTCTGCCTTCAAC TCCGATGGCACCACTAGCTATGCAGATTCTGTGAAAGGCAGATTCACCATCT CTCAGGACAAGGCCAAGAATACCGTGTACCTCCAGATGAACAGCCTGAAGC CAGAGGATACCGCTATGTACTATTGCAAGACAGATCCTCACGTGCAATCCTC TGGTGGCTACTGTCCGCCCTACTGGGGCCAGGGCACACAGGTAACGGTTAG TTCC (SEQ ID NO: 78) |
| hIL23R VHH2 | CAGGTGCAGCTCCAGGAATCTGGCGGAGGTTCCGTGCAGGCCGGTGGCAGC CTGAGGCTCAGCTGCGCCGCGTCCGGGTATACCTACTGTTCCTACGATATGT CCTGGTATCGGCAGGCTCCGGGTAAAAAGAGAGAGTTTGTGTCCAGCTTTA ACAGCGACGGCAGTACATCTTACGCTGACTCCGTGAAGGGTCGCTTCACCA TTAGCCAGGATAACGCAAAAAACACAGTGTACCTTCAGATGAACAGTCTGA AGCCAGAGGACACCGCCATGTATTACTGCAAGACGGACCCGCACGCTGATT GGGGTGCCCCTTGCGGGGGCGATTATTGGGGCCAAGGCACCCAGGTGACTG TTTCTTCC (SEQ ID NO: 79) |
| hIL23R VHH3 | CAGGTGCAGCTCCAGGAATCTGGGGGCGGTTCTGTGCAAGCGGGCGAGAGC CTGAGACTGAGCTGCGCCGCGAGCGGCTACACCTACTGTACCTATGACATG ACTTGGTACAGACAGGCCCCCGGAAAAAAGCGCGAGTTCGTCAGCGGTATC CATAGCGACGGTACTACCTCTTACGCAGATTCCGTGAAAGGCCGCTTCACA ATTTCTCAGGACAATGCCGAAAACACCGTGTACCTCCAGATGAACTCCCTG AAGCCAGAGGATACCGCGATGTATTACTGCAAGACAGACCCCATCGCCACC ATCACCCGCCGGTGCGACTCATACTGGGGGCAGGGCACTCAGGTCACAGTC TCATCT (SEQ ID NO: 80) |
| hIL23R VHH4 | CAGGTGCAACTTCAGGAATCAGGAGGCGGTAGTGTGCAAGCGGGCGGAAG TCTGCGCCTGAGCTGCGCTGCCTCCGGGAGCACGTATTGTACGTATGATATG ACGTGGTACAGGCAGGCCCCTGGCAAGCGCAGGGAGTTCGTGAGTGCAATC AACTCAGATGGCAGCACCTCTTATGCTGACAGCGTGAAAGGGAGATTCACT ATCTCCCAGGACAACGCAAAAAACACCGTCTATCTCCAGATGAACTCTCTG AAGCCCGAAGACACCGCGATGTATTACTGTAAGACTGATCCTAACAGCGGA TGGGGCGCTCCTTGCGGTGGCGATTATTGGGGACAGGGCACCCAAGTGACA GTTAGCAGC (SEQ ID NO: 81) |

TABLE 2-continued

| DNA Sequences Encoding VHHs of Table 1 | |
|---|---|
| Name | DNA Sequence |
| hIL23R VHH5 | CAGGTGCAGCTTCAGGAAAGCGGTGGGGGCTCCGTCCAGGCAGGCGGTTCC CTTCGCCTTTCTTGTGCCGCTTCTGGTTATACTTACTGTTCATACGATATGTC TTGGTATCGCCAGGCTCCCGGCAAAAAGCGTGAGTTCGTCTCTGCCATCGCC TCCGATGGCTCAACGTCCTACGCGGACAGTCTCAAGGGTCGCTTCACCATTT CCCAGGATAATGCAAAGAACACCGTGTATCTCCAGATGAACTCACTGAAGC CCGAAGACACAGCCATGTACTATTGCAAGACTGACCCACACGTACAGTCTT CCGGCGGATACTGCCCACCTTACTGGGGACAGGGAACCCAGGTGACAGTGA GTTCT (SEQ ID NO: 82) |
| hIL23R VHH6 | CAGGTGCAGCTTCAGGAAAGTGGCGGGGGTCTGGTGCAGCCGGGCGGGTCC CTCCGGCTGTCCTGTGCTGCCAGCGGCTACACCTATTGCAGCTATGATATGG GCTGGTATCGCCAGGCCCCTGGAAAAAAGAGAAAGTTTGTGTCCAGCATTA ACAGCGATGGGACCACTTCTTACGCTGACAGTGTTAAAGGGCGTTTCACGA TCTCCCAGGACAACGCTAAAAACACCGTGTATCTCCAGATGAATAGCCTGA AGCCCGAGGACACCGCAATGTATTACTGTAAAACTGACCCCCAGACACGTC CCGGTAAGCCATGTGCTGATTATTGGGGCCAGGGGACCCAGGTGACCGTCA GCTCC (SEQ ID NO: 83) |
| hIL23R VHH7 | CAGGTGCAGCTCCAGGAGTCCGGTGGCGGGTCTGTCCAAGCTGGCGGTTCC CTTCGCCTGTCCTGTGCAGCCAGTGGATATACGTATTGCAACTACGACATCG CCTGGTATAGACAGGCCCCTGGCAAAGAGCGCAAGTTCGTATCCGCAATCG CCAGTGACGGTATCACCTCTTATGCTGACTCTGTGAAGGGTCGGTTCACTAT CTCCCAGGATAACGCTAAGAACACAGTCTACCTCCAGATGAACAGCTTGAA GCCGGAGGACACTGCGATGTACTATTGCAAGACTGATCCGATTTCCACCATC ACAAGGATCTGCGACCCGTACTGGGGCCAGGGCACCCAAGTGACTGTGTCA TCA (SEQ ID NO: 84) |
| hIL23R VHH8 | CAAGTGCAGTTGCAGGAGAGCGGTGGCGATTCTGTGCAGGCCGGAGGCTCC CTCCGCCTGTCCTGTGCCGCTTCAGGCTACACGTATTGTTCTTATGATATGA AGTGGTATCGCCAGGCCCCAGGTAAGGAACGCGAGTTCGTCAGCGGTATTG ATTCCGACGGCAGTATTAGCTACGCCGACTCCGTGAAAGGCCGCTTCACAA TTAGCCAGGACAACGCGAAAAACACCGTGTACCTCCAGATGAACTCTCTGA AGCCAGAGGATACCGCCATGTACTATTGCAAGACTGAGGGCACTATCCCCG TAGGTGCATGTCCTAACTACTGGGGCCAGGGCACTCAGGTAACCGTCAGTA GC (SEQ ID NO: 85) |
| hIL23R VHH9 | CAAGTCCAGCTCCAGGAGAGCGGCGGTGGCTTGGTGCAGGCCGGTGGCTCC CTGAGACTGAGCTGTGCAGCCTCCGGGTATACATATTGCAGCTACGACATG AGTTGGTATCGCCAGGCACCGGGCAAGGAGAGAAAGTTTGTGTCCTCTATC AATTCAGATGGCACAACCTCCTACGCCGACTCAGTCAAGGGTCGTTTCACTA TTTCTCAGGACAACGCTAAGAACACCGTGTACCTCCAGATGAACAGCCTGA AGCCTGAGGATACGGCCATGTACTATTGCAAAACTGACCCCCAGACTAGAC CTGGCAAGCCGTGCGCGGACTATTGGGGTCAGGGCACGCAAGTCACCGTGT CCTCA (SEQ ID NO: 86) |
| hIL23R VHH10 | CAGGTGCAGTTGCAGGAGAGCGGCGGAGGGTCTGTGCAGGCTGGAGGTAG CCTGAAGCTGTCCTGTGCTGCCAGCGGCTACACCTACTGTAACTACGATATC GCGTGGTATCGGCAAGCGCCCGGCAAAGAGCGTAAGTTCGTGTCCGCTATC GCCTCCGATGGCTCTACTTCCTATGCCGACAGCGTTAAAGGTCGCTTCACCA TCTCCCAAGACAACGCCAAAAATACAGTGTATCTTCAGATGAACTCTCTGA AACCCGAGGATACTGCGATGTATTACTGCAAGACTGATCCAATCGCTACCA TGACCAGGCGCTGCGACCCTTACTGGGGCCAGGGCACCCAGGTGACGGTAT CCTCA (SEQ ID NO: 87) |
| hIL23R VHH11 | CAAGTCCAGCTTCAGGAGTCTGGTGGGGGCTCTGTCCAGGCCGGGGGCTCT CTGAGACTGTCTTGTGCAGCCTCCGGGTACACCTACTGTTCCTATGACATGA CTTGGTATCGTCAAGCACCTGGCAAAAAGCGTGAGTTCGTGTCTGCCATCGA CTCCGACGGCTCTACCTCCTACGCCGACTCTGTGAAAGGTAGGTTCACAATC TCCCAGGATAACGCAAAGAATACTGTGTACTTGCAGATGAACTCCTTGAAG CCCGAGGATACTGCCATGTACTATTGCAAGACAGACCCTATTGCTACTATCT CTCGTAGGTGTGATAGTTACTGGGGACAAGGCACCCAGGTTACCGTATCCA GT (SEQ ID NO: 88) |

TABLE 2-continued

| DNA Sequences Encoding VHHs of Table 1 | |
|---|---|
| Name | DNA Sequence |
| hIL23R VHH12 | CAGGTGCAGCTCCAAGAATCTGGTGGAGGGTCAGTGCAGGCCGGAGGCAGC CTGCGCCTGTCTTGCGCTGCAAGCGGTTACACCAGCTCCTCTCGCTGTATGG GATGGTTCCGGCAAGCTCCGGGCAAGGAAAGGGAAGGAGTCGCTCGTATCT ACACCCCAACCAGAACTACGTGGTACGCCGATAGCGTCAAGGGGCGCTTCA CCATCAGCCAGGATAACGCCAAGAATACCGTGTACCTGGAGATGGCCAGCC TCAAGCCAGAGGACACGGCGAAGTATTTTTGCGCTGCCGGGGCGTCCTGCG CCGTGGATTTGTTCTCTTACTGGGGTCAGGGCACTCAGGTCACCGTGTCAAG C (SEQ ID NO: 89) |
| hIL23R VHH13 | CAGGTTCAGCTCCAGGAGTCCGGCGGTGGCTCTGTGCAGGCCGGTGGCTCC CTGAGACTGTCCTGCGCGGCTTCAGGATACACGTACTGCTCCTATGATATGA AGTGGTATCGTCAGGCTCCAGGCAAAAAGAGGGAGTTCGTGAGCGCGATTG ATTCCGATGGGAGTACCTCCTACGCGGACTCTGTGAAGGGACGCTTTACTAT TTCCCAGGACAACGCGAAGAATACGGTCTACCTGCAAATGAACTCCCTCAA GCCGGAGGATACCGCTATGTATTACTGTAAAACCGAGGGAACAATTCCTGT CGGCGTCTGCCCTAATTATTGGGGGCAGGGCACACAAGTGACTGTCTCCTCC (SEQ ID NO: 90) |
| hIL23R VHH14 | CAAGTCCAGCTGCAAGAGTCTGGTGGGGGCCTGGTGCAACCAGGGGGCAGC TTGAGACTCTCCTGCGCTGCCAGCGGGTATACATACTGTAGCTATGATATGA AGTGGTACAGGCAAGCCCCTGGCAAAAAGCGCGAGTTCGTGTCCGCCATCG ACTCCGACGGTTCCACTAGCTACGCGGATTCCGTGAAGGGAAGGTTCACTA TTTCTCAGGATAACGCCAAGAACACCGTCTACCTCCAGATGAACTCCCTGAA GCCAGAGGACACCGCCATGTACTATTGTAAGACCGAGGGCACAGTGCCTGT GGGCGTCTGTCCAAATTATTGGGGTCAAGGCACCCAGGTCACAGTATCCTCT (SEQ ID NO: 91) |
| hIL23R VHH15 | CAAGTGCAGCTGCAAGAGAGCGGTGGCGGGTCCGTGCAAGCAGGTGGCTCC TTGCGCCTGTCCTGCGCTGCCAGCCCCGGCACCTACACATCCCGTTATATGG GATGGTTTCGCCAGGCACCTGGAAAGGAACGCGAGGGGGTTGCGACTATCT GGCCCGCTGGCGGTAACACCGTTTACGCCGATAGCGTGAAAGGGCGCTTCA CCATTAGTCAAGACGGGGCCAAAAAGACCGTGTACCTCCAGATGAACTCCC TGAAACCTGAAGACACTGCTATGTACTATTGTGCCGCAGCTAAGTACGGCG GGACTAGCCTGGCTCCTTACACATATAACTACTGGGGCCAAGGCACCCAGG TGACAGTCTCTTCT (SEQ ID NO: 92) |
| hIL23R VHH16 | CAGGTCCAACTCCAGGAATCCGGTGGGGGCAGCGTCGAGGCCGGGGGCGC ACTCACCCTCTCCTGCGTCGCAAGCGGCTATACGTACTGTAACTACGACATT GCTTGGTATCGCCAGGCCCCAGGCAAGGAGCGCAAGTTCGTTTCCGCCATC GCCTCTGATGGAAGCACAAGTTACGCAGATTCCGTGAAAGGCCGGTTCACA ATCTCACAGGACAACGCTAAGAACACCGTCTACTTGCAGATGAACAGTCTG AAGCCCGAAGACACCGCCATGTATTACTGCAAGACCGATCCCATCGCCACT ATGACACGTCGCTGTGACCCCTACTGGGGCCAAGGCACTCAGGTGACCGTG AGTTCC (SEQ ID NO: 93) |
| hIL23R VHH17 | CAGGTACAGCTCCAAGAATCTGGCGGTGGCTCCGTGCAGGCCGGTGGCTCC TTGCGTCTGTCCTGCACCGCCAGTGGATATACTTTCTCCACCATGAAGTACA TGGGATGGTTCCGCCAGGCTCCGGGAAAGGAGAGGGAGGGCGTTGCGGCC ATTTGGATCGCCGCTGGCAACACTTATTACGCCGATTCCGTGAAAGGCCGCT TTACCATTTCCCAGGACAACACAAAGAACACCGTTTACCTCCAGATGAATA GCCTGAAGCCAGAGGATACCGCCCTCTACTATTGCGCGGCAGCCAGGTACG GCTTTGTCCCCAGCACTTGGTATCTCCCCGAGCGTTACAACTATTGGGGCCA GGGAACTCAGGTGACTGTCAGTTCC (SEQ ID NO: 94) |
| hIL23R VHH18 | CAGGTGCAGTTGCAGGAGTCCGGCGGTGGGTCTGTGCAGGCGGGCGGGAGC CTGCGCTTGGCCTGCGCCGCAAGCGGTTATACCTACTGCAATTACGACATCG CGTGGTATCGGCAGGCCCCCGGTAAGGAGCGTAAGTTCGTGTCCGCCATCG CGTCTGACGGAAGCACCTCTTATGCCGATAGCGTGAAAGGAAGATTTACAA TCTCCCAGGATAACGCCAAAAACACCGTCTATTTGCAGATGAATAGTCTGA AGCCAGAGGACACGGCTATGTATTACTGCAAGACCGATCCAATCGCTACCA TGACCAGGCGCTGCGACCCATATTGGGGCCAGGGCACGCAGGTCACCGTAT CCTCC (SEQ ID NO: 95) |

TABLE 2-continued

| DNA Sequences Encoding VHHs of Table 1 | |
|---|---|
| Name | DNA Sequence |
| hIL23R VHH19 | CAGGTCCAGTTGCAGGAAAGCGGCGGTGGATCAGTCCAGGCTGGTGGGAGT CTGCGTCTGAGCTGTGCTGCCAGCGGTTATACATCCTGCTCTTACGATATGT CTTGGTACAGACAGGCCCCTGGCAAGAAAAGAGAGTTCGTTTCCGCCATTC ATAGTGATGGCACAACCTCCTACGCCGACAGCATGAAGGGGAGGTTCACTA TCTCCCAGGATAATGCTAAGAATACCGTTTATCTCCAGATGAACTCACTGAA ACCGGAGGACACCGCAATGTACTATTGCAAGACGGACCCTAACTACTCAGA CCACGTGTGCCCGCCTTACTGGGGACGCGGTACTCAAGTGACTGTGTCAAG C (SEQ ID NO: 96) |

In some embodiments, the IL23R binding molecule comprises a single domain antibody (sdAb) that specifically binds to the extracellular domain of murine IL23R (mIL23R).

In some embodiments, the IL23R binding molecule consists of, optionally consists essentially of, or optionally comprises a single domain antibody (sdAb) having at least 80%, alternatively at least 85%, alternatively at least 90%, alternatively at least 95%, alternatively at least 98%, alternatively at least 99% identity (or being identical except for 1, 2, 3, or 4 amino acids that optionally are conserved substitutions) or 10000 identity to a polypeptide sequence of any one of SEQ ID NOS, as shown in Table 3 below.

TABLE 3

| mIL23 ECD Generated VHHs and CDRs | | |
|---|---|---|
| Name | VHH Amino Acid Sequence (CDRs underlined | SEQ ID NO |
| mIL23R VHH1 | QVQLQESGGGSVQAGGSLRLSCAASGYTYSSCTMGWYRQAPGKER ELVSMLISDGSTFYADSVKGRFTFSQEYAKNTVYLQMNSLKPEDTA MYYCGCATLGSRTVWGQGTQVTVSS | 97 |
| mIL23R VHH2 | QVQLQESGGGSVQAGGSLTLSCTAPGFTFRLAAMRWVRQAPGKGL EWVSGIDSRGSTIYADSVKGRFTISKDNAKNTLYLQLNSLKTEDTA MYYCAQGVYGDTYSGSQGTQVTVSS | 98 |
| mIL23R VHH3 | QVQLQESGGGSVQAGGSLRLSCTASVNTYCEYNMSWYRQAPGKE REFVSGVDSDGSTRYSESVKGRFTISQDNAKNTMYLQMNGLKPEDT AMYYCKTYVCTFCSGNSCYYEYKYYYEGQGTQVTVSS | 99 |
| mIL23R VHH4 | QVQLQESGGGSVQAGGSLRLSCAASGYTYSNNCMGWFRQAPGKD RERIANIYTGGGRTTYADSVKGRFTISQDSAKSTVYLQMNSLKPE DTAMYYCAAGSCGSARSEYSYWGQGTQVTVSS | 100 |
| mIL23R VHH5 | QVQLQESGGGSVQAGGSLRLSCAASGYTFCMAWFRQAPGKEREGV ARFYTRDGYTYYSDSVKGRFTISQNNAKNTLYLQMNSLKSEDTAM YYCAADLARCSSNKNDFRYWGQGTQVTVSS | 101 |
| mIL23R VHH6 | QVQLQESGGGSVQAGGSLRLSCAASGYTSGNYWMGWFRQAPGKE REGVATLWTGGASTFYGDSVKGRFTISRDNFKNTLYLQMNSLKVE DTAMYYCAADPALRLGANILRPAEYKYWGQGTQVTVSS | 102 |
| mIL23R VHH7 | QVQLQESGGGLVQPGGSLRLSCAASGFTFSRSAMTWVRQAPGKGL DWVSGIDSGGTTVYADSVKGRFTISRDSAKNTLYLQMNSLKTEDTA VYYCAIGLPWGNTWRTRGQGTQVTVSS | 103 |
| mIL23R VHH8 | QVQLQESGGGSVQAGGSLRLSCTASRYTYSSCTMGWYRQAPGKER ELVSMVFSDGSTFYADSVKGRFTFSQENAKNTVYLQMNSLKPEDT AMYYCGCATLGSRTIWGQGTQVTVSS | 104 |
| mIL23R VHH9 | QVQLQESGGGLVQPGGSLRLSCATSGFTFRLTAMRWVRQAPGKGV EWVSGIDSAGSTIYADSVKGRFTISKDNAKNTLYLQMNSLKTEDTA MYYCAQGVYGDTYSGSQGTQVTVSS | 105 |
| mIL23R VHH10 | QVQLQESGGGSVQAGGSLRLSCAASGDTYSSCTMGWYRQAPGKER DLVSMLMGDGSTFYADSVKGRFTFSQENAKNTVYLQMNSLKPEDT AMYYCGCATLGSRTIWGQGTQVTVSS | 106 |
| mIL23R VHH11 | QVQLQESGGGSVQAGGSLRLSCAASGYTYSSCTMGWYRQAPGKER ELVSMLISDGSTFYADSVKGRFTFSQENAKSTVYLQMNSLKPEDTA MYYCGCATLGSRTVWGQGTQVTVSS | 107 |
| mIL23R VHH12 | QVQLQESGGGSVQAGGSLRLSCAASGYTYSSCTMGWYRQAPGKER ELVSMLISDGSTFYADSVKGRFTFSQENAKNTVYLQMNSLKPEDTA MYYCGCATLGSRTVWGQGTQVTVSS | 108 |

TABLE 3-continued

| mIL23 ECD Generated VHHs and CDRs | | |
|---|---|---|
| Name | VHH Amino Acid Sequence (CDRs underlined | SEQ ID NO |
| mIL23R VHH13 | QVQLQESGGGLVQPGGSLRLSCATSGFTFRLAAMRWVRQAPGKGLEWVSGIDSRGSTIYADSVKGRFTISKDNAKNTLYLQLNSLKTEDTAMYYCAQGVYGDTYSGSQGTQVTVSS | 109 |
| mIL23R VHH14 | QVQLQESGGGLVQPGGSLRLSCAASGFTFRTSAMTWVRQAPGKGLDWVSGIDSGGTTVYADSVKGRFTISRDSAKNTLYLQMNSLKTEDTAVYYCAMGLPWGNTWRTRGQGTQVTVSS | 110 |
| mIL23R VHH15 | QVQLQESGGGSVQAGGSLRLSCAASGYTYSSCTMGWYRQAPGKERELVSMVFSDGSTFYADSVKGRFTFSQENAKNTVYLQMNSLKPEDTAMYYCGCATLGSRTIWGQGTQVTVSS | 111 |
| mIL23R VHH16 | QVQLQESGGGSVQAGGSLRLSCAASGDTYSSCTMGWYRQAPGKERDLVSMLMGDGSTFYADSVKGRFTFSQENAKNTVYLQMNNLKPEDTAMYYCGCATLGSRTIWGQGTQVTVSS | 112 |
| mIL23R VHH17 | QVQLQESGGGSVQAGGSLRLSCAASGFTFRLTAMRWVRQAPGKGLEWVSGIDSRGSTIYADSVKGRFTISKDNAKNTLYLQLNSLKTEDTAMYYCAQGVYGDTYSGSQGTQVTVSS | 113 |
| mIL23R VHH18 | QVQLQESGGGLVQPGGSLRLSCAASGFTFRLTAMRWVRQAPGKGLEWVSGIDSRGSTIYADSVKGRFTISKDNAKNTLYLQLNSLKTEDTAMYYCAQGVYGDTYSGSQGTQVTVSS | 114 |
| mIL23R VHH19 | QVQLQESGGGLVQPGGSLRLSCAASGFTFRLSAMRWVRQAPGKGLEWVSGIDSRGSTIYADSVKGRFTISKDNAKNTLYLQLNSLKTEDTAMYYCAQGVYGDTYSGSQGTQVTVSS | 115 |
| mIL23R VHH20 | QVQLQESGGGLVQPGGSLRLSCAASGFTFSSSAMTWVRQAPGKGLDWVSGIDSGGTTVYADSVKGRATILKDNAKNTLYLQMNSLKTEDTAVYYCATGLPWGNTWRTRGQGTQVTVSS | 116 |
| mIL23R VHH21 | QVQLQESGGGLVQPGGSLRLSCATSGFTFSSSAMTWVRQAPGKGLDWVSGIDSGGTTVYADSVKGRFTISKDNAKNTLYLQMNSLKTEDTAVYYCATGLPWGNTWRTTGQGTQVTVSS | 117 |
| mIL23R VHH22 | QVQLQESGGGSVQAGGSLRLSCAASGYTFCMAWFRQAPGKEREGVARFYTRDSYTYYSDSVKGRFTISQNNAKNTLYLQMNSLKSEDTAMYYCAADLTRCSSNKNDFRYWGQGTQVTVSS | 118 |
| mIL23R VHH23 | QVQLQESGGGLVQPGGSLRLSCAASGFNFRLYAMRWVRQAPGKGVEWVSGIDSGGSTIYADSVKGRFTISKDNAKNTLYLQLNSLKTEDTAMYYCAQGVYGDTYSGSQGTQVTVSS | 119 |
| mIL23R VHH24 | QVQLQESGGGSVQAGGSLRLSCAVSGYTFCMAWFRQAPGKEREGVARFYTRDGYTYYSGSVKGRFTISQNNAKNTLYLQMNSLKSEDTAMYYCAADLTRCSSNKNDFRYWGQGTQVTVSS | 120 |
| mIL23R VHH25 | QVQLQESGGGSVQAGGSLRLSCAASGYTYSSCTMGWYRQAPGKERELVSMLISDGSTFYADSVKGRFTFSQENAKNTVYLQMNSLKPEDTAMYFCGCATLGSRTVWGQGTQVTVSS | 121 |
| mIL23R VHH26 | QVQLQESGGGSVQAGGSLRLSCAASGYTFCMAWFRQAPGKEREGVARFYTRDGYTYYSDSVKGRFTISQNNAKNTLYLQMNSLKSEDTAMYYCAADLTRCSSNKNDFRYWGQGTQVTVSS | 122 |
| mIL23R VHH27 | QVQLQESGGGSVQAGGSLRLSCAASGYTYSSCTMGWYRQAPGKERELVSMLISDGSTFYADSVKGRFTSSQENAKNTVYLQMNSLKPEDTAMYYCGCATLGSRTVWGQGTQVTVSS | 123 |
| mIL23R VHH28 | QVQLQESGGGLVQPGGSLRLSCAASGFTFRLTAMRWVRQAPGKGLEWVSGIDSRGSTIYADSVKGRFTISRDNAKNTLYLQLNSLKTEDAAMYYCAQGVYGDTYSGSQGTQVTVSS | 124 |
| mIL23R VHH29 | QVQLQESGGGLVQPGGSLRLSCAASGFTFSTSAMTWVRQAPGKGLDWVSGIDSGGTTVYADSVKGRFTISKDNAKNTLYLQMNSLKTEDTAVYYCATGLPWGNTWRTRGQGTQVTVSS | 125 |
| mIL23R VHH30 | QVQLQESGGGLVQPGGSLRLSCAASGFTFRLTAMRWVRQAPGKGLEWVSGIDSRGSTIYADSVKGRFTISKDNAKNTLYLQLNSLKTEDTAMYYCAQGVYGDTYSGSLGTQVTVSS | 126 |
| mIL23R VHH31 | QVQLQESGGGLVQPGGSLRLSCAASGFTFRLTAMRWVRQAPGKGLEWVSGIDSRGSTIYADSVKGRFTISRDNAKNTLYLQLNSLKTEDTAMYYCAQGVYGDTYSGSQGTQVTVSS | 127 |

TABLE 3-continued mIL23 ECD Generated VHHs and CDRs

| Name | VHH Amino Acid Sequence (CDRs underlined | SEQ ID NO |
|---|---|---|
| mIL23R VHH32 | QVQLQESGGGLVRPGGSLRLSCAASGFTFSRSAMTWVRQAPGKGL DWVSGIDSGGTTVYADSVKGRFTISRDSAKNTLYLQMNSLKTEDTA VYYCAIGLPWGNTWRTRGQGTQVTVSS | 128 |
| mIL23R VHH33 | QVQLQESGGGLVQPGGSLRLSCTTSGFTFSSSAMTWVRQAPGKGLD WVSGIDSGGTTVYADSVKGRFTISKDNAKNTLYLQMNSLKTEDTA VYYCATGLPWGNTWRTTGQGTQVTVSS | 129 |
| mIL23R VHH34 | QVQLQESGGGLVQPGGSLRLSCAASGFTFRLTAMRWVRQAPGKGL EWVSGIDSRGSTIYADSVKGRFTISKDNAKNTLYLQLNSLKTEDTA MYYCAQGVYGDTHSGSQGTQVTVSS | 130 |
| mIL23R VHH35 | QVQLQESGGGLVQPGGSLRLACSASGFTFSSSAMTWVRQAPGKGL DWVSGIDSGGTTVYADSVKGRATILKDNAKNTLYLQMNSLKTEDT AVYYCATGLPWGNTWRTRGQGTQVTVSS | 131 |
| mIL23R VHH36 | QVQLQESGGGSVQAGGSLRLSCAASGDTYSSCTMGWYRQAPGKER DLVSMVFSDGSTFYADSVKGRFTFSQENAKNTVYLQMNSLKPEDT AMYYCGCATLGSRTIWGQGTQVTVSS | 132 |
| mIL23R VHH37 | QVQLQESGGGLVQPGGSLRLSCATSGFTFSSGAMTWVRQAPGKGL DWVSGIDSGGTTVYADSVKGRFTISKDNAKNTLYLQMNSLKTEDT AVYYCATGLPWGNTWRTTGQGTQVTVSS | 133 |
| mIL23R VHH38 | QVQLQESGGGLVQPGGSLRLSCAASGFTFSTSAMTWVRQAPGKGL DWVSGIDSGGTTVYADSVKGRFTISKDNAKNTLYLQMNSLKTEDT AVYYCATGLPWGNIWRTRGQGTQVTVSS | 134 |
| mIL23R VHH39 | QVQLQESGGGLVQPGGSLRLSCAASGFTFSRSAMTWVRQAPGKGL DWVSGIDSGGTTVYADSVKGRFTISRDSAKNTLYLQMNGLKTEDT AVYYCAIGLPWGNTWRTRGQGTQVTVSS | 135 |
| mIL23R VHH40 | QVQLQESGGGLVQPGGSLRLSCAASGFTFRLTAMRWVRQAPGKGL EWVSGIDSRGSTIYADSVKGRFTISKDNAKNTLYLQLNSLKSEDTA MYYCAQGVYGDTYSGSQGTQVTVSS | 136 |
| mIL23R VHH41 | QVQLQESGGGLVQPGGSLRLTCAASGFTFSTSAMTWVRQAPGKGL DWVSGIDSGGTTVYADSVKGRFTISKDNAKNTLYLQMNSLKTEDT AVYYCATGLPWGNTWRTRGQGTQVTVSS | 137 |
| mIL23R VHH42 | QVQLQESGGGLVQPGGSLRLSCAASGFTFSNYAMRWVRQAPGKGL EWVSGIDSRGSTIYADSVKGRFTISKDNAKNTLYLQLNSLKTEDTA MYYCAQGVYGDTYSGSQGTQVTVSS | 138 |
| mIL23R VHH43 | QVQLQESGGGSVQAGGSLRLSCAASGYTFCMAWFRQAPGKEREGV ARFYTRDGYTYYSDSVKGRFTISQDNAKNTLYLQMNSLKSEDTAM YYCAADLTRCSSNKNDFRYWGQGTQVTVSS | 139 |
| mIL23R VHH44 | QVQLQESGGGLVQPGGSLRLSCAASGFTFRLSAMRWVRQAPGKGF EWVSGIDSRGSTIYADSVKGRFTISKDNAKNTLYLQLNSLKTEDTA MYYCAQGVYGDTYSGSQGTQVTVSS | 140 |
| mIL23R VHH45 | QVQLQESGGGLVQPGGSLRLSCAASGFTFRLSAMRWVRQAPGKGL EWVSGIDSRGSTIYADSVEGRFTISKDNAKNTLYLQLNSLKTEDTA MYYCAQGVYGDTYSGSQGTQVTVSS | 141 |
| mIL23R VHH46 | QVQLQESGGGLVQPGGSLRLSCAASGFTFRLSAMRWVRQAPGKGL EWVSGIDSRGSTIYADSVKGRFTISKDDAKNTLYLQLNSLKTEDTA MYYCAQGVYGDTYSGSQGTQVTVSS | 142 |

In some embodiments, the IL23R binding molecule is a sdAb, the sdAb comprising a set of CDRs corresponding to CDR1, CDR2, and CDR3 as shown in a row of Table 4 below.

In some embodiments, the IL23R binding molecule comprises a CDR1, a CDR2, and a CDR3 as described in a row of Table 1 below, in which the CDR1, CDR2, and CDR3 can each, independently, comprise at least 90% (e.g., 91%, 92%, 93%, 94%, 95%, 96%, 97%, 98%, 99%, or 100%) sequence identity, or have 0, 1, 2, or 3 amino acid changes, optionally conservative amino acid changes, relative to the sequence described in a row of Table 5 below.

TABLE 4 mIL23R ECD Generated VHH CDRs

| CDR1 (AA Seq) | SEQ ID NO | CDR2 (AA Seq) | SEQ ID NO | CDR3 (AA Seq) | SEQ ID NO |
|---|---|---|---|---|---|
| YTYSSCTMG | 143 | MLISDGSTFYADSVKG | 144 | ATLGSRTV | 145 |
| FTFRLAAMR | 146 | GIDSRGSTIYADSVKG | 147 | GVYGDTYS | 148 |
| NTYCEYNMS | 149 | GVDSDGSTRYSESVKG | 150 | YVCTFCSGNSCYYEYKYYY | 151 |
| YTYSNNCMG | 152 | NIYTGGGRTTYADSVKG | 153 | GSCGSARSEYSY | 154 |
| YTFCMA | 155 | RFYTRDGYTYYSDSVKG | 156 | DLARCSSNKNDFRY | 157 |
| YTSGNYWMG | 158 | TLWTGGASTFYGDSVKG | 159 | DPALRLGANILRPAEYKY | 160 |
| FTFSRSAMT | 161 | GIDSGGTTVYADSVKG | 162 | GLPWGNTWRT | 163 |
| YTYSSCTMG | 164 | MVFSDGSTFYADSVKG | 165 | ATLGSRTI | 166 |
| FTFRLTAMR | 167 | GIDSAGSTIYADSVKG | 168 | GVYGDTYS | 169 |
| DTYSSCTMG | 170 | MLMGDGSTFYADSVKG | 171 | ATLGSRTI | 172 |
| YTYSSCTMG | 173 | MLISDGSTFYADSVKG | 174 | ATLGSRTV | 175 |
| YTYSSCTMG | 176 | MLISDGSTFYADSVKG | 177 | ATLGSRTV | 178 |
| FTFRLAAMR | 179 | GIDSRGSTIYADSVKG | 180 | GVYGDTYS | 181 |
| FTFRTSAMT | 182 | GIDSGGTTVYADSVKG | 183 | GLPWGNTWRT | 184 |
| YTYSSCTMG | 185 | MVFSDGSTFYADSVKG | 186 | ATLGSRTI | 187 |
| DTYSSCTMG | 188 | MLMGDGSTFYADSVKG | 189 | ATLGSRTI | 190 |
| FTFRLTAMR | 191 | GIDSRGSTIYADSVKG | 192 | GVYGDTYS | 193 |
| FTFRLTAMR | 194 | GIDSRGSTIYADSVKG | 195 | GVYGDTYS | 196 |
| FTFRLSAMR | 197 | GIDSRGSTIYADSVKG | 198 | GVYGDTYS | 199 |
| FTFSSSAMT | 200 | GIDSGGTTVYADSVKG | 201 | GLPWGNTWRT | 202 |
| FTFSSSAMT | 203 | GIDSGGTTVYADSVKG | 204 | GLPWGNTWRT | 205 |
| YTFCMA | 206 | RFYTRDSYTYYSDSVKG | 207 | DLTRCSSNKNDFRY | 208 |
| FNFRLYAMR | 209 | GIDSGGSTIYADSVKG | 210 | GVYGDTYS | 211 |
| YTFCMA | 212 | RFYTRDGYTYYSGSVKG | 213 | DLTRCSSNKNDFRY | 214 |
| YTYSSCTMG | 215 | MLISDGSTFYADSVKG | 216 | ATLGSRTV | 217 |
| YTFCMA | 218 | RFYTRDGYTYYSDSVKG | 219 | DLTRCSSNKNDFRY | 220 |
| YTYSSCTMG | 221 | MLISDGSTFYADSVKG | 222 | ATLGSRTV | 223 |
| FTFRLTAMR | 224 | GIDSRGSTIYADSVKG | 225 | GVYGDTYS | 226 |
| FTFSTSAMT | 227 | GIDSGGTTVYADSVKG | 228 | GLPWGNTWRT | 229 |
| FTFRLTAMR | 230 | GIDSRGSTIYADSVKG | 231 | GVYGDTYS | 232 |
| FTFRLTAMR | 233 | GIDSRGSTIYADSVKG | 234 | GVYGDTYS | 235 |
| FTFSRSAMT | 236 | GIDSGGTTVYADSVKG | 237 | GLPWGNTWRT | 238 |
| FTFSSSAMT | 239 | GIDSGGTTVYADSVKG | 240 | GLPWGNTWRT | 241 |
| FTFRLTAMR | 242 | GIDSRGSTIYADSVKG | 243 | GVYGDTHS | 244 |
| FTFSSSAMT | 245 | GIDSGGTTVYADSVKG | 246 | GLPWGNTWRT | 247 |
| DTYSSCTMG | 248 | MVFSDGSTFYADSVKG | 249 | ATLGSRTI | 250 |
| FTFSSGAMT | 251 | GIDSGGTTVYADSVKG | 252 | GLPWGNTWRT | 253 |

TABLE 4-continued

| mIL23R ECD Generated VHH CDRs | | | | | |
|---|---|---|---|---|---|
| CDR1 (AA Seq) | SEQ ID NO | CDR2 (AA Seq) | SEQ ID NO | CDR3 (AA Seq) | SEQ ID NO |
| FTFSTSAMT | 254 | GIDSGGTTVYADSVKG | 255 | GLPWGNIWRT | 256 |
| FTFSRSAMT | 257 | GIDSGGTTVYADSVKG | 258 | GLPWGNTWRT | 259 |
| FTFRLTAMR | 260 | GIDSRGSTIYADSVKG | 261 | GVYGDTYS | 262 |
| FTFSTSAMT | 263 | GIDSGGTTVYADSVKG | 264 | GLPWGNTWRT | 265 |
| FTFSNYAMR | 266 | GIDSRGSTIYADSVKG | 267 | GVYGDTYS | 268 |
| YTFCMA | 269 | RFYTRDGYTYYSDSVKG | 270 | DLTRCSSNKNDFRY | 271 |
| FTFRLSAMR | 272 | GIDSRGSTIYADSVKG | 273 | GVYGDTYS | 274 |
| FTFRLSAMR | 275 | GIDSRGSTIYADSVEG | 276 | GVYGDTYS | 277 |
| FTFRLSAMR | 278 | GIDSRGSTIYADSVKG | 279 | GVYGDTYS | 280 |

In some embodiments, the foregoing sets of CDRs are incorporated in a humanized VHH framework to provide "humanized" sdAb IL23R binding molecules.

The disclosure further provides methods of chemical or recombinant processes for the preparation of the IL23R binding molecules of the present disclosure.

The disclosure further provides nucleic acids encoding the IL23R binding molecules. Table 5 below provides examples of DNA sequences encoding IL23R binding molecules as described herein.

TABLE 5

| Nucleic Acid sequences Encoding IL23 VHHs of Table 3 | | |
|---|---|---|
| Name | DNA Sequence | SEQ ID NO |
| mIL23R VHH1 | CAAGTGCAGCTGCAAGAATCTGGCGGAGGCTTGTGCAAGCTGGC GGTTCCTTGCGTCTGAGCTGCGCCGCATCTGGGTATACCTACAGT AGCTGCACAATGGGTTGGTATAGACAAGCGCCCGGTAAGGAGCG GGAACTGGTGTCCATGCTGATCTCTGACGGCAGTACTTTTTACGC CGACTCCGTGAAGGGCAGATTCACATTCTCCCAGGAGTACGCCA AGAACACCGTCTACCTTCAGATGAACAGTCTGAAGCCTGAGGAC ACCGCTATGTACTATTGCGGCTGCGCAACGCTCGGCTCCCGCACG GTCTGGGGTCAGGGCACCCAGGTCACCGTGTCCTCT | 281 |
| mIL23R VHH2 | CAGGTTCAGCTTCAGGAGTCTGGTGGCGGTTCCGTACAGGCCGG GGGCTCCCTTACTCTCAGCTGTACCGCGCCGGGTTTTACTTTCCG GTTGGCGGCCATGCGCTGGGTTCGCCAGGCTCCGGGAAAAGGAC TGGAGTGGGTTAGCGGCATTGATTCCAGGGGCTCCACCATCTATG CCGACTCTGTGAAGGGGAGGTTCACAATTAGCAAAGATAATGCC AAAAACACTCTTTACCTTCAGCTCAATTCTTTGAAAACTGAGGAT ACTGCAATGTATTACTGCGCCCAGGGCGTATACGGCGACACTTAC TCCGGGAGCCAAGGAACACAGGTGACTGTATCTTCT | 282 |
| mIL23R VHH3 | CAGGTCCAGTTGCAAGAGTCAGGGGGTGGGTCCGTACAGGCAGG AGGTTCCCTCCGCCTCAGCTGCACTGCCTCTGTCAACACATACTG CGAATACAATATGTCCTGGTATCGGCAGGCCCCTGGCAAGGAGA GAGAGTTCGTGTCCGGCGTTGACTCTGATGGTTCCACCCGCTACA GCGAGAGCGTTAAGGGGCGCTTCACCATCTCCCAGGACAACGCC AAGAACACTATGTACCTCCAGATGAATGGTCTGAAGCCCGAGGA CACCGCTATGTACTATTGTAAGACATACGTTTGTACCTTCTGTTC AGGCAACAGCTGCTACTATGAATATAAGTACTATTACGAGGGCC AGGGAACGCAGGTTACCGTATCCTCT | 283 |

TABLE 5-continued

Nucleic Acid sequences Encoding IL23 VHHs of Table 3

| Name | DNA Sequence | SEQ ID NO |
|---|---|---|
| mIL23R VHH4 | CAGGTGCAACTCCAGGAGTCCGGCGGGGGTAGCGTCCAGGCTGG<br>GGGCTCCCTCCGCCTGAGTTGTGCTGCCAGCGGTTATACTTACTC<br>TAATAATTGCATGGGCTGGTTTAGGCAAGCTCCGGGCAAGGACC<br>GCGAGAGAATTGCCAATATCTACACAGGAGGTGGCAGAACTACC<br>TACGCAGATAGTGTGAAGGGCCGGTTCACCATTTCTCAGGACAG<br>TGCGAAGTCCACTGTGTACCTCCAGATGAACTCACTGAAGCCGG<br>AGGACACCGCGATGTATTACTGCGCCGCTGGCTCCTGTGGGAGC<br>GCTCGTTCCGAATACTCATACTGGGGCCAGGGCACCCAGGTGAC<br>CGTGTCCTCC | 284 |
| mIL23R VHH5 | CAAGTGCAGCTCCAGGAATCTGGGGGGGGTCTGTCCAAGCTGG<br>CGGGAGCCTCCGCCTGAGTTGTGCTGCCTCTGGGTACACCTTTTG<br>TATGGCTTGGTTCCGCCAAGCGCCTGGGAAGGAACGCGAGGGTG<br>TCGCACGCTTCTATACACGTGATGGATACACATATTACTCTGACA<br>GCGTTAAGGGCAGATTCACTATCTCTCAGAATAACGCTAAGAAT<br>ACCCTCTACTTGCAGATGAACTCTCTGAAAAGCGAGGACACCGC<br>TATGTACTATTGCGCAGCGGATTTGGCCCGCTGTTCCAGCAACAA<br>GAATGACTTTCGTTACTGGGGTCAGGGGACACAGGTGACAGTTA<br>GTAGC | 285 |
| mIL23R VHH6 | CAGGTCCAGCTCCAGGAGTCAGGAGGTGGCTCCGTTCAGGCTGG<br>TGGCTCCCTCCGGCTGTCCTGTGCCGCAAGCGGATACACGTCTGG<br>AAACTACTGGATGGGATGGTTCCGTCAAGCCCCCGGCAAAGAAC<br>GCGAGGGCGTGGCTACTCTGTGGACTGGTGGAGCCTCAACCTTCT<br>ACGGCGACTCTGTTAAGGGCCGTTTCACCATTAGTCGCGATAACT<br>TCAAAAACACACTCTACCTTCAGATGAACTCCCTGAAGGTCGAG<br>GATACAGCCATGTATTACTGCGCCGCTGACCCTGCCCTGCGTCTG<br>GGAGCTAACATCCTGCGCCCTGCTGAATACAAATATTGGGGTCA<br>AGGGACACAGGTGACTGTCAGCTCA | 286 |
| mIL23R VHH7 | CAGGTGCAGCTCCAGGAGTCCGGCGGTGGCCTGGTACAGCCCGG<br>TGGCAGCTTGCGCCTGAGCTGCGCCGCTTCTGGATTTACATTCTC<br>CCGCAGCGCCATGACATGGGTTCGCCAGGCTCCAGGCAAGGGCC<br>TCGACTGGGTGTCCGGCATTGACAGTGGCGGAACTACCGTGTAC<br>GCAGATTCTGTTAAGGGAAGATTCACCATCTCCCGCGACTCCGCC<br>AAGAACACCCTGTACTTGCAAATGAACAGCCTCAAGACAGAAGA<br>CACAGCCGTGTATTACTGTGCCATCGGACTGCCGTGGGGCAACA<br>CATGGCGTACCAGGGGACAGGGCACACAGGTGACAGTCTCCTCA | 287 |
| mIL23R VHH8 | CAGGTGCAGTTGCAGGAGTCCGGCGGAGGCAGCGTGCAAGCCGG<br>AGGTAGCCTCCGCCTGAGCTGCACAGCGAGCCGCTACACCTATA<br>GCAGTTGCACTATGGGTTGGTATCGTCAGGCCCCCGGCAAGGAG<br>AGGGAACTCGTGTCAATGGTGTTTTCTGACGGTTCCACCTTCTAC<br>GCCGACTCCGTTAAAGGTCGGTTCACCTTCTCTCAGGAAAACGCC<br>AAAAACACCGTGTACCTCCAGATGAACTCCCTGAAACCCGAGGA<br>TACCGCTATGTACTATTGCGGATGCGCTACACTCGGCTCAAGAAC<br>TATCTGGGGCCAAGGCACTCAGGTGACTGTCTCCTCC | 288 |
| mIL23R VHH9 | CAGGTGCAGCTCCAGGAAAGCGGAGGTGGCCTCGTGCAGCCTGG<br>TGGCTCCCTGAGACTGTCTTGCGCAACATCTGGATTCACCTTCAG<br>GCTCACTGCTATGCGTTGGGTGAGACAAGCCCCAGGGAAGGGCG<br>TCGAATGGGTGTCTGGAATCGACTCCGCTGGCTCTACGATCTACG<br>CCGACAGCGTGAAGGGCCGCTTCACTATCTCCAAAGATAATGCT<br>AAGAACACTCTGTATCTGCAAATGAACAGCCTCAAAACCGAAGA<br>CACAGCTATGTACTATTGTGCGCAGGGTGTCTACGGTGATACCTA<br>CAGCGGTTCTCAGGGCACTCAGGTGACGGTGTCCAGC | 289 |
| mIL23R VHH10 | CAGGTCCAGCTCCAGGAGAGCGGCGGGGGCAGCGTGCAGGCTGG<br>GGGTTCCCTGAGACTGTCCTGTGCTGCCTCCGGCGATACCTACAG<br>TTCATGTACTATGGGCTGGTATCGCCAGGCTCCGGGCAAGGAGC<br>GCGACCTCGTGAGCATGTTGATGGGCGATGGTAGCACCTTTTACG<br>CCGATAGTGTGAAGGGCCGTTTCACCTTTAGCCAGGAGAACGCT<br>AAAAACACTGTGTACTTGCAGATGAACAGCTTGAAGCCCGAGGA<br>CACTGCAATGTATTACTGTGGCTGCGCCACGCTGGGCTCCCGCAC<br>AATTTGGGGCCAGGGCACCCAGGTGACCGTTTCTAGC | 290 |
| mIL23R VHH11 | CAGGTCCAGCTCCAGGAAAGCGGCGGTGGAAGCGTGCAGGCCGG<br>TGGCAGTCTTCGCCTGTCTTGCGCTGCGTCTGGTTACACCTACTCC<br>TCATGCACTATGGGTTGGTACAGGCAGGCCCCAGGGAAGGAGCG<br>CGAGCTGGTATCCATGCTCATTTCTGACGGGTCCACCTTCTACGC<br>CGATTCTGTCAAGGGCAGGTTTACCTTTTCCCAGGAAAACGCCAA<br>GTCCACTGTCTATCTGCAAATGAACTCCTTGAAGCCCGAAGACAC<br>TGCCATGTATTACTGTGGCTGTGCGACGCTTGGCTCAAGGACGGT<br>GTGGGGCCAGGGCACGCAGGTAACCGTTTCCAGC | 291 |

TABLE 5-continued

Nucleic Acid sequences Encoding IL23 VHHs of Table 3

| Name | DNA Sequence | SEQ ID NO |
|---|---|---|
| mIL23R VHH12 | CAGGTGCAGCTCCAAGAGTCTGGCGGAGGCTCCGTGCAGGCTGG CGGGAGCCTGCGCTTGTCCTGCGCAGCCAGCGGCTATACCTACTC CTCTTGTACTATGGGCTGGTATAGGCAAGCGCCTGGCAAGGAGC GCGAACTCGTCAGCATGTTGATCTCTGACGGAAGCACCTTCTACG CTGATTCTGTGAAGGGGCGTTTTACCTTCAGCCAGGAGAACGCTA AGAACACCGTGTACCTCCAGATGAACTCTCTGAAACCTGAAGAT ACCGCTATGTACTATTGCGGATGCGCTACCCTGGGTTCTAGGACC GTTTGGGGTCAGGGAACACAGGTGACAGTATCTTCC | 292 |
| mIL23R VHH13 | CAGGTCCAGCTCCAGGAATCTGGCGGGGGCCTCGTGCAACCAGG GGGTTCCCTGAGATTGTCTTGCGCAACCAGTGGTTTTACCTTCCG CCTCGCTGCCATGCGTTGGGTGCGGCAAGCGCCCGGCAAGGGCC TGGAGTGGGTGTCTGGGATTGATTCTCGGGGCTCCACAATCTACG CGGACAGCGTCAAGGGTCGCTTCACTATCTCTAAGGACAATGCT AAGAACACTCTGTACCTTCAGTTGAACTCTCTGAAAACCGAGGAT ACCGCTATGTATTACTGTGCTCAGGGAGTGTATGGCGATACATAC TCCGGCTCCCAGGGGACGCAAGTGACTGTGAGTTCT | 293 |
| mIL23R VHH14 | CAGGTGCAGCTTCAGGAGTCCGGCGGGGGCCTGGTTCAGCCCGG TGGGTCCCTGCGCCTGTCATGCGCAGCTTCCGGCTTCACCTTTAG GACATCTGCCATGACTTGGGTGCGTCAGGCTCCTGGCAAGGGCCT CGACTGGGTGAGCGGCATCGACAGCGGGGGAACCACAGTGTATG CCGACTCCGTCAAGGGACGCTTCACCATTAGCCGCGACTCCGCCA AGAACACCCTCTACCTTCAGATGAACAGCCTGAAGACGGAAGAC ACCGCCGTTTATTACTGCGCAATGGGGCTGCCTTGGGGCAACACC TGGAGGACTCGGGGCCAGGGAACTCAGGTGACCGTGTCTTCC | 294 |
| mIL23R VHH15 | CAGGTGCAGCTTCAGGAGTCAGGCGGGGGCAGCGTGCAGGCCGG AGGCTCCTTGAGGCTGAGTTGCGCGGCCAGCGGCTACACATATTC TAGCTGCACAATGGGGTGGTATCGCCAGGCACCCGGAAAGGAGA GGGAACTCGTGTCTATGGTGTTCTCTGACGGCTCCACATTCTACG CCGATTCTGTGAAGGGCCGGTTTACCTTCTCACAGGAGAATGCCA AAAACACCGTGTATCTCCAGATGAACTCTTTGAAGCCAGAGGAC ACAGCCATGTATTACTGTGGATGCGCTACCCTGGGCTCCCGTACC ATCTGGGGTCAGGGCACCCAGGTGACTGTCAGCTCT | 295 |
| mIL23R VHH16 | CAAGTCCAGCTCCAGGAGAGCGGGGGCGGTTCCGTCCAGGCGGG CGGAAGCCTCCGCCTTTCATGTGCAGCTAGTGGCGACACGTACA GCTCCTGTACTATGGGCTGGTACAGGCAGGCCCCAGGTAAGGAG CGCGATCTGGTGTCTATGCTGATGGGCGACGGCAGTACCTTTTAC GCTGATAGCGTCAAGGGCCGTTTCACCTTTTCTCAGGAGAACGCC AAGAATACCGTCTATCTTCAAATGAATAACCTCAAGCCAGAAGA TACTGCTATGTACTATTGTGGTTGTGCCACCCTGGGGTCCAGAAC AATCTGGGGACAGGGCACCCAGGTCACTGTGTCCTCT | 296 |
| mIL23R VHH17 | CAAGTCCAGCTTCAGGAGTCTGGCGGGGGCTCAGTGCAAGCAGG AGGTAGCCTGAGGCTGAGCTGCGCTGCCAGTGGTTTTACTTTCCG CCTCACCGCCATGCGCTGGGTGCGCCAGGCCCCCGGCAAGGGCC TGGAGTGGGTGAGCGGAATCGACTCCAGGGGCAGCACTATTTAT GCCGACTCAGTGAAGGGGAGATTTACTATCTCCAAGGACAATGC AAAAAACACCCTTTACCTTCAACTGAACTCTTTGAAGACCGAGG ACACGGCCATGTATTACTGCGCACAGGGAGTCTACGGGGACACC TACTCTGGCTCTCAGGGCACCCAGGTCACTGTGTCTAGC | 297 |
| mIL23R VHH18 | CAAGTCCAGCTCCAGGAGAGCGGCGGGGGCCTGGTGCAGCCCGG TGGCTCTTTGAGGCTCAGCTGTGCTGCCTCCGGCTTCACATTCCG CCTGACTGCAATGCGTTGGGTGAGGCAGGCTCCTGGCAAGGGTC TGGAGTGGGTCTCTGGTATCGACAGTAGAGGCTCCACCATCTACG CAGATAGCGTAAAGGGACGCTTCACCATCTCCAAAGATAACGCT AAGAACACCCTCTACCTCCAGCTTAACAGCCTGAAGACCGAGGA CACAGCTATGTACTATTGTGCACAAGGCGTCTACGGCGATACCTA TTCCGGTTCCCAGGGCACTCAGGTGACCGTCTCCTCC | 298 |
| mIL23R VHH19 | CAGGTTCAGCTTCAGGAGAGCGGCGGTGGCCTGGTCCAACCTGG GGGAAGCCTCCGTCTGAGCTGCGCCGCATCTGGATTCACCTTTAG GCTGTCAGCTATGCGCTGGGTCCGTCAGGCCCCAGGGAAGGGCC TGGAATGGGTTAGCGGGATCGACTCTCGCGGGTCTACGATTTATG CCGACTCAGTCAAGGGGCGCTTCACGATCTCTAAGGACAACGCT AAGAACACCCTGTACTTGCAGCTGAACAGCCTGAAGACCGAGGA TACGGCTATGTATTACTGTGCGCAGGGGGTCTACGGGGACACCT ACTCAGGATCACAGGGCACCCAAGTGACCGTGAGTTCC | 299 |

TABLE 5-continued

Nucleic Acid sequences Encoding IL23 VHHs of Table 3

| Name | DNA Sequence | SEQ ID NO |
|---|---|---|
| mIL23R VHH20 | CAGGTACAGCTCCAGGAGTCCGGCGGAGGCCTTGTGCAGCCTGG TGGCTCCTTGAGACTGAGCTGTGCCGCTTCCGGTTTTACATTCTCC AGCTCAGCCATGACATGGGTGAGACAGGCCCCTGGAAAGGGACT GGACTGGGTTTCTGGCATTGACTCAGGGGGCACGACCGTGTATG CTGACTCTGTTAAGGGCCGCGCCACCATCCTCAAGGACAACGCT AAGAACACACTCTACCTCCAGATGAACTCCCTGAAGACTGAGGA CACAGCTGTCTACTATTGTGCTACTGGTCTGCCTTGGGGTAACAC CTGGCGGACCAGGGGCCAGGGCACTCAGGTGACTGTCTCCTCA | 300 |
| mIL23R VHH21 | CAGGTGCAGCTCCAGGAGTCAGGCGGTGGACTCGTTCAGCCGGG TGGCTCCCTGCGCCTCAGTTGTGCGACCTCTGGCTTTACCTTCTCC AGCTCCGCTATGACCTGGGTGAGGCAAGCACCTGGGAAGGGCCT CGATTGGGTCTCCGGCATTGATTCTGGAGGCACCACTGTCTACGC CGACAGCGTGAAGGGCAGATTCACAATCAGTAAGGACAACGCTA AGAACACTCTGTACCTGCAAATGAACAGCCTGAAGACCGAGGAC ACCGCTGTTTATTACTGCGCAACGGGACTGCCTTGGGGTAATACT TGGAGGACTACCGGCCAGGGAACTCAGGTGACTGTGAGTTCC | 301 |
| mIL23R VHH22 | CAGGTGCAGCTCCAGGAATCCGGTGGAGGCTCCGTGCAAGCGGG CGGGTCCCTGCGCCTCAGCTGTGCAGCTTCTGGCTATACCTTCTG CATGGCCTGGTTTCGCCAGGCCCCTGGGAAGGAGAGGGAGGGGG TGGCCCGCTTTTACACTAGAGACAGCTATACTTACTATAGCGACT CCGTGAAGGGGCGCTTTACGATTAGCCAGAATAACGCCAAGAAT ACCTTGTACCTCCAGATGAATAGTCTGAAGTCCGAGGACACCGC CATGTATTACTGTGCTGCCGACCTTACGAGGTGCAGCTCCAATAA GAACGACTTCCGCTACTGGGGCCAGGGTACTCAGGTCACTGTGTC CAGC | 302 |
| mIL23R VHH23 | CAAGTGCAGCTCCAGGAAAGCGGAGGCGGTCTGGTCCAACCAGG AGGGTCCCTGCGTCTGTCCTGCGCGGCCTCCGGCTTTAATTTCAG ACTGTATGCGATGCGTTGGGTTCGTCAAGCGCCCGGTAAGGGCG TGGAGTGGGTGTCCGGTATCGACTCAGGAGGCTCTACCATCTATG CTGACTCTGTGAAGGGCCGCTTTACCATCAGCAAGGACAACGCT AAAAATACCCTGTACTTGCAGCTGAACTCTCTGAAAACCGAGGA CACTGCCATGTATTACTGCGCCCAGGGTGTGTACGGCGACACCTA CTCTGGTTCCCAAGGCACCCAGGTGACGGTCTCCTCC | 303 |
| mIL23R VHH24 | CAAGTGCAGCTCCAGGAGAGCGGTGGCGGTTCTGTGCAAGCGGG TGGGTCCCTGCGGCTGAGCTGCGCTGTGTCTGGTTATACCTTCTG TATGGCCTGGTTCCGCCAGGCTCCGGGAAAGGAGCGCGAAGGCG TGGCTCGGTTCTACACCAGAGACGGTTACACATACTATTCCGGCA GCGTGAAGGGCAGGTTCACGATCAGCCAGAATAACGCTAAAAAC ACCCTGTACCTGCAAATGAACAGCCTGAAGAGCGAGGATACCGC GATGTATTACTGCGCAGCCGACTTGACCAGATGCTCTTCCAACAA AAACGACTTCCGCTACTGGGGTCAGGGCACCCAAGTCACTGTGT CCTCC | 304 |
| mIL23R VHH25 | CAAGTCCAGCTCCAGGAGAGTGGAGGCGGAAGCGTGCAGGCCG GTGGCTCCCTGAGACTTTCATGCGCAGCGTCCGGCTATACATATT CTTCCTGCACTATGGGCTGGTACAGACAAGCGCCGGGCAAGGAG CGTGAGTTGGTGAGTATGCTCATCAGCGATGGCAGTACCTTTTAT GCGGACTCTGTCAAGGGCCGCTTCACCTTCTCTCAAGAGAACGCT AAAAACACAGTTTACCTCCAGATGAACTCCCTGAAGCCCGAAGA CACTGCCATGTATTTTTGTGGGTGTGCCACTCTTGGCTCCAGGAC GGTGTGGGGCCAGGGCACCCAGGTTACCGTGAGCAGT | 305 |
| mIL23R VHH26 | CAGGTCCAGCTGCAAGAGTCTGGAGGGGGCAGCGTGCAGGCTGG CGGTTCTCTGCGCCTGAGCTGCGCTGCGAGTGGGTACACTTTCTG TATGGCATGGTTTCGCCAAGCTCCCGGTAAGGAGCGCGAAGGTG TGGCCCGCTTTTATACTAGGGACGGTTACACATATTACTCAGACT CTGTGAAGGGCCGTTTTACCATTTCCCAAAACAATGCAAAAAAC ACCCTGTACCTTCAGATGAACTCTCTCAAAAGCGAGGATACTGCT ATGTATTACTGCGCCGCAGACCTGACCAGATGTTCATCCAATAAG AATGACTTCCGCTACTGGGGCCAAGGGACCCAGGTGACCGTGAG CAGT | 306 |
| mIL23R VHH27 | CAGGTCCAGCTGCAAGAATCTGGTGGGGGTTCCGTGCAAGCCGG AGGCAGCCTGAGGCTCAGCTGCGCCGCAAGCGGATACACATATT CCTCTTGCACTATGGGTTGGTATCGCCAGGCCCCAGGCAAGGAA CGTGAGCTGGTCTCTATGCTCATCAGTGATGGCAGCACCTTTTAC GCTGATTCTGTGAAGGGCAGATTTACCTCTTCCCAGGAGAACGCT AAAAACACTGTGTACCTTCAGATGAACAGCCTGAAGCCAGAGGA CACCGCGATGTACTATTGCGGCTGCGCAACCCTGGGGAGCAGGA CAGTGTGGGGGCAGGGCACACAGGTGACCGTCTCCTCA | 307 |

TABLE 5-continued

| Nucleic Acid sequences Encoding IL23 VHHs of Table 3 | | |
|---|---|---|
| Name | DNA Sequence | SEQ ID NO |
| mIL23R VHH28 | CAGGTCCAGCTGCAAGAGAGCGGAGGCGGGCTCGTGCAGCCGGG TGGCAGCCTGCGCCTTTCCTGCGCTGCGTCTGGCTTCACCTTCAG GCTCACCGCTATGAGATGGGTTAGACAAGCTCCCGGCAAGGGTC TGGAATGGGTGAGCGGCATCGACAGCAGAGGTAGCACGATCTAC GCTGATTCCGTCAAGGGACGGTTCACAATTTCCAGAGACAACGC CAAGAACACACTGTACCTTCAGTTGAACTCCCTGAAGACCGAAG ACGCCGCTATGTACTATTGTGCGCAGGGCGTGTACGGCGATACCT ACTCAGGCTCCCAGGGCACCCAGGTAACGGTGAGTTCC | 308 |
| mIL23R VHH29 | CAGGTACAGCTGCAAGAGAGTGGCGGAGGCCTCGTTCAACCCGG AGGGAGTCTGCGCCTGTCTTGTGCTGCCTCCGGCTTCACCTTTTCC ACTTCCGCTATGACCTGGGTCAGGCAGGCCCCCGGCAAGGGACT GGACTGGGTAAGTGGCATCGACTCCGGTGGCACTACCGTGTACG CGGACTCCGTGAAAGGCCGCTTCACTATTAGCAAGGACAACGCT AAAAACACACTCTACCTCCAGATGAACAGCCTCAAGACAGAGGA CACTGCCGTGTACTATTGCGCGACCGGCCTGCCTTGGGGCAACAC CTGGCGCACAAGAGGTCAAGGGACACAGGTCACTGTGAGCAGC | 309 |
| mIL23R VHH30 | CAGGTGCAGCTGCAAGAAAGCGGAGGCGGACTTGTTCAGCCTGG GGGCTCCTTGCGGCTGTCCTGTGCTGCCTCAGGCTTTACTTTTCGT CTGACAGCCATGCGGTGGGTGCGGCAGGCCCCTGGCAAGGGTCT CGAATGGGTTTCCGGTATTGACTCTCGCGGCTCTACTATCTACGC CGACTCTGTGAAGGGCCGTTTCACCATCTCCAAGGATAATGCCAA AAACACGCTGTACTTGCAGCTTAATAGCTTGAAGACCGAGGATA CGGCCATGTACTATTGTGCTCAGGGCGTTTACGGCGACACTTATT CTGGCTCCCTTGGCACGCAGGTCACGGTTTCTAGC | 310 |
| mIL23R VHH31 | CAGGTGCAGCTCCAGGAGAGCGGAGGCGGACTGGTGCAGCCAG GTGGCAGCCTGAGGCTCTCCTGTGCGGCCTCAGGTTTTACCTTTC GCCTGACAGCCATGCGGTGGGTCAGACAAGCGCCTGGGAAAGGT CTGGAGTGGGTGTCTGGTATCGACTCTCGCGGTTCCACCATCTAC GCCGATTCTGTGAAGGGGCGCTTTACAATTAGCCGCGACAACGC CAAGAACACCCTGTACCTCCAGCTCAATTCCCTGAAGACCGAGG ACACCGCGATGTACTATTGTGCGCAAGGCGTCTATGGGGATACCT ATAGCGGTTCTCAGGGAACCCAGGTGACTGTTTCCAGC | 311 |
| mIL23R VHH32 | CAGGTGCAGCTCCAGGAATCTGGGGGAGGCCTGGTTCGCCCTGG GGGTAGCCTGAGACTGAGCTGTGCAGCCTCTGGATTCACTTTCTC CCGTTCCGCAATGACCTGGGTCCGCCAGGCCCCAGGCAAGGGGT TGGATTGGGTGTCTGGCATTGATTCCGGGGGCACCACTGTGTACG CGGACTCCGTGAAGGGCCGCTTCACCATCAGCCGCGATAGCGCC AAAAACACGCTGTATCTCCAGATGAACAGCCTGAAGACCGAGGA CACTGCCGTCTACTATTGTGCTATCGGCCTGCCCTGGGGCAACAC ATGGCGTACACGCGGTCAGGGCACGCAGGTGACCGTGTCTTCT | 312 |
| mIL23R VHH33 | CAGGTCCAGCTTCAGGAAAGCGGAGGCGGACTGGTGCAGCCCGG AGGCAGTCTGCGTCTCAGCTGTACGACCAGCGGGTTTACTTTCTC TAGTAGCGCAATGACTTGGGTGAGGCAGGCTCCGGGCAAGGGTC TGGACTGGGTCAGCGGTATCGACAGCGGCGGGACGACTGTGTAT GCCGATTCAGTGAAAGGACGGTTCACTATCTCAAAGGACAACGC CAAAAACACACTGTACCTTCAGATGAACTCCCTGAAGACCGAAG ACACAGCGGTGTATTACTGCGCCACAGGGTTGCCTTGGGGCAAC ACTTGGCGCACCACTGGACAAGGGACGCAGGTGACCGTTTCCTC T | 313 |
| mIL23R VHH34 | CAGGTGCAGCTCCAAGAGAGTGGCGGAGGCCTGGTGCAGCCCGG TGGCTCTCTGAGGTTGTCTTGTGCTGCCTCTGGCTTTACCTTCAGA CTGACAGCCATGCGCTGGGTCCGCCAGGCTCCTGGTAAGGGACT GGAGTGGGTAAGCGGTATCGACTCCAGAGGGAGCACCATCTATG CTGATTCCGTTAAGGGACGGTTCACCATCTCTAAGGATAATGCCA AGAACACCCTGTATCTCCAGTTGAACTCCCTGAAAACCGAGGAC ACCGCGATGTACTATTGCGCACAGGGCGTGTATGGCGACACTCA CAGCGGCTCTCAAGGCACCCAGGTGACCGTGTCTTCC | 314 |
| mIL23R VHH35 | CAGGTCCAGCTCCAAGAATCCGGCGGAGGGCTGGTACAGCCAGG AGGCAGTCTTAGGCTGGCTTGCTCTGCGTCCGGCTTCACATTTTC CAGCTCTGCCATGACCTGGGTGCGCCAGGCACCCGGAAAGGGCC TGGACTGGGTGAGCGGGATTGATAGCGGAGGCACCACGGTGTAT GCTGACAGTGTAAAAGGACGCGCCACTATCCTGAAGGACAATGC CAAGAACACCCTCTATTTGCAGATGAACAGCCTGAAGACTGAAG ATACTGCTGTGTATTACTGTGCAACGGGCCTGCCTTGGGGAAACA CTTGGCGGACGCGGGGCCAGGGCACGCAGGTGACCGTGTCTTCC | 315 |

TABLE 5-continued

| Nucleic Acid sequences Encoding IL23 VHHs of Table 3 | | |
|---|---|---|
| Name | DNA Sequence | SEQ ID NO |
| mIL23R VHH36 | CAGGTTCAGCTGCAAGAATCTGGTGGCGGAAGCGTGCAAGCGGG TGGCTCTCTTCGTCTCTCTTGTGCTGCATCCGGCGACACCTACAG CTCCTGCACAATGGGGTGGTATCGTCAGGCCCCTGGCAAGGAGC GGGATCTGGTCAGCATGGTCTTCTCTGACGGCAGCACATTCTACG CTGACTCCGTCAAGGGACGTTTCACCTTCTCTCAGGAGAACGCGA AGAATACTGTGTATCTTCAGATGAACAGCCTGAAGCCGGAGGAT ACAGCAATGTATTACTGCGGTTGCGCGACCCTGGGTAGCAGGAC CATCTGGGGTCAAGGCACCCAGGTGACAGTGTCCTCC | 316 |
| mIL23R VHH37 | CAGGTCCAGCTTCAGGAATCAGGAGGCGGGCTTGTGCAGCCGGG AGGCAGCCTGCGCCTGTCCTGCGCAACCTCCGGCTTTACCTTCTC CAGCGGAGCCATGACCTGGGTGCGGCAGGCCCCCGGTAAGGGCC TGGATTGGGTGTCTGGCATCGACTCCGGCGGAACCACTGTGTACG CTGATTCTGTGAAGGGTCGCTTCACAATTAGTAAGGACAACGCTA AGAACACCCTGTACCTCCAGATGAACTCATTGAAGACAGAGGAT ACCGCCGTGTACTATTGTGCAACCGGCCTCCCCTGGGGGAACACC TGGCGCACCACTGGTCAGGGAACACAAGTAACCGTGAGCAGC | 317 |
| mIL23R VHH38 | CAGGTCCAGCTCCAGGAGAGTGGCGGGGGACTCGTGCAGCCTGG TGGCTCTTTGCGCCTGAGCTGCGCGGCAAGCGGATTTACATTTTC CACCAGTGCTATGACCTGGGTGCGCCAGGCTCCCGGCAAGGGAC TGGACTGGGTAAGCGGTATTGATTCCGGCGGAACGACTGTGTAC GCTGATAGCGTAAAGGGCCGCTTTACCATCAGCAAAGACAACGC CAAAAATACCCTTTACCTGCAAATGAACTCTTTGAAGACGGAGG ACACCGCTGTGTATTACTGCGCCACTGGCCTCCCTTGGGGCAACA TCTGGAGAACCCGTGGTCAGGGCACCCAGGTTACCGTGTCCTCC | 318 |
| mIL23R VHH39 | CAGGTCCAACTCCAGGAGTCCGGCGGAGGCTTGGTGCAGCCTGG AGGCTCTCTGCGGCTGTCCTGCGCCGCATCAGGTTTTACGTTTTCT CGGTCTGCCATGACCTGGGTCAGACAGGCACCAGGCAAGGGCCT GGATTGGGTGTCCGGTATTGACTCTGGTGGCACTACCGTGTATGC CGACTCCGTTAAGGGCCGTTTCACCATCTCCAGGGACTCTGCCAA GAACACATTGTATTTGCAAATGAACGGCCTCAAAACTGAGGACA CCGCAGTCTACTATTGTGCAATCGGGCTTCCGTGGGGCAACACGT GGAGAACCAGGGGCCAGGGGACTCAGGTCACCGTGTCATCC | 319 |
| mIL23R VHH40 | CAGGTCCAGCTCCAGGAGTCAGGTGGAGGCCTGGTGCAACCCGG AGGCTCCCTCCGCCTGTCCTGTGCAGCCTCCGGCTTTACCTTTCGC CTGACCGCGATGAGGTGGGTTCGGCAGGCCCCTGGCAAAGGGCT GGAGTGGGTTAGCGGCATCGACTCCAGGGGCTCCACCATTTACG CCGACTCTGTCAAGGGGCGTTTCACCATTTCTAAGGACAACGCTA AGAATACCCTCTACCTCCAGCTCAACTCCCTGAAGAGTGAAGAC ACCGCCATGTATTACTGTGCCCAGGGCGTCTACGGAGACACTTAC AGCGGGTCCCAGGGTACTCAGGTGACCGTGTCTTCC | 320 |
| mIL23R VHH41 | CAAGTCCAGTTGCAGGAGTCAGGAGGTGGCCTGGTGCAACCCGG TGGCTCCCTCCGTCTGACCTGCGCTGCGTCTGGTTTCACTTTCTCA ACTTCAGCTATGACATGGGTCCGCCAGGCACCGGGGAAGGGCCT CGACTGGGTATCTGGGATCGACAGCGGAGGCACCACTGTCTATG CCGATTCCGTGAAAGGACGCTTCACTATTAGCAAGGACAACGCT AAAAACACCCTGTATTTGCAGATGAATAGCCTCAAAACTGAAGA TACTGCCGTTTACTATTGCGCCACTGGCCTCCCCTGGGGCAACAC CTGGCGCACAAGGGGTCAGGGTACTCAGGTAACCGTGTCCTCT | 321 |
| mIL23R VHH42 | CAGGTGCAGCTGCAAGAGTCCGGTGGCGGTCTGGTGCAGCCCGG AGGCAGTCTGAGGCTCTCCTGCGCTGCCTCTGGATTCACCTTCAG CAACTACGCTATGCGCTGGGTGCGGCAGGCCCCCGGCAAGGGCC TGGAGTGGGTCAGTGGCATCGACAGTCGCGGAAGTACTATTTAT GCCGACTCCGTGAAGGGAAGGTTCACTATTTCCAAGGACAACGC CAAAAACACTCTGTACTTGCAGCTGAACTCCTTGAAGACTGAGG ACACTGCCATGTACTATTGCGCCCAGGGAGTCTATGGGGACACCT ATTCCGGGAGCCAGGGCACTCAGGTGACCGTGTCAAGT | 322 |
| mIL23R VHH43 | CAGGTTCAGCTCCAGGAATCCGGTGGAGGGTCCGTGCAGGCCGG GGGCAGCCTGAGACTGTCCTGTGCTGCCTCTGGTTATACGTTTTG CATGGCGTGGTTCCGGCAGGCTCCTGGAAAAGAGCGCGAGGGCG TGGCAAGATTCTACACTAGAGATGGTTACACCTATTACTCCGACT CTGTCAAGGGGAGGTTTACCATCTCTCAGGACAACGCCAAGAAC ACTTTGTACCTCCAGATGAACTCCCTGAAGTCTGAGGACACCGCC ATGTATTACTGTGCAGCCGATCTGACCCGGTGCAGTTCCAACAAG AACGATTTCCGCTATTGGGGCCAGGGCACACAGGTCACAGTCTC CTCC | 323 |

TABLE 5-continued

| Nucleic Acid sequences Encoding IL23 VHHs of Table 3 | | |
|---|---|---|
| Name | DNA Sequence | SEQ ID NO |
| mIL23R VHH44 | CAAGTACAGCTCCAAGAGTCTGGGGGAGGTCTTGTGCAGCCCGG AGGCTCTTTGCGTCTGTCATGTGCGGCCAGCGGATTCACATTCAG GCTGTCTGCAATGCGTTGGGTGCGCCAAGCGCCTGGCAAGGGGT TTGAATGGGTGTCTGGAATTGATTCCCGTGGCTCTACCATCTATG CCGATTCTGTTAAAGGCCGCTTTACCATCTCCAAGGATAACGCAA AAAACACACTGTACTTGCAGCTGAATAGCCTGAAAACTGAGGAC ACCGCTATGTATTACTGCGCTCAGGGAGTGTATGGCGACACTTAT TCCGGCAGCCAGGGCACTCAGGTGACAGTTAGCTCC | 324 |
| mIL23R VHH45 | CAGGTGCAGCTCCAGGAGTCCGGCGGTGGACTCGTGCAACCCGG CGGTTCCCTTAGATTGTCTTGCGCCGCTTCAGGTTTTACCTTTCGC TTGTCCGCTATGCGGTGGGTTCGCCAAGCGCCAGGAAAAGGCCT GGAGTGGGTCTCCGGTATTGATTCCAGAGGCTCCACCATCTACGC CGACTCTGTCGAGGGCAGGTTCACCATCAGCAAGGACAACGCAA AGAACACCCTGTATCTTCAGCTTAATAGTCTGAAGACCGAGGAC ACTGCGATGTATTACTGCGCTCAGGGAGTGTACGGTGATACCTAC TCCGGCTCCCAGGGAACTCAGGTGACCGTCTCCAGC | 325 |
| mIL23R VHH46 | CAAGTTCAGTTGCAGGAGAGCGGAGGGGGCCTGGTTCAGCCGGG AGGCTCCCTGAGGCTGTCCTGCGCTGCGAGTGGCTTCACTTTTAG GTTGTCCGCTATGCGCTGGGTGCGCCAGGCTCCTGGGAAGGGTCT GGAGTGGGTGTCTGGGATTGACTCCAGAGGTAGTACCATTTACG CCGACTCCGTCAAGGGACGCTTCACCATCTCCAAGGACGATGCC AAGAACACCCTGTATCTCCAGCTGAACTCACTCAAGACCGAAGA CACGGCAATGTATTACTGTGCCCAGGGTGTGTATGGTGACACTTA CTCTGGCTCTCAGGGCACTCAAGTGACCGTTTCTTCC | 326 |

The disclosure further provides recombinant viral and non-viral vectors comprising a nucleic acid encoding the IL23R binding molecules of the present disclosure or the CDRs of the IL23R binding molecules of the present disclosure.

The disclosure further provides host cells comprising recombinant viral and non-viral vectors comprising a nucleic acid the IL23R binding molecules of the present disclosure or the CDRs of the IL23R binding molecules of the present disclosure.

The disclosure further provides host cells comprising recombinant viral and non-viral vectors comprising a nucleic acid the IL23R binding molecules of the present disclosure or the CDRs of the IL23R binding molecules of the present disclosure.

The disclosure further provides pharmaceutical formulations comprising the recombinant viral and non-viral vectors comprising a nucleic acid the IL23R binding molecules of the present disclosure and methods of use thereof in the treatment or prevention of diseases, disorders or conditions in a mammalian subject.

The disclosure further kits comprising the IL23R binding molecules of the present disclosure.

In another aspect, the present disclosure provides constructs for the targeted delivery of therapeutic agents to a cell expressing the IL23R receptor, wherein the IL23R binding molecule is conjugated to one or more therapeutic agents, optionally through a chemical or polypeptide linker. The disclosure further provides methods of use of the foregoing in the treatment of disease associated with expression of the IL23R in a subject, the method comprising the administration of a therapeutically effective amount of the IL23R binding molecule conjugated to the therapeutic agent to a subject in need to treatment, alone or in combination with one or more additional therapeutic agents. In some embodiments, the diseases amenable to treatment are diseases, disorders or conditions associated with signaling from receptor comprising the IL23R. In some embodiments, the IL23R binding molecules of the present disclosure are useful in the treatment of diseases associated with dysregulated T cell or B cell activity. In some embodiments, the IL23R binding molecules of the present disclosure are useful in the treatment of autoimmune disease associated with aberrant cell activity arising from dysregulated signaling in cells expressing the IL23R. In some embodiments, the IL23R binding molecules of the present disclosure are useful in the treatment of neoplastic diseases associated with aberrant cell activity arising from dysregulated signaling in cells expressing the IL23R.

In another aspect, the present disclosure provides constructs for the identification of cells expressing the IL23R receptor wherein the IL23R binding molecule is conjugated to one or more imaging agents, optionally through a chemical or polypeptide linker. The disclosure further provides methods of use of the foregoing in the identification of cells expressing the IL23R receptor in a subject, the method comprising the administration of a effective amount of the IL23R binding molecule conjugated to the imaging agent to a subject in need to treatment and evaluating the subject for the presence of the imaging agent that is conjugated to the IL23R binding molecule.

In another aspect, the present disclosure provides IL23R binding molecules which have been modified for extended duration of action in vivo wherein the IL23R binding molecule is conjugated to one or more carrier molecules.

The present disclosure provides IL23R binding molecules comprising a polypeptide sequence that specifically binds to the extracellular domain of the IL23R and methods of use thereof in the isolation, depletion or enrichment of cells expressing the IL23R in a biological sample.

DETAILED DESCRIPTION OF THE INVENTION

Introduction

In order for the present disclosure to be more readily understood, certain terms and phrases are defined below as well as throughout the specification. The definitions provided herein are non-limiting and should be read in view of the knowledge of one of skill in the art would know.

Before the present methods and compositions are described, it is to be understood that this disclosure is not limited to particular method or composition described, as such may, of course, vary.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited.

It should be noted that as used herein and in the appended claims, the singular forms “a”, “an”, and “the” include plural referents unless the context clearly dictates otherwise. Thus, for example, reference to “a cell” includes a plurality of such cells and reference to “the peptide” includes reference to one or more peptides and equivalents thereof, e.g., polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

It will be appreciated that throughout this disclosure reference is made to amino acids according to the single letter or three letter codes. For the reader’s convenience, the single and three letter amino acid codes are provided in Table 6 below:

TABLE 6

Amino Acid Abbreviations

| Single Letter Abbreviation | Name | 3-letter abbreviation |
|---|---|---|
| G | Glycine | Gly |
| P | Proline | Pro |
| A | Alanine | Ala |
| V | Valine | Val |
| L | Leucine | Leu |
| I | Isoleucine | Ile |
| M | Methionine | Met |

TABLE 6-continued

Amino Acid Abbreviations

| Single Letter Abbreviation | Name | 3-letter abbreviation |
|---|---|---|
| C | Cysteine | Cys |
| F | Phenylalanine | Phe |
| Y | Tyrosine | Tyr |
| W | Tryptophan | Trp |
| H | Histidine | His |
| K | Lysine | Lys |
| R | Arginine | Arg |
| Q | Glutamine | Gln |
| N | Asparagine | Asn |
| E | Glutamic Acid | Glu |
| D | Aspartic Acid | Asp |
| S | Serine | Ser |
| T | Threonine | Thr |

Standard methods in molecular biology are described in the scientific literature (see, e.g., Sambrook and Russell (2001) Molecular Cloning, 3rd ed., Cold Spring Harbor Laboratory Press, Cold Spring Harbor, N.Y.; and Ausubel, et al. (2001) Current Protocols in Molecular Biology, Vols. 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4)). The scientific literature describes methods for protein purification, including immunoprecipitation, chromatography, electrophoresis, centrifugation, and crystallization, as well as chemical analysis, chemical modification, post-translational modification, production of fusion proteins, and glycosylation of proteins (see, e.g., Coligan, et al. (2000) Current Protocols in Protein Science, Vols. 1-2, John Wiley and Sons, Inc., NY).

Definitions

Unless otherwise indicated, the following terms are intended to have the meaning set forth below. Other terms are defined elsewhere throughout the specification.

Activate: As used herein the term “activate” is used in reference to a receptor or receptor complex to reflect a biological effect, directly and/or by participation in a multicomponent signaling cascade, arising from the binding of an agonist ligand to a receptor responsive to the binding of the ligand.

Activity: As used herein, the term “activity” is used with respect to a molecule to describe a property of the molecule with respect to a test system (e.g., an assay) or biological or chemical property (e.g., the degree of binding of the molecule to another molecule) or of a physical property of a material or cell (e.g., modification of cell membrane potential). Examples of such biological functions include but are not limited to catalytic activity of a biological agent, the ability to stimulate intracellular signaling, gene expression, cell proliferation, the ability to modulate immunological activity such as inflammatory response. “Activity” is typically expressed as a level of a biological activity per unit of agent tested such as [catalytic activity]/[mg protein], [immunological activity]/[mg protein], international units (IU) of activity, [STAT5 phosphorylation]/[mg protein], [proliferation]/[mg protein], plaque forming units (pfu), etc. As used herein, the term proliferative activity refers to an activity that promotes cell proliferation and replication, including dysregulated cell division such as that observed in neoplastic diseases, inflammatory diseases, fibrosis, dysplasia, cell transformation, metastasis, and angiogenesis.

Administer/Administration: The terms "administration" and "administer" are used interchangeably herein to refer the act of contacting a subject, including contacting a cell, tissue, organ, or biological fluid of the subject in vitro, in vivo or ex vivo with an agent (e.g., an a IL23R binding molecule or an engineered cell expressing an IL23R binding molecule, a chemotherapeutic agent, an antibody, or a pharmaceutical formulation comprising one or more of the foregoing). Administration of an agent may be achieved through any of a variety of art recognized methods including but not limited to the topical administration, intravascular injection (including intravenous or intraarterial infusion), intradermal injection, subcutaneous injection, intramuscular injection, intraperitoneal injection, intracranial injection, intratumoral injection, transdermal, transmucosal, iontophoretic delivery, intralymphatic injection, intragastric infusion, intraprostatic injection, intravesical infusion (e.g., bladder), inhalation (e.g respiratory inhalers including dry-powder inhalers), intraocular injection, intraabdominal injection, intralesional injection, intraovarian injection, intracerebral infusion or injection, intracerebroventricular injection (ICVI), and the like. The term "administration" includes contact of an agent to the cell, tissue or organ as well as the contact of an agent to a fluid, where the fluid is in contact with the cell, tissue or organ.

Affinity: As used herein the term "affinity" refers to the degree of specific binding of a first molecule (e.g., a ligand) to a second molecule (e.g., a receptor) and is measured by the equilibrium dissociation constant ($K_D$), a ratio of the dissociation rate constant between the molecule and its target ($K_{off}$) and the association rate constant between the molecule and its target ($K_{on}$).

Agonist: As used herein, the term "agonist" refers a first agent that specifically binds a second agent ("target") and interacts with the target to cause or promote an increase in the activation of the target. In some instances, agonists are activators of receptor proteins that modulate cell activation, enhance activation, sensitize cells to activation by a second agent, or up-regulate the expression of one or more genes, proteins, ligands, receptors, biological pathways, that may result in cell proliferation or pathways that result in cell cycle arrest or cell death such as by apoptosis. In some embodiments, an agonist is an agent that binds to a receptor and alters the receptor state resulting in a biological response that mimics the effect of the endogenous ligand of the receptor. The term "agonist" includes partial agonists, full agonists and superagonists. An agonist may be described as a "full agonist" when such agonist which leads to a substantially full biological response (i.e. the response associated with the naturally occurring ligand/receptor binding interaction) induced by receptor under study, or a partial agonist. A "superagonist" is a type of agonist that can produce a maximal response greater than the endogenous agonist for the target receptor, and thus has an activity of more than 100% of the native ligand. A super agonist is typically a synthetic molecule that exhibits greater than 110%, alternatively greater than 120%, alternatively greater than 130%, alternatively greater than 140%, alternatively greater than 150%, alternatively greater than 160%, or alternatively greater than 170% of the response in an evaluable quantitative or qualitative parameter of the naturally occurring form of the molecule when evaluated at similar concentrations in a comparable assay. It should be noted that the biological effects associated with the full agonist may differ in degree and/or in kind from those biological effects of partial or superagonists. In contrast to agonists, antagonists may specifically bind to a receptor but do not result the signal cascade typically initiated by the receptor and may to modify the actions of an agonist at that receptor. Inverse agonists are agents that produce a pharmacological response that is opposite in direction to that of an agonist.

Antagonist: As used herein, the term "antagonist" or "inhibitor" refers a molecule that opposes the action(s) of an agonist. An antagonist prevents, reduces, inhibits, or neutralizes the activity of an agonist, and an antagonist can also prevent, inhibit, or reduce constitutive activity of a target, e.g., a target receptor, even where there is no identified agonist. Inhibitors are molecules that decrease, block, prevent, delay activation, inactivate, desensitize, or down-regulate, e.g., a gene, protein, ligand, receptor, biological pathway including an immune checkpoint pathway, or cell.

Antibody: As used herein, the term "antibody" refers collectively to: (a) a glycosylated or non-glycosylated immunoglobulin that specifically binds to target molecule, and (b) immunoglobulin derivatives thereof, including but not limited to antibody fragments such as single domain antibodies. In some embodiments the immunoglobulin derivative competes with the immunoglobulin from which it was derived for binding to the target molecule. The term antibody is not restricted to immunoglobulins derived from any particular species and includes murine, human, equine, camelids, antibodies of cartilaginous fishes including, but not limited to, sharks. The term "antibody" encompasses antibodies isolatable from natural sources or from animals following immunization with an antigen and as well as engineered antibodies including monoclonal antibodies, bispecific antibodies, tri-specific, chimeric antibodies, humanized antibodies, human antibodies, CDR-grafted, veneered, or deimmunized (e.g., to remove T-cell epitopes) antibodies, camelized (in the case of VHHs), or molecules comprising binding domains of antibodies (e.g., CDRs) in non-immunoglobulin scaffolds. The term "antibody" should not be construed as limited to any particular means of synthesis and includes naturally occurring antibodies isolatable from natural sources and as well as engineered antibodies molecules that are prepared by "recombinant" means including antibodies isolated from transgenic animals that are transgenic for human immunoglobulin genes or a hybridoma prepared therefrom, antibodies isolated from a host cell transformed with a nucleic acid construct that results in expression of an antibody, antibodies isolated from a combinatorial antibody library including phage display libraries. In one embodiment, an "antibody" is a mammalian immunoglobulin of the IgG1, IgG2, IgG3 or IgG4 class. In some embodiments, the antibody is a "full length antibody" comprising variable and constant domains providing binding and effector functions. The term "single domain antibody" (sdAb) as used herein refers an antibody fragment consisting of a monomeric variable antibody domain that is able to bind specifically to an antigen and compete for binding with the parent antibody from which it is derived. The term "single domain antibody" includes scFv and VHH molecules. As used herein, the term "VHH" refers to a single domain antibody derived from camelid antibody typically obtained from immunization of camelids (including camels, llamas and alpacas (see, e.g., Hamers-Casterman, et al. (1993) Nature 363:446-448). VHHs are also referred to as heavy chain antibodies or Nanobodies® as Single domain antibodies may also be derived from non-mammalian sources such as VHHs obtained from IgNAR antibodies immunization of cartilaginous fishes including, but not limited to, sharks.

Biological Sample: As used herein, the term "biological sample" or "sample" refers to a sample obtained (or derived) from a subject. By way of example, a biological sample comprises a material selected from the group consisting of body fluids, blood, whole blood, plasma, serum, mucus secretions, saliva, cerebrospinal fluid (CSF), bronchoalveolar lavage fluid (BALF), fluids of the eye (e.g., vitreous fluid, aqueous humor), lymph fluid, lymph node tissue, spleen tissue, bone marrow, tumor tissue, including immunoglobulin enriched or cell-type specific enriched fractions derived from one or more of such tissues.

IL23R cell: The terms "IL23R cell", "IL23R-expressing cell", "IL23R-positive cell" and "IL23R+" cell are used interchangeably herein to refer to a cell which expresses and displays the IL23R antigen on the extracellular surface of the cell membrane. Similarly, the terms "IL23R-negative cell", "IL23R− cells" as are used interchangeably herein to describe cells which do not express or display IL23R antigen on the cell surface.

CDR: As used herein, the term "CDR" or "complementarity determining region" is intended to mean the non-contiguous antigen combining sites found within the variable region of both heavy and light chain immunoglobulin polypeptides. CDRs have been described by Kabat et al., J. Biol. Chem. 252:6609-6616 (1977); Kabat, et al., U.S. Dept. of Health and Human Services publication entitled "Sequences of proteins of immunological interest" (1991) (also referred to herein as "Kabat 1991" or "Kabat"); by Chothia, et al. (1987) J. Mol. Biol. 196:901-917 (also referred to herein as "Chothia"); and MacCallum, et al. (1996) J. Mol. Biol. 262:732-745, where the definitions include overlapping or subsets of amino acid residues when compared against each other. Nevertheless, application of either definition to refer to a CDR of an antibody or grafted antibodies or variants thereof is intended to be within the scope of the term as defined and used herein. The term "Chothia Numbering" as used herein is recognized in the arts and refers to a system of numbering amino acid residues based on the location of the structural loop regions (Chothia et al. 1986, Science 233:755-758; Chothia & Lesk 1987, JMB 196:901-917; Chothia et al. 1992, JMB 227:799-817). For purposes of the present disclosure, unless otherwise specifically identified, the positioning of CDRs2 and 3 in the variable region of an antibody follows Kabat numbering or simply, "Kabat." The positioning of CDR1 in the variable region of an antibody follows a hybrid of Kabat and Chothia numbering schemes.

Comparable: As used herein, the term "comparable" is used to describe the degree of difference in two measurements of an evaluable quantitative or qualitative parameter. For example, where a first measurement of an evaluable quantitative parameter and a second measurement of the evaluable parameter do not deviate beyond a range that the skilled artisan would recognize as not producing a statistically significant difference in effect between the two results in the circumstances, the two measurements would be considered "comparable." In some instances, measurements may be considered "comparable" if one measurement deviates from another by less than 35%, alternatively by less than 30%, alternatively by less than 25%, alternatively by less than 20%, alternatively by less than 15%, alternatively by less than 10%, alternatively by less than 7%, alternatively by less than 5%, alternatively by less than 4%, alternatively by less than 3%, alternatively by less than 2%, or by less than 1%. In particular embodiments, one measurement is comparable to a reference standard if it deviates by less than 15%, alternatively by less than 10%, or alternatively by less than 5% from the reference standard.

Derived From: As used herein in the term "derived from", in the context of an amino acid sequence is meant to indicate that the polypeptide or nucleic acid has a sequence that is based on that of a reference polypeptide or nucleic acid and is not meant to be limiting as to the source or method in which the protein or nucleic acid is made. By way of example, the term "derived from" includes homologs or variants of reference amino acid or DNA sequences.

Effective Concentration (EC): As used herein, the terms "effective concentration" or its abbreviation "EC" are used interchangeably to refer to the concentration of an agent in an amount sufficient to effect a change in a given parameter in a test system. The abbreviation "E" refers to the magnitude of a given biological effect observed in a test system when that test system is exposed to a test agent. When the magnitude of the response is expressed as a factor of the concentration ("C") of the test agent, the abbreviation "EC" is used. In the context of biological systems, the term Emax refers to the maximal magnitude of a given biological effect observed in response to a saturating concentration of an activating test agent. When the abbreviation EC is provided with a subscript (e.g., $EC_{40}$, $EC_{50}$, etc.) the subscript refers to the percentage of the Emax of the biological response observed at that concentration. For example, the concentration of a test agent sufficient to result in the induction of a measurable biological parameter in a test system that is 30% of the maximal level of such measurable biological parameter in response to such test agent, this is referred to as the "$EC_{30}$" of the test agent with respect to such biological parameter. Similarly, the term "$EC_{100}$" is used to denote the effective concentration of an agent that results the maximal (100%) response of a measurable parameter in response to such agent. Similarly, the term $EC_{50}$ (which is commonly used in the field of pharmacodynamics) refers to the concentration of an agent sufficient to results in the half-maximal (about 50%) change in the measurable parameter. The term "saturating concentration" refers to the maximum possible quantity of a test agent that can dissolve in a standard volume of a specific solvent (e.g., water) under standard conditions of temperature and pressure. In pharmacodynamics, a saturating concentration of a drug is typically used to denote the concentration sufficient of the drug such that all available receptors are occupied by the drug, and $EC_{50}$ is the drug concentration to give the half-maximal effect.

Enriched: As used herein in the term "enriched" refers to a sample that is non-naturally manipulated so that a species (e.g., a molecule or cell) of interest is present in: (a) a greater concentration (e.g., at least 3-fold greater, alternatively at least 5-fold greater, alternatively at least 10-fold greater, alternatively at least 50-fold greater, alternatively at least 100-fold greater, or alternatively at least 1000-fold greater) than the concentration of the species in the starting sample, such as a biological sample (e.g., a sample in which the molecule naturally occurs or in which it is present after administration); or (b) a concentration greater than the environment in which the molecule was made (e.g., a recombinantly modified bacterial or mammalian cell).

Extracellular Domain: As used herein the term "extracellular domain" or its abbreviation "ECD" refers to the portion of a cell surface protein (e.g., a cell surface receptor) which is external to of the plasma membrane of a cell. The cell surface protein may be transmembrane protein, a cell surface or membrane associated protein.

Identity: The term "identity," as used herein in reference to polypeptide or DNA sequences, refers to the subunit sequence identity between two molecules. When a subunit position in both of the molecules is occupied by the same monomeric subunit (i.e., the same amino acid residue or nucleotide), then the molecules are identical at that position. The similarity between two amino acid or two nucleotide sequences is a direct function of the number of identical positions. In general, the sequences are aligned so that the highest order match is obtained. If necessary, identity can be calculated using published techniques and widely available computer programs, such as BLAST 2.0 algorithms, which are described in Altschul et al. (1990) *J Mol. Biol.* 215: 403-410 and Altschul, et al. (1977) *Nucleic Acids Res.* 25: 3389-3402. Software for performing BLAST analyses is publicly available through the National Center for Biotechnology Information (NCBI) web site. The algorithm involves first identifying high scoring sequence pairs (HSPs) by identifying short words of length W of the query sequence, which either match or satisfy some positive-valued threshold score "T" when aligned with a word of the same length in a database sequence. T is referred to as the neighborhood word score threshold (Altschul, et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters "M" (the reward score for a pair of matching residues; always >0) and "N" (the penalty score for mismatching residues; always <0). For amino acid sequences, a scoring matrix is used to calculate the cumulative score. Extension of the word hits in each direction are halted when: (a) the cumulative alignment score falls off by the quantity X from its maximum achieved value; the cumulative score goes to zero or below, due to the accumulation of one or more negative-scoring residue alignments; or (b) the end of either sequence is reached. The BLAST algorithm parameters "W", "T", and "X" determine the sensitivity and speed of the alignment. The BLASTN program (for nucleotide sequences) functions similarly but uses as defaults a word size ("W") of 28, an expectation ("E") of 10, M=1, N=−2, and a comparison of both strands. For amino acid sequences, the BLASTP program uses as defaults a word size (W) of 3, an expectation (E) of 10, and the BLOSUM62 scoring matrix (see Henikoff & Henikoff, (1989) PNAS (USA) 89:10915-10919).

In An Amount Sufficient Amount to Cause a Response: As used herein the phrase "in an amount sufficient to cause a response" is used in reference to the amount of a test agent sufficient to provide a detectable change in the level of an indicator measured before (e.g., a baseline level) and after the application of a test agent to a test system. In some embodiments, the test system is a cell, tissue or organism. In some embodiments, the test system is an in vitro test system such as a fluorescent assay. In some embodiments, the test system is an in vivo system which involves the measurement of a change in the level a parameter of a cell, tissue, or organism reflective of a biological function before and after the application of the test agent to the cell, tissue, or organism. In some embodiments, the indicator is reflective of biological function or state of development of a cell evaluated in an assay in response to the administration of a quantity of the test agent. In some embodiments, the test system involves the measurement of a change in the level an indicator of a cell, tissue, or organism reflective of a biological condition before and after the application of one or more test agents to the cell, tissue, or organism. The term "in an amount sufficient to effect a response" may be sufficient to be a therapeutically effective amount but may also be more or less than a therapeutically effective amount.

In Need of Treatment: The term "in need of treatment" as used herein refers to a judgment made by a physician or other caregiver with respect to a subject that the subject requires or will potentially benefit from treatment. This judgment is made based on a variety of factors that are in the realm of the physician's or caregiver's expertise.

In Need of Prevention: As used herein the term "in need of prevention" refers to a judgment made by a physician or other caregiver with respect to a subject that the subject requires or will potentially benefit from preventative care. This judgment is made based upon a variety of factors that are in the realm of a physician's or caregiver's expertise.

Inhibitor: As used herein the term "inhibitor" refers to a molecule that decreases, blocks, prevents, delays activation of, inactivates, desensitizes, or down-regulates, e.g., a gene, protein, ligand, receptor, or cell. An inhibitor can also be defined as a molecule that reduces, blocks, or inactivates a constitutive activity of a cell or organism.

Intracellular Domain: As used herein the term "intracellular domain" or its abbreviation "ICD" refers to the portion of a cell surface protein (e.g., a cell surface receptor) which is inside of the plasma membrane of a cell. The ICD may include the entire cytoplasmic portion of a transmembrane protein or membrane associated protein, or intracellular protein.

Isolated: As used herein the term "isolated" is used in reference to a polypeptide of interest that, if naturally occurring, is in an environment different from that in which it can naturally occur. "Isolated" is meant to include polypeptides that are within samples that are substantially enriched for the polypeptide of interest and/or in which the polypeptide of interest is partially or substantially purified. Where the polypeptide is not naturally occurring, "isolated" indicates that the polypeptide has been separated from an environment in which it was synthesized, for example isolated from a recombinant cell culture comprising cells engineered to express the polypeptide or by a solution resulting from solid phase synthetic means.

Kabat Numbering: The term "Kabat numbering" as used herein is recognized in the art and refers to a system of numbering amino acid residues which are more variable than other amino acid residues (e.g., hypervariable) in the heavy and light chain regions of immunoglobulins (Kabat, et al., (1971) *Ann. NY Acad. Sci.* 190:382-93; Kabat, et al., (1991) *Sequences of Proteins of Immunological Interest*, Fifth Edition, U.S. Department of Health and Human Services, NIH Publication No. 91-3242). For purposes of the present disclosure, unless otherwise specifically identified, the positioning of CDRs in the variable region of an antibody follows Kabat numbering or simply, "Kabat."

Ligand: As used herein, the term "ligand" refers to a molecule that specifically binds a receptor and causes a change in the receptor so as to effect a change in the activity of the receptor or a response in cell that expresses that receptor. In one embodiment, the term "ligand" refers to a molecule or complex thereof that can act as an agonist or antagonist of a receptor. As used herein, the term "ligand" encompasses natural and synthetic ligands. "Ligand" also encompasses small molecules, peptide mimetics of cytokines and antibodies. The complex of a ligand and receptor is termed a "ligand-receptor complex." A ligand may comprise one domain of a polyprotein or fusion protein (e.g., either domain of an antibody/ligand fusion protein).

Modulate: As used herein, the terms "modulate", "modulation" and the like refer to the ability of a test agent to cause a response, either positive or negative or directly or indirectly, in a system, including a biological system, or biochemical pathway. The term modulator includes both agonists (including partial agonists, full agonists and superagonists) and antagonists.

Neoplastic Disease: As used herein, the term "neoplastic disease" refers to disorders or conditions in a subject arising from cellular hyper-proliferation or unregulated (or dysregulated) cell replication. The term neoplastic disease refers to disorders arising from the presence of neoplasms in the subject. Neoplasms may be classified as: (1) benign (2) pre-malignant (or "pre-cancerous"); and (3) malignant (or "cancerous"). The term "neoplastic disease" includes neoplastic-related diseases, disorders and conditions referring to conditions that are associated, directly or indirectly, with neoplastic disease, and includes, e.g., angiogenesis and precancerous conditions such as dysplasia or smoldering multiple myeloma. Examples of benign disorders arising from dysregulated cell replication include hypertrophic scars such as keloid scars.

Nucleic Acid: The terms "nucleic acid", "nucleic acid molecule", "polynucleotide" and the like are used interchangeably herein to refer to a polymeric form of nucleotides of any length, either deoxyribonucleotides or ribonucleotides, or analogs thereof. Non-limiting examples of polynucleotides include linear and circular nucleic acids, messenger RNA (mRNA), complementary DNA (cDNA), recombinant polynucleotides, vectors, probes, primers and the like.

Operably Linked: The term "operably linked" is used herein to refer to the relationship between molecules, typically polypeptides or nucleic acids, which are arranged in a construct such that each of the functions of the component molecules is retained although the operable linkage may result in the modulation of the activity, either positively or negatively, of the individual components of the construct. For example, the operable linkage of a polyethylene glycol (PEG) molecule to a wild-type protein may result in a construct where the biological activity of the protein is diminished relative to the to the wild-type molecule, however the two are nevertheless considered operably linked. When the term "operably linked" is applied to the relationship of multiple nucleic acid sequences encoding differing functions, the multiple nucleic acid sequences when combined into a single nucleic acid molecule that, for example, when introduced into a cell using recombinant technology, provides a nucleic acid which is capable of effecting the transcription and/or translation of a particular nucleic acid sequence in a cell. For example, the nucleic acid sequence encoding a signal sequence may be considered operably linked to DNA encoding a polypeptide if it results in the expression of a preprotein whereby the signal sequence facilitates the secretion of the polypeptide; a promoter or enhancer is considered operably linked to a coding sequence if it affects the transcription of the sequence; or a ribosome binding site is considered operably linked to a coding sequence if it is positioned so as to facilitate translation. Generally, in the context of nucleic acid molecules, the term "operably linked" means that the nucleic acid sequences being linked are contiguous, and, in the case of a secretory leader or associated subdomains of a molecule, contiguous and in reading phase. However, certain genetic elements such as enhancers may function at a distance and need not be contiguous with respect to the sequence to which they provide their effect but nevertheless may be considered operably linked.

Parent Polypeptide: As used herein, the terms "parent polypeptide" or "parent protein" are used interchangeably to designate the source of a second polypeptide (e.g., a derivative, mutein or variant) which is modified with respect to a first "parent" polypeptide. In some instances, the parent polypeptide is a wild-type or naturally occurring form of a protein. In some instance, the parent polypeptide may be a modified form a naturally occurring protein that is further modified. The term "parent polypeptide" may refer to the polypeptide itself or compositions that comprise the parent polypeptide (e.g., glycosylated or PEGylated forms and/or fusion proteins comprising the parent polypeptide).

Partial Agonist: As used herein, the term "partial agonist" refers to a molecule that specifically binds that bind to and activate a given receptor but possess only partial activation the receptor relative to a full agonist. Partial agonists may display both agonistic and antagonistic effects. For example, when both a full agonist and partial agonist are present, the partial agonist acts as a competitive antagonist by competing with the full agonist for the receptor binding resulting in net decrease in receptor activation relative to the contact of the receptor with the full agonist in the absence of the partial agonist. Partial agonists can be used to activate receptors to give a desired submaximal response in a subject when inadequate amounts of the endogenous ligand are present, or they can reduce the overstimulation of receptors when excess amounts of the endogenous ligand are present. The maximum response ($E_{max}$) produced by a partial agonist is called its intrinsic activity and may be expressed on a percentage scale where a full agonist produced a 100% response. An partial agonist may have greater than 10% but less than 100%, alternatively greater than 20% but less than 100%, alternatively greater than 30% but less than 100%, alternatively greater than 40% but less than 100%, alternatively greater than 50% but less than 100%, alternatively greater than 60% but less than 100%, alternatively greater than 70% but less than 100%, alternatively greater than 80% but less than 100%, or alternatively greater than 90% but less than 100%, of the activity of the reference polypeptide when evaluated at similar concentrations in a given assay system.

Polypeptide: As used herein the terms "polypeptide," "peptide," and "protein", used interchangeably herein, refer to a polymeric form of amino acids of any length, which can include genetically coded and non-genetically coded amino acids, chemically or biochemically modified or derivatized amino acids, and polypeptides having modified polypeptide backbones. The term polypeptide include fusion proteins, including, but not limited to, fusion proteins with a heterologous amino acid sequence; fusion proteins with heterologous and homologous leader sequences; fusion proteins with or without N-terminal methionine residues; fusion proteins with amino acid sequences that facilitate purification such as chelating peptides; fusion proteins with immunologically tagged proteins; fusion proteins comprising a peptide with immunologically active polypeptide fragment (e.g., antigenic diphtheria or tetanus toxin or toxoid fragments) and the like.

Prevent: As used herein the terms "prevent", "preventing", "prevention" and the like refer to a course of action initiated with respect to a subject prior to the onset of a disease, disorder, condition or symptom thereof so as to prevent, suppress, inhibit or reduce, either temporarily or permanently, a subject's risk of developing a disease, disorder, condition or the like (as determined by, for example, the absence of clinical symptoms) or delaying the onset thereof. A course of action to prevent a disease, disorder or condition in a subject is typically applied in the context of a subject who is predisposed to developing a disease, disorder or condition due to genetic, experiential or environmental factors of developing a particular disease, disorder or condition. In certain instances, the terms "prevent", "preventing", "prevention" are also used to refer to the slowing of the progression of a disease, disorder or condition from an existing state to a more deleterious state.

Receptor: As used herein, the term "receptor" refers to a polypeptide having a domain that specifically binds a ligand that binding of the ligand results in a change to at least one biological property of the polypeptide. In some embodiments, the receptor is a cell membrane associated protein that comprises and extracellular domain (ECD) and a membrane associated domain which serves to anchor the ECD to the cell surface. In some embodiments of cell surface receptors, the receptor is a membrane spanning polypeptide comprising an intracellular domain (ICD) and extracellular domain (ECD) linked by a membrane spanning domain typically referred to as a transmembrane domain (TM). The binding of a cognate ligand to the receptor results in a conformational change in the receptor resulting in a measurable biological effect. In some instances, where the receptor is a membrane spanning polypeptide comprising an ECD, TM and ICD, the binding of the ligand to the ECD results in a measurable intracellular biological effect mediated by one or more domains of the ICD in response to the binding of the ligand to the ECD. In some embodiments, a receptor is a component of a multi-component complex to facilitate intracellular signaling. For example, the ligand may bind a cell surface receptor that is not associated with any intracellular signaling alone but upon ligand binding facilitates the formation of a heteromultimeric (including heterodimeric, heterotrimeric, etc.) or homomultimeric (including homodimeric, homotrimeric, homotetrameric, etc.) complex that results in a measurable biological effect in the cell such as activation of an intracellular signaling cascade (e.g., the Jak/STAT pathway). In some embodiments, a receptor is a membrane spanning single chain polypeptide comprising ECD, TM and ICD domains wherein the ECD, TM and ICD domains are derived from the same or differing naturally occurring receptor variants or synthetic functional equivalents thereof.

Recombinant: As used herein, the term "recombinant" is used as an adjective to refer to the method by which a polypeptide, nucleic acid, or cell was modified using recombinant DNA technology. A "recombinant protein" is a protein produced using recombinant DNA technology and is frequently abbreviated with a lower case "r" preceding the protein name to denote the method by which the protein was produced (e.g., recombinantly produced human growth hormone is commonly abbreviated "rhGH"). Similarly a cell is referred to as a "recombinant cell" if the cell has been modified by the incorporation (e.g., transfection, transduction, infection) of exogenous nucleic acids (e.g., ssDNA, dsDNA, ssRNA, dsRNA, mRNA, viral or non-viral vectors, plasmids, cosmids and the like) using recombinant DNA technology. The techniques and protocols for recombinant DNA technology are well known in the art such as those can be found in Sambrook, et al. (1989) Molecular Cloning: A Laboratory Manual (2d ed., Cold Spring Harbor Laboratory Press, Plainview, N.Y.) and other standard molecular biology laboratory manuals.

Response: The term "response," for example, of a cell, tissue, organ, or organism, encompasses a quantitative or qualitative change in a evaluable biochemical or physiological parameter, (e.g., concentration, density, adhesion, proliferation, activation, phosphorylation, migration, enzymatic activity, level of gene expression, rate of gene expression, rate of energy consumption, level of or state of differentiation) where the change is correlated with the activation, stimulation, or treatment, with or contact with exogenous agents or internal mechanisms such as genetic programming. In certain contexts, the terms "activation", "stimulation", and the like refer to cell activation as regulated by internal mechanisms, as well as by external or environmental factors; whereas the terms "inhibition", "down-regulation" and the like refer to the opposite effects. A "response" may be evaluated in vitro such as through the use of assay systems, surface plasmon resonance, enzymatic activity, mass spectroscopy, amino acid or protein sequencing technologies. A "response" may be evaluated in vivo quantitatively by evaluation of objective physiological parameters such as body temperature, bodyweight, tumor volume, blood pressure, results of X-ray or other imaging technology or qualitatively through changes in reported subjective feelings of well-being, depression, agitation, or pain. In some embodiments, the level of proliferation of CD3 activated primary human T-cells may be evaluated in a bioluminescent assay that generates a luminescent signal that is proportional to the amount of ATP present which is directly proportional to the number of viable cells present in culture as described in Crouch, et al. (1993) J. Immunol. Methods 160: 81-8 or using commercially available assays such as the CellTiter-Glo® 2.0 Cell Viability Assay or CellTiter-Glo® 3D Cell Viability kits commercially available from Promega Corporation, Madison WI 53711 as catalog numbers G9241 and G9681 in substantial accordance with the instructions provided by the manufacturer. In some embodiments, the level of activation of T cells in response to the administration of a test agent may be determined by flow cytometric methods as described as determined by the level of STAT (e.g., STAT1, STAT3, STAT5) phosphorylation in accordance with methods well known in the art.

Significantly Reduced Binding: As used herein, the term "exhibits significantly reduced binding" is used with respect a variant of a first molecule (e.g., a ligand or antibody) which exhibits a significant reduction in the affinity for a second molecule (e.g., receptor or antigen) relative the parent form of the first molecule. With respect to antibody variants, an antibody variant "exhibits significantly reduced binding" if the affinity of the variant antibody for an antigen if the variant binds to the native form of the receptor with and affinity of less than 20%, alternatively less than about 10%, alternatively less than about 8%, alternatively less than about 6%, alternatively less than about 4%, alternatively less than about 2%, alternatively less than about 1%, or alternatively less than about 0.5% of the parent antibody from which the variant was derived. Similarly, with respect to variant ligands, a variant ligand "exhibits significantly reduced binding" if the affinity of the variant ligand binds to a receptor with an affinity of less than 20%, alternatively less than about 10%, alternatively less than about 8%, alternatively less than about 6%, alternatively less than about 4%, alternatively less than about 2%, alternatively less than about 1%, or alternatively less than about 0.5% of the parent ligand from which the variant ligand was derived. Similarly, with respect to variant receptors, a variant ligand "exhibits significantly reduced binding" if the affinity of the variant receptors binds to a with an affinity of less than 20%, alternatively less than about 10%, alternatively less than about 8%, alternatively less than about 6%, alternatively less than about 4%, alternatively less than about 2%, alternatively less than about 1%, or alternatively less than about 0.5% of the parent receptor from which the variant receptor was derived.

Small Molecule(s): The term "small molecules" refers to chemical compounds (typically pharmaceutically active compounds) having a molecular weight that is less than about 10 kDa, less than about 2 kDa, or less than about 1 kDa. Small molecules include, but are not limited to, inorganic molecules, organic molecules, organic molecules containing an inorganic component, molecules comprising a radioactive atom, and synthetic molecules. The term "small molecule" is a term well understood to those of ordinary skill in the pharmaceutical arts and is typically used to distinguish organic chemical compounds from biologics.

Specifically Binds: As used herein the term "specifically binds" refers to the degree of affinity for which a first molecule exhibits with respect to a second molecule. In the context of binding pairs (e.g., ligand/receptor, antibody/antigen) a first molecule of a binding pair is said to specifically bind to a second molecule of a binding pair when the first molecule of the binding pair does not bind in a significant amount to other components present in the sample. A first molecule of a binding pair is said to specifically bind to a second molecule of a binding pair when the first molecule of the binding pair when the affinity of the first molecule for the second molecule is at least two-fold greater, alternatively at least five times greater, alternatively at least ten times greater, alternatively at least 20-times greater, or alternatively at least 100-times greater than the affinity of the first molecule for other components present in the sample. In a particular embodiment, where the first molecule of the binding pair is an antibody, the antibody specifically binds to the antigen (or antigenic determinant (epitope) of a protein, antigen, ligand, or receptor) if the equilibrium dissociation constant ($K_D$) between antibody and the antigen is lesser than about $10^{-6}$ M, alternatively lesser than about $10^{-8}$ M, alternatively lesser than about $10^{-10}$ M, alternatively lesser than about $10^{-11}$ M, lesser than about $10^{-12}$ M as determined by, e.g., Scatchard analysis (Munsen, et al. (1980) Analyt. Biochem. 107:220-239) or BIACORE®. In one embodiment where the ligand is an ILR binding sdAb and the receptor comprises an ILR, the ILR binding sdAb specifically binds if the equilibrium dissociation constant ($K_D$) of the ILR binding sdAb/ILR ECD is lesser than about $10^{-5}$M, alternatively lesser than about $10^{-6}$ M, alternatively lesser than about $10^{-7}$M, alternatively lesser than about $10^{-8}$M, alternatively lesser than about $10^{-9}$ M, alternatively lesser than about $10^{-10}$ M, or alternatively lesser than about $10^{-11}$ M. Specific binding may be assessed using techniques known in the art including but not limited to competition ELISA assays, radioactive ligand binding assays (e.g., saturation binding, Scatchard plot, nonlinear curve fitting programs and competition binding assays); non-radioactive ligand binding assays (e.g., fluorescence polarization (FP), fluorescence resonance energy transfer (FRET); liquid phase ligand binding assays (e.g., real-time polymerase chain reaction (RT-qPCR), and immunoprecipitation); and solid phase ligand binding assays (e.g., multiwell plate assays, on-bead ligand binding assays, on-column ligand binding assays, and filter assays)) and surface plasmon resonance assays (see, e.g., Drescher et al., (2009) Methods Mol Biol 493:323-343 with commercially available instrumentation such as the Biacore 8+, Biacore 5200, Biacore T200 (GE Healthcare Bio-Sciences, 100 Results Way, Marlborough MA 01752). In some embodiments, the present disclosure provides molecules (e.g., ILR binding sdAbs) that specifically bind to the hILR. As used herein, the binding affinity of an ILR binding molecule for the ILR, the binding affinity may be determined and/or quantified by surface plasmon resonance ("SPR"). In evaluating binding affinity of an ILR binding molecule for the ILR, either member of the binding pair may be immobilized, and the other element of the binding pair be provided in the mobile phase. In some embodiments, the sensor chip on which the protein of interest is to be immobilized is conjugated with a substance to facilitate binding of the protein of interest such as nitrilotriacetic acid (NTA) derivatized surface plasmon resonance sensor chips (e.g., Sensor Chip NTA available from Cytiva Global Life Science Solutions USA LLC, Marlborough MA as catalog number BR100407), as anti-His tag antibodies (e.g. anti-histidine CM5 chips commercially available from Cytiva, Marlborough MA), protein A or biotin. Consequently, to evaluate binding, it is frequently necessary to modify the protein to provide for binding to the substance conjugated to the surface of the chip. For example, the one member of the binding pair to be evaluated by incorporation of a chelating peptide comprising polyhistidine sequence (e.g., 6×His (SEQ ID NO: 330) or 8×His (SEQ ID NO: 331)) for retention on a chip conjugated with NTA. In some embodiments, the ILR binding molecule may be immobilized on the chip and ILR (or ECD fragment thereof) be provided in the mobile phase. Alternatively, the ILR (or ECD fragment thereof) may be immobilized on the chip and the ILR binding molecule be provided in the mobile phase. In either circumstance, it should be noted that modifications of some proteins for immobilization on a coated SPR chip may interfere with the binding properties of one or both components of the binding pair to be evaluated by SPR. In such cases, it may be necessary to switch the mobile and bound elements of the binding pair or use a chip with a binding agent that facilitates non-interfering conjugation of the protein to be evaluated. Alternatively, when evaluating the binding affinity of ILR binding molecule for ILR using SPR, the ILR binding molecule may be derivatized by the C-terminal addition of a poly-His sequence (e.g., 6×His (SEQ ID NO: 330) or 8×His (SEQ ID NO: 331)) and immobilized on the NTA derivatized sensor chip and the ILR receptor subunit for which the ILR VHH's binding affinity is being evaluated is provided in the mobile phase. The means for incorporation of a poly-His sequence into the C-terminus of the ILR binding molecule produced by recombinant DNA technology is well known to those of skill in the relevant art of biotechnology. In some embodiments, the binding affinity of ILR binding molecule for an ILR comprises using SPR substantially in accordance with the teaching of the Examples.

Subject: The terms "recipient", "individual", "subject", and "patient", are used interchangeably herein and refer to any mammalian subject for whom diagnosis, treatment, or therapy is desired, particularly humans. "Mammal" for purposes of treatment refers to any animal classified as a mammal, including humans, domestic and farm animals, and zoo, sports, or pet animals, such as dogs, horses, cats, cows, sheep, goats, pigs, etc. In some embodiments, the mammal is a human being.

Substantially Pure: As used herein, the term "substantially pure" indicates that a component of a composition makes up greater than about 50%, alternatively greater than about 60%, alternatively greater than about 70%, alternatively greater than about 80%, alternatively greater than about 90%, alternatively greater than about 95% of the total content of the composition. A protein that is "substantially pure" comprises greater than about 50%, alternatively greater than about 60%, alternatively greater than about 70%, alternatively greater than about 80%, alternatively greater than about 90%, alternatively greater than about 95% of the total content of the composition.

Suffering From: As used herein, the term "suffering from" refers to a determination made by a physician with respect to a subject based on the available objective or subjective information accepted in the field for the identification of a disease, disorder or condition including but not limited to X-ray, CT-scans, conventional laboratory diagnostic tests (e.g., blood count, etc.), genomic data, protein expression data, immunohistochemistry, that the subject requires or will benefit from treatment. The term suffering from is typically used in conjunction with a particular disease state such as "suffering from a neoplastic disease" refers to a subject which has been diagnosed with the presence of a neoplasm.

T-cell: As used herein the term "T-cell" or "T cell" is used in its conventional sense to refer to a lymphocytes that differentiates in the thymus, possess specific cell-surface antigen receptors, and include some that control the initiation or suppression of cell-mediated and humoral immunity and others that lyse antigen-bearing cells. In some embodiments the T cell includes without limitation naïve $CD8^+$ T cells, cytotoxic $CD8^+$ T cells, naïve $CD4^+$ T cells, helper T cells, e.g., $T_H1$, $T_H2$, $T_H9$, $T_H11$, $T_H22$, $T_{FH}$; regulatory T cells, e.g., $T_R1$, Tregs, inducible Tregs; memory T cells, e.g., central memory T cells, effector memory T cells, NKT cells, tumor infiltrating lymphocytes (TILs) and engineered variants of such T-cells including but not limited to CAR-T cells, recombinantly modified TILs and TCR-engineered cells. In some embodiments the T cell is a T cell expressing the IL23R isoform referred to interchangeably as IL23R cell, IL23R+ cell, IL23R T cell, or IL23R+ T cell).

Terminus/Terminal: As used herein in the context of the structure of a polypeptide, "N-terminus" (or "amino terminus") and "C-terminus" (or "carboxyl terminus") refer to the extreme amino and carboxyl ends of the polypeptide, respectively, while the terms "N-terminal" and "C-terminal" refer to relative positions in the amino acid sequence of the polypeptide toward the N-terminus and the C-terminus, respectively, and can include the residues at the N-terminus and C-terminus, respectively. "Immediately N-terminal" refers to the position of a first amino acid residue relative to a second amino acid residue in a contiguous polypeptide sequence, the first amino acid being closer to the N-terminus of the polypeptide. "Immediately C-terminal" refers to the position of a first amino acid residue relative to a second amino acid residue in a contiguous polypeptide sequence, the first amino acid being closer to the C-terminus of the polypeptide.

Therapeutically Effective Amount: As used herein to the phrase "therapeutically effective amount" refers to the quantity of an agent when administered to a subject, either alone or as part of a pharmaceutical composition or treatment regimen, in a single dose or as part of a series of doses, provides a positive effect on any quantitative or qualitative symptom, aspect, or characteristic of a disease, disorder or condition. A therapeutically effective amount can be ascertained by measuring relevant physiological effects, and it may be adjusted in connection with a dosing regimen and in response to diagnostic analysis of the subject's condition. The parameters for evaluation to determine a therapeutically effective amount of an agent are determined by the physician using art accepted diagnostic criteria including but not limited to indicia such as age, weight, sex, general health, ECOG score, observable physiological parameters, blood levels, blood pressure, electrocardiogram, computerized tomography, X-ray, and the like. Alternatively, or in addition, other parameters commonly assessed in the clinical setting may be monitored to determine if a therapeutically effective amount of an agent has been administered to the subject such as body temperature, heart rate, normalization of blood chemistry, normalization of blood pressure, normalization of cholesterol levels, or any symptom, aspect, or characteristic of the disease, disorder or condition, biomarkers (such as inflammatory cytokines, IFN-γ, granzyme, and the like), reduction in serum tumor markers, improvement in Response Evaluation Criteria In Solid Tumors (RECIST), improvement in Immune-Related Response Criteria (irRC), increase in duration of survival, extended duration of progression free survival, extension of the time to progression, increased time to treatment failure, extended duration of event free survival, extension of time to next treatment, improvement objective response rate, improvement in the duration of response, reduction of tumor burden, complete response, partial response, stable disease, and the like that that are relied upon by clinicians in the field for the assessment of an improvement in the condition of the subject in response to administration of an agent. In one embodiment, a therapeutically effective amount is an amount of an agent when used alone or in combination with another agent provides an provides a positive effect on any quantitative or qualitative symptom, aspect, or characteristic of a disease, disorder or condition and does not result in non-reversible serious adverse events in the course of administration of the agent to the mammalian subject.

Transmembrane Domain: The term "transmembrane domain" or "TM" refers to a polypeptide domain of a membrane spanning polypeptide (e.g., a transmembrane receptor) which, when the membrane spanning polypeptide is associated with a cell membrane, is which is embedded in the cell membrane and is in peptidyl linkage with the extracellular domain (ECD) and the intracellular domain (ICD) of a membrane spanning polypeptide. A transmembrane domain may be homologous (naturally associated with) or heterologous (not naturally associated with) with either or both of the extracellular and/or intracellular domains. In some embodiments, where the receptor is chimeric receptor comprising the intracellular domain derived from a first parental receptor and a second extracellular domains are derived from a second different parental receptor, the transmembrane domain of the chimeric receptor is the transmembrane domain normally associated with either the ICD or the ECD of the parent receptor from which the chimeric receptor is derived.

Treat: The terms "treat", "treating", treatment" and the like refer to a course of action (such as contacting the subject with pharmaceutical composition comprising a IL23R binding sdAb alone or in combination with a supplementary agent) that is initiated with respect to a subject in response to a diagnosis that the subject is suffering from a disease, disorder or condition, or a symptom thereof, the course of action being initiated so as to eliminate, reduce, suppress, mitigate, or ameliorate, either temporarily or permanently, at least one of: (a) the underlying causes of such disease, disorder, or condition afflicting a subject; and/or (b) at least one of the symptoms associated with such disease, disorder, or condition. In some embodiments, treating includes a course of action taken with respect to a subject suffering from a disease where the course of action results in the inhibition (e.g., arrests the development of the disease, disorder or condition or ameliorates one or more symptoms associated therewith) of the disease in the subject.

Treg Cell or Regulatory T Cell. The terms "regulatory T cell", "Treg cell", or "Treg" are interchangeably herein to refers to a type of $CD4^+$ T cell that can suppress the responses of other T cells including but not limited to effector T cells ($T_{eff}$). Treg cells are typically characterized by expression of CD4 (CD4+), the CD25 subunit of the IL2 receptor (CD25+), and the transcription factor forkhead box P3 (FOXP3+) (Sakaguchi, Annu Rev Immunol 22, 531-62 (2004). In some instances, the term "conventional $CD4^+$ T cells" is used to distinguish non-Treg $CD4^+$ T cells from $CD4^+$ Tregs.

Variant: The terms "variant", "protein variant" or "variant protein" or "variant polypeptide" are used interchangeably herein to refer to a polypeptide that differs from a parent polypeptide by virtue of at least one amino acid modification, substitution, or deletion. The parent polypeptide may be a naturally occurring or wild-type (WT) polypeptide or may be a modified version of a WT polypeptide. The term variant polypeptide may refer to the polypeptide itself, a composition comprising the polypeptide, or the nucleic acid sequence that encodes it. In some embodiments, the variant polypeptide comprises from about one to about ten, alternatively about one to about eight, alternatively about one to about seven, alternatively about one to about five, alternatively about one to about four, alternatively from about one to about three alternatively from one to two amino acid modifications, substitutions, or deletions, or alternatively a single amino acid amino acid modification, substitution, or deletion compared to the parent polypeptide. A variant may be at least about 99% identical, alternatively at least about 98% identical, alternatively at least about 97% identical, alternatively at least about 95% identical, or alternatively at least about 90% identical to the parent polypeptide from which the variant is derived.

VHH: As used herein, the term "$V_HH$" is a type of sdAb that has a single monomeric heavy chain variable antibody domain. Such antibodies can be found in or produced from Camelid mammals (e.g., camels, llamas) which are naturally devoid of light chains $V_HHs$ can be obtained from immunization of camelids (including camels, llamas, and alpacas (see, e.g., Hamers-Casterman, et al. (1993) Nature 363:446-448) or by screening libraries (e.g., phage libraries) constructed in $V_HH$ frameworks. Antibodies having a given specificity may also be derived from non-mammalian sources such as $V_HHs$ obtained from immunization of cartilaginous fishes including, but not limited to, sharks. In a particular embodiment, a $V_HH$ in a bispecific $V_HH^2$ binding molecule described herein binds to a receptor (e.g., the first receptor or the second receptor of the natural or non-natural receptor pairs) if the equilibrium dissociation constant ($K_D$) between the $V_HH$ and the receptor is lesser than about $10^{-6}$ M, alternatively lesser than about $10^{-8}$ M, alternatively lesser than about $10^{-10}$ M, alternatively lesser than about $10^{-11}$ M, alternatively lesser than about $10^{-10}$ M, lesser than about $10^{-12}$ M as determined by, e.g., Scatchard analysis (Munsen, et al. 1980 Analyt. Biochem. 107:220-239). Standardized protocols for the generation of single domain antibodies from camelids are well known in the scientific literature. See, e.g., Vincke, et al (2012) Chapter 8 in *Methods in Molecular Biology*, Walker, J. editor (Humana Press, Totowa NJ). Specific binding may be assessed using techniques known in the art including but not limited to competition ELISA, BIACORE® assays and/or KINEXA® assays. In some embodiments, a $V_HH$ described herein can be humanized to contain human framework regions. Examples of human germlines that could be used to create humanized $V_HHs$ include, but are not limited to, VH3-23 (e.g., UniProt ID: P01764), VH3-74 (e.g., UniProt ID: A0A0B4J1X5), VH3-66 (e.g., UniProt ID: A0A0C4DH42), VH3-30 (e.g., UniProt ID: P01768), VH3-11 (e.g., UniProt ID: P01762), and VH3-9 (e.g., UniProt ID: P01782).

Clonotype: As used herein, a clonotype refers to a collection of binding molecules that originate from the same B-cell progenitor cell. The term "clonotype" is used to refer to a collection of antigen binding molecules that belong to the same germline family, have the same CDR3 lengths, and have 70% or greater homology in CDR3 sequence.

Wild Type: By "wild type" or "WT" or "native" herein is meant an amino acid sequence or a nucleotide sequence that is found in nature, including allelic variations. A wild-type protein, polypeptide, antibody, immunoglobulin, IgG, etc. has an amino acid sequence or a nucleotide sequence that has not been modified by the hand of man.

IL23R

The IL23R binding molecules of the present disclosure specifically bind to the extracellular domain of the IL23R.

Human IL23R

In one embodiment, specifically bind to the extracellular domain of the human IL23R receptor subunit (hIL23R). hIL23R is expressed as a 629 amino acid precursor comprising a 23 amino acid N-terminal signal sequence which is post-translationally cleaved to provide an 606 amino acid mature protein. The canonical full-length acid hIL23R precursor (including the signal peptide) is a 629 amino acid polypeptide having the amino acid sequence:

```
                                           (SEQ ID NO: 1)
MNQVTIQWDAVIALYILFSWCHGGITNINCSGHIWVEPATIFKMGMNIS

IYCQAAIKNCQPRKLHFYKNGIKERFQITRINKTTARLWYKNFLEPHAS

MYCTAECPKHFQETLICGKDISSGYPPDIPDEVTCVIYEYSGNMTCTWN

AGKLTYIDTKYVVHVKSLETEEEQQYLTSSYINISTDSLQGGKKYLVWV

QAANALGMEESKQLQIHLDDIVIPSAAVISRAETINATVPKTIIYWDSQ

TTIEKVSCEMRYKATTNQTWNVKEFDTNFTYVQQSEFYLEPNIKYVFQV

RCQETGKRYWQPWSSLFFHKTPETVPQVTSKAFQHDTWNSGLTVASIST

GHLTSDNRGDIGLLLGMIVFAVMLSILSLIGIFNRSFRTGIKRRILLLI

PKWLYEDIPNMKNSNVVKMLQENSELMNNNSSEQVLYVDPMITEIKEIF

IPEHKPTDYKKENTGPLETRDYPQNSLFDNTTVVYIPDLNTGYKPQISN

FLPEGSHLSNNNEITSLTLKPPVDSLDSGNNPRLQKHPNFAFSVSSVNS

LSNTIFLGELSLILNQGECSSPDIQNSVEEETTMLLENDSPSETIPEQT

LLPDEFVSCLGIVNEELPSINTYFPQNILESHFNRISLLEK.
```

For purposes of the present disclosure, the numbering of amino acid residues of the human gp130 polypeptides as described herein is made in accordance with the numbering of this canonical sequence (UniProt Reference No Q5VWK5, SEQ ID NO:1). Amino acids 1-23 of SEQ ID NO:1 are identified as the signal peptide of hIL23R, amino acids 24-355 of SEQ ID NO:1 are identified as the extracellular domain, amino acids 356-376 of SEQ ID NO:1 are identified as the transmembrane domain, and amino acids 377-629 of SEQ ID NO:1 are identified as the intracellular domain.

For the purposes of generating antibodies that bind to the ECD of IL23R, immunization may be performed with the extracellular domain of the hIL23R. The extracellular domain of hIL23R is a 332 amino acid polypeptide of the sequence:

```
                                       (SEQ ID NO: 327)
GITNINCSGHIWVEPATIFKMGMNISIYCQAAIKNCQPRKLHFYKNGIK

ERFQITRINKTTARLWYKNFLEPHASMYCTAECPKHFQETLICGKDISS

GYPPDIPDEVTCVIYEYSGNMTCTWNAGKLTYIDTKYVVHVKSLETEEE

QQYLTSSYINISTDSLQGGKKYLVWVQAANALGMEESKQLQIHLDDIVI

PSAAVISRAETINATVPKTIIYWDSQTTIEKVSCEMRYKATTNQTWNVK

EFDTNFTYVQQSEFYLEPNIKYVFQVRCQETGKRYWQPWSSLFFHKTPE

TVPQVTSKAFQHDTWNSGLTVASISTGHLTSDNRGDIG.
```

Mouse IL23R

In one embodiment, specifically bind to the extracellular domain of the mouse or murine IL23R receptor subunit (mIL23R). mIL23R is expressed as a 644 amino acid precursor comprising a 23 amino acid N-terminal signal sequence which is post-translationally cleaved to provide a 621 amino acid mature protein. The canonical full-length acid mIL23R precursor (including the 23 amino acid signal peptide) is a 644 amino acid polypeptide having the amino acid sequence:

```
                                       (SEQ ID NO: 328)
MSHLTLQLHVVIALYVLFRWCHGGITSINCSGDMWVEPGEIFQMGMNVS

IYCQEALKHCRPRNLYFYKNGFKEEFDITRINRTTARIWYKGFSEPHAY

MHCTAECPGHFQETLICGKDISSGHPPDAPSNLTCVIYEYSGNMTCTWN

TGKPTYIDTKYIVHVKSLETEEEQQYLASSYVKISTDSLQGSRKYLVWV

QAVNSLGMENSQQLHVHLDDIVIPSASIISRAETTNDTVPKTIVYWKSK

TMIEKVFCEMRYKTTTNQTWSVKEFDANFTYVQQSEFYLEPDSKYVFQV

RCQETGKRNWQPWSSPFVHQTSQETGKRNWQPWSSPFVHQTSQTVSQVT

AKSSHEPQKMEMLSATIFRGHPASGNHQDIGLLSGMVFLAIMLPIFSLI

GIFNRSLRIGIKRKVLLMIPKWLYEDIPNMENSNVAKLLQEKSVFENDN

ASEQALYVDPVLTEISEISPLEHKPTDYKEERLTGLLETRDCPLGMLST

SSSVVYIPDLNTGYKPQVSNVPPGGNLFINRDERDPTSLETTDDHFARL

KTYPNFQFSASSMALLNKTLILDELCLVLNQGEFNSLDIKNSRQEETSI

VLQSDSPSETIPAQTLLSDEFVSCLAIGNEDLPSINSYFPQNVLESHFS

RISLFQK
```

For purposes of the present disclosure, the numbering of amino acid residues of the mIL23R polypeptides as described herein is made in accordance with the numbering of this canonical sequence (UniProt Reference No. Q8K4B4, SEQ ID NO:328). Amino acids 1-23 of SEQ ID NO:328 are identified as the signal peptide of mIL23R, amino acids 24-374 of SEQ ID NO: 328 are identified as the extracellular domain, amino acids 375-395 of SEQ ID NO: 328 are identified as the transmembrane domain, and amino acids 396-644 of SEQ ID NO: 328 are identified as the intracellular domain.

For the purposes of generating antibodies that bind to the ECD of IL23R, immunization may be performed with the extracellular domain of the mIL23R. The extracellular domain of the mIL23R receptor is a 351 amino acid polypeptide of the sequence:

```
                                       (SEQ ID NO: 329)
GITSINCSGDMWVEPGEIFQMGMNVSIYCQEALKHCRPRNLYFYKNGFK

EEFDITRINRTTARIWYKGFSEPHAYMHCTAECPGHFQETLICGKDISS

GHPPDAPSNLTCVIYEYSGNMTCTWNTGKPTYIDTKYIVHVKSLETEEE

QQYLASSYVKISTDSLQGSRKYLVWVQAVNSLGMENSQQLHVHLDDIVI

PSASIISRAETTNDTVPKTIVYWKSKTMIEKVFCEMRYKTTTNQTWSVK

EFDANFTYVQQSEFYLEPDSKYVFQVRCQETGKRNWQPWSSPFVHQTSQ

ETGKRNWQPWSSPFVHQTSQTVSQVTAKSSHEPQKMEMLSATIFRGHPA

SGNHQDIG
```

Cross Reactivity:

In some instances, due to sequence or structural similarities between the extracellular domains of IL23R receptors from various mammalian species, immunization with an antigen derived from a IL23R of a first mammalian species (e.g., the hIL23R-ECD) may provide antibodies which specifically bind to IL23R receptors of one or more additional mammalian species. Such antibodies are termed "cross reactive." For example, immunization of a camelid with a human derived antigen (e.g., the hIL23R-ECD) may generate antibodies that are cross-reactive the murine and human receptors. Evaluation of cross-reactivity of antibody with respect to the receptors derived from other mammalian species may be readily determined by the skilled artisan, for example using the methods relating to evaluation of binding affinity and/or specific binding described elsewhere herein such as flow cytometry or SPR. Consequently, the use of the term "human IL23R VHH" or "hIL23R VHH" merely denotes that the species of the IL23R antigen used for immunization of the camelid from which the VHH was derived was the human IL23R (e.g., the hIL23R ECD, SEQ ID NO:327) but should not be understood as limiting with respect to the specific binding affinity of the VHH for IL23R molecules of other mammalian species. Similarly, the use of the term "mouse IL23R VHH" or "mIL23R VHH" merely denotes that the species of the IL23R antigen used for immunization of the camelid from which the VHH was derived was the murine IL23R (e.g., the mIL23R ECD, SEQ ID NO:329) but should not be understood as limiting with respect to the specific binding affinity of the VHH for IL23R molecules of other mammalian species.

IL23R Binding Molecules and Single Domain Antibodies

In some embodiments, a IL23R binding molecule of the present disclosure is a single domain antibody (sdAb). The present disclosure relates to IL23R binding molecules comprising single domain antibodies (sdAbs) that specifically bind to the extracellular domain of the human IL23R isoform (hIL23R) which are found on all IL23R-expressing cells.

A single-domain antibody (sdAb) is an antibody containing a single monomeric variable antibody domain. Like a full-length antibody, sdAbs are able to bind specifically to an antigenic determinant. hIL23R binding VHH single-domain antibodies can be engineered from heavy chain antibodies isolated from Camelidae mammals (e.g., camels, llamas, dromedary, alpaca, and guanaco) immunized with the extracellular domain of hIL23R or an immunologically active fragment thereof. Descriptions of sdAbs and VHHs can be found in, e.g., De Greve et al., (2019) Curr Opin Biotechnol. 61:96-101; Ciccarese, et al., (2019) Front Genet. 10:997: Chanier and Chames (2019) *Antibodies* (Basel) 8(1); and De Vlieger, et al. (2018) *Antibodies* (Basel) 8(1). Alternatively, hIL23R single domain antibodies may be engineered from heavy chain antibodies isolated from the IgNAR heavy chain antibodies isolated from cartilaginous fishes immunized with the extracellular domain of hIL23R or an immunologically active fragment thereof hIL23R binding sdAbs may also be obtained by splitting the dimeric variable domains from immunoglobulin G (IgG) isotypes from other mammalian species including humans, rats, rabbits immunized with the extracellular domain of hIL23R or an immunologically active fragment thereof. Although most research into sdAbs is currently based on heavy chain variable domains, sdAbs derived from light chains have also been shown to bind specifically to the target proteins comprising the antigenic immunization sequence. Moller et al., *J Biol Chem.* 285(49):38348-38361, 2010.

In some embodiments, the sdAb is a VHH. A VHH is a type of sdAb that has a single monomeric heavy chain variable antibody domain. Similar to a traditional antibody, a VHH is able to bind specifically to a specific antigen. An exemplary VHH has a molecular weight of approximately 12-15 kDa which is much smaller than traditional mammalian antibodies (150-160 kDa) composed of two heavy chains and two light chains. VHHs can be found in or produced from Camelidae mammals (e.g., camels, llamas, dromedary, alpaca, and guanaco) which are naturally devoid of light chains.

The present disclosure provides IL23R binding molecules comprising a polypeptide having at least 75%, alternatively 80%, alternatively 90%, alternatively 95%, alternatively 98%, or alternatively 99% or 100% identity to a polypeptide of any one of SEQ ID NOS:2-20.

The present disclosure provides IL23R binding molecules comprising a polypeptide having at least 75%, alternatively 80%, alternatively 90%, alternatively 95%, alternatively 98%, or alternatively 99% or 100% identity to a polypeptide of any one of SEQ ID NOS:97-142.

The present disclosure provides IL23R binding molecules comprising a CDR1, a CDR2, and a CDR3 as described in a row of Table 1 provided herein. In some embodiments, the CDR1, CDR2, and CDR3 can each, independently, comprise at least 90% (e.g., 91%, 92%, 93%, 94%, 95%, 96%, 97%, 98%, 99%, or 100%) sequence identity, or have 0, 1, 2, or 3 amino acid changes, optionally conservative amino acid changes, relative to the sequence described in a row of Table 1 provided herein.

The present disclosure provides IL23R binding molecules comprising a CDR1, a CDR2, and a CDR3 as described in a row of Table 4 provided herein. In some embodiments, the CDR1, CDR2, and CDR3 can each, independently, comprise at least 90% (e.g., 91%, 92%, 93%, 94%, 95%, 96%, 97%, 98%, 99%, or 100%) sequence identity, or have 0, 1, 2, or 3 amino acid changes, optionally conservative amino acid changes, relative to the sequence described in a row of Table 4 provided herein.

Modified Forms of Single Domain Antibodies

CDR Grafted sdAbs

In some embodiments, the IL23R binding sdAb of the present disclosure is a CDR grafted IL23R binding sdAb. CDRs obtained from antibodies, heavy chain antibodies, and sdAbs derived therefrom may be grafted onto alternative frameworks as described in Saerens, et al. (2005) J. Mol Biol 352:597-607 to generate CDR-grafted sdAbs. In some embodiments, the present disclosure provides a IL23R binding molecule comprising a CDR grafted IL23R binding sdAb, said CDR-grafted IL23R binding sdAb comprising a set of CDRs1, 2, and 3 as shown in a row of the Table 1A above. In some embodiments, the present disclosure provides a IL23R binding molecule comprising a CDR grafted IL23R binding sdAb, said CDR-grafted IL23R binding sdAb comprising a set of CDRs1, 2, and 3 as shown in a row of the Table 1B above.

Elimination of N-Linked Glycosylation Sites

In some embodiments, it is possible that an amino acid sequence (particularly a CDR sequence) of the IL23R binding sdAb may contain a glycosylation motif, particularly an N-linked glycosylation motif of the sequence Asn-X-Ser (N-X-S) or Asn-X-Thr (N-X-T), wherein X is any amino acid except for proline. In such instances, it is desirable to eliminate such N-linked glycosylation motifs by modifying the sequence of the N-linked glycosylation motif to prevent glycosylation. In some embodiments, the N-linked glycosylation motif is disrupted by the incorporation of conservative amino acid substitution of the Asn (N) residue of the N-linked glycosylation. As procaryotic host cells do not provide the mechanism for glycosylation of recombinant proteins, when employing a procaryotic expression system to produce a recombinant IL23R binding sdAb the modification of the sequence to eliminate the N-linked glycosylation sites may be obviated.

Chimeric and Humanized sdAbs

Any framework region can be used with the CDRs as described herein. In some embodiments, the IL23R binding sdAb is a chimeric sdAb, in which the CDRs are derived from one species (e.g., camel) and the framework and/or constant regions are derived from another species (e.g., human or mouse). In specific embodiments, the framework regions are human or humanized sequences. Thus, humanized IL23R binding sdAbs derived from hIL23R binding VHHs are considered within the scope of the present disclosure. The techniques for humanization of camelid single domain antibodies are well known in the art. See, e.g., Vincke, et al. (2009) General Strategy to Humanize a Camelid Single-domain Antibody and *Identification of a Universal Humanized Nanobody Scaffold* J. Biol. Chem. 284(5)3273-3284.

In some embodiments, a VHH described herein can be humanized to contain human framework regions. Examples of human germlines that could be used to create humanized VHHs include, but are not limited to, VH3-23 (e.g., UniProt ID: P01764), VH3-74 (e.g., UniProtID: A0A0B4J1X5), VH3-66 (e.g., UniProtID: A0A0C4DH42), VH3-30 (e.g., UniProt ID: P01768), VH3-11 (e.g., UniProt ID: P01762), and VH3-9 (e.g., UniProt ID: P01782).

IL23R Binding Molecules Comprising Additional Agents

In some embodiments, a IL23R binding molecule of the present disclosure comprises a IL23R single domain antibody (sdAb) conjugated to one or more additional biologically active agents including but not limited to, therapeutic agents, chemically, optically or radioactively active agents, including combinations thereof. The conjugation of at least one such biologically, chemically, optically or radioactively active agent confer additional biological or chemical properties to IL23R binding sdAb, the combination providing a IL23R binding molecule possessing additional or alternative utilities.

For example, the additional agent may be a molecule selected from one or more of: immunomodulatory agents (e.g., immunogens); molecules that improve aqueous solubility (e.g., water soluble polymers and hydrophilic molecules such as sugars); carrier molecules that extend in vivo half-life (e.g., PEGylation, Fc fusions or acylation); generation of antibodies for use in detection assays (e.g., epitope tags), enhance ease of purification (e.g., chelating peptides such as poly-His tags); targeting domains that provide selective targeting IL23R binding molecule to a particular cell or tissue type; therapeutic agents (e.g., therapeutic agents including small molecule or polypeptide agents); agents that visibility to optical or electromagnetic sensors (e.g., radionucleotides or fluorescent agents). In some embodiments, the linker is a cleavable linker or a non-cleavable linker. The use of a cleavable linker in a IL23R binding molecule as contemplated herein facilitates the release of a therapeutic agent into the intracellular cytoplasm upon internalization of the IL23R binding molecule. A non-cleavable linker would allow release upon digestion of the IL23R binding molecule of or it could be used with an agent that does not require release from the antibody (e.g., an imaging agent).

In some embodiments, where the IL23R binding molecule comprises a IL23R binding sdAb in stable association with an additional agent joined via a linker. A linker is a covalent linkage between two elements of a IL23R binding molecule (e.g., a hIL23R binding VHH and PEG polymer). A linker can be a covalent bond, chemical linker or a peptide linker. Suitable linkers include "flexible linkers" which are generally of sufficient length to permit some movement between the IL23R binding sdAb and the linked agent(s). Examples of chemical linkers include aryl acetylene, ethylene glycol oligomers containing 2-10 monomer units, diamines, diacids, amino acids, or combinations thereof. In some embodiments, the linker is a peptide linker. Suitable peptide linkers can be readily selected and can be of any suitable length, such as 1 amino acid (e.g., Gly), 2, 3, 4, 5, 6, 7, 8, 9, 10, 10-20, 20-30, 30-50 or more than 50 amino acids. Suitable peptide linkers are known in the art, and include, for example, peptide linkers containing flexible amino acid residues such as glycine and serine. Examples of flexible linkers include glycine polymers $(G)_n$, glycine-serine polymers, glycine-alanine polymers, alanine-serine polymers, and other flexible linkers. Glycine and glycine-serine polymers are relatively unstructured, and therefore can serve as a neutral tether between components. Further examples of flexible linkers include glycine polymers $(G)_n$, glycine-alanine polymers, alanine-serine polymers, glycine-serine polymers. Glycine and glycine-serine polymers are relatively unstructured, and therefore may serve as a neutral tether between components. A multimer (e.g., 1, 2, 3, 4, 5, 6, 7, 8, 9, 10, 10-20, 20-30, or 30-50) of such linker sequences may be linked together to provide flexible linkers that may be used to conjugate a heterologous amino acid sequence to IL23R binding sdAbs disclosed herein. In some embodiments the linkers have the formula (GGGS)n (SEQ ID NO: 332), (GGGSG)n (SEQ ID NO: 333), or (GGSG)n (SEQ ID NO: 334), wherein n is an integer selected from 1, 2, 3, 4, 5, 6, 7, 8, 9 and 10.

Immunomodulatory Agents

In some embodiments, a IL23R binding molecule of the present disclosure comprises an immunomodulatory agent (immunoconjugates). Immunomodulatory agents that may conjugated to the hIL23R binding sdAb of the present disclosure include, but are not limited to, inactivated virus particles, inactivated bacterial toxins such as toxoid from diphtheria, tetanus, cholera, or leukotoxin molecules, inactivated bacteria and dendritic cells. Such immunoconjugates are useful in facilitating an immune response against the IL23R or cells expressing the IL23R.

Flag Tags

In one embodiment, the present disclosure provides a IL23R binding molecule comprising an antigenic tag, such as a FLAG sequence. FLAG sequences are recognized by biotinylated, highly specific, anti-FLAG antibodies, as described herein (see e.g., Blanar et al. (1992) Science 256:1014 and LeClair, et al. (1992) PNAS-USA 89:8145). In some embodiments, the IL23R binding sdAb polypeptide further comprises a C-terminal c-myc epitope tag.

Chelating Peptides

In one embodiment, the present disclosure provides a IL23R binding molecule comprising one or more transition metal chelating polypeptide sequences. The incorporation of such a transition metal chelating domain facilitates purification immobilized metal affinity chromatography (IMAC) as described in Smith, et al. U.S. Pat. No. 4,569,794 issued Feb. 11, 1986. Examples of transition metal chelating polypeptides useful in the practice of the present IL23R binding molecule are described in Smith, et al. supra and Dobeli, et al. U.S. Pat. No. 5,320,663 issued May 10, 1995, the entire teachings of which are hereby incorporated by reference. Particular transition metal chelating polypeptides useful in the practice of the present IL23R binding molecule are polypeptides comprising 3-6 contiguous histidine residues (SEQ ID NO: 335) such as a six-histidine $(His)_6$ peptide (SEQ ID NO: 330) and are frequently referred to in the art as "His-tags." In addition to providing a purification "handle" for the recombinant proteins or to facilitate immobilization on SPR sensor chips, such the conjugation of the hIL23R binding molecule to a chelating peptide facilitates the targeted delivery to IL23R expressing cells of transition metal ions as kinetically inert or kinetically labile complexes in substantial accordance with the teaching of Anderson, et al., (U.S. Pat. No. 5,439,829 issued Aug. 8, 1995 and Hale, J. E (1996) Analytical Biochemistry 231(1):46-49. The transition metal ion is a reporter molecule such as a fluorescent compound or radioactive agent, including as radiological imaging or therapeutic agents Carrier Molecules In some embodiments the IL23R binding sdAbs of the present disclosure may be conjugated to one or more carrier molecules. Carrier molecules are typically large, slowly metabolized macromolecules which provide for stabilization and/or extended duration of action in vivo to distinguish such molecules from conventional carrier molecules used in the preparation of pharmaceutical formulations as described below. Examples of in vivo carriers that may be incorporated into IL23R binding molecules, but are not limited to: proteins (including but not limited to human serum albumin); fatty acids (acylation); polysaccharides (including but not limited to (N- and O-linked) sugars, sepharose, agarose, cellulose, or cellulose); polypeptides amino acid copolymers; acylation, or polysialylation, an polyethylene glycol (PEG) polymers.

Water Soluble Polymers

In some embodiments, the IL23R binding sdAb is conjugated to one or more water-soluble polymers. Examples of water soluble polymers useful in the practice of the present IL23R binding molecule include polyethylene glycol (PEG), poly-propylene glycol (PPG), polysaccharides (polyvinylpyrrolidone, copolymers of ethylene glycol and propylene glycol, poly(oxyethylated polyol), polyolefinic alcohol, polysaccharides, poly-alpha-hydroxy acid, polyvinyl alcohol (PVA), polyphosphazene, polyoxazolines (POZ), poly (N-acryloylmorpholine), or a combination thereof.

Polyethylene Glycol

In one embodiment, the carrier molecule is a polyethylene glycol ("PEG") polymer. Conjugation of PEG polymers to proteins (PEGylation) is a well-established method for the extension of serum half-life of biological agents. The PEGylated polypeptide may be further referred to as monopegylated, dipegylated, tripegylated (and so forth) to denote a polypeptide comprising one, two, three (or more) PEG moieties attached to the polypeptide, respectively. In some embodiments, the PEG may be covalently attached directly to the sdAb (e.g., through a lysine side chain, sulfhydryl group of a cysteine or N-terminal amine) or optionally employ a linker between the PEG and the sdAb. In some embodiments, a IL23R binding molecule comprises more than one PEG molecules each of which is attached to a different amino acid residue. In some embodiments, the sdAb may be modified by the incorporation of non-natural amino acids with non-naturally occurring amino acid side chains to facilitate site specific PEGylation. In other embodiments, cysteine residues may be substituted at one or more positions within the sdAb to facilitate site-specific PEGylation via the cysteine sulfhydryl side chain.

In some instances, the IL23R binding molecules of the present disclosure possess an N-terminal glutamine ("1Q") residue. N-terminal glutamine residues have been observed to spontaneously cyclyize to form pyroglutamate (pE) at or near physiological conditions. (See e.g., Liu, et al (2011) J. Biol. Chem. 286(13): 11211-11217). In some embodiments, the formation of pyroglutamate complicates N-terminal PEG conjugation particularly when aldehyde chemistry is used for N-terminal PEGylation. Consequently, when PEGylating the IL23R binding molecules of the present disclosure, particularly when aldehyde chemistry is to be employed, the IL23R binding molecules possessing an amino acid at position 1 (e.g., 1Q) are substituted at position 1 with an alternative amino acid or are deleted at position 1 (e.g., des-1Q). In some embodiments, the IL23R binding molecules of the present disclosure comprise an amino acid substitution selected from the group Q1E and Q1D.

PEGs suitable for conjugation to a polypeptide sequence are generally soluble in water at room temperature, and have the general formula

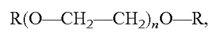

$$R(O{-}CH_2{-}CH_2)_nO{-}R,$$

where R is hydrogen or a protective group such as an alkyl or an alkanol group, and where n is an integer from 1 to 1000. When R is a protective group, it generally has from 1 to 8 carbons. The PEG can be linear or branched. Branched PEG derivatives, "star-PEGs" and multi-armed PEGs are contemplated by the present disclosure.

A molecular weight of the PEG used in a IL23R binding molecule is not restricted to any particular range. The PEG component of a IL23R binding molecule can have a molecular mass greater than about 5 kDa, greater than about 10 kDa, greater than about 15 kDa, greater than about 20 kDa, greater than about 30 kDa, greater than about 40 kDa, or greater than about 50 kDa. In some embodiments, the molecular mass is from about 5 kDa to about 10 kDa, from about 5 kDa to about 15 kDa, from about 5 kDa to about 20 kDa, from about 10 kDa to about 15 kDa, from about 10 kDa to about 20 kDa, from about 10 kDa to about 25 kDa or from about 10 kDa to about 30 kDa. Linear or branched PEG molecules having molecular weights from about 2,000 to about 80,000 daltons, alternatively about 2,000 to about 70,000 daltons, alternatively about 5,000 to about 50,000 daltons, alternatively about 10,000 to about 50,000 daltons, alternatively about 20,000 to about 50,000 daltons, alternatively about 30,000 to about 50,000 daltons, alternatively about 20,000 to about 40,000 daltons, alternatively about 30,000 to about 40,000 daltons. In one embodiment of the IL23R binding molecule, the PEG is a 40 kD branched PEG comprising two 20 kD arms.

The present disclosure also contemplates a IL23R binding molecule comprising more than one PEG moiety wherein the PEGs have different sizes values, and thus the various different PEGs are present in specific ratios. For example, in the preparation of a PEGylated IL23R binding molecule, some compositions comprise a mixture of mono-, di-, tri-, and quadra-PEGylated sdAb conjugates. In some compositions, the percentage of monoPEGylated species is 18-25%, the percentage of di-PEGylated species is 50-66%, the percentage of tri-pegylated species is 12-16%, and the percentage of quadra-pegylated species up to 5%. Such complex compositions can be produced by reaction conditions and purification methods known in the art. Chromatography may be used to resolve conjugate fractions, and a fraction is then identified which contains the conjugate having, for example, the desired number of PEGs attached, purified free from unmodified protein sequences and from conjugates having other numbers of PEGs attached.

PEGylation most frequently occurs at the α-amino group at the N-terminus of the polypeptide, the epsilon amino group on the side chain of lysine residues, and the imidazole group on the side chain of histidine residues. Since most recombinant polypeptides possess a single alpha and a number of epsilon amino and imidazole groups, numerous positional isomers can be generated depending on the linker chemistry.

Two widely used first generation activated monomethoxy PEGs (mPEGs) are succinimdyl carbonate PEG (SC-PEG; see, e.g., Zalipsky, et al. (1992) Biotehnol. Appl. Biochem 15:100-114) and benzotriazole carbonate PEG (BTC-PEG; see, e.g., Dolence, et al. U.S. Pat. No. 5,650,234), which react preferentially with lysine residues to form a carbamate linkage but are also known to react with histidine and tyrosine residues. Use of a PEG-aldehyde linker targets a single site on the N-terminus of a polypeptide through reductive amination.

The PEG can be bound to a IL23R binding molecule of the present disclosure via a terminal reactive group (a "spacer") which mediates a bond between the free amino or carboxyl groups of one or more of the polypeptide sequences and polyethylene glycol. The PEG having the spacer which can be bound to the free amino group includes N-hydroxysuccinylimide polyethylene glycol, which can be prepared by activating succinic acid ester of polyethylene glycol with N-hydroxysuccinylimide.

In some embodiments, the PEGylation of the sdAb is facilitated by the incorporation of non-natural amino acids bearing unique side chains to facilitate site specific PEGylation. The incorporation of non-natural amino acids into polypeptides to provide functional moieties to achieve site specific PEGylation of such polypeptides is known in the art. See e.g., Ptacin, et al., PCT International Application No. PCT/US2018/045257 filed Aug. 3, 2018 and published Feb. 7, 2019 as International Publication Number WO 2019/028419A1.

The PEG moiety of the of a PEGylated IL23R binding molecule may be linear or branched. Branched PEG derivatives, "star-PEGs" and multi-armed PEGs are contemplated by the present disclosure. Specific embodiments PEGs useful in the practice of the present disclosure include a 10 kDa linear PEG-aldehyde (e.g., Sunbright® ME-100AL, NOF America Corporation, One North Broadway, White Plains, NY 10601 USA), 10 kDa linear PEG-NHS ester (e.g., Sunbright® ME-100CS, Sunbright® ME-100AS, Sunbright® ME-100GS, Sunbright® ME-100HS, NOF), a 20 kDa linear PEG-aldehyde (e.g., Sunbright® ME-200AL, NOF, a 20 kDa linear PEG-NHS ester (e.g., Sunbright® ME-200CS, Sunbright® ME-200AS, Sunbright® ME-200GS, Sunbright® ME-200HS, NOF), a 20 kDa 2-arm branched PEG-aldehyde the 20 kDA PEG-aldehyde comprising two 10 kDA linear PEG molecules (e.g., Sunbright® GL2-200AL3, NOF), a 20 kDa 2-arm branched PEG-NHS ester the 20 kDA PEG-NHS ester comprising two 10 kDA linear PEG molecules (e.g., Sunbright® GL2-200TS, Sunbright® GL200GS2, NOF), a 40 kDa 2-arm branched PEG-aldehyde the 40 kDA PEG-aldehyde comprising two 20 kDA linear PEG molecules (e.g., Sunbright® GL2-400AL3), a 40 kDa 2-arm branched PEG-NHS ester the 40 kDA PEG-NHS ester comprising two 20 kDA linear PEG molecules (e.g., Sunbright® GL2-400AL3, Sunbright® GL2-400GS2, NOF), a linear 30 kDa PEG-aldehyde (e.g., Sunbright® ME-300AL) and a linear 30 kDa PEG-NHS ester.

Fc Fusions

In some embodiments, the carrier molecule is a Fc molecule or a monomeric subunit thereof. In some embodiments, the dimeric Fc molecule may be engineered to possess a "knob-into-hole modification." The knob-into-hole modification is more fully described in Ridgway, et al. (1996) Protein Engineering 9(7):617-621 and U.S. Pat. No. 5,731,168, issued Mar. 24, 1998, U.S. Pat. No. 7,642,228, issued Jan. 5, 2010, U.S. Pat. No. 7,695,936, issued Apr. 13, 2010, and U.S. Pat. No. 8,216,805, issued Jul. 10, 2012. The knob-into-hole modification refers to a modification at the interface between two immunoglobulin heavy chains in the CH3 domain, wherein: i) in a CH3 domain of a first heavy chain, an amino acid residue is replaced with an amino acid residue having a larger side chain (e.g., tyrosine or tryptophan) creating a projection from the surface ("knob") and ii) in the CH3 domain of a second heavy chain, an amino acid residue is replaced with an amino acid residue having a smaller side chain (e.g., alanine or threonine), thereby generating a cavity ("hole") within at interface in the second CH3 domain within which the protruding side chain of the first CH3 domain ("knob") is received by the cavity in the second CH3 domain. In one embodiment, the "knob-into-hole modification" comprises the amino acid substitution T366W and optionally the amino acid substitution S354C in one of the antibody heavy chains, and the amino acid substitutions T366S, L368A, Y407V and optionally Y349C in the other one of the antibody heavy chains. Furthermore, the Fc domains may be modified by the introduction of cysteine residues at positions S354 and Y349 which results in a stabilizing disulfide bridge between the two antibody heavy chains in the Fe region (Carter, et al. (2001) Immunol Methods 248, 7-15). The knob-into-hole format is used to facilitate the expression of a first polypeptide (e.g., an IL23R binding sdAb) on a first Fc monomer with a "knob" modification and a second polypeptide on the second Fc monomer possessing a "hole" modification to facilitate the expression of heterodimeric polypeptide conjugates.

Targeting Domains

In some embodiments, the IL23R binding molecule is provided as a component of a multivalent (e.g., bivalent) fusion protein with a polypeptide sequence ("targeting domain") to facilitate selective binding to particular cell type or tissue expressing a cell surface molecule that specifically binds to such targeting domain, optionally incorporating a linker between the IL23R binding sdAb sequence and the sequence of the targeting domain of the fusion protein.

In some embodiments of the IL23R binding molecule, the IL23R binding molecule may be targeted to a particular cell type cell by incorporation of a targeting domain into the structure of the IL23R binding molecules. As used herein, the term targeting domain refers to a moiety that specifically binds to a molecule expressed on the surface of a target cell. The targeting domain may be any moiety that specifically binds to one or more cell surface molecules (e.g., T cell receptor) expressed on the surface of a target cell. In some embodiments, the target cell is a T cell. In some embodiments, the target cell is a IL23R+ T cell.

In some embodiments, the targeting domain is a ligand for a receptor. In some embodiments, the targeting domain is a ligand for a receptor expressed on the surface of a T cell. In some embodiments, the ligand is a cytokine. In some embodiments, the cytokine includes but is not limited to the group consisting interleukins, interferons, and functional derivatives thereof. In some embodiments, the cytokine includes but is not limited to the group consisting IL2, IL3, IL4, IL7, IL9, IL12, IL15, IL18, IL21, IL22, IL23, IL27, IL28, IL34, and modified versions or fragments thereof that bind to their cognate ligand expressed on the surface of a T-cell. In some embodiments, the cytokine includes but is not limited to the group consisting of interferon alpha, interferon a2b, interferon gamma, or interferon lambda and modified versions or fragments thereof that bind to their cognate ligand expressed on the surface of a T-cell.

In another aspect, the present disclosure provides a multivalent binding molecule, the multivalent binding molecule comprising: (a) a IL23R binding molecule and (b) a second binding molecule that specifically binds to the extracellular domain of a second cell surface molecule, wherein the IL23R binding molecule and second binding molecule are operably linked, optionally through a chemical or polypeptide linker. In some embodiments, the IL23R binding molecules of the present disclosure are useful in the preparation of the multivalent binding molecules described in Gonzalez, et al. PCT/US2018/021301 published as WO 2018/182935 A1 on Oct. 4, 2018. In some aspects, the second binding molecule specifically binds to the extracellular domain of: (i) a component of cytokine receptor that activates the JAK/STAT pathway in the cell; (ii) a receptor tyrosine kinase; or (iii) a TNFR superfamily member. In some embodiments, the second surface molecule is a tyrosine kinase selected from EGFR, ErbB2, ErbB3, ErbB4, InsR, IGF1R, InsRR, PDGFRα, PDGFRβ, CSF1R/Fms, cKit, Flt-3/Flk2, VEGFR1, VEGFR2, VEGFR3, FGFR1, FGFR2, FGFR3, FGFR4, PTK7/CCK4, TrkA, TrkB, TrkC, Ror1, Ror2, MuSK, Met, Ron, Axl, Mer, Tyro3, Tie1, Tie2, EphA1-8, EphA10, EphB1-4, EphB6, Ret, Ryk, DDR1, DDR2, Ros, LMR1, LMR2, LMR3, ALK, LTK, SuRTK106/STYK1. In some embodiments, the second surface molecule is a TNFR superfamily member is selected from TNFR1 (TNFRSF1A), TNFR2 (TNFRSF1B; TNFRSF2), 41-BB (TNFRSF9); AITR (TNFRSF18); BCMA (TNFRSF17), CD27 (TNFRSF7), CD30 (TNFRSF8), CD40 (TNFRSF5), Death Receptor 1 (TNFRSF10C), Death Receptor-3 (TNFRSF25), Death Receptor 4 (TNFRSF10A), Death Receptor 5 (TNFRSF10B), Death Receptor-6 (TNFRSF21), Decoy Receptor-3 (TNFRSF6B), Decoy Receptor 2 (TNFRSF10D), EDAR, Fas (TNFRSF6), HVEM (TNFRSF14), LTBR (TNFRSF3), OX40 (TNFRSF4), RANK (TNFRSF11A), TAC1 (TNFRSF13B), Troy (TNFRSF19), XEDAR (TNFRSF27), Osteoprotegerin (TNFRSF11B), TWEAK receptor (TNFRSF12A), BAFF Receptor (TNFRSF13C), NGF receptor (TNFRSF16).

In some embodiments, the targeting domain is a polypeptide that specifically binds to a cell surface molecule associated with a tumor cell (e.g., a cognate ligand for a tumor cell receptor) selected from the group consisting of GD2, BCMA, CD19, CD33, CD38, CD70, GD2, IL3Ra2, CD19, mesothelin, Her2, EpCam, Mucd, ROR1, CD133, CEA, EGRFRVIII, PSCA, GPC3, Pan-ErbB and FAP.

In some embodiments, the targeting domain of the IL23R binding molecule is an antibody (as defined hereinabove to include molecules such as VHHs, scFvs, etc.) Examples of antibodies that may incorporated as a targeting domain of a IL23R binding molecule include but are not limited to the group consisting of: anti-GD2 antibodies, anti-BCMA antibodies, anti-CD19 antibodies, anti-CD33 antibodies, anti-CD38 antibodies, anti-CD70 antibodies, anti-GD2 antibodies and IL3Ra2 antibodies, anti-CD19 antibodies, anti-mesothelin antibodies, anti-Her2 antibodies, anti-EpCam antibodies, anti-Muc antibodies, anti-ROR1 antibodies, anti-CD133 antibodies, anti-CEA antibodies, anti-PSMA antibodies, anti-EGRFRVIII antibodies, anti-PSCA antibodies, anti-GPC3 antibodies, anti-Pan-ErbB antibodies, and anti-FAP antibodies.

The antibody or antigen-binding fragment thereof can also be linked to another antibody to form, e.g., a bispecific or a multispecific antibody Labels In some embodiments, IL23R binding molecules of the present disclosure comprise a label. In some embodiments, the label is incorporated to facilitate use as imaging agent, diagnostic agent, or for use in cell sorting procedures. The term labels includes but is not limited to fluorescent labels, a biologically active enzyme labels, a radioisotopes (e.g., a radioactive ions), a nuclear magnetic resonance active labels, a luminescent labels, or a magnetic compound. In one embodiment a IL23R binding sdAb (e.g., a IL23R binding VHH) molecule in stable association (e.g., covalent, coordinate covalent) with an imaging labels. The term imaging labels is used to describe any of a variety of compounds a signature that facilitates identification, tracing and/or localization of the IL23R binding sdAb (or its metabolites) using diagnostic procedures. Examples of imaging labels include, but are not limited to, fluorescent compounds, radioactive compounds, and compounds opaque to imaging methods (e.g., X-ray, ultrasound). Examples of radioactive compounds useful as imaging label include but are not limited to Technetium-99m ($^{99m}$Tc), Indium-111 ($^{111}$In), Iodine-131 ($^{131}$I), Iodine-123 ($^{123}$I), Iodine-125 ($^{125}$I), Gallium-67 ($^{67}$Ga), and Lutetium-177 ($^{17}$Lu), phosphorus ($^{32}$P), carbon ($^{14}$C), tritium ($^{3}$H), yttrium ($^{90}$Y), actinium ($^{225}$Ac), astatine ($^{211}$At), rhenium ($^{186}$Re), bismuth ($^{212}$Bi or $^{213}$Bi), and rhodium ($^{188}$Rh).

Therapeutic Agents

In some embodiments, IL23R binding molecules of the present disclosure comprise a therapeutic agent. Examples of therapeutic agents include therapeutic small molecule (e.g., chemotherapeutic agents) or biologic therapeutic agents including antibodies, cytoxic or cytostatic compounds, a radioisotope, molecules of plant, fungal, or bacterial origin, or biological proteins (e.g., protein toxins) or particles (e.g., nano-particles or recombinant viral particles, e.g., via a viral coat protein), therapeutic antibodies antibodies, chemotherapeutic agents, as described more fully herein.

In some embodiments, the therapeutic agent which may be incorporated into the IL23R binding molecules of the present disclosure is short-range radiation emitters, including, for example, short-range, high-energy a-emitters. Examples of such radioisotope include an alpha-emitter, a beta-emitter, a gamma-emitter or a beta/gamma emitter. Radioisotopes useful as therapeutic agents include yttrium 90 ($^{90}$Y), lutetium-177 ($^{77}$Lu), actinium-225 ($^{225}$Ac), astatine-211 ($^{211}$At), rhenium-186 ($^{186}$Re), bismuth-212 ($^{212}$Bi), bismuth-213 ($^{213}$Bi), and rhodium-188 ($^{188}$Rh).

In some embodiments, the IL23R binding molecules comprises a cytotoxic agent (or derivative thereof), such maytansinol or the DM1 maytansinoid), a taxane, or a calicheamicin, *Pseudomonas* exotoxin A, deBouganin, ricin toxin, diphtheria toxin, an amatoxin, such as a-amanitin, saporin, maytansine, a maytansinoid, an auristatin, an anthracycline, a calicheamicin, irinotecan, SN-38, a duocarmycin, a pyrrolobenzodiazepine, a pyrrolobenzodiazepine dimer, an indolinobenzodiazepine, and an indolinobenzodiazepine dimer, or a variant thereof.

Multispecific Binding Format

The sdAbs can be combined to provide multispecific targeting and selection including in combination with bi-specific and tri-specific constructs which bind to one or more cell surface antigens.

Synthesis of IL23R Binding Molecules:

In some embodiments, the IL23R binding molecules of the present disclosure are polypeptides. However, in some embodiments, only a portion of the IL23R binding molecule is a polypeptide, for example where the IL23R binding molecule comprises a non-peptidyl domain (e.g., a PEG IL23R binding sdAb conjugate, a radionucleotide IL23R binding sdAb conjugate, or a small molecule IL23R binding sdAb conjugate). The following provides guidance to enable the solid phase and recombinant synthesis of the polypeptide portions (domains) of IL23R binding molecules of the present disclosure. In those embodiments where only a portion of the IL23R binding molecule is a polypeptide, it will be understood that the peptidyl domain(s) of the IL23R binding molecule are an intermediate in the process which may undergo further processing to complete the synthesis of the desired IL23R binding molecules. The polypeptide domains of IL23R binding molecules may be produced by conventional methodology for the construction of polypeptides including recombinant or solid phase syntheses as described in more detail below.

Chemical Synthesis

In addition to generating mutant polypeptides via expression of nucleic acid molecules that have been altered by recombinant molecular biological techniques, polypeptide domains of IL23R binding molecules can be chemically synthesized. Chemically synthesized polypeptides are routinely generated by those of skill in the art. Chemical synthesis includes direct synthesis of a peptide by chemical means of the polypeptide domains of IL23R binding molecules exhibiting the properties described. This method can incorporate both natural and unnatural amino acids at desired positions that facilitate linkage of particular molecules (e.g., PEG).

In some embodiments, the polypeptide domains of IL23R binding molecules of the present disclosure may be prepared by chemical synthesis. The chemical synthesis of the polypeptide domains of IL23R binding molecules may proceed via liquid-phase or solid-phase. Solid-phase peptide synthesis (SPPS) allows the incorporation of unnatural amino acids and/or peptide/protein backbone modification. Various forms of SPPS are available for synthesizing the polypeptide domains of IL23R binding molecules of the present disclosure are known in the art (e.g., Ganesan A. (2006) Mini Rev. Med. Chem. 6:3-10; and Camarero J. A. et al., (2005) Protein Pept Lett. 12:723-8). In the course of chemical synthesis, the alpha functions and any reactive side chains may protected with acid-labile or base-labile groups that are stable under the conditions for linking amide bonds but can readily be cleaved without impairing the peptide chain that has formed.

In the solid phase synthesis, either the N-terminal or C-terminal amino acid may be coupled to a suitable support material. Suitable support materials are those which are inert towards the reagents and reaction conditions for the stepwise condensation and cleavage reactions of the synthesis process and which do not dissolve in the reaction media being used. Examples of commercially available support materials include styrene/divinylbenzene copolymers which have been modified with reactive groups and/or polyethylene glycol; chloromethylated styrene/divinylbenzene copolymers; hydroxymethylated or aminomethylated styrene/divinylbenzene copolymers; and the like. The successive coupling of the protected amino acids can be carried out according to conventional methods in peptide synthesis, typically in an automated peptide synthesizer.

At the end of the solid phase synthesis, the peptide is cleaved from the support material while simultaneously cleaving the side chain protecting groups. The peptide obtained can be purified by various chromatographic methods including but not limited to hydrophobic adsorption chromatography, ion exchange chromatography, distribution chromatography, high pressure liquid chromatography (HPLC) and reversed-phase HPLC.

Recombinant Production

Alternatively, polypeptide domains of IL23R binding molecules of the present disclosure may be produced by recombinant DNA technology. In the typical practice of recombinant production of polypeptides, a nucleic acid sequence encoding the desired polypeptide is incorporated into an expression vector suitable for the host cell in which expression will be accomplish, the nucleic acid sequence being operably linked to one or more expression control sequences encoding by the vector and functional in the target host cell. The recombinant protein may be recovered through disruption of the host cell or from the cell medium if a secretion leader sequence (signal peptide) is incorporated into the polypeptide. The recombinant protein may be purified and concentrated for further use including incorporation.

Synthesis of Nucleic Acid Sequences Encoding the IL23R Binding Molecule

In some embodiments, the polypeptide domains of IL23R binding molecule is produced by recombinant methods using a nucleic acid sequence encoding the polypeptide domains of IL23R binding molecule (or fusion protein comprising the polypeptide domains of IL23R binding molecule). The nucleic acid sequence encoding the desired polypeptide domains of IL23R binding molecule can be synthesized by chemical means using an oligonucleotide synthesizer.

The nucleic acid molecules are not limited to sequences that encode polypeptides; some or all of the non-coding sequences that lie upstream or downstream from a coding sequence (e.g., the coding sequence of the polypeptide domains of IL23R binding molecule) can also be included. Those of ordinary skill in the art of molecular biology are familiar with routine procedures for isolating nucleic acid molecules. They can, for example, be generated by treatment of genomic DNA with restriction endonucleases, or by performance of the polymerase chain reaction (PCR). In the event the nucleic acid molecule is a ribonucleic acid (RNA), molecules can be produced, for example, by in vitro transcription.

The nucleic acid molecules encoding the polypeptide domains of IL23R binding molecule (and fusions thereof) may contain naturally occurring sequences or sequences that differ from those that occur naturally, but, due to the degeneracy of the genetic code, encode the same polypeptide. These nucleic acid molecules can consist of RNA or DNA (for example, genomic DNA, cDNA, or synthetic DNA, such as that produced by phosphoramidite-based synthesis), or combinations or modifications of the nucleotides within these types of nucleic acids. In addition, the nucleic acid molecules can be double-stranded or single-stranded (i.e., either a sense or an antisense strand).

Nucleic acid sequences encoding the polypeptide domains of the IL23R binding molecule may be obtained from various commercial sources that provide custom synthesis of nucleic acid sequences. Amino acid sequence variants of the HUMAN IL23R binding molecules of the present disclosure are prepared by introducing appropriate nucleotide changes into the coding sequence based on the genetic code which is well known in the art. Such variants represent insertions, substitutions, and/or specified deletions of, residues as noted. Any combination of insertion, substitution, and/or specified deletion can be made to arrive at the final construct, provided that the final construct possesses the desired biological activity as defined herein.

Methods for constructing a DNA sequence encoding the polypeptide domains of IL23R binding molecule and expressing those sequences in a suitably transformed host include, but are not limited to, using a PCR-assisted mutagenesis technique. Mutations that consist of deletions or additions of amino acid residues to polypeptide domains of IL23R binding molecule can also be made with standard recombinant techniques. In the event of a deletion or addition, the nucleic acid molecule encoding polypeptide domains of IL23R binding molecule is optionally digested with an appropriate restriction endonuclease. The resulting fragment can either be expressed directly or manipulated further by, for example, ligating it to a second fragment. The ligation may be facilitated if the two ends of the nucleic acid molecules contain complementary nucleotides that overlap one another, but blunt-ended fragments can also be ligated. PCR-generated nucleic acids can also be used to generate various mutant sequences.

A polypeptide domain of IL23R binding molecules of the present disclosure may be produced recombinantly not only directly, but also as a fusion polypeptide with a heterologous polypeptide, e.g., a signal sequence or other polypeptide having a specific cleavage site at the N-terminus or C-terminus of the mature IL23R binding molecule. In general, the signal sequence may be a component of the vector, or it may be a part of the coding sequence that is inserted into the vector. The heterologous signal sequence selected preferably is one that is recognized and processed (i.e., cleaved by a signal peptidase) by the host cell. In some embodiments, the signal sequence is the signal sequence that is natively associated with the IL23R binding molecule (i.e. the human IL23R signal sequence). The inclusion of a signal sequence depends on whether it is desired to secrete the IL23R binding molecule from the recombinant cells in which it is made. If the chosen cells are prokaryotic, it generally is preferred that the DNA sequence not encode a signal sequence. If the chosen cells are eukaryotic, it generally is preferred that a signal sequence be encoded and most preferably that the wild type IL-2 signal sequence be used. Alternatively, heterologous mammalian signal sequences may be suitable, such as signal sequences from secreted polypeptides of the same or related species, as well as viral secretory leaders, for example, the herpes simplex gD signal. When the recombinant host cell is a yeast cell such as *Saccharomyces cerevisiae*, the alpha mating factor secretion signal sequence may be employed to achieve extracellular secretion of the IL23R binding molecule into the culture medium as described in Singh, U.S. Pat. No. 7,198,919 B1.

In the event the polypeptide domain of IL23R binding molecules to be expressed is to be expressed as a chimera (e.g., a fusion protein comprising a IL23R binding molecule and a heterologous polypeptide sequence), the chimeric protein can be encoded by a hybrid nucleic acid molecule comprising a first sequence that encodes all or part of the polypeptide domains of IL23R binding molecule and a second sequence that encodes all or part of the heterologous polypeptide. For example, polypeptide domains of IL23R binding molecules described herein may be fused to a hexa-histidine tag (SEQ ID NO: 330) to facilitate purification of bacterially expressed protein, or to a hemagglutinin tag to facilitate purification of protein expressed in eukaryotic cells. By first and second, it should not be understood as limiting to the orientation of the elements of the fusion protein and a heterologous polypeptide can be linked at either the N-terminus and/or C-terminus of the polypeptide domains of IL23R binding molecule. For example, the N-terminus may be linked to a targeting domain and the C-terminus linked to a hexa-histidine tag (SEQ ID NO: 330) purification handle.

The complete amino acid sequence of the polypeptide domain of IL23R binding molecule (or fusion/chimera) to be expressed can be used to construct a back-translated gene. A DNA oligomer containing a nucleotide sequence coding for the polypeptide domain of IL23R binding molecules can be synthesized. For example, several small oligonucleotides coding for portions of the desired polypeptide can be synthesized and then ligated. The individual oligonucleotides typically contain 5' or 3' overhangs for complementary assembly.

In some embodiments, the nucleic acid sequence encoding the polypeptide domain of the IL23R binding molecule may be "codon optimized" to facilitate expression in a particular host cell type. Techniques for codon optimization in a wide variety of expression systems, including mammalian, yeast and bacterial host cells, are well known in the and there are online tools to provide for a codon optimized sequences for expression in a variety of host cell types. See e.g., Hawash, et al., (2017) 9:46-53 and Mauro and Chappell in *Recombinant Protein Expression in Mammalian Cells: Methods and Protocols*, edited by David Hacker (Human Press New York). Additionally, there are a variety of web based on-line software packages that are freely available to assist in the preparation of codon optimized nucleic acid sequences.

Expression Vectors

Once assembled (by synthesis, site-directed mutagenesis or another method), the nucleic acid sequence encoding polypeptide domains of IL23R binding molecule will be inserted into an expression vector. A variety of expression vectors for uses in various host cells are available and are typically selected based on the host cell for expression. An expression vector typically includes, but is not limited to, one or more of the following: an origin of replication, one or more marker genes, an enhancer element, a promoter, and a transcription termination sequence. Vectors include viral vectors, plasmid vectors, integrating vectors, and the like. Plasmids are examples of non-viral vectors. To facilitate efficient expression of the recombinant polypeptide, the nucleic acid sequence encoding the polypeptide sequence to be expressed is operably linked to transcriptional and translational regulatory control sequences that are functional in the chosen expression host.

Expression vectors typically contain a selection gene, also termed a selectable marker. This gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media.

Expression vectors for polypeptide domain of IL23R binding molecules of the present disclosure contain a regulatory sequence that is recognized by the host organism and is operably linked to nucleic acid sequence encoding the polypeptide domains of IL23R binding molecule. The terms "regulatory control sequence," "regulatory sequence" or "expression control sequence" are used interchangeably herein to refer to promoters, enhancers, and other expression control elements (e.g., polyadenylation signals). See, for example, Goeddel (1990) in Gene Expression Technology: Methods in Enzymology 185 (Academic Press, San Diego, CA USA Regulatory sequences include those that direct constitute expression of a nucleotide sequence in many types of host cells and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. In selecting an expression control sequence, a variety of factors understood by one of skill in the art are to be considered. These include, for example, the relative strength of the sequence, its controllability, and its compatibility with the actual DNA sequence encoding the subject IL23R binding molecule, particularly as regards potential secondary structures.

In some embodiments, the regulatory sequence is a promoter, which is selected based on, for example, the cell type in which expression is sought. Promoters are untranslated sequences located upstream (5') to the start codon of a structural gene (generally within about 100 to 1000 bp) that control the transcription and translation of particular nucleic acid sequence to which they are operably linked. Such promoters typically fall into two classes, inducible and constitutive. Inducible promoters are promoters that initiate increased levels of transcription from DNA under their control in response to some change in culture conditions, e.g., the presence or absence of a nutrient or a change in temperature. A large number of promoters recognized by a variety of potential host cells are well known.

A T7 promoter can be used in bacteria, a polyhedrin promoter can be used in insect cells, and a cytomegalovirus or metallothionein promoter can be used in mammalian cells. Also, in the case of higher eukaryotes, tissue-specific and cell type-specific promoters are widely available. These promoters are so named for their ability to direct expression of a nucleic acid molecule in a given tissue or cell type within the body. Skilled artisans are well aware of numerous promoters and other regulatory elements which can be used to direct expression of nucleic acids.

Transcription from vectors in mammalian host cells may be controlled, for example, by promoters obtained from the genomes of viruses such as polyoma virus, fowlpox virus, adenovirus (such as human adenovirus serotype 5), bovine papilloma virus, avian sarcoma virus, cytomegalovirus, a retrovirus (such as murine stem cell virus), hepatitis-B virus and most preferably Simian Virus 40 (SV40), from heterologous mammalian promoters, e.g., the actin promoter, PGK (phosphoglycerate kinase), or an immunoglobulin promoter, from heat-shock promoters, provided such promoters are compatible with the host cell systems. The early and late promoters of the SV40 virus are conveniently obtained as an SV40 restriction fragment that also contains the SV40 viral origin of replication.

Transcription by higher eukaryotes is often increased by inserting an enhancer sequence into the vector. Enhancers are cis-acting elements of DNA, usually about from 10 to 300 bp, which act on a promoter to increase its transcription. Enhancers are relatively orientation and position independent, having been found 5' and 3' to the transcription unit, within an intron, as well as within the coding sequence itself. Many enhancer sequences are now known from mammalian genes (globin, elastase, albumin, alpha-fetoprotein, and insulin). Typically, however, one will use an enhancer from a eukaryotic cell virus. Examples include the SV40 enhancer on the late side of the replication origin, the cytomegalovirus early promoter enhancer, the polyoma enhancer on the late side of the replication origin, and adenovirus enhancers. The enhancer may be spliced into the expression vector at a position 5' or 3' to the coding sequence but is preferably located at a site 5' from the promoter. Expression vectors used in eukaryotic host cells will also contain sequences necessary for the termination of transcription and for stabilizing the mRNA. Such sequences are commonly available from the 5' and, occasionally 3', untranslated regions of eukaryotic or viral DNAs or cDNAs. Construction of suitable vectors containing one or more of the above-listed components employs standard techniques.

In addition to sequences that facilitate transcription of the inserted nucleic acid molecule, vectors can contain origins of replication, and other genes that encode a selectable marker. For example, the neomycin-resistance (neoR) gene imparts G418 resistance to cells in which it is expressed, and thus permits phenotypic selection of the transfected cells. Additional examples of marker or reporter genes include beta-lactamase, chloramphenicol acetyltransferase (CAT), adenosine deaminase (ADA), dihydrofolate reductase (DHFR), hygromycin-B-phosphotransferase (HPH), thymidine kinase (TK), lacZ (encoding beta-galactosidase), and xanthine guanine phosphoribosyltransferase (XGPRT). Those of skill in the art can readily determine whether a given regulatory element or selectable marker is suitable for use in a particular experimental context. Proper assembly of the expression vector can be confirmed by nucleotide sequencing, restriction mapping, and expression of a biologically active polypeptide in a suitable host.

Host Cells

The present disclosure further provides prokaryotic or eukaryotic cells that contain and express a nucleic acid molecule that encodes a polypeptide domains of IL23R binding molecule. A cell of the present disclosure is a transfected cell, i.e., a cell into which a nucleic acid molecule, for example a nucleic acid molecule encoding a polypeptide domains of IL23R binding molecule, has been introduced by means of recombinant DNA techniques. The progeny of such a cell are also considered within the scope of the present disclosure.

Host cells are typically selected in accordance with their compatibility with the chosen expression vector, the toxicity of the product coded for by the DNA sequences of this IL23R binding molecule, their secretion characteristics, their ability to fold the polypeptides correctly, their fermentation or culture requirements, and the ease of purification of the products coded for by the DNA sequences. Suitable host cells for cloning or expressing the DNA in the vectors herein are the prokaryote, yeast, or higher eukaryote cells.

In some embodiments the recombinant polypeptide domains of IL23R binding molecule or biologically active variants thereof can also be made in eukaryotes, such as yeast or human cells. Suitable eukaryotic host cells include insect cells (examples of Baculovirus vectors available for expression of proteins in cultured insect cells (e.g., Sf9 cells) include the pAc series (Smith et al. (1983) Mol. Cell Biol. 3:2156-2165) and the pVL series (Lucklow and Summers (1989) Virology 170:31-39)); yeast cells (examples of vectors for expression in yeast *S. cerevisiae* include pYepSecl (Baldari et al. (1987) EMBO J. 6:229-234), pMFa (Kurjan and Herskowitz (1982) Cell 30:933-943), pJRY88 (Schultz et al. (1987) Gene 54:113-123), pYES2 (Invitrogen Corporation, San Diego, Calif.), and pPicZ (Invitrogen Corporation, San Diego, Calif)); or mammalian cells (mammalian expression vectors include pCDM8 (Seed (1987) Nature 329:840) and pMT2PC (Kaufman et al. (1987) EMBO J. 6:187:195)).

Examples of useful mammalian host cell lines are mouse L cells (L-M[TK-], ATCC #CRL-2648), monkey kidney CV1 line transformed by SV40 (COS-7, ATCC CRL 1651); human embryonic kidney line (HEK293 or HEK293 cells subcloned for growth in suspension culture; baby hamster kidney cells (BHK, ATCC CCL 10); Chinese hamster ovary cells/-DHFR (CHO); mouse sertoli cells (TM4); monkey kidney cells (CV1 ATCC CCL 70); African green monkey kidney cells (VERO-76, ATCC CRL-1 587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells; MRC 5 cells; FS4 cells; and a human hepatoma line (Hep G2). In mammalian cells, the expression vector's control functions are often provided by viral regulatory elements. For example, commonly used promoters are derived from polyoma, Adenovirus 2, cytomegalovirus, and Simian Virus 40.

The polypeptide domains of IL23R binding molecule can be produced in a prokaryotic host, such as the bacterium *E. coli*, or in a eukaryotic host, such as an insect cell (e.g., an Sf21 cell), or mammalian cells (e.g., COS cells, NIH 3T3 cells, or HeLa cells). These cells are available from many sources, including the American Type Culture Collection (Manassas, Va.). Artisans or ordinary skill are able to make such a determination. Furthermore, if guidance is required in selecting an expression system, skilled artisans may consult Ausubel et al. (Current Protocols in Molecular Biology, John Wiley and Sons, New York, N.Y., 1993) and Pouwels et al. (Cloning Vectors: A Laboratory Manual, 1985 Suppl. 1987).

In some embodiments, the recombinant polypeptide domains of IL23R binding molecule may be glycosylated or unglycosylated depending on the host organism used to produce the IL23R binding molecule. If bacteria are chosen as the host then the polypeptide domains of IL23R binding molecule produced will be aglycosylated. Eukaryotic cells, on the other hand, will glycosylate the recombinant polypeptide domains of IL23R binding molecule.

For other additional expression systems for both prokaryotic and eukaryotic cells, see Chapters 16 and 17 of Sambrook et al. (1989) Molecular Cloning: A Laboratory Manual (2nd ed., Cold Spring Harbor Laboratory Press, Plainview, N.Y.). See, Goeddel (1990) in Gene Expression Technology: Methods in Enzymology 185 (Academic Press, San Diego, Calif.).

Transfection

The expression constructs of the can be introduced into host cells to thereby produce the recombinant polypeptide domains of IL23R binding molecule disclosed herein or to produce biologically active muteins thereof. Vector DNA can be introduced into prokaryotic or eukaryotic cells via conventional transformation or transfection techniques. Suitable methods for transforming or transfecting host cells can be found in Sambrook et al. (1989) Molecular Cloning: A Laboratory Manual (2d ed., Cold Spring Harbor Laboratory Press, Plainview, N.Y.) and other standard molecular biology laboratory manuals.

In order to facilitate transfection of the target cells, the target cell may be exposed directly with the non-viral vector may under conditions that facilitate uptake of the non-viral vector. Examples of conditions which facilitate uptake of foreign nucleic acid by mammalian cells are well known in the art and include but are not limited to chemical means (such as Lipofectamine®, Thermo-Fisher Scientific), high salt, and magnetic fields (electroporation).

Cell Culture

Cells may be cultured in conventional nutrient media modified as appropriate for inducing promoters, selecting transformants, or amplifying the genes encoding the desired sequences. Mammalian host cells may be cultured in a variety of media. Commercially available media such as Ham's F10 (Sigma), Minimal Essential Medium ((MEM), Sigma), RPMI 1640 (Sigma), and Dulbecco's Modified Eagle's Medium ((DMEM), Sigma) are suitable for culturing the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics, trace elements, and glucose or an equivalent energy source. Any other necessary supplements may also be included at appropriate concentrations that would be known to those skilled in the art. The culture conditions, such as temperature, pH and the like, are those previously used with the host cell selected for expression and will be apparent to the ordinarily skilled artisan.

Recovery of Recombinant Proteins

Recombinantly-produced IL23R binding polypeptides can be recovered from the culture medium as a secreted polypeptide if a secretion leader sequence is employed. Alternatively, the IL23R binding polypeptides can also be recovered from host cell lysates. A protease inhibitor, such as phenyl methyl sulfonyl fluoride (PMSF) may be employed during the recovery phase from cell lysates to inhibit proteolytic degradation during purification, and antibiotics may be included to prevent the growth of adventitious contaminants.

Purification

Various purification steps are known in the art and find use, e.g., affinity chromatography. Affinity chromatography makes use of the highly specific binding sites usually present in biological macromolecules, separating molecules on their ability to bind a particular ligand. Covalent bonds attach the ligand to an insoluble, porous support medium in a manner that overtly presents the ligand to the protein sample, thereby using natural specific binding of one molecular species to separate and purify a second species from a mixture. Antibodies are commonly used in affinity chromatography. Size selection steps may also be used, e.g., gel filtration chromatography (also known as size-exclusion chromatography or molecular sieve chromatography) is used to separate proteins according to their size. In gel filtration, a protein solution is passed through a column that is packed with semipermeable porous resin. The semipermeable resin has a range of pore sizes that determines the size of proteins that can be separated with the column.

The recombinant polypeptide domains of IL23R binding molecule produced by the transformed host can be purified according to any suitable method. IL23R binding molecules can be isolated from inclusion bodies generated in *E. coli*, or from conditioned medium from either mammalian or yeast cultures producing a given IL23R binding molecule sing cation exchange, gel filtration, and or reverse phase liquid chromatography.

The substantially purified forms of the recombinant polypeptides can be used, e.g., as therapeutic agents, as described herein.

The biological activity of the recombinant polypeptide domains of IL23R binding molecule produced in accordance with the foregoing can be confirmed by a IL23R binding using procedures well known in the art including but not limited to competition ELISA, radioactive ligand binding assays (e.g., saturation binding, Scatchard plot, nonlinear curve fitting programs and competition binding assays); non-radioactive ligand binding assays (e.g., fluorescence polarization (FP), fluorescence resonance energy transfer (FRET) and surface plasmon resonance assays (see, e.g., Drescher et al., Methods Mol Biol 493:323-343 (2009) with instrumentation commercially available from GE Healthcare Bio-Sciences such as the Biacore 8+, Biacore S200, Biacore T200 (GE Healthcare Bio-Sciences, 100 Results Way, Marlborough MA 01752)); liquid phase ligand binding assays (e.g., real-time polymerase chain reaction (RT-qPCR), and immunoprecipitation); and solid phase ligand binding assays (e.g., multiwell plate assays, on-bead ligand binding assays, on-column ligand binding assays, and filter assays).

Methods of Use

Inhibition of IL23R Receptor Activity

In one embodiment, the present disclosure provides a method of modulating the activity of cells expressing the IL23R by the administration of a IL23R binding molecule to a subject in an amount sufficient to interfere with the activity of receptors comprising the of IL23R. The present disclosure further provides a method of modulating the activity of cells expressing the IL23R in a mixed population of cells comprising contacting said population of cells, in vivo and/or ex vivo, with a IL23R binding molecule or complex of the present disclosure to in an amount sufficient to interfere with the activity of receptors comprising the IL23R.

Autoimmune and Inflammatory Diseases

In one embodiment the present disclosure provides a method of treating a T cell mediated autoimmune disease, the method comprising the administration of a IL23R binding molecule to a subject in an amount effective to inhibit a T-cell mediated immune response. IL23R binding molecules of the present disclosure specifically bind to the ECD of the IL23R, either alone or associated with other molecules, and are useful in modulating the function of the cells expressing the IL23R isoform and are useful in the treatment or prevention of diseases, disorders or conditions associated with inflammation or autoimmunity where immunological memory is involved in the cause, maintenance or exacerbation of the disease, disorder or condition.

Autoimmune and inflammatory diseases, disorders or conditions amenable to treatment or prophylaxis with the compositions of the present disclosure include autoimmune diseases, such as, rheumatoid arthritis, psoriasis, psoriatic arthritis, autoimmune thyroiditis, Graves disease, type I and type II diabetes, multiple sclerosis, Crohn's disease (CD), inflammatory bowel disease (IBD), ulcerative colitis (UC), systemic lupus erythematosus (SLE), graft versus host disease (GVHD), psoriasis, and dermatitis. The tolerogenic properties IL23R antibodies and complexes thereof of the present disclosure are useful in the induction of tolerance to alloantigens, autoantigens, allergens, bacterial antigens and conditions arising therefore including allergic contact dermatitis, and/or allergies, including allergic asthma.

In the treatment of autoimmune diseases, the IL23R binding molecule of the present disclosure may be administered alone or combination with one or more immunomodulatory or anti-inflammatory agents. Examples of immunomodulatory or anti-inflammatory agents which may be combined with administration IL23R binding molecule or incorporation by conjugated to a IL23R binding molecule include but are not limited to cyclosporins such as cyclosporine A, cyclosporine G, FK-506, ABT-281, ASM 981; an mTOR inhibitor, e.g., rapamycin, 40-O-(2-hydroxy) ethyl-rapamycin, CC1779, ABT578, AP23573, AP23464, AP23675, AP23841, TAFA-93, biolimus-7 or bioimus-9; a corticosteroid; cyclophosphamide; azathioprine; methotrexate; a SIP receptor agonist, e.g., FTY 720 or an analogue thereof, leflunomide or analogs thereof, mizoribine; mycophenolic acid; mycophenolate mofetil; 15-deoxyspergualine or analogs thereof, immunosuppressive monoclonal antibodies, e.g., monoclonal antibodies to leukocyte receptors, e.g., MHC, CD2, CDS, CD4, CD11a/CD18. CD7, CD25, CD27, B7, CD40, CD58, CD137, ICOS, CD150 (SLAM), OX40, 4-1BB or their ligands, e.g., CD154; or other immunomodulatory compounds, e.g., a recombinant binding molecule having at least a portion of the extracellular domain of CTLA4 or a mutant thereof, e.g., an at least extracellular portion of CTLA4 or a mutant thereof joined to a non-CTLA4 protein sequence, e.g., CTLA41g (e.g., designated ATCC 68629) or a mutant thereof, e.g., LEA29Y, or other adhesion molecule inhibitors, e.g., mAbs or low molecular weight inhibitors including LFA-1 antagonists, selectin antagonists and VLA-4 antagonists.

Treatment of Neoplastic Disease

The present disclosure provides methods of use of IL23R binding molecules in the treatment of subjects suffering from a neoplastic disease disorder or condition by the administration of a therapeutically effective amount of a IL23R binding molecule (or nucleic acid encoding an IL23R binding molecule including recombinant vectors encoding IL23R binding molecules) as described herein. The compositions and methods of the present disclosure are useful in the treatment of subject suffering from a neoplastic disease characterized by the presence neoplasms, including benign and malignant neoplasms, and neoplastic disease.

Examples of benign neoplasms amenable to treatment using the compositions and methods of the present disclosure include but are not limited to adenomas, fibromas, hemangiomas, and lipomas. Examples of pre-malignant neoplasms amenable to treatment using the compositions and methods of the present disclosure include but are not limited to hyperplasia, atypia, metaplasia, and dysplasia. Examples of malignant neoplasms amenable to treatment using the compositions and methods of the present disclosure include but are not limited to carcinomas (cancers arising from epithelial tissues such as the skin or tissues that line internal organs), leukemias, lymphomas, and sarcomas typically derived from bone fat, muscle, blood vessels or connective tissues). Also included in the term neoplasms are viral induced neoplasms such as warts and EBV induced disease (i.e., infectious mononucleosis), scar formation, hyperproliferative vascular disease including intimal smooth muscle cell hyperplasia, restenosis, and vascular occlusion and the like.

The term "neoplastic disease" includes cancers characterized by solid tumors and non-solid tumors including but not limited to breast cancers; sarcomas (including but not limited to osteosarcomas and angiosarcomas and fibrosarcomas), leukemias, lymphomas, genitourinary cancers (including but not limited to ovarian, urethral, bladder, and prostate cancers); gastrointestinal cancers (including but not limited to colon esophageal and stomach cancers); lung cancers; myelomas; pancreatic cancers; liver cancers; kidney cancers; endocrine cancers; skin cancers; and brain or central and peripheral nervous (CNS) system tumors, malignant or benign, including gliomas and neuroblastomas, astrocytomas, myelodysplastic disorders; cervical carcinoma-in-situ; intestinal polyposes; oral leukoplakias; histiocytoses, hyperprofroliferative scars including keloid scars, hemangiomas; hyperproliferative arterial stenosis, psoriasis, inflammatory arthritis; hyperkeratoses and papulosquamous eruptions including arthritis.

The term neoplastic disease includes carcinomas. The term "carcinoma" refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. The term neoplastic disease includes adenocarcinomas. An "adenocarcinoma" refers to a carcinoma derived from glandular tissue or in which the tumor cells form recognizable glandular structures.

As used herein, the term "hematopoietic neoplastic disorders" refers to neoplastic diseases involving hyperplastic/neoplastic cells of hematopoietic origin, e.g., arising from myeloid, lymphoid or erythroid lineages, or precursor cells thereof.

Myeloid neoplasms include, but are not limited to, myeloproliferative neoplasms, myeloid and lymphoid disorders with eosinophilia, myeloproliferative/myelodysplastic neoplasms, myelodysplastic syndromes, acute myeloid leukemia and related precursor neoplasms, and acute leukemia of ambiguous lineage. Exemplary myeloid disorders amenable to treatment in accordance with the present disclosure include, but are not limited to, acute promyeloid leukemia (APML), acute myelogenous leukemia (AML) and chronic myelogenous leukemia (CML).

Lymphoid neoplasms include, but are not limited to, precursor lymphoid neoplasms, mature B-cell neoplasms, mature T-cell neoplasms, Hodgkin's Lymphoma, and immunodeficiency-associated lymphoproliferative disorders. Exemplary lymphic disorders amenable to treatment in accordance with the present disclosure include, but are not limited to, acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM).

In some instances, the hematopoietic neoplastic disorder arises from poorly differentiated acute leukemias (e.g., erythroblastic leukemia and acute megakaryoblastic leukemia). As used herein, the term "hematopoietic neoplastic disorders" refers malignant lymphomas including, but are not limited to, non-Hodgkins lymphoma and variants thereof, peripheral T cell lymphomas, adult T-cell leukemia/lymphoma (ATL), cutaneous T cell lymphoma (CTCL), large granular lymphocytic leukemia (LGF), Hodgkin's disease and Reed-Steinberg disease.

The determination of whether a subject is "suffering from a neoplastic disease" refers to a determination made by a physician with respect to a subject based on the available information accepted in the field for the identification of a disease, disorder or condition including but not limited to X-ray, CT-scans, conventional laboratory diagnostic tests (e.g., blood count, etc.), genomic data, protein expression data, immunohistochemistry, that the subject requires or will benefit from treatment.

Isolation, Enrichment or Depletion of IL23R+ Cells from a Biological Sample

In one embodiment, the present disclosure provides a method of use of the IL23R binding molecules of the present disclosure useful in a process for in the isolation, enrichment or depletion of IL23R+ cells from a biological sample comprising IL23R+ cells. The biological sample may comprise cells of blood origin such as PBMC, T cells, B cells of cell culture origin or of tissue origin such as brain or bone marrow. Processes suitable for the isolation, enrichment or depletion of IL23R+ cells comprise centrifugation, filtration, magnetic cell sorting and fluorescent cell sorting by techniques well known in the art. The present disclosure further provides a method for the treatment of a subject suffering from a disease, disorder or condition by the administration of a therapeutically effective amount of a cell product enriched or depleted of IL23R+ cells through the use of a IL23R binding molecule as described herein.

In one embodiment, the sorting procedure employs a IL23R binding molecule comprising a fluorescent label for use in FACS isolation or depletion of IL23R+ cells from a sample. The fluorescent label may be attached to the sdAb of the IL23R binding molecule directly (e.g., by chemical conjugation optionally employing a linker) or indirectly (e.g., by biotinylation of the sdAb and binding of the biotinylated antibody to a streptavidin fluorochrome conjugate). Such fluorescently labelled IL23R+ cells may be separated from a mixed cell population using conventional FACS technology.

In an alternative embodiment, the selection procedure employs IL23R binding molecules of the present disclosure (e.g., a IL23R binding VHH) conjugated to magnetic particles which provide magnetic labeling of the IL23R+ cells for use in magnetic cell separation procedures. In one embodiment the method comprises: (a) conjugation of one or more IL23R binding molecule of the present disclosure (e.g., a IL23R binding VHH) to a magnetic particle; (b) creating a mixture by contacting the biological sample with a quantity of the magnetic particles conjugated to IL23R binding molecule; (c) subjecting to a magnetic field such that the magnetically labelled IL23R+ cells are retained; (d) removing the non-magnetically labelled cells from the mixture; and (e) removal of the magnetic field enabling isolation of the IL23R+ cells.

The cell selection procedure (e.g., FACS or magnetic separation) results in two products: (a) a population of cells depleted of IL23R+ cells and (b) a population of cells enriched for IL23R+ cells. Each of these populations may be further processed by convention procedures to identify particular IL23R+ or IL23R− cell subsets which may be useful in research, diagnostic or clinical applications. For example, isolation of specific IL23R+ T cell subsets that also express one or more of CD4, CD8, CD19, CD25, and CD62L, further iterations of the using one or more antibodies that specifically bind to CD4, CD8, CD19, CD25, and CD62L antigens respectively by FACS or magnetic field separation by techniques well known in the art.

In one embodiment of the IL23R binding molecule a humanized antibody or fragment thereof as disclosed herein may be used for depletion of IL23R-expressing cells from a biological sample comprising IL23R-expressing cells such peripheral blood or lymphoid tissue which may optionally be further processed for further isolation of IL23R+ naïve T cell subsets, isolation human IL23R+ memory T cells from a population of CD4+ or CD8+ cells, or isolation of human IL23RRA+ naïve T cells from presorted CD4+ or CD8+ cells by depletion of IL23R+ cells. In one embodiment, the IL23R binding molecule provides a method of generating a population of cells enriched for naïve Tregs from a biological sample, the method comprising depleting IL23R+ cells using a IL23R binding molecule of the present disclosure as described above, optionally further comprising the steps of depleting CD8+ and/or CD19+ cells. The IL23R+ depleted cell population may optionally be further expanded in vitro for particular cell types to in the preparation of a cell product comprising a therapeutically effective amount of the IL23R+ depleted cell product which may be administered to a subject suffering from a disease, disorder or condition.

The IL23R+ enriched cell population may optionally be further expanded in vitro to in the preparation of a cell product comprising a therapeutically effective amount of the IL23R+ cells.

Combination with Supplementary Therapeutic Agents

The present disclosure provides for the use of the IL23R binding molecules of the present disclosure in combination with one or more additional active agents ("supplementary agents"). Such further combinations are referred to interchangeably as "supplementary combinations" or "supplementary combination therapy" and those therapeutic agents that are used in combination with IL23R binding molecules of the present disclosure are referred to as "supplementary agents." As used herein, the term "supplementary agents" includes agents that can be administered or introduced separately, for example, formulated separately for separate administration (e.g., as may be provided in a kit) and/or therapies that can be administered or introduced in combination with the IL23R binding molecules.

As used herein, the term "in combination with" when used in reference to the administration of multiple agents to a subject refers to the administration of a first agent at least one additional (i.e. second, third, fourth, fifth, etc.) agent to a subject. For purposes of the present invention, one agent (e.g., IL23R binding molecule) is considered to be administered in combination with a second agent (e.g., a modulator of an immune checkpoint pathway) if the biological effect resulting from the administration of the first agent persists in the subject at the time of administration of the second agent such that the therapeutic effects of the first agent and second agent overlap. For example, the PD1 immune checkpoint inhibitors (e.g., nivolumab or pembrolizumab) are typically administered by IV infusion every two weeks or every three weeks while the IL23R binding molecules of the present disclosure are typically administered more frequently, e.g., daily, BID, or weekly. However, the administration of the first agent (e.g., pembrolizumab) provides a therapeutic effect over an extended time and the administration of the second agent (e.g., an IL23R binding molecule) provides its therapeutic effect while the therapeutic effect of the first agent remains ongoing such that the second agent is considered to be administered in combination with the first agent, even though the first agent may have been administered at a point in time significantly distant (e.g., days or weeks) from the time of administration of the second agent. In one embodiment, one agent is considered to be administered in combination with a second agent if the first and second agents are administered simultaneously (within 30 minutes of each other), contemporaneously or sequentially. In some embodiments, a first agent is deemed to be administered "contemporaneously" with a second agent if first and second agents are administered within about 24 hours of each another, preferably within about 12 hours of each other, preferably within about 6 hours of each other, preferably within about 2 hours of each other, or preferably within about 30 minutes of each other. The term "in combination with" shall also understood to apply to the situation where a first agent and a second agent are co-formulated in single pharmaceutically acceptable formulation and the co-formulation is administered to a subject. In certain embodiments, the IL23R binding molecule and the supplementary agent(s) are administered or applied sequentially, e.g., where one agent is administered prior to one or more other agents. In other embodiments, the IL23R binding molecule and the supplementary agent(s) are administered simultaneously, e.g., where two or more agents are administered at or about the same time; the two or more agents may be present in two or more separate formulations or combined into a single formulation (i.e., a co-formulation). Regardless of whether the agents are administered sequentially or simultaneously, they are considered to be administered in combination for purposes of the present disclosure.

Chemotherapeutic Agents

In some embodiments, the supplementary agent is a chemotherapeutic agent. In some embodiments the supplementary agent is a "cocktail" of multiple chemotherapeutic agents. In some embodiments the chemotherapeutic agent or cocktail is administered in combination with one or more physical methods (e.g., radiation therapy). The term "chemotherapeutic agents" includes but is not limited to alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamime; nitrogen mustards such as chiorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins such as bleomycin A2, cactinomycin, calicheamicin, carabicin, caminomycin, carzinophilin, chromomycins, dactinomycin, daunorubicin and derivaties such as demethoxy-daunomycin, 11-deoxydaunorubicin, 13-deoxydaunorubicin, detorubicin, 6-diazo-5-oxo-L-norleucine, doxorubicin, epirubicin, esorubicin, idarubicin, marcellomycin, mitomycins such as mitomycin C, N-methyl mitomycin C; mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate, dideazatetrahydrofolic acid, and folinic acid; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside (Ara-C); cyclophosphamide; thiotepa; taxoids, e.g., paclitaxel, nab-paclitaxel and doxetaxel; chlorambucil; gemcitabine; 6-thioguanine; mercaptopurine; methotrexate; platinum and platinum coordination complexes such as cisplatin, oxaplatin and carboplatin; vinblastine; etoposide (VP-16); ifosfamide; mitomycin C; mitoxantrone; vincristine; vinorelbine; navelbine; novantrone; teniposide; daunomycin; aminopterin; xeloda; ibandronate; CPT11; topoisomerase inhibitors; difluoromethylomithine (DMFO); retinoic acid; esperamicins; capecitabine; taxanes such as paclitaxel, docetaxel, cabazitaxel; carminomycin, adriamycins such as 4'-epiadriamycin, 4-adriamycin-14-benzoate, adriamycin-14-octanoate, adriamycin-14-naphthaleneacetate; cholchicine and pharmaceutically acceptable salts, acids or derivatives of any of the above.

The term "chemotherapeutic agents" also includes anti-hormonal agents that act to regulate or inhibit hormone action on tumors such as anti-estrogens, including for example tamoxifen, raloxifene, aromatase inhibiting 4(5)-imidazoles, 4-hydroxytamoxifen, trioxifene, keoxifene, onapristone, and toremifene; and antiandrogens such as flutamide, nilutamide, bicalutamide, leuprolide, and goserelin; and pharmaceutically acceptable salts, acids or derivatives of any of the above.

In some embodiments, a supplementary agent is one or more chemical or biological agents identified in the art as useful in the treatment of neoplastic disease, including, but not limited to, a cytokines or cytokine antagonists such as IL-12, INFα, or anti-epidermal growth factor receptor, irinotecan; tetrahydrofolate antimetabolites such as pemetrexed; antibodies against tumor antigens, a complex of a monoclonal antibody and toxin, a T-cell adjuvant, bone marrow transplant, or antigen presenting cells (e.g., dendritic cell therapy), anti-tumor vaccines, replication competent viruses, signal transduction inhibitors (e.g., Gleevec® or Herceptin®) or an immunomodulator to achieve additive or synergistic suppression of tumor growth, non-steroidal anti-inflammatory drugs (NSAIDs), cyclooxygenase-2 (COX-2) inhibitors, steroids, TNF antagonists (e.g., Remicade® and Enbrel®), interferon-μ1a (Avonex®), and interferon-β1b (Betaseron®) as well as combinations of one or more of the foregoing as practiced in known chemotherapeutic treatment regimens including but not limited to TAC, FOLFOX, TPC, FEC, ADE, FOLFOX-6, EPOCH, CHOP, CMF, CVP, BEP, OFF, FLOX, CVD, TC, FOLFIRI, PCV, FOLFOXIRI, ICE-V, XELOX, and others that are readily appreciated by the skilled clinician in the art.

In some embodiments, the IL23R binding molecule is administered in combination with BRAF/MEK inhibitors, kinase inhibitors such as sunitinib, PARP inhibitors such as olaparib, EGFR inhibitors such as osimertinib (Ahn, et al. (2016) J Thorac Oncol 11:S115), IDO inhibitors such as epacadostat, and oncolytic viruses such as talimogene laherparepvec (T-VEC).

Therapeutic Antibodies

In some embodiments, a "supplementary agent" is a therapeutic antibody (including bi-specific and tri-specific antibodies which bind to one or more tumor associated antigens including but not limited to bispecific T cell engagers (BITEs), dual affinity retargeting (DART) constructs, and trispecific killer engager (TriKE) constructs).

In some embodiments, the therapeutic antibody is an antibody that binds to at least one tumor antigen selected from the group consisting of HER2 (e.g., trastuzumab, pertuzumab, ado-trastuzumab emtansine), nectin-4 (e.g., enfortumab), CD79 (e.g., polatuzumab vedotin), CTLA4 (e.g., ipilumumab), CD22 (e.g., moxetumomab pasudotox), CCR4 (e.g., magamuizumab), IL23p19 (e.g., tildrakizumab), PDL1 (e.g., durvalumab, avelumab, atezolizumab), IL17a (e.g., ixekizumab), CD38 (e.g., daratumumab), SLAMF7 (e.g., elotuzumab), CD20 (e.g., rituximab, tositumomab, ibritumomab and ofatumumab), CD30 (e.g., brentuximab vedotin), CD33 (e.g., gemtuzumab ozogamicin), CD52 (e.g., alemtuzumab), EpCam, CEA, fpA33, TAG-72, CAIX, PSMA, PSA, folate binding protein, GD2 (e.g., dinuntuximab), GD3, IL6 (e.g., silutxumab) GM2, $Le^y$, VEGF (e.g., bevacizumab), VEGFR, VEGFR2 (e.g., ramucirumab), PDGFR (e.g., olartumumab), EGFR (e.g., cetuximab, panitumumab and necitumumab), ERBB2 (e.g., trastuzumab), ERBB3, MET, IGF1R, EPHA3, TRAIL R1, TRAIL R2, RANKL RAP, tenascin, integrin □V□3, and integrin □4□1.

Cell Therapy Agents and Methods as Supplementary Agents

In some embodiments, the methods of the disclosure may include the administration of a IL23R binding molecule of the present disclosure in combination with supplementary agents in the form of cell therapies for the treatment of neoplastic, autoimmune or inflammatory diseases. Examples of cell therapies that are amenable to use in combination with the methods of the present disclosure include but are not limited to engineered T cell products comprising one or more first, second, third or fourth generation. CAR-T cells, engineered TCR cells, tumor infiltrating lymphocytes (TILs), and engineered Treg cells. In some embodiments, the extracellular domain of the chimeric antigen receptor of the CAR T cell is a polypeptide that specifically binds to one or more cell surface molecules preferentially or uniquely expressed on the extracellular surface of neoplastic cell (e.g., a tumor antigen) selected from the group consisting of GD2, BCMA, CD19, PSMA, CD33, CD38, CD70, GD2, IL3R□2, CD2, mesothelin, Her2, EpCam, Mucd, ROR1, CD133, CEA, EGRFRVIII, PSCA, GPC3, Pan-ErbB and FAP.

Physical Methods

In some embodiments, the supplementary agent is an anti-neoplastic physical method including but not limited to radiotherapy, cryotherapy, hyperthermic therapy, surgery, laser ablation, and proton therapy.

Formulations

The present disclosure further provides pharmaceutically acceptable formulations of the IL23R binding molecules of the present disclosure. The preferred formulation depends on the intended mode of administration and therapeutic application. Pharmaceutical dosage forms of the IL23R binding molecules described herein comprise physiologically acceptable carriers that are inherently non-toxic and non-therapeutic. Examples of such carriers include ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts, or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, and PEG. Carriers for topical or gel-based forms of polypeptides include polysaccharides such as sodium carboxymethylcellulose or methylcellulose, polyvinylpyrrolidone, polyacrylates, polyoxyethylene-polyoxypropylene-block polymers, PEG, polymeric amino acids, amino acid copolymers, and lipid aggregates (such as oil droplets or liposomes).

The pharmaceutical compositions may also comprise pharmaceutically-acceptable, non-toxic carriers, excipients, stabilizers, or diluents, which are defined as vehicles commonly used to formulate pharmaceutical compositions for animal or human administration. The diluent is selected so as not to affect the biological activity of the combination. Acceptable carriers, excipients, or stabilizers are non-toxic to recipients at the dosages and concentrations employed, and include buffers such as phosphate, citrate, and other organic acids; antioxidants including ascorbic acid and methionine; preservatives (such as octadecyidimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

Formulations to be used for in vivo administration are typically sterile. Sterilization of the compositions of the present disclosure may readily accomplished by filtration through sterile filtration membranes.

Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above (Langer, *Science* 249: 1527, 1990 and Hanes, *Advanced Drug Delivery Reviews* 28: 97-119, 1997). The agents of this disclosure can be administered in the form of a depot injection or implant preparation which can be formulated in such a manner as to permit a sustained or pulsatile release of the active ingredient. The pharmaceutical compositions are generally formulated as sterile, substantially isotonic and in full compliance with all Good Manufacturing Practice (GMP) regulations of the U.S. Food and Drug Administration.

Vector Delivery of Polypeptide IL23R Binding Molecules

In those embodiments where the IL23R binding molecule is a polypeptide, such IL23R binding molecules may also be delivered to a subject through the administration of a recombinant vectors comprising a nucleic acid sequence encoding the peptidyl IL23R binding molecule operably linked to an expression control sequence in the cells of the tissues of the subject.

Expression vectors may be viral vectors or non-viral vectors. The term "nonviral vector" refers to an autonomously replicating, extrachromosomal circular DNA molecule, distinct from the normal genome and nonessential for cell survival under nonselective conditions capable of effecting the expression of an coding sequence in the target cell. Plasmids are examples of non-viral vectors. In order to facilitate transfection of the target cells, the target cell may be exposed directly with the non-viral vector may under conditions that facilitate uptake of the non-viral vector. Examples of conditions which facilitate uptake of foreign nucleic acid by mammalian cells are well known in the art and include but are not limited to chemical means (such as Lipofectamine®, Thermo-Fisher Scientific), high salt, magnetic fields (electroporation)

In one embodiment, a non-viral vector may be provided in a non-viral delivery system. Non-viral delivery systems are typically complexes to facilitate transduction of the target cell with a nucleic acid cargo wherein the nucleic acid is complexed with agents such as cationic lipids (DOTAP, DOTMA), surfactants, biologicals (gelatin, chitosan), metals (gold, magnetic iron) and synthetic polymers (PLG, PEI, PAMAM). Numerous embodiments of non-viral delivery systems are well known in the art including lipidic vector systems (Lee et al. (1997) Crit Rev Ther Drug Carrier Syst. 14:173-206); polymer coated liposomes (Marin et al., U.S. Pat. No. 5,213,804, issued May 25, 1993; Woodle, et al., U.S. Pat. No. 5,013,556, issued May 7, 1991); cationic liposomes (Epand et al., U.S. Pat. No. 5,283,185, issued Feb. 1, 1994; Jessee, J. A., U.S. Pat. No. 5,578,475, issued Nov. 26, 1996; Rose et al, U.S. Pat. No. 5,279,833, issued Jan. 18, 1994; Gebeyehu et al., U.S. Pat. No. 5,334,761, issued Aug. 2, 1994).

In another embodiment, the expression vector may be a viral vector. As used herein, the term viral vector is used in its conventional sense to refer to any of the obligate intracellular parasites having no protein-synthesizing or energy-generating mechanism and generally refers to any of the enveloped or non-enveloped animal viruses commonly employed to deliver exogenous transgenes to mammalian cells. A viral vector may be replication competent (e.g., substantially wild-type), conditionally replicating (recombinantly engineered to replicate under certain conditions) or replication deficient (substantially incapable of replication in the absence of a cell line capable of complementing the deleted functions of the virus). The viral vector can possess certain modifications to make it "specifically replicating," i.e. that it replicates preferentially in certain cell types or phenotypic cell states, e.g., cancerous. Viral vector systems useful in the practice of the instant IL23R binding molecule include, for example, naturally occurring or recombinant viral vector systems. Examples of viruses useful in the practice of the present IL23R binding molecule include recombinantly modified enveloped or non-enveloped DNA and RNA viruses. For example, viral vectors can be derived from the genome of human or bovine adenoviruses, vaccinia virus, lentivirus, herpes virus, adeno-associated virus, human immunodeficiency virus, sindbis virus, and retroviruses (including but not limited to Rous sarcoma virus), and hepatitis B virus. Typically, genes of interest are inserted into such vectors to allow packaging of the gene construct, typically with accompanying viral genomic sequences, followed by infection of a sensitive host cell resulting in expression of the gene of interest (e.g., a targeting antigen).

The expression vector may encode one or more polypeptides in addition to the targeting antigen. When expressing multiple polypeptides as in the practice of the present IL23R binding molecule, each polypeptide may be operably linked to an expression control sequence (monocistronic) or multiple polypeptides may be encoded by a polycistronic construct where multiple polypeptides are expressed under the control of a single expression control sequence. In one embodiment, the expression vector encoding the targeting antigen may optionally further encode one or more immunological modulators. Examples of immunological modulators useful in the practice of the present IL23R binding molecule include but are not limited to cytokines. Examples of such cytokines are interleukins including but not limited to one more or of IL-1, IL-2, IL-3, IL-4, IL-12, TNF-alpha, interferon alpha, interferon alpha-2b, interferon-beta, interferon-gamma, GM-CSF, MIP1-alpha, MIP1-beta, MIP3-alpha, TGF-beta and other suitable cytokines capable of modulating immune response. The expressed cytokines can be directed for intracellular expression or expressed with a signal sequence for extracellular presentation or secretion.

The expression vector may optionally provide an additional expression cassette comprising a nucleic acid sequence encoding a "rescue" gene. A "rescue gene" is a nucleic acid sequence, the expression of which renders the cell susceptible to killing by external factors or causes a toxic condition in the cell such that the cell is killed. Providing a rescue gene enables selective cell killing of transduced cells. Thus, the rescue gene provides an additional safety precaution when said constructs are incorporated into the cells of a mammalian subject to prevent undesirable spreading of transduced cells or the effects of replication competent vector systems. In one embodiment, the rescue gene is the thymidine kinase (TK) gene (see e.g., Woo, et al. U.S. Pat. No. 5,631,236 issued May 20, 1997 and Freeman, et al. U.S. Pat. No. 5,601,818 issued Feb. 11, 1997) in which the cells expressing the TK gene product are susceptible to selective killing by the administration of gancyclovir.

Dosage

The present disclosure further provides the administration of therapeutically or prophylactically effective dose of IL23R binding molecule or a recombinant vector or cell comprising a nucleic acid sequence encoding a polypeptide IL23R binding molecule to a subject suffering from or at risk of developing, respectively, a disease, disorder or condition. The dosage of the pharmaceutical composition comprising the IL23R binding molecules, vector or cell depends on factors including the route of administration, the disease to be treated, and physical characteristics, e.g., age, weight, general health, of the subject. Typically, the amount of a IL23R binding molecule contained within a single dose may be an amount that effectively prevents, delays, or treats the disease without inducing significant toxicity. A pharmaceutical composition of the disclosure may include a dosage of a IL23R binding molecule described herein ranging from 0.01 to 500 mg/kg (e.g., from 0.01 to 450 mg, from 0.01 to 400 mg, from 0.01 to 350 mg, from 0.01 to 300 mg, from 0.01 to 250 mg, from 0.01 to 200 mg, from 0.01 to 150 mg, from 0.01 to 100 mg, from 0.01 to 50 mg, from 0.01 to 10 mg, from 0.01 to 1 mg, from 0.1 to 500 mg/kg, from 1 to 500 mg/kg, from 5 to 500 mg/kg, from 10 to 500 mg/kg, from 50 to 500 mg/kg, from 100 to 500 mg/kg, from 150 to 500 mg/kg, from 200 to 500 mg/kg, from 250 to 500 mg/kg, from 300 to 500 mg/kg, from 350 to 500 mg/kg, from 400 to 500 mg/kg, or from 450 to 500 mg/kg) and, in a more specific embodiment, about 1 to about 100 mg/kg (e.g., about 1 to about 90 mg/kg, about 1 to about 80 mg/kg, about 1 to about 70 mg/kg, about 1 to about 60 mg/kg, about 1 to about 50 mg/kg, about 1 to about 40 mg/kg, about 1 to about 30 mg/kg, about 1 to about 20 mg/kg, about 1 to about 10 mg/kg, about 10 to about 100 mg/kg, about 20 to about 100 mg/kg, about 30 to about 100 mg/kg, about 40 to about 100 mg/kg, about 50 to about 100 mg/kg, about 60 to about 100 mg/kg, about 70 to about 100 mg/kg, about 80 to about 100 mg/kg, or about 90 to about 100 mg/kg). In some embodiments, a pharmaceutical composition of the disclosure may include a dosage of a binding protein described herein ranging from 0.01 to 20 mg/kg (e.g., from 0.01 to 15 mg/kg, from 0.01 to 10 mg/kg, from 0.01 to 8 mg/kg, from 0.01 to 6 mg/kg, from 0.01 to 4 mg/kg, from 0.01 to 2 mg/kg, from 0.01 to 1 mg/kg, from 0.01 to 0.1 mg/kg, from 0.01 to 0.05 mg/kg, from 0.05 to 20 mg/kg, from 0.1 to 20 mg/kg, from 1 to 20 mg/kg, from 2 to 20 mg/kg, from 4 to 20 mg/kg, from 6 to 20 mg/kg, from 8 to 20 mg/kg, from 10 to 20 mg/kg, from 15 to 20 mg/kg). The dosage may be adapted by the physician in accordance with conventional factors such as the extent of the disease and different parameters of the subject.

A pharmaceutical composition containing a IL23R binding molecule described herein can be administered to a subject in need thereof, for example, one or more times (e.g., 1-10 times or more) daily, weekly, monthly, biannually, annually, or as medically necessary. Dosages may be provided in either a single or multiple dosage regimens. The timing between administrations may decrease as the medical condition improves or increase as the health of the patient declines. A course of therapy may be a single dose or in multiple doses over a period of time. In some embodiments, a single dose is used. In some embodiments, two or more split doses administered over a period of 1, 2, 3, 4, 5, 6, 7, 8, 9, 10, 11, 12, 13, 14, 21, 28, 30, 60, 90, 120 or 180 days are used. Each dose administered in such split dosing protocols may be the same in each administration or may be different. Multi-day dosing protocols over time periods may be provided by the skilled artisan (e.g., physician) monitoring the administration, taking into account the response of the subject to the treatment including adverse effects of the treatment and their modulation as discussed above.

For prophylactic applications, pharmaceutical compositions or medicaments are administered to a patient susceptible to, or otherwise at risk of disease in an amount sufficient to eliminate or reduce the risk, lessen the severity, or delay the outset of the disease, including biochemical, histologic and/or behavioral symptoms of the disease, its complications and intermediate pathological phenotypes presenting during development of the disease.

In some embodiments the condition to be treated is a chronic condition (e.g., a chronic infection, i.e., an infection that is not cleared by the host immune system within a period of up to 1 week, 2 weeks, etc.). In some cases, chronic condition involve integration of pathogen genetic elements into the host genome, e.g., retroviruses, lentiviruses, Hepatitis B virus, etc. In other cases, chronic infections, for example certain intracellular bacteria or protozoan pathogens, result from a pathogen cell residing within a host cell. Additionally, in some embodiments, the infection is in a latent stage, as with herpes viruses or human papilloma viruses. In such instances, the course of therapy may involve the administration of the IL23R binding molecule over an extended period of time including continued administration in the substantial absence of the symptoms of the chronic condition to prevent recurrence of the chronic conditions or symptoms thereof.

In prophylactic applications, a relatively low dosage may be administered at relatively infrequent intervals over a long period of time. Some patients continue to receive treatment for the rest of their lives. In other therapeutic applications, a relatively high dosage at relatively short intervals is sometimes required until progression of the disease is reduced or terminated, and preferably until the patient shows partial or complete amelioration of symptoms of disease. Thereafter, the patent can be administered a prophylactic regime.

Routes of Administration

Administration of a IL23R binding molecules described herein may be achieved through any of a variety of art recognized methods including but not limited to the topical, intravascular injection (including intravenous or intraarterial infusion), intradermal injection, subcutaneous injection, intramuscular injection, intraperitoneal injection, intracranial injection, intratumoral injection, intranodal injection, transdermal, transmucosal, iontophoretic delivery, intralymphatic injection (Senti and Kundig (2009) *Current Opinions in Allergy and Clinical Immunology* 9(6):537-543), intragastric infusion, intraprostatic injection, intravesical infusion (e.g., bladder), respiratory inhalers including nebulizers, intraocular injection, intraabdominal injection, intralesional injection, intraovarian injection, intracerebral infusion or injection, intracerebroventricular injection (ICVI), and the like. Administration to the subject may be achieved by intravenous, as a bolus or by continuous infusion over a period of time. Examples of parenteral routes of administration include, for example, intravenous, intradermal, subcutaneous, transdermal (topical), transmucosal, and rectal administration. The IL23R binding molecule can be administered once, continuously, such as by continuous pump, or at periodic (e.g., daily, bi-weekly, monthly) intervals over a period of time can occur over the period of one week, two weeks, one month, two months, three months or more. Desired time intervals of multiple doses of the IL23R binding molecule may be determined by one of skill in the art.

As described hereinabove, the compositions of the present disclosure may be used in combination with one or more additional therapeutically effective agents. As used herein, the term "in combination with" when used in reference to the administration of multiple agents to a subject refers to the administration of a first agent at least one additional (i.e. second, third, fourth, fifth, etc.) supplementary agent to a subject. For purposes of the present disclosure, one agent (e.g., a IL23R binding molecule) is considered to be administered in combination with a supplementary agent if the biological effect resulting from the administration of the first agent persists in the subject at the time of administration of the supplementary agent such that the therapeutic effects of the first agent and second agent overlap. The administration of the first agent may provide a therapeutic effect over an extended time and the administration of the supplementary agent provides its therapeutic effect while the therapeutic effect of the first agent remains ongoing such that the supplementary agent is considered to be administered in combination with the first agent, even though the first agent may have been administered at a point in time significantly distant (e.g., days or weeks) from the time of administration of the supplementary agent. In one embodiment, one agent is considered to be administered in combination with a supplementary agent if the first and second agents are administered simultaneously (within 30 minutes of each other), contemporaneously or sequentially. In some embodiments, a first agent is deemed to be administered "contemporaneously" with a supplementary agent if first and supplementary agents are administered within about 24 hours of each another, preferably within about 12 hours of each other, preferably within about 6 hours of each other, preferably within about 2 hours of each other, or preferably within about 30 minutes of each other. The term "in combination with" shall also understood to apply to the situation where a first agent and a supplementary agent are co-formulated in single pharmaceutically acceptable formulation and the co-formulation is administered to a subject. In certain embodiments, first agent and the supplementary agent(s) are administered or applied sequentially, e.g., where one agent is administered prior to one or more other agents. In other embodiments, the first agent and the supplementary agent(s) are administered simultaneously, for example where two or more agents are administered at or about the same time; the two or more agents may be present in two or more separate formulations or combined into a single formulation (i.e., a co-formulation). Regardless of whether the agents are administered sequentially or simultaneously, they are considered to be administered in combination for purposes of the present disclosure.

Kits

The present disclosure also contemplates kits comprising pharmaceutical compositions of IL23R binding molecules. In some embodiments, the kit further comprises supplementary pharmaceutical compositions comprising supplementary agents as discussed above for use in combination therapy with IL23R binding molecules. The kits are generally in the form of a physical structure housing various components, as described below, and can be utilized, for example, in practicing the methods described above. A kit may comprise a IL23R binding molecule in the form of a pharmaceutical composition suitable for administration to a subject that is ready for use or in a form or requiring preparation for example, thawing, reconstitution or dilution prior to administration. When the IL23R binding molecule is in a form that requires reconstitution by a user, the kit may also comprise a sterile container providing a reconstitution medium comprising buffers, pharmaceutically acceptable excipients, and the like. A kit of the present disclosure can be designed for conditions necessary to properly maintain the components housed therein (e.g., refrigeration or freezing). A kit may further contain a label or packaging insert including identifying information for the components therein and instructions for their use. Each component of the kit can be enclosed within an individual container, and all of the various containers can be within a single package. Labels or inserts can include manufacturer information such as lot numbers and expiration dates. The label or packaging insert can be, e.g., integrated into the physical structure housing the components, contained separately within the physical structure, or affixed to a component of the kit (e.g., an ampule, syringe or vial). Labels or inserts may be provided in a physical form or a computer readable medium. In some embodiments, the actual instructions are not present in the kit, but rather the kit provides a means for obtaining the instructions from a remote source, e.g., via an internet site, including by secure access by providing a password (or scannable code such as a barcode or QR code on the container of the IL23R binding molecule or kit comprising) in compliance with governmental regulations (e.g., HIPAA) are provided.

EXAMPLES

The following examples are put forth so as to provide those of ordinary skill in the art with a complete disclosure and description of how to make and use the present IL23R binding molecule, and are not intended to limit the scope of what the inventors regard as their IL23R binding molecule nor are they intended to represent that the experiments below were performed and are all of the experiments that can be performed. It is to be understood that exemplary descriptions written in the present tense were not necessarily performed, but rather that the descriptions can be performed to generate the data and the like described therein. Efforts have been made to ensure accuracy with respect to numbers used (e.g., amounts, temperature, etc.), but some experimental errors and deviations should be accounted for. Variations of the particularly described procedures employed may become apparent to individuals or skill in the art and it is expected that those skilled artisans may employ such variations as appropriate. Accordingly, it is intended that the IL23R binding molecule be practiced otherwise than as specifically described herein, and that the invention includes all modifications and equivalents of the subject matter recited in the claims appended hereto as permitted by applicable law.

Unless indicated otherwise, parts are parts by weight, molecular weight is weight average molecular weight, temperature is in degrees Celsius (° C.), and pressure is at or near atmospheric. Standard abbreviations are used, including the following: bp=base pair(s); kb=kilobase(s); pl=picoliter(s); s or sec=second(s); min=minute(s); h or hr=hour(s); aa=amino acid(s); kb=kilobase(s); nt=nucleotide(s); pg=picogram; ng=nanogram; μg=microgram; mg=milligram; g=gram; kg=kilogram; dl or dL=deciliter; μl or μL=microliter; ml or mL=milliliter; l or L=liter; μM=micromolar; mM=millimolar; M=molar; kDa=kilodalton; i.m.=intramuscular(ly); i.p.=intraperitoneal (ly); SC or SQ=subcutaneous(ly); QD=daily; BID=twice daily; QW=weekly; QM=monthly; HPLC=high performance liquid chromatography; BW=body weight; U=unit; ns=not statistically significant; PBS=phosphate-buffered saline; PCR=polymerase chain reaction; NHS=N-hydroxysuccinimide; HSA=human serum albumin; MSA=mouse serum albumin; DMEM=Dulbeco's Modification of Eagle's Medium; GC=genome copy; EDTA=ethylenediaminetetraacetic acid; PBMCs=primary peripheral blood mononuclear cells; FBS=fetal bovine serum; FCS=fetal calf serum; HEPES=4-(2-hydroxyethyl)-1piperazineethanesulfonic acid; LPS=lipopolysaccharide; ATCC=American Type Culture Collection

Example 1. Immunization Protocol

The process for isolation of the anti-hIL23R VHHs was initiated by immunization of a camel with a 332 amino acid polypeptide corresponding to amino acids 24-355 of hIL23R, (UNIPROT Reference No. Q5VWK5). The process for isolation of the anti-m IL23R VHHs was the initiated by immunization of a camel with the with the 351 amino acid extracellular domain of the mIL23R, amino acids 24-374 of the m IL23R precursor (UNIPROT Reference No. Q8K4B4). With respect to each antigen, the following methodology was used to identify and isolate the VHHs.

The synthetic DNA sequence encoding the antigen was inserted into the pFUSE_hIgG1_Fc2 vector (Generay Biotechnology) and transfected into the HEK293F mammalian cell host cell for expression. The antigen is expressed as an Fc fusion protein which is purified using Protein A chromatography. The antigen was diluted with 1×PBS (antigen total about 1 mg). The quality was estimated by SDS-PAGE to ensure the purity was sufficient (>80%) for immunization. The camel was acclimated at the facility for at least 7 days before immunization. The immunization with the antigen was conducted using once weekly administration of the antigen over a period of 7 weeks. For the initial immunization, the immunogen was prepared as follows: 10 mL of complete Freund's Adjuvant (CFA) was added into mortar, then 10 mL antigen in 1×PBS was slowly added into the mortar with the pestle grinding and sample ground until the antigen was emulsified until milky white and hard to disperse. For the subsequent six immunizations (weeks 2-7) in the immunization protocol, immunogen was prepared as above except that Incomplete Freund's Adjuvant (IFA) was used in place of CFA. At least six sites on the camel were injected subcutaneously with approximately 2 ml of the emulsified antigen for a total of approximately 10 mL per camel. When injecting the antigen, the needle is maintained in the in the subcutaneous space for approximately 10 to 15 seconds after each injection to avoid leakage of the emulsion.

Example 2. Phage Library Construction

A blood sample was collected from the camel three days following the last injection in the immunization protocol. RNA was extracted from blood and transcribed to cDNA. The approximately 900 bp reverse transcribed sequences encoding the VH-CH1-hinge-CH2-CH3 constructs were isolated from the approximately desired 700 bp fragments encoding the VHH-hinge-CH2-CH3 species. The purified approximately 700 bp fragments were amplified by nested PCR. The amplified sequences were digested using Pst1 and Not1. The approximately 400 bp PST1/Not1 digested fragments were inserted into a Pst1/Not1 digested pMECS phagemid vector such that the sequence encoding the VHH was in frame with a DNA sequence encoding a HA/His sequence. The PCR generated sequences and the vector of pMECS phagemid were digested with PstI and NotI, subsequently, ligated to pMECS/Nb recombinant. After ligation, the products were transformed into *Escherichia coli* (*E. coli*) TG1 cells by electroporation. The transformants were enriched in growth medium, followed by transfer to 2YT+2% glucose agar plates.

Example 3: Isolation of Antigen Specific VHHs

Bio-panning of the phage library was conducted to identify VHHs that bind IL23R. A 96-well plate was coated with IL23R and the phage library was incubated in each well to allow phage-expressing IL23R reactive VHH to bind to the IL23R on the plate. Non-specifically bound phage were washed off and the specifically bound phage isolated. After the selection, the enriched phage library expressing IL23R reactive VHH were amplified in TG1 cells. The aforementioned bio-panning process was repeated for 2-3 rounds to enrich the library for VHH selective for IL23R. Once biopanning was complete, three 96-well plates of individual phage clones were isolated in order to perform an ELISA on IL23R coated plates to identify positive VHH binders. Positive clones were sequenced, and sequences analyzed to identify unique clonotypes.

Experimental

The single domain antibodies of the present disclosure were obtained from camels by immunization with an extracellular domain of a IL-23 receptor. IL-23 VHH molecules of the present disclosure of the present disclosure were generated in substantial accordance with the teaching of the Examples. Briefly, a camel was sequentially immunized with the ECD of the human IL-23 and mouse IL-23 over a period several weeks of by the subcutaneous an adjuvanted composition containing a recombinantly produced fusion proteins comprising the extracellular domain of the IL-23, the human IgG1 hinge domain and the human IgG1 heavy chain Fc. Following immunization, RNAs extracted from a blood sample of appropriate size VHH-hinge-CH2-CH3 species were transcribed to generate DNA sequences, digested to identify the approximately 400 bp fragment comprising the nucleic acid sequence encoding the VHH domain was isolated. The isolated sequence was digested with restriction endonucleases to facilitate insertion into a phagemid vector for in frame with a sequence encoding a his-tag and transformed into *E. coli* to generate a phage library. Multiple rounds of biopanning of the phage library were conducted to identify VHHs that bound to the ECD of IL-23 (human or mouse as appropriate). Individual phage clones were isolated for periplasmic extract ELISA (PE-ELISA) in a 96-well plate format and selective binding confirmed by colorimetric determination. The IL-23 binding molecules that demonstrated specific binding to the IL-23 antigen were isolated and sequenced and sequences analyzed to identify VHH sequences, CDRs and identify unique VHH clonotypes. As used herein, the term "clonotypes" refers a collection of binding molecules that originate from the same B-cell progenitor cell, in particular collection of antigen binding molecules that belong to the same germline family, have the same CDR3 lengths, and have 70% or greater homology in CDR3 sequence. The VHH molecules demonstrating specific binding to the hIL-23 ECD antigen (anti-human IL-23 VHHs) and the CDRs isolated from such VHHs are provided in Table 1. The VHH molecules demonstrating specific binding to the mIL-23 ECD antigen (anti-mouse IL-23 VHHs) are provided in Table 4 and the CDRs isolated from such VHHs are provided in Table 3. Nucleic acid sequences encoding the VHHs of Table 1 and 4 are provide in Tables 2 and 5 respectively.

In some instances, due to sequence or structural similarities between the extracellular domains of IL-23 receptors from various mammalian species, immunization with an antigen derived from a IL-23 of a first mammalian species (e.g., the hIL-23-ECD) may provide antibodies which specifically bind to IL-23 receptors of one or more additional mammalian species. Such antibodies are termed "cross reactive." For example, immunization of a camelid with a human derived antigen (e.g., the hIL-23-ECD) may generate antibodies that are cross-reactive the murine and human receptors. Evaluation of cross-reactivity of antibody with respect to the receptors derived from other mammalian species may be readily determined by the skilled artisan, for example using the methods relating to evaluation of binding affinity and/or specific binding described elsewhere herein such as flow cytometry or SPR. Consequently, the use of the term "human IL-23 VHH" or "hIL-23 VHH" merely denotes that the species of the IL-23 antigen used for immunization of the camelid from which the VHH was derived was the human IL-23 (e.g., the hIL-23, ECD, SEQ ID NO:327 but should not be understood as limiting with respect to the specific binding affinity of the VHH for hIL-23 molecules of other mammalian species. Similarly, the use of the term "mouse IL-23 VHH" or "mIL-23" merely denotes that the species of the IL-23 antigen used for immunization of the camelid from which the VHH was derived was the murine IL-23 (e.g., the mIL-23 ECD, SEQ ID NO:329) but should not be understood as limiting with respect to the specific binding affinity of the VHH for IL-23 molecules of other mammalian species.

It is understood that the examples and embodiments described herein are for illustrative purposes only and that various modifications or changes in light thereof will be suggested to persons skilled in the art and are to be included within the spirit and purview of this application and scope of the appended claims. All publications, sequence accession numbers, patents, and patent applications cited herein are hereby incorporated by reference in their entirety for all purposes.

The invention claimed is:

1. A 1IL23R binding molecule that specifically binds to the extracellular domain of IL23R, wherein the IL23R binding molecule comprises a single domain antibody (sdAb), wherein the sdAb comprises a complementary determining region 1 (CDR1), a CDR2, and a CDR3 as shown in a row of the table below:

| CDR1 | CDR2 | CDR3 |
|---|---|---|
| YTYCSYDMS (SEQ ID NO: 21) | AFNSDGTTSYADSVKG (SEQ ID NO: 22) | DPHVQSSGGYCPPY (SEQ ID NO: 23) |

-continued

| CDR1 | CDR2 | CDR3 |
|---|---|---|
| YTYCSYDMS (SEQ ID NO: 24) | SFNSDGSTSYADSVKG (SEQ ID NO: 25) | DPHADWGAPCGGDY (SEQ ID NO: 26) |
| YTYCSYDMS (SEQ ID NO: 33) | AIASDGSTSYADSLKG (SEQ ID NO: 34) | DPHVQSSGGYCPPY (SEQ ID NO: 35) |
| YTYCSYDMG (SEQ ID NO: 36) | SINSDGTTSYADSVKG (SEQ ID NO: 37) | DPQTRPGKPCADY (SEQ ID NO: 38) |
| YTYCSYDMK (SEQ ID NO: 42) | GIDSDGSISYADSVKG (SEQ ID NO: 43) | EGTIPVGACPNY (SEQ ID NO: 44) |
| YTYCSYDMS (SEQ ID NO: 45) | SINSDGTTSYADSVKG (SEQ ID NO: 46) | DPQTRPGKPCADY (SEQ ID NO: 47) |
| YTYCSYDMT (SEQ ID NO: 51) | AIDSDGSTSYADSVKG (SEQ ID NO: 52) | DPIATISRRCDSY (SEQ ID NO: 53) |
| YTYCSYDMK (SEQ ID NO: 57) | AIDSDGSTSYADSVKG (SEQ ID NO: 58) | EGTIPVGVCPNY (SEQ ID NO: 59) |
| YTYCSYDMK (SEQ ID NO: 60) | AIDSDGSTSYADSVKG (SEQ ID NO: 61) | EGTVPVGVCPNY (SEQ ID NO: 62) |
| YTSCSYDMS (SEQ ID NO: 75) | AIHSDGTTSYADSMKG (SEQ ID NO: 76) | DPNYSDHVCPPY (SEQ ID NO: 77). |

2. The IL23R binding molecule of claim 1, wherein the sdAb has at least 95% identity to a polypeptide sequence of any one of SEQ ID NOS: 2, 3, 6, 7, 9, 10, 12, 14, 15, and 20.

3. The IL23R binding molecule of claim 1, wherein the sdAb is humanized or otherwise comprises CDRs grafted onto a heterologous framework.

4. The IL23R binding molecule of claim 1, further comprising a labeling agent, an imaging agent, and/or a therapeutic agent.

5. A method for isolating, depleting, or enriching IL23R+ cells in a biological sample, comprising contacting the biological sample with the IL23R binding molecule of claim 1.

6. A pharmaceutical preparation comprising the IL23R binding molecule of claim 1.

7. A kit comprising the IL23R binding molecule of claim 1.

8. The IL23R binding molecule of claim 1, wherein the sdAb is linked to a second binding molecule that specifically binds to the extracellular domain of a second cell surface molecule.

9. The IL23R binding molecule of claim 1, wherein the sdAb comprises the CDR1, the CDR2, and the CDR3 of SEQ ID NOS:21, 22, and 23, respectively.

10. The IL23R binding molecule of claim 9, wherein the sdAb has at least 95% identity to a polypeptide sequence of SEQ ID NO:2.

11. The IL23R binding molecule of claim 1, wherein the sdAb comprises the CDR1, the CDR2, and the CDR3 of SEQ ID NOS:24, 25, and 26, respectively.

12. The IL23R binding molecule of claim 11, wherein the sdAb has at least 95% identity to a polypeptide sequence of SEQ ID NO:3.

13. The IL23R binding molecule of claim 1, wherein the sdAb comprises the CDR1, the CDR2, and the CDR3 of SEQ ID NOS:33, 34, and 35, respectively.

14. The IL23R binding molecule of claim 13, wherein the sdAb has at least 95% identity to a polypeptide sequence of SEQ ID NO:6.

15. The IL23R binding molecule of claim 1, wherein the sdAb comprises the CDR1, the CDR2, and the CDR3 of SEQ ID NOS:36, 37, and 38, respectively.

16. The IL23R binding molecule of claim 15, wherein the sdAb has at least 95% identity to a polypeptide sequence of SEQ ID NO:7.

17. The IL23R binding molecule of claim 1, wherein the sdAb comprises the CDR1, the CDR2, and the CDR3 of SEQ ID NOS:42, 43, and 44, respectively.

18. The IL23R binding molecule of claim 17, wherein the sdAb has at least 95% identity to a polypeptide sequence of SEQ ID NO:9.

19. The IL23R binding molecule of claim 1, wherein the sdAb comprises the CDR1, the CDR2, and the CDR3 of SEQ ID NOS:45, 46, and 47, respectively.

20. The IL23R binding molecule of claim 19, wherein the sdAb has at least 95% identity to a polypeptide sequence of SEQ ID NO:10.

21. The IL23R binding molecule of claim 1, wherein the sdAb comprises the CDR1, the CDR2, and the CDR3 of SEQ ID NOS:51, 52, and 53, respectively.

22. The IL23R binding molecule of claim 21, wherein the sdAb has at least 95% identity to a polypeptide sequence of SEQ ID NO:12.

23. The IL23R binding molecule of claim 1, wherein the sdAb comprises the CDR1, the CDR2, and the CDR3 of SEQ ID NOS:57, 58, and 59, respectively.

24. The IL23R binding molecule of claim 23, wherein the sdAb has at least 95% identity to a polypeptide sequence of SEQ ID NO:14.

25. The IL23R binding molecule of claim 1, wherein the sdAb comprises the CDR1, the CDR2, and the CDR3 of SEQ ID NOS:60, 61, and 62, respectively.

26. The IL23R binding molecule of claim 25, wherein the sdAb has at least 95% identity to a polypeptide sequence of SEQ ID NO:15.

27. The IL23R binding molecule of claim 1, wherein the sdAb comprises the CDR1, the CDR2, and the CDR3 of SEQ ID NOS:75, 76, and 77, respectively.

28. The IL23R binding molecule of claim 27, wherein the sdAb has at least 95% identity to a polypeptide sequence of SEQ ID NO:20.

29. The IL23R binding molecule of claim 1, wherein the sdAb is a VHH.

30. A nucleic acid sequence encoding the IL23R binding molecule of claim 1.

31. A recombinant viral or non-viral vector comprising a nucleic acid of claim 30.

32. A host cell comprising a nucleic acid of claim 30.

33. The nucleic acid sequence of claim 30, encoding the IL23R binding molecule comprising the sdAb having the CDR1, the CDR2, and the CDR3 of SEQ ID NOS:21, 22, and 23, respectively.

34. The nucleic acid sequence of claim 30, encoding the IL23R binding molecule comprising the sdAb having the CDR1, the CDR2, and the CDR3 of SEQ ID NOS:24, 25, and 26, respectively.

35. The nucleic acid sequence of claim 30, encoding the IL23R binding molecule comprising the sdAb having the CDR1, the CDR2, and the CDR3 of SEQ ID NOS:33, 34, and 35, respectively.

36. The nucleic acid sequence of claim 30, encoding the IL23R binding molecule comprising the sdAb having the CDR1, the CDR2, and the CDR3 of SEQ ID NOS:36, 37, and 38, respectively.

37. The nucleic acid sequence of claim 30, encoding the IL23R binding molecule comprising the sdAb having the CDR1, the CDR2, and the CDR3 of SEQ ID NOS:42, 43, and 44, respectively.

38. The nucleic acid sequence of claim 30, encoding the IL23R binding molecule comprising the sdAb having the CDR1, the CDR2, and the CDR3 of SEQ ID NOS:45, 46, and 47, respectively.

39. The nucleic acid sequence of claim 30, encoding the IL23R binding molecule comprising the sdAb having the CDR1, the CDR2, and the CDR3 of SEQ ID NOS:51, 52, and 53, respectively.

40. The nucleic acid sequence of claim 30, encoding the IL23R binding molecule comprising the sdAb having the CDR1, the CDR2, and the CDR3 of SEQ ID NOS:57, 58, and 59, respectively.

41. The nucleic acid sequence of claim 30, encoding the IL23R binding molecule comprising the sdAb having the CDR1, the CDR2, and the CDR3 of SEQ ID NOS:60, 61, and 62, respectively.

42. The nucleic acid sequence of claim 30, encoding the IL23R binding molecule comprising the sdAb having the CDR1, the CDR2, and the CDR3 of SEQ ID NOS:75, 76, and 77, respectively.

* * * * *